US008389705B2

(12) United States Patent
Allen et al.

(10) Patent No.: US 8,389,705 B2
(45) Date of Patent: Mar. 5, 2013

(54) NITRATE TRANSPORT COMPONENTS

(75) Inventors: Stephen M. Allen, Wilmington, DE (US); Kanwarpal Singh Dhugga, Johnston, IA (US); Kevin Fengler, Wilmington, DE (US); Howard P. Hershey, Cumming, IA (US); Lu Liu, Palo Alto, CA (US); Victor Llaca, Newark, DE (US); Dale Loussaert, Clive, IA (US); Xiaomu Niu, Johnston, IA (US); Haiyin Wang, Johnston, IA (US)

(73) Assignees: E. I. du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 13/166,835

(22) Filed: Jun. 23, 2011

(65) Prior Publication Data

US 2012/0005775 A1 Jan. 5, 2012

Related U.S. Application Data

(62) Division of application No. 11/504,116, filed on Aug. 15, 2006, now Pat. No. 7,999,093.

(60) Provisional application No. 60/785,143, filed on Mar. 23, 2006, provisional application No. 60/784,618, filed on Mar. 22, 2006, provisional application No. 60/708,318, filed on Aug. 15, 2005.

(51) Int. Cl.
*C07H 21/04* (2006.01)
*A01H 1/00* (2006.01)
*C07K 14/415* (2006.01)
*C12N 15/00* (2006.01)

(52) U.S. Cl. ........ 536/23.6; 435/6.1; 435/468; 435/419; 435/320.1; 530/370; 536/23.1; 800/278; 800/295

(58) Field of Classification Search .................. 435/6.1, 435/69.1, 468, 183, 419, 320.1; 536/23.2, 536/23.6; 800/278, 295
See application file for complete search history.

(56) References Cited

U.S. PATENT DOCUMENTS

2004/0214272 A1 10/2004 La Rosa et al.

OTHER PUBLICATIONS

E. J. Hewitt et al., Nitrate Metabolism, Chapter 20, pp. 633-681, 1976.
Mathilde Orsel et al., Analysis of the NRT2 Nitrate Transporter Family in *Arabidopsis*. Structure and Gene Expression, Plant Physiology, vol. 129:886-896, 2002.
Yiping Tong et al., A Two-Component, High-Affinity Nitrate Uptake System in Barley, The Plant Journal, vol. 41:442-450, 2005.
National Center for Biotechnology Information General Identifier No. 29412128, Mar. 31, 2003, Accession No. AY129953, S. Quaggiotti et al., Expression of a Putative High-Affinity NO3-Transporter and of a H+-ATPase in Relation to Whole Plant Nitrate Transport Physiology in Two Maize Genotypes Differently Responsive to Low Nitrogen Availability.
National Center for Biotechnology Information General Identifier No. 33941728, Aug. 19, 2003, Accession No. CG069548, C. A. Whitelaw et al., Maize Genomics Consortium.
National Center for Biotechnology Information General Identifier No. 34245424, Aug. 26, 2003, Accession No. CG328158, C.A. Whitelaw et al., Consortium for Maize Genomics.
National Center for Biotechnology Information General Identifier No. 32105143, Jun. 19, 2003, Accession No. CC700367, C. A. Whitelaw et al., Consortium for Maize Genomics.
National Center for Biotechnology Information General Identifier No. 34245411, Aug. 26, 2003, Accession No. CG328145, C. A. Whitelaw et al., Consortium for Maize Genomics.
National Center for Biotechnology Information General Identifier No. 34082540, Aug. 21, 2003, Accession No. CG191479, C. A. Whitelaw et al., Maize Genomics Consortium.
National Center for Biotechnology Information General Identifier No. 33992813, Aug. 20, 2003, Accession No. CG109376, C. A. Whitelaw et al., Maize Genomics Consortium.
National Center for Biotechnology Information General Identifier No. 34913806, Nov. 9, 2004, Accession No. NP_918250, The NCBI Genome Assembly Consortium.
National Center for Biotechnology Information General Identifier No. 50904699, Nov. 9, 2004, Accession No. XP_463838, The NCBI Genome Assembly Consortium.
National Center for Biotechnology Information General Identifier No. 13624657, Apr. 12, 2001, Accession No. CAC36942, J. J. Zhou et al., Functional Expression and Kinetic Characterisation of NAR2 Gene of *Arabidopsis* in *Xenopus oocyte*.
Henk Doddema et al., Uptake of Nitrate by Mutants of *Arabidopsis thaliana*, Disturbed in Uptake or Reduction of Nitrate, Physiol. Plant, vol. 45:332-338, 1979.
WPC Stemmer, PNAS, DNA Shuffling by Random Fragmentation and Reassembly: In Vitro Recombination for Molecular Evolution, vol. 91:10747-10751, 1994.
Andreas Crameri et al., DNA Shuffling of a Family of Genes From Diverse Species Accelerates Directed Evolution, Nature, vol. 391:288-291, 1998.
Jon E. Ness et al., DNA Shuffling of Subgenomic Sequences of Subtilisin, Nature Biotechnology, vol. 17:893-896, 1999.
A. A. Meharg et al., NO-3 Transport Across the Plasma Membrane of *Arabidopsis thaliana* Root Hairs: Kinetic Control by PH and Membrane Voltage, J. Membrane Biol., vol. 145:49-66, 1995.
Bruno Touraine et al., NO3- and ClO3- Fluxes in the CHL1-5 Mutant of *Arabidopsis thaliana*, Plant Physiol., vol. 114:137-144, 1997.
Kun-Hsiang Liu et al., CHL1 is a Dual-Affinity Nitrate Transporter of *Arabidopsis* Involved in Multiple Phases of Nitrate Uptake, The Plant Cell, vol. 11:865-874, 1999.

(Continued)

*Primary Examiner* — Phuong T Bui

(57) ABSTRACT

This invention relates to isolated nucleic acid fragments encoding high affinity nitrate transport components. The invention also relates to the construction of recombinant DNA constructs encoding all or a portion of nitrate transport components, in sense or antisense orientation, wherein expression of the recombinant DNA construct may alter levels of the nitrate transport components in a transformed host cell.

11 Claims, 7 Drawing Sheets

OTHER PUBLICATIONS

Figure 1:
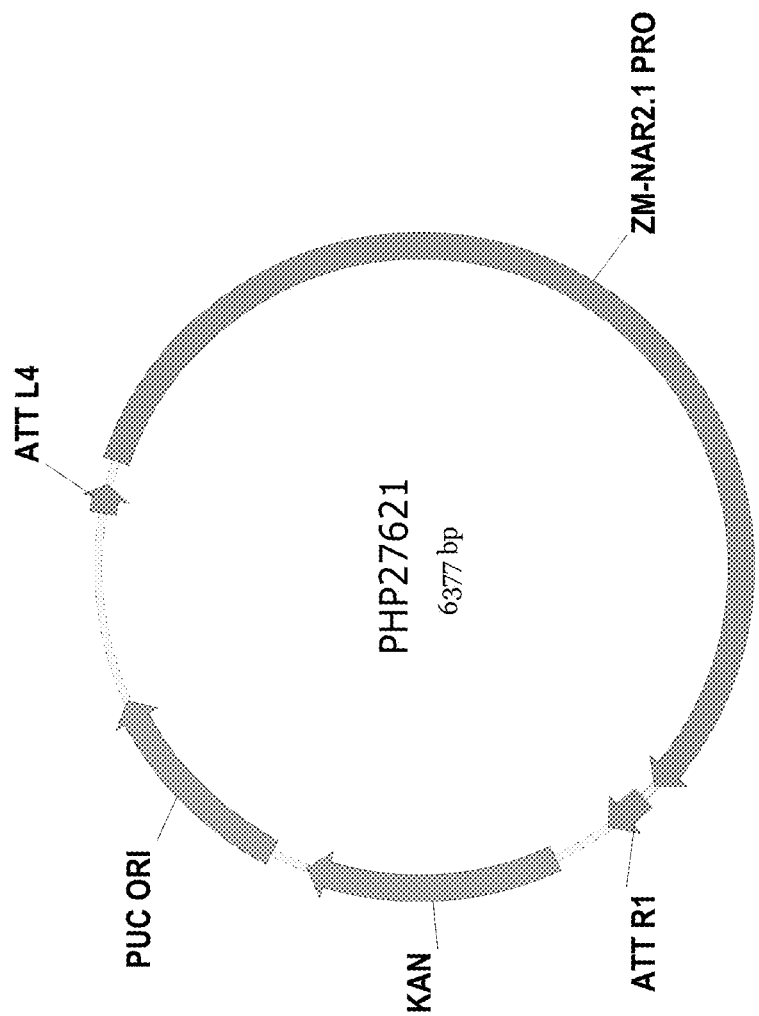

Quaggiotti, S. et al., Expression of a Putative High-Affinity NO3 Transporter and of a H+-ATPase in Relation to Whole Plant Nitrate Transport Physiology in Two Maize Genotypes Differently Responsive to Low Nitrogen Availability, J. of Exp. Botany, vol. 54:1023-1031, 2003.

Vidmar, J. J. et al., Isolation and Characterization of HVNRT 2.3 and HVNRT 2.4, CDNAS Encoding High Affinity Transporters From Roots of Barley, Plant Physiology, vol. 122:783-792, 2000.

Santi, S. et al., Induction of Nitrate Uptake in Maize Roots: Expression of a Putative High-Affinity Nitrate Transporter and Plasma Membrane H+-ATPase Isoforms, J. of Exp. Botany, vol. 54:1851-1864, 2003.

Quaggiotti, S. et al., Effect of Low Molecular Size Humic Substances on Nitrate Uptake and Expression Gens Involves in Nitrate Transport in Maize (*Zea mays* L.), J. of Exp. Botany, vol. 55(398):803-813, 2004.

Barton, G. J., Protein Sequence Alignment and Database Scanning,, Protein Structure Prediction, A Practical Approach, pp. 31-63, 1996.

George, D. G. et al., Current Methods in Sequence Comparison and Analysis, Macromolecular Sequencing and Synthesis Selected Methods and Applications, pp. 127-149,, 1988.

Sheila E. Unkles et al., Two perfectly conserved arginine residues are required for substrate binding in a high-affinity nitrate transporter, PNAS, Dec. 14, 2004, pp. 17549-17554, vol. 101, No. 50.

Laurence J. Trueman et al., Molecular cloning of higher plant homologues of the high-affinity nitrate transporters of *Chlamydomonas reinhardtii* and *Aspergillus nidulans*, Elsevier Science B.V. Gene, 1996, pp. 223-231, vol. 175.

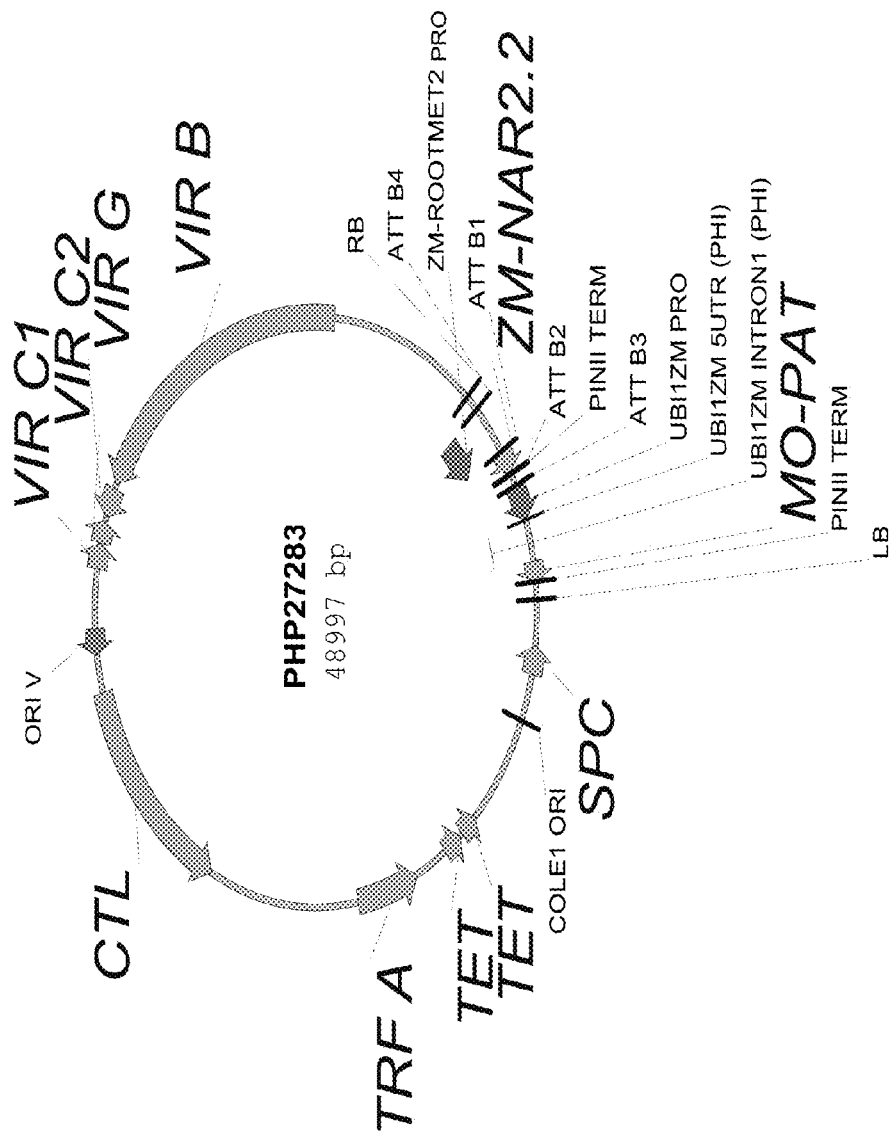

SEQUENCE LISTING

```
<160> NUMBER OF SEQ ID NOS: 96

<210> SEQ ID NO 1
<211> LENGTH: 25
<212> TYPE: DNA
<213> ORGANISM: Artificial
<220> FEATURE:
<223> OTHER INFORMATION: Primer

<400> SEQUENCE: 1
ccaactggag tccaacaccc acaaa                                        25

<210> SEQ ID NO 2
<211> LENGTH: 21
<212> TYPE: DNA
<213> ORGANISM: Artificial
<220> FEATURE:
<223> OTHER INFORMATION: Primer

<400> SEQUENCE: 2
catgctgctc gtccactgcg g                                            21

<210> SEQ ID NO 3
<211> LENGTH: 20
<212> TYPE: DNA
```

```
<213> ORGANISM: Artificial
<220> FEATURE:
<223> OTHER INFORMATION: Primer

<400> SEQUENCE: 3
taatacgact cactataggg                                           20

<210> SEQ ID NO 4
<211> LENGTH: 19
<212> TYPE: DNA
<213> ORGANISM: Artificial
<220> FEATURE:
<223> OTHER INFORMATION: Primer

<400> SEQUENCE: 4
tatttaggtg acactatag                                            19

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
atgttgttgg tggtgagctg                                           20

<210> SEQ ID NO 6
<211> LENGTH: 18
<212> TYPE: DNA
<213> ORGANISM: Artificial
<220> FEATURE:
<223> OTHER INFORMATION: Primer

<400> SEQUENCE: 6
acacgaggtt ggccatgc                                             18

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
gtttgacacc cctttctag caagg                                      25

<210> SEQ ID NO 8
<211> LENGTH: 25
<212> TYPE: DNA
<213> ORGANISM: Artificial
<220> FEATURE:
<223> OTHER INFORMATION: Primer

<400> SEQUENCE: 8
ccttgctaga aagggggtgt caaac                                     25

<210> SEQ ID NO 9
<211> LENGTH: 27
<212> TYPE: DNA
<213> ORGANISM: Artificial
<220> FEATURE:
<223> OTHER INFORMATION: Primer

<400> SEQUENCE: 9
ggtcccgttt ggttagagag actaatc                                   27
```

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
gcgcaacgaa atgcattggt ca                                           22

<210> SEQ ID NO 11
<211> LENGTH: 25
<212> TYPE: DNA
<213> ORGANISM: Artificial
<220> FEATURE:
<223> OTHER INFORMATION: Primer

<400> SEQUENCE: 11
aggggagaga agagaaaaag cgggt                                        25

<210> SEQ ID NO 12
<211> LENGTH: 28
<212> TYPE: DNA
<213> ORGANISM: Artificial
<220> FEATURE:
<223> OTHER INFORMATION: Primer

<400> SEQUENCE: 12
gctgcatgtt tacgactaca atctttgg                                     28

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
tttgtgggtg ttggactcca gttgg                                        25

<210> SEQ ID NO 14
<211> LENGTH: 23
<212> TYPE: DNA
<213> ORGANISM: Artificial
<220> FEATURE:
<223> OTHER INFORMATION: Primer

<400> SEQUENCE: 14
tttgtgggtg ttggactcca gtt                                          23

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
tttgtgggtg ttggactcca                                              20

<210> SEQ ID NO 16
<211> LENGTH: 17
<212> TYPE: DNA
<213> ORGANISM: Artificial
<220> FEATURE:
<223> OTHER INFORMATION: Primer -continued

<400> SEQUENCE: 16
gggatgacgc cgaaggt                                              17

<210> SEQ ID NO 17
<211> LENGTH: 17
<212> TYPE: DNA
<213> ORGANISM: Artificial
<220> FEATURE:
<223> OTHER INFORMATION: Primer

<400> SEQUENCE: 17
cttcggcgtc atccoct                                              17

<210> SEQ ID NO 18
<211> LENGTH: 17
<212> TYPE: DNA
<213> ORGANISM: Artificial
<220> FEATURE:
<223> OTHER INFORMATION: Primer

<400> SEQUENCE: 18
aaggggatga cgccgaa                                              17

<210> SEQ ID NO 19
<211> LENGTH: 17
<212> TYPE: DNA
<213> ORGANISM: Artificial
<220> FEATURE:
<223> OTHER INFORMATION: Primer

<400> SEQUENCE: 19
ttcggcgtca tcccctt                                              17

<210> SEQ ID NO 20
<211> LENGTH: 21
<212> TYPE: DNA
<213> ORGANISM: Artificial
<220> FEATURE:
<223> OTHER INFORMATION: Primer

<400> SEQUENCE: 20
cacatcgccg tgggcatcct t                                         21

<210> SEQ ID NO 21
<211> LENGTH: 18
<212> TYPE: DNA
<213> ORGANISM: Artificial
<220> FEATURE:
<223> OTHER INFORMATION: Primer

<400> SEQUENCE: 21
aggatgccca cggcgatg                                             18

<210> SEQ ID NO 22
<211> LENGTH: 21
<212> TYPE: DNA
<213> ORGANISM: Artificial
<220> FEATURE:
<223> OTHER INFORMATION: Primer

<400> SEQUENCE: 22
cacatcgccg tgggcatcct t                                         21

<210> SEQ ID NO 23
<211> LENGTH: 21
<212> TYPE: DNA

```
<213> ORGANISM: Artificial
<220> FEATURE:
<223> OTHER INFORMATION: Primer

<400> SEQUENCE: 23
aaggatgccc acggcgatgt g                                              21

<210> SEQ ID NO 24
<211> LENGTH: 18
<212> TYPE: DNA
<213> ORGANISM: Artificial
<220> FEATURE:
<223> OTHER INFORMATION: Primer

<400> SEQUENCE: 24
tgccccgcgg ttagcaca                                                  18

<210> SEQ ID NO 25
<211> LENGTH: 18
<212> TYPE: DNA
<213> ORGANISM: Artificial
<220> FEATURE:
<223> OTHER INFORMATION: Primer

<400> SEQUENCE: 25
tgtgctaacc gcggggca                                                  18

<210> SEQ ID NO 26
<211> LENGTH: 18
<212> TYPE: DNA
<213> ORGANISM: Artificial
<220> FEATURE:
<223> OTHER INFORMATION: Primer

<400> SEQUENCE: 26
gcggttagca caaggatg                                                  18

<210> SEQ ID NO 27
<211> LENGTH: 18
<212> TYPE: DNA
<213> ORGANISM: Artificial
<220> FEATURE:
<223> OTHER INFORMATION: Primer

<400> SEQUENCE: 27
catccttgtg ctaaccgc                                                  18

<210> SEQ ID NO 28
<211> LENGTH: 25
<212> TYPE: DNA
<213> ORGANISM: Artificial
<220> FEATURE:
<223> OTHER INFORMATION: Primer

<400> SEQUENCE: 28
ggtagttggc gacggcgtgc cagag                                          25

<210> SEQ ID NO 29
<211> LENGTH: 22
<212> TYPE: DNA
<213> ORGANISM: Artificial
<220> FEATURE:
<223> OTHER INFORMATION: Primer

<400> SEQUENCE: 29
gcgacggcgt gccagagcac cc                                             22
```

```
<210> SEQ ID NO 30
<211> LENGTH: 25
<212> TYPE: DNA
<213> ORGANISM: Artificial
<220> FEATURE:
<223> OTHER INFORMATION: Primer

<400> SEQUENCE: 30
caggttctcc cggatgatgg ggatc                                           25

<210> SEQ ID NO 31
<211> LENGTH: 26
<212> TYPE: DNA
<213> ORGANISM: Artificial
<220> FEATURE:
<223> OTHER INFORMATION: Primer

<400> SEQUENCE: 31
gatccccatc atccgggaga acctgg                                          26

<210> SEQ ID NO 32
<211> LENGTH: 25
<212> TYPE: DNA
<213> ORGANISM: Artificial
<220> FEATURE:
<223> OTHER INFORMATION: Primer

<400> SEQUENCE: 32
gatccccatc atccgggaga acctg                                           25

<210> SEQ ID NO 33
<211> LENGTH: 26
<212> TYPE: DNA
<213> ORGANISM: Artificial
<220> FEATURE:
<223> OTHER INFORMATION: Primer

<400> SEQUENCE: 33
ccaggttctc ccggatgatg gggatc                                          26

<210> SEQ ID NO 34
<211> LENGTH: 3924
<212> TYPE: DNA
<213> ORGANISM: Zea mays

<400> SEQUENCE: 34
ttcgagggca atgggttcca aagaatgtca tttgaattag acacttagtt atttatgaaa      60
aggttttttc tccccgagtt aatttgcttc caaactataa ttaaccctaa gcaaggtgtt     120
agttatttgt tttgacggtt tatatatccg tgttagcttg gtggctagct tgtatccatt     180
tgacttgacg gcacatgcat gcatgcgtgg agtgcaccgt gcggcggttt gtgacgcggt     240
gccaaacgtg caattgactc attgagtagt catcagcagg cttgcgatca ttagacacta     300
acaagcatta atatttgctg catatatata tatacacaca catgcttcac tgacgacgct     360
tgcaacttga tcttgttaat tattatatat cctaagcaca acgaacaaac cttagatatg     420
cgaccatgcc ttgagtagag cgtgaaaaat aggggggtgaa aaaaagggac gagtaattat     480
agatgacact atttgatatt gtttaaagat gagataggga atgtgctgaa tagatcaatt     540
tttaatcagg gatggtaggg actagtattt cctctatgat tttccatgta acacctttga     600
atatacaata ataataagaa gccaccaacc tttgaattat tatctgttcc aatatattag     660
atgaggggtg tatcggaatt tgacttccga gttgttcttg cgtgtccgta cgctcgtacg     720
```

```
gtagctcgtt gggttgttgt accagccatc ctgctactgc gcaacgaaat gcattggtca    780
tctcaattaa gtccaaagat tgtagtcgta aacatgcagc caataagagc aaggataata    840
gtttagccat tgatatgtct tctaaagcta attattactg tattggaccc acctcgtact    900
ctcattctct caccacttgt ttcggaatct gtactgctac aaccagctct tagtcgactg    960
ataattaact acccgctttt tctcttctct cccctccaac tgcaaaaatc taatgtggca   1020
aaccatttag cctgcttaca tcgtcaaaaa tctaatgtgg taaagtgtga agtgtcctaa   1080
agttttagtc cttaatttct ttcaataaac taaactaaac tttagaaaac tcaaacaagt   1140
cctcatgttt gcacatttta ggtctcgttt ggtttgaggg actaaagatt agtccctcca   1200
ttttagtccc atttagttac taaattacca aacagtagga ctaaacagg gactaaattg    1260 ttttagtccc tagtccctta agatggctaa aagggactaa accatattaa ttccacattt   1320 gccctcatt tagttcaatt gtactaatag caggagaatg ttaaaagtca ttttaatctt    1380
cttatgagtc atttaggccc tgtttggttc cattagtcat agaactaaag tttagttgta   1440
gggactaaat agattctaaa tacattaaat gcaacacata aagaccaaaa tgccctttt    1500 tgtttgacac ccctttttcta gcaagggtat ttggagtaaa tgttgccctt tggtcccttt   1560
tagcacccat gtgagggact agagactaaa accaattagt ccctacttta gtcattccgt   1620
ttagcaaaat agagactaaa cgagactaaa acgagaggc taaagattag tctctctaac    1680
caaacgggac ctaaaattac tatctgtatg tatctgttgg atggaaaagt cagaacgtcg   1740 tgggaccac cacgctacca catggtacgg taatgtcaga aagtcgctat cttcttcgat    1800
ctgcatctcc actccagcca gcgctgctta tcatcagcat tcacgaagcc gcccaacgat   1860
aataaaaaat gtcagcgcga tcgcgcactg cctataaaac cccggccgtc gcgtccatgg   1920
cgtttcagga tccgagcacc agaaagaagc tgagttagct agggtcaaga aagtagtcag   1980
cactcagcag gaaaagaagc agagactaca catcatggcg agtgacgccg cgcatggtag   2040
ctcgctggac ggggtgacgc cgtcgagcaa gttcgacctg ccggtggact cggagcacaa   2100
ggccaagacc atccgcctgc tctccttcgc gaacccgcac atgcgtacct tccacctctc   2160
ctggatgtcc ttcttcacct gcgtcgtctc caccttcgcg gcggcgccgc tgatccccat   2220
catccgggag aacctgggcc tgaccaaggc cgacatcggc aacgccgggg tggcctccgt   2280
ctcgggcgcc atcttctcgc gcctcgccat gggcgccgtc tgcgacctgc tgggcccgcg   2340
ctacggctgc gccttcgtcg tcatgctggc ggcgcccgcg gtgttctgca tggccgtcat   2400
cgacagcgcc gcgggctacg tcgcgtgccg cttcctcatc ggcttctccc tcgccacctt   2460
cgtctcctgc cagtactgga ccagcaccat gttcaacatc aagatcatcg gcaccgtcaa   2520
cgcgctggcg tcggggtggg cgacatggg cggcggcgcc acgcagctca tcatgccctt    2580
cgtctacgag gccatcctcc gctgcggcgc cacgccgttc gccgcgtggc gcatcgccta   2640
cttcgtgccg gggatcatgc acatcgccgt gggcatcctt gtgctaaccg cggggcagga   2700
cctccccgac ggcaacctcc gcagcctccg gaagcagcag cagcagcagc agcagggtga   2760
cggcggcgat gccagctgct gccgcaggga cagcttctcc agggtgctct ggcacgccgt   2820
cgccaactac cgcacctggg tcttcgtctt cgtgtacggc tacagcatgg gcgtgcagct   2880
caccaccaac aacatcatcg ccgagttcta ctacgaccag ttcgagctcg acatccgcgt   2940
ggccggcatc atcgccgcct gcttcggcat ggccaacctc gtgtcgcggc cctgggcgg    3000 cgtgctctcc gacctcggcg cgcggtactg gggcatgcgc gcgcgcctct ggaacatctg   3060
gatcctccag accgccggcg gcgcgttctg cttctggctc ggccgcgcca gcgagctccc   3120
```

```
ggcctccgtc accgccatgg tgctcttctc cttctgcgcg caggccgcct gcggcgccac    3180
cttcggcgta tccccttcg tctcccgccg ctcgctgggc gtcatctccg ggctcacggg    3240
cgccggcggc aacgtgggcg ccgggctcac gcagctgctc ttcttcacca cgtccagcta    3300
ctccacgagg aagggcatcg agaacatggg catcatggcc atggcgtgca cgctgccgct    3360
cgtcctcgtg cacttcccgc agtggggttc catgctcctg ccgcccagcg ccgacgccga    3420
cgaggagcgt actatgcct ccgagtggag cgaggacgag aagagcgtag gccgtcacag    3480
cgcaagccta agttcgccg agaacagccg gtccgagcgt ggcaagcgca acgccgtcgc    3540
cgtcctcgcc acgccgcgg ccacgccgga gcacgtcgtg taacaactag cgtacgtact    3600
tgtaggttct gatcgagcat acagcaaact gtgtaatgta ctctagcagt ctagcttgct    3660
ccgatactcc tgcttccaac aaaattatga aacataggct aatatggatc ggtgtacacg    3720
tacgtcgtag tatttcctgt gcaacataca caattcagta aatgaacaaa ctttgctcat    3780
gtgcattctt ctgcaaagta caaataaaat caaatagaga ggccaggaca acgtctatga    3840
tctatcaact tggttgttaa aattaaagaa aaccaactgg agtccaacac ccacaaaaca    3900
ttttgtctct aacacgttgt tgtc                                          3924
```

<210> SEQ ID NO 35
<211> LENGTH: 1569
<212> TYPE: DNA
<213> ORGANISM: Zea mays

<400> SEQUENCE: 35

```
atggcgagtg acgccgcgca tggtagctcg ctggacgggg tgacgccgtc gagcaagttc      60
gacctgccgg tggactcgga gcacaaggcc aagaccatcc gcctgctctc cttcgcgaac     120
ccgcacatgc gtaccttcca cctctcctgg atgtccttct tcacctgcgt cgtctccacc     180
ttcgcggcgg cgccgctgat ccccatcatc cgggagaacc tgggcctgac caaggccgac     240
atcggcaacg ccggggtggc ctccgtctcg gcgccatct tctcgcgcct cgccatgggc     300
gccgtctgcg acctgctggg cccgcgctac ggctgcgcct tcgtcgtcat gctggcggcg     360
cccgcggtgt tctgcatggc cgtcatcgac agcgccgcgg gctacgtcgc gtgccgcttc     420
ctcatcggct tctcccctcgc caccttcgtc tcctgccagt actggaccag caccatgttc     480
aacatcaaga tcatcggcac cgtcaacgcg ctggcgtcgg ggtggggcga catgggcggc     540
ggcgccacgc agctcatcat gcccttcgtc tacgaggcca tcctccgctg cggcgccacg     600
ccgttcgccg cgtggcgcat cgcctacttc gtgccgggga tcatgcacat cgccgtgggc     660
atccttgtgc taaccgcggg gcaggacctc cccgacggca acctccgcag cctccggaag     720
cagcagcagc agcagcagca gggtgacggc ggcgatgcca gctgctgccg cagggacagc     780
ttctccaggg tgctctggca cgccgtcgcc aactaccgca cctgggtctt cgtcttcgtg     840
tacggctaca gcatgggcgt gcagctcacc accaacaaca tcatcgccga gttctactac     900
gaccagttcg agctcgacat ccgcgtggcc ggcatcatcg ccgcctgctt cggcatggcc     960
aacctcgtgt cgcggcccct gggcggcgtg ctctccgacc tcggcgcgcg gtactgggc     1020 atgcgcgcgc gcctctggaa catctggatc ctccagaccg ccggcggcgc gttctgcttc     1080 tggctccggcc gcgccagcga gctccccggcc tccgtcaccg ccatggtgct cttctccttc     1140
tgcgcgcagg ccgcctgcgg cgccaccttc ggcgtcatcc ccttcgtctc ccgccgctcg     1200
ctgggcgtca tctccgggct cacgggcgcc ggcggcaacg tgggcgccgg gctcacgcag     1260
ctgctcttct tcaccacgtc cagctactcc acgaggaagg gcatcgagaa catgggcatc     1320
```

```
atggccatgg cgtgcacgct gccgctcgtc ctcgtgcact tcccgcagtg gggttccatg    1380
ctcctgccgc ccagcgccga cgccgacgag gagcggtact atgcctccga gtggagcgag    1440
gacgagaaga gcgtaggccg tcacagcgca agcctaaagt tcgccgagaa cagccggtcc    1500
gagcgtggca agcgcaacgc cgtcgccgtc ctcgccacgg ccgcggccac gccggagcac    1560
gtcgtgtaa                                                            1569
```

<210> SEQ ID NO 36
<211> LENGTH: 522
<212> TYPE: PRT
<213> ORGANISM: Zea mays

<400> SEQUENCE: 36

```
Met Ala Ser Asp Ala Ala His Gly Ser Ser Leu Asp Gly Val Thr Pro
1               5                   10                  15

Ser Ser Lys Phe Asp Leu Pro Val Asp Ser Glu His Lys Ala Lys Thr
            20                  25                  30

Ile Arg Leu Leu Ser Phe Ala Asn Pro His Met Arg Thr Phe His Leu
        35                  40                  45

Ser Trp Met Ser Phe Phe Thr Cys Val Val Ser Thr Phe Ala Ala Ala
    50                  55                  60

Pro Leu Ile Pro Ile Ile Arg Glu Asn Leu Gly Leu Thr Lys Ala Asp
65                  70                  75                  80

Ile Gly Asn Ala Gly Val Ala Ser Val Ser Gly Ala Ile Phe Ser Arg
                85                  90                  95

Leu Ala Met Gly Ala Val Cys Asp Leu Leu Gly Pro Arg Tyr Gly Cys
            100                 105                 110

Ala Phe Val Val Met Leu Ala Ala Pro Ala Val Phe Cys Met Ala Val
        115                 120                 125

Ile Asp Ser Ala Ala Gly Tyr Val Ala Cys Arg Phe Leu Ile Gly Phe
    130                 135                 140

Ser Leu Ala Thr Phe Val Ser Cys Gln Tyr Trp Thr Ser Thr Met Phe
145                 150                 155                 160

Asn Ile Lys Ile Ile Gly Thr Val Asn Ala Leu Ala Ser Gly Trp Gly
                165                 170                 175

Asp Met Gly Gly Gly Ala Thr Gln Leu Ile Met Pro Phe Val Tyr Glu
            180                 185                 190

Ala Ile Leu Arg Cys Gly Ala Thr Pro Phe Ala Ala Trp Arg Ile Ala
        195                 200                 205

Tyr Phe Val Pro Gly Ile Met His Ile Ala Val Gly Ile Leu Val Leu
    210                 215                 220

Thr Ala Gly Gln Asp Leu Pro Asp Gly Asn Leu Arg Ser Leu Arg Lys
225                 230                 235                 240

Gln Gln Gln Gln Gln Gln Gly Asp Gly Gly Asp Ala Ser Cys Cys
                245                 250                 255

Arg Arg Asp Ser Phe Ser Arg Val Leu Trp His Ala Val Ala Asn Tyr
            260                 265                 270

Arg Thr Trp Val Phe Val Phe Val Tyr Gly Tyr Ser Met Gly Val Gln
        275                 280                 285

Leu Thr Thr Asn Asn Ile Ile Ala Glu Phe Tyr Tyr Asp Gln Phe Glu
    290                 295                 300

Leu Asp Ile Arg Val Ala Gly Ile Ile Ala Cys Phe Gly Met Ala
305                 310                 315                 320

Asn Leu Val Ser Arg Pro Leu Gly Gly Val Leu Ser Asp Leu Gly Ala
                325                 330                 335
```

```
Arg Tyr Trp Gly Met Arg Ala Arg Leu Trp Asn Ile Trp Ile Leu Gln
                340                 345                 350
Thr Ala Gly Gly Ala Phe Cys Phe Trp Leu Gly Arg Ala Ser Glu Leu
            355                 360                 365
Pro Ala Ser Val Thr Ala Met Val Leu Phe Ser Phe Cys Ala Gln Ala
        370                 375                 380
Ala Cys Gly Ala Thr Phe Gly Val Ile Pro Phe Val Ser Arg Arg Ser
385                 390                 395                 400
Leu Gly Val Ile Ser Gly Leu Thr Gly Ala Gly Gly Asn Val Gly Ala
                405                 410                 415
Gly Leu Thr Gln Leu Leu Phe Phe Thr Thr Ser Ser Tyr Ser Thr Arg
            420                 425                 430
Lys Gly Ile Glu Asn Met Gly Ile Met Ala Met Ala Cys Thr Leu Pro
        435                 440                 445
Leu Val Leu Val His Phe Pro Gln Trp Gly Ser Met Leu Leu Pro Pro
    450                 455                 460
Ser Ala Asp Ala Asp Glu Glu Arg Tyr Tyr Ala Ser Glu Trp Ser Glu
465                 470                 475                 480
Asp Glu Lys Ser Val Gly Arg His Ser Ala Ser Leu Lys Phe Ala Glu
                485                 490                 495
Asn Ser Arg Ser Glu Arg Gly Lys Arg Asn Ala Val Ala Val Leu Ala
            500                 505                 510
Thr Ala Ala Ala Thr Pro Glu His Val Val
        515                 520

<210> SEQ ID NO 37
<211> LENGTH: 2014
<212> TYPE: DNA
<213> ORGANISM: Zea mays

<400> SEQUENCE: 37
ttcgagggca atgggttcca agaatgtca  tttgaattag acacttagtt atttatgaaa      60
aggttttttc tccccgagtt aatttgcttc caaactataa ttaaccctaa gcaaggtgtt     120
agttatttgt tttgacggtt tatatatccg tgttagcttg gtggctagct tgtatccatt     180
tgacttgacg gcacatgcat gcatgcgtgg agtgcaccgt gcggcggttt gtgacgcggt     240
gccaaacgtg caattgactc attgagtagt catcagcagg cttgcgatca ttagacacta     300
acaagcatta atatttgctg catatatata tatacacaca catgcttcac tgacgacgct     360
tgcaacttga tcttgttaat tattatatat cctaagcaca acgaacaaac cttagatatg     420
cgaccatgcc ttgagtagag cgtgaaaaat aggggtgaa aaaaagggac gagtaattat      480
agatgacact atttgatatt gtttaaagat gagatagga atgtgctgaa tagatcaatt     540
tttaatcagg gatggtaggg actagtattt cctctatgat tttccatgta acacctttga     600
atatacaata ataataagaa gccaccaacc tttgaattat tatctgttcc aatatattag     660
atgaggggtg tatcggaatt tgacttccga gttgttcttg cgtgtccgta cgctcgtacg     720
gtagctcgtt gggttgttgt accagccatc ctgctactgc gcaacgaaat gcattggtca     780
tctcaattaa gtccaaagat tgtagtcgta acatgcagc caataagagc aaggataata      840
gtttagccat tgatatgtct tctaaagcta attattactg tattggaccc acctcgtact     900
ctcattctct caccacttgt ttcggaatct gtactgctac aaccagctct tagtcgactg     960
ataattaact acccgctttt tctcttctct ccccctccaac tgcaaaaatc taatgtggca    1020
aaccattag cctgcttaca tcgtcaaaaa tctaatgtgg taaagtgtga agtgtcctaa     1080
```

```
agttttagtc cttaatttct ttcaataaac taaactaaac tttagaaaac tcaaacaagt    1140
cctcatgttt gcacatttta ggtctcgttt ggtttgaggg actaaagatt agtccctcca    1200
ttttagtccc atttagttac taaattacca aacagtagga ctaaacagg gactaaattg     1260 ttttagtccc tagtccctta agatggctaa aagggactaa accatattaa ttccacattt    1320
gcccctcatt tagttcaatt gtactaatag caggagaatg ttaaaagtca ttttaatctt    1380
cttatgagtc atttaggccc tgtttggttc cattagtcat agaactaaag tttagttgta    1440
gggactaaat agattctaaa tacattaaat gcaacacata aagaccaaaa tgcccttttt    1500
tgtttgacac cccttttcta gcaagggtat ttggagtaaa tgttgccctt tggtcccttt    1560
tagcacccat gtgagggact agagactaaa accaattagt ccctacttta gtcattccgt    1620
ttagcaaaat agagactaaa cgagactaaa aacgagaggc taaagattag tctctctaac    1680
caaacgggac ctaaaattac tatctgtatg tatctgttgg atggaaaagt cagaacgtcg    1740
tggggaccac cacgctacca catggtacgg taatgtcaga aagtcgctat cttcttcgat    1800
ctgcatctcc actccagcca gcgctgctta tcatcagcat tcacgaagcc gcccaacgat    1860
aataaaaaat gtcagcgcga tcgcgcactg cctataaaac cccggccgtc gcgtccatgg    1920
cgtttcagga tccgagcacc agaaagaagc tgagttagct agggtcaaga aagtagtcag    1980
cactcagcag gaaaagaagc agagactaca catc                                2014

<210> SEQ ID NO 38
<211> LENGTH: 1014
<212> TYPE: DNA
<213> ORGANISM: Zea mays

<400> SEQUENCE: 38
tgcaaaaatc taatgtggca aaccatttag cctgcttaca tcgtcaaaaa tctaatgtgg      60
taaagtgtga agtgtcctaa agttttagtc cttaatttct ttcaataaac taaactaaac    120
tttagaaaac tcaaacaagt cctcatgttt gcacatttta ggtctcgttt ggtttgaggg    180
actaaagatt agtccctcca ttttagtccc atttagttac taaattacca aacagtagga    240 ctaaacagg gactaaattg ttttagtccc tagtccctta agatggctaa aagggactaa     300
accatattaa ttccacattt gcccctcatt tagttcaatt gtactaatag caggagaatg    360
ttaaaagtca ttttaatctt cttatgagtc atttaggccc tgtttggttc cattagtcat    420
agaactaaag tttagttgta gggactaaat agattctaaa tacattaaat gcaacacata    480
aagaccaaaa tgcccttttt tgtttgacac cccttttcta gcaagggtat ttggagtaaa    540
tgttgccctt tggtcccttt tagcacccat gtgagggact agagactaaa accaattagt    600
ccctacttta gtcattccgt ttagcaaaat agagactaaa cgagactaaa aacgagaggc    660
taaagattag tctctctaac caaacgggac ctaaaattac tatctgtatg tatctgttgg    720
atggaaaagt cagaacgtcg tggggaccac cacgctacca catggtacgg taatgtcaga    780
aagtcgctat cttcttcgat ctgcatctcc actccagcca gcgctgctta tcatcagcat    840
tcacgaagcc gcccaacgat aataaaaaat gtcagcgcga tcgcgcactg cctataaaac    900
cccggccgtc gcgtccatgg cgtttcagga tccgagcacc agaaagaagc tgagttagct    960
agggtcaaga aagtagtcag cactcagcag gaaaagaagc agagactaca catc         1014

<210> SEQ ID NO 39
<211> LENGTH: 18
<212> TYPE: DNA
<213> ORGANISM: Artificial
```

```
<220> FEATURE:
<223> OTHER INFORMATION: Primer

<400> SEQUENCE: 39
cggggttcgc cagcctcc                                                      18

<210> SEQ ID NO 40
<211> LENGTH: 17
<212> TYPE: DNA
<213> ORGANISM: Artificial
<220> FEATURE:
<223> OTHER INFORMATION: Primer

<400> SEQUENCE: 40
agtgggctcc ctctccg                                                       17

<210> SEQ ID NO 41
<211> LENGTH: 18
<212> TYPE: DNA
<213> ORGANISM: Artificial
<220> FEATURE:
<223> OTHER INFORMATION: Primer

<400> SEQUENCE: 41
gctcgtcatg ccgctcgc                                                      18

<210> SEQ ID NO 42
<211> LENGTH: 18
<212> TYPE: DNA
<213> ORGANISM: Artificial
<220> FEATURE:
<223> OTHER INFORMATION: Primer

<400> SEQUENCE: 42
gcactggatg tcgggcat                                                      18

<210> SEQ ID NO 43
<211> LENGTH: 20
<212> TYPE: DNA
<213> ORGANISM: Artificial
<220> FEATURE:
<223> OTHER INFORMATION: Primer

<400> SEQUENCE: 43
aattaaccct cactaaaggg                                                    20

<210> SEQ ID NO 44
<211> LENGTH: 22
<212> TYPE: DNA
<213> ORGANISM: Artificial
<220> FEATURE:
<223> OTHER INFORMATION: Primer

<400> SEQUENCE: 44
gtaatacgac tcactatagg gc                                                 22

<210> SEQ ID NO 45
<211> LENGTH: 5812
<212> TYPE: DNA
<213> ORGANISM: Zea mays

<400> SEQUENCE: 45
ggttggcgag cgggtgtggt ctgggcagtg gcaatggcgg gggcagcgaa gaggagggcg        60 gtggggagg gagtggcgag agaggggagga aagagagatg aggcgtgtgc aacaacagga       120
gacgtacgtc ggcgcttgtc agggtttcgt gcaatgagat atgggtgtgt gggttgattc       180
```

```
taaagtaatg ttgggagtgt tttgaaaaaa tttgacgcag gacgaccgtt gaaactagtg    240
ctttaagtat agtagagatt taaaattaaa gtggacacat ggcccacata ctgaatatta    300
aactgcagat attacactt  atcttagcca aaaggtcgag aaatgtatga gttaaaaaag    360
gagacatgcc cttttataac tcactcggtc gcttgtccta cttcaactat taagtttgta    420
ctattcgaga acgttgtatt acatgtggtt ttgtgtcata ttgggtttgg gtgttttctc    480
actaactatc tgggtgrtaa gattgctaga cgagacgtag aggagaaaaa catatctact    540
ctacaccgtt tcatgcgtga catgatatac gaaacccaag ttttaaagga gtaaaaataa    600
aaataaagat agataaacca taaattacta tctacaaaaa cgtagacagc aggctagata    660
ccaaggaggg caaggcaag  atggccgagg cacttgtgcc cgccggagct ttggatgcaa    720
gatgcaacac actagctgtt cggagacaat cggtgtatca aagaagtaaa aaaatttgga    780
tgaaacacac aagctgttac agtggctcta aggaaagat  tgggattttc attttctgat    840
gcattcttta cgcagggcaa gagtgttatt tctgctgatg tacacataat tagaagactc    900 tcttttttt  taattggtgc attttcctta tgaaccacat gcgtaaaaaa ctgggccgaa    960
gttcatcacg tcgttgtgcc ctggcacgtc accaatcgca acgctcagct agaagctgct   1020
gctgaatgcg caccacagac tcttgggcga aaccagttca tctgtttttt ttttacgcgc   1080
agagcggcag agacgacaga gatatgacga tgtatattat ggattaatta aaagcgatc    1140 cggagtttta gatgtctatt tccaccctga ggagccaaaa aggattcatc ggagattcag   1200
gaatttctgc atctgcaatc attggaccag agcggcggta gtatattccg atctacaggc   1260
ttgcccggcc gagatcctct ggggtcaacc tcgctgctac gcgggagggc gggcgcagcc   1320
cctgggcctc acggagagac tccttcacgt ctccgggccc actacagaag gccgagtagt   1380
ggcatccgac gctcctgggc ccacttgccg tctcgagtca ccatacgcgc gggcccccag   1440
cccacgtaat taaagtgtga ctgggttagt cctgtccgag gctagcgcag agtgggatgc   1500
gatgcgacaa aacggccgct agattggatt attagtatag agagtataca gattagagag   1560
ttctggaagg ttggttagct catggagttg atcgattccc gctcgtgtca aacacgtata   1620
tgttcacctt catatttatc attcgtgtaa attcacggag agtaatatac attgcttact   1680
ggagttttgt gtcaaccaat aaccgatcaa agatgttgtt atttactgca tccacactaa   1740
taaaacacat aatgtgttct aattttgtct tgggktaatt ttgtcctgga gatgactta    1800 gcttgagggt ggtgttacga cgaaaaacaa tgccgtatag ttctaaggtt agattttgc    1860 aattaatcaa tcacatcgat atgctaatgc taaattgcta atgctatgct ttaaattgct   1920
aatgcaatga ggtgatggca gcagccgca  gtcccttttc atggcctcgg ggagccggtg   1980
gtaggcacgt acaaaagcca cacggacatg caacgcggcg ccctgcatgc acccgccgcg   2040
acaccgcttg ccctccgcct tctcgttctc ggtccaccac cttctattcc attccacac    2100 ccatcaccac acacatttaa aaccaccagc gagtatctaa acctttcacc ccattggtcg   2160
cccacaggtc tggaactagt agccactagc tccattctct gcttggctgt ggtagatctc   2220
ttcctgcaca gccacgaggc caggcaggca gacgtcacta gctatggtgg cgatgggaa    2280 aaagcagcag ctggccgacg acgaagagaa ctgctgctac ggcgtcggca gctctgaggc   2340
ggagtgcggg gtcgatgccg agttcagggc gacggatctg cgccctctgt cactgctgtc   2400
gccgcacacg caggcgttcc acctcgcctg gctctcctc  ttcgcctgct tcttcgcggc   2460 cttgccgcc  ccgccatcc  tccctgcgct gcggccggcg ctcgtgctcg cgccctcgga   2520 cgccccgcc  gccgcagtgg gctccctctc cgccacgctg gtcggcaggc ttgccatggg   2580
```

```
gcccgcatgc gacctcctcg gcccgcgccg cgcgtcgggg ttcgccagcc tcctggccgc   2640
gctcgccgtc gcggtcaccg cggtcaccgc gtcgtcgccc gcggggttcg tcgcgctgcg   2700
cttcgtggcg ggcctctccc tcgccaactt cgtcgccaac cagcactgga tgtcgggcat   2760
cttcgcgccc tccgccgtgg ggctcgccaa cgccgtcacg gccggctggg ccaacgtcgg   2820
cagcgccgcg gcgcagctcg tcatgccgct cgcgtacgag ctcgtcctcc gcctcggcgt   2880
gcccatcacc gtcgcctggc gcgtcaccta cctcctcccc tgcgcgctcc tcatcaccac   2940
gggcctcgcc gtcctcgcct tcccytacga cctcccgcgc ggcgccggcg tcggcggcgg   3000
agccaagacc ggcaagagct tgtggaaggt ggtgcgcgga ggggtcagca actaccgcgc   3060
gtgggtgctc gcgctcacct acggctactg ctacggcgtc gagctcatca tggagaacgt   3120
ggccgccgac ttcttccgga aacgtttcca cctccccatg gaggctgcgg gcgccgcggc   3180
ggcgtgcttc ggcgcgatga acgcggtggc gcggcccgcg ggcgggttgg cgtcggacgc   3240
ggtggcgaga ctgttcggca tgcgcgggag gctgtggctt ctctgggccg tgcagaccac   3300
cggcgcggca ctgtgcgtgc tggtcggcag gatgggcgca gcggaagcgc cgtcgctggc   3360
ggccaccatg gcgtcatgg tgctgtgcgc gcgtttgtg caggcctcgt cggggctcac   3420
cttcggcatc gtcccgttcg tgtccaagag gtgaatccaa caaacttctt acaacatcta   3480
atacagatta ttttgcgtcg gattaattca aaaatagtta tatatagatt ctaagtatat   3540
attcacatat agatttttt tccacccaaa aagttataac ttacaaggaa ggacatctat   3600
catgcatgtt tcataaacaa attaactaaa gattttctg tgtttggtta tttagatata   3660
aatagatctt gaattatata ttgacgtaca gatccctcc ctcaaagtta taacgtaaat   3720
aataagggca aagacgttga agctgatata tacctctcaa ttgaaagatg gccacgccag   3780
ctagcttttt gaagatattt tctaagcaca caaacaccta attactgctc cgttcattta   3840
aaattatagc tttaaaaatt aaatcaaag cgtttaatta gaaaaatcta aaattcttca   3900
agctataagt ttaattagaa aaatcaaaac atttaataat ttaaaataga tgaaacatac   3960
ccaactaaga gggccacatc gttatcatag gccctaatat agattctata gtagaatcct   4020
ggtatactac tattgttgat gttcacctgt tttctgatat ttgtggacga aaataatcag   4080
agaggtttcc aacaataaag caactcatta attatttctc tgaacatata ggaggacgtg   4140
tttggttgcc acgctagcca tgtccaagct cacgcgcgtg tacttggtta tctgcatgta   4200
attaacaaag cgaactcgca cgcacgcgta caacctaagc accttttcca cctcctacat   4260
gcatatgtag ggaagcggcc gggtccgcgc gagtcaggag ctctcaactc acaaaccaat   4320
cacgtccata acaaccaagg actgtaaaat gtggcgtaca tattttttat gtctaagggc   4380
tagtttgaga ctccattatc ctaagagaaa gtgaattaat tagattccta aactagccct   4440
gatatgaaaa agaaacaccg gaaaaactac ggtagcaaaa tagccagtgg aaaataaact   4500
tgtcgtcaca agttactctt ctattccaat acctcttgta tatgtatttt aaagacacgg   4560
ccttaaacat ttttttaaa aaaaaaaat ccatctaatg aattagccta ggaatatcat   4620
gcatggtttt ctcaaaataa tgtcttcgac cccatttggt cacaaattaa tttatctaaa   4680
ctagatctaa ctcgtagcat gagttttaga gcgccagagg caatttgtta ttacagaaag   4740
attaaggtca tgtttgatac acttcagctt tacaggtgaa ggtgttttaa aaaaaaataa   4800
cttcaccaat aacgattgga gaaggaaatg aggaagaaag ctacccaaag ttacttttc    4860 ggcttcacct ctgtctaatt ctgcgtctga gcataaaaag gagttttacc tatgaatctt   4920
tttgaaaaaa aagaatgttt acaaaaaaat aaatagctca acaacttata aagcttctga   4980
```

```
ttaatctgta ctaaaaaaga actaactata aacaaaggtc aaagaaacca tgacacattt    5040
cttacggctt gtgttgggtc acttaatttc ggtggtgtgt gtgcaggtcg ttgggcgtgg    5100
tgtccgggat gacggcgagc ggcggcgcgg tgggcgcgat cgtgacgaac cggctcttct    5160
tcagcgggtc gcggtacacc attgaggagg cyatctcgtt gaccggcgcc gccagcctcg    5220
tgtgcacgct cccgctggcc ctcgtccact cccgcgcca cggtggcatg ctctgcggcc    5280
caaccgccgt cgtcgatggc gacgatgcag gatacgacaa cgataatagt gctggagatt    5340
acacgctcct caaatgaatt gaggaacaaa tgtatgcaac ggggggggtcg catgtgaact    5400 ttgtacatag cacatccaat ggccttgata gattagcaaa cgattactca tggtttgttt    5460
caggatcagg ggtgcgatat gagcgacaca cggatagaaa tatgtcgagt ggcttcgtct    5520
gtcgatcacc tgcacataaa tagatagaga gtagagatgg ctcgtaggtt gttcacgtgt    5580
cgctgccgca ttggcaattg cgtgtcttat gtttgtgttg gttcgaagag tgagacaata    5640
ataagttgtc ggtgttcgaa tcagtaccaa cgagtaaatt gtgtatgcgt gcatgttttg    5700
gatttggatg atgtgttcag tgaacgcaag atttatactg attcggatag aacgtcccta    5760
cttctagtct tcgatggctc gcgtaatcga taacttcttg ctgaatgctc at           5812

<210> SEQ ID NO 46
<211> LENGTH: 2263
<212> TYPE: DNA
<213> ORGANISM: Zea mays

<400> SEQUENCE: 46
ggttggcgag cgggtgtggt ctgggcagtg gcaatggcgg gggcagcgaa gaggagggcg      60 gtggggagg gagtggcgag agagggagga aagagagatg aggcgtgtgc aacaacagga     120
gacgtacgtc ggcgcttgtc agggtttcgt gcaatgagat atgggtgtgt gggttgattc     180
taaagtaatg ttgggagtgt tttgaaaaaa tttgacgcag gacgaccgtt gaaactagtg     240 cttttaagtat agtagagatt taaaattaaa gtggacacat ggcccacata ctgaatatta     300
aactgcagat attacacttt atcttagcca aaaggtcgag aaatgtatga gttaaaaaag     360
gagacatgcc ttttataac tcactcggtc gcttgtccta cttcaactat taagtttgta     420
ctattcgaga acgttgtatt acatgtggtt ttgtgtcata ttgggtttgg gtgttttctc     480
actaactatc tgggtgrtaa gattgctaga cgagacgtag aggagaaaaa catatctact     540
ctacaccgtt tcatgcgtga catgatatac gaaacccaag ttttaaagga gtaaaaataa     600
aaataaagat agataaacca taaattacta tctacaaaaa cgtagacagc aggctagata     660
ccaaggaggg caagggcaag atggccgagg cacttgtgcc cgccggagct ttggatgcaa     720
gatgcaacac actagctgtt cggagacaat cggtgtatca aagaagtaaa aaaatttgga     780
tgaaacacac aagctgttac agtggctcta gaggaaagat tgggatttc attttctgat     840 gcattcttta cgcagggcaa gagtgttatt tctgctgatg tacacataat tagaagactc     900 tcttttttttt taattggtgc attttccta tgaaccacat gcgtaaaaaa ctgggccgaa     960
gttcatcacg tcgttgtgcc ctggcacgtc accaatcgca acgctcagct agaagctgct    1020
gctgaatgcg caccacagac tcttgggcga aaccagttca tctgtttttt ttttacgcgc    1080
agagcggcag agacgacaga gatatgcga tgtatattat ggattaatta aaaagcgatc    1140
cggagtttta gatgtctatt tccaccctga ggagccaaaa aggattcatc ggagattcag    1200
gaatttctgc atctgcaatc attggaccag agcggcggta gtatattccg atctacaggc    1260
ttgcccggcc gagatcctct ggggtcaacc tcgctgctac gcgggagggc gggcgcagcc    1320
```

-continued

| | |
|---|---|
| cctgggcctc acggagagac tccttcacgt ctccgggccc actacagaag gccgagtagt | 1380 |
| ggcatccgac gctcctgggc ccacttgccg tctcgagtca ccatacgcgc gggcccccag | 1440 |
| cccacgtaat taaagtgtga ctgggttagt cctgtccgag gctagcgcag agtgggatgc | 1500 |
| gatgcgacaa aacggccgct agattggatt attagtatag agagtataca gattagagag | 1560 |
| ttctggaagg ttggttagct catggagttg atcgattccc gctcgtgtca aacacgtata | 1620 |
| tgttcacctt catatttatc attcgtgtaa attcacggag agtaatatac attgcttact | 1680 |
| ggagttttgt gtcaaccaat aaccgatcaa agatgttgtt atttactgca tccacactaa | 1740 |
| taaaacacat aatgtgttct aattttgtct tgggktaatt ttgtcctgga gatgacttta | 1800 |
| gcttgagggt ggtgttacga cgaaaaacaa tgccgtatag ttctaaggtt agattttgc | 1860 |
| aattaatcaa tcacatcgat atgctaatgc taaattgcta atgctatgct ttaaattgct | 1920 |
| aatgcaatga ggtgatggca ggcagccgca gtccctttc atggcctcgg ggagccggtg | 1980 |
| gtaggcacgt acaaaagcca cacggacatg caacgcggcg ccctgcatgc acccgccgcg | 2040 |
| acaccgcttg ccctccgcct tctcgttctc ggtccaccac cttctattcc atttccacac | 2100 |
| ccatcaccac acacatttaa aaccaccagc gagtatctaa acctttcacc ccattggtcg | 2160 |
| cccacaggtc tggaactagt agccactagc tccattctct gcttggctgt ggtagatctc | 2220 |
| ttcctgcaca gccacgaggc caggcaggca gacgtcacta gct | 2263 |

<210> SEQ ID NO 47
<211> LENGTH: 1263
<212> TYPE: DNA
<213> ORGANISM: Zea mays

<400> SEQUENCE: 47

| | |
|---|---|
| acgctcagct agaagctgct gctgaatgcg caccacagac tcttgggcga aaccagttca | 60 |
| tctgtttttt ttttacgcgc agagcggcag agacgacaga gatatgacga tgtatattat | 120 |
| ggattaatta aaaagcgatc cggagtttta gatgtctatt tccaccctga ggagccaaaa | 180 |
| aggattcatc ggagattcag gaatttctgc atctgcaatc attggaccag agcggcggta | 240 |
| gtatattccg atctacaggc ttgcccggcc gagatcctct ggggtcaacc tcgctgctac | 300 |
| gcgggagggc gggcgcagcc cctgggcctc acggagagac tccttcacgt ctccgggccc | 360 |
| actacagaag gccgagtagt ggcatccgac gctcctgggc ccacttgccg tctcgagtca | 420 |
| ccatacgcgc gggcccccag cccacgtaat taaagtgtga ctgggttagt cctgtccgag | 480 |
| gctagcgcag agtgggatgc gatgcgacaa aacggccgct agattggatt attagtatag | 540 |
| agagtataca gattagagag ttctggaagg ttggttagct catggagttg atcgattccc | 600 |
| gctcgtgtca aacacgtata tgttcacctt catatttatc attcgtgtaa attcacggag | 660 |
| agtaatatac attgcttact ggagttttgt gtcaaccaat aaccgatcaa agatgttgtt | 720 |
| atttactgca tccacactaa taaaacacat aatgtgttct aattttgtct tgggktaatt | 780 |
| ttgtcctgga gatgacttta gcttgagggt ggtgttacga cgaaaaacaa tgccgtatag | 840 |
| ttctaaggtt agattttgc aattaatcaa tcacatcgat atgctaatgc taaattgcta | 900 |
| atgctatgct ttaaattgct aatgcaatga ggtgatggca ggcagccgca gtccctttc | 960 |
| atggcctcgg ggagccggtg gtaggcacgt acaaaagcca cacggacatg caacgcggcg | 1020 |
| ccctgcatgc acccgccgcg acaccgcttg ccctccgcct tctcgttctc ggtccaccac | 1080 |
| cttctattcc atttccacac ccatcaccac acacatttaa aaccaccagc gagtatctaa | 1140 |
| acctttcacc ccattggtcg cccacaggtc tggaactagt agccactagc tccattctct | 1200 |

```
gcttggctgt ggtagatctc ttcctgcaca gccacgaggc caggcaggca gacgtcacta    1260
gct                                                                  1263

<210> SEQ ID NO 48
<211> LENGTH: 1455
<212> TYPE: DNA
<213> ORGANISM: Zea mays

<400> SEQUENCE: 48
atggtggcga tggggaaaaa gcagcagctg gccgacgacg aagagaactg ctgctacggc     60
gtcggcagct ctgaggcgga gtgcggcgtc gatgccgagt tcagggcgac ggatctgcgc    120
cctctgtcac tgctgtcgcc gcacacgcag gcgttccacc tcgcctggct ctccctcttc    180
gcctgcttct tcgcggccct tgccgccccg cccatcctcc ctgcgctgcg gccggcgctc    240
gtgctcgcgc cctcggacgc ccccgccgcc gcagtgggct ccctctccgc cacgctggtc    300
ggcaggcttg ccatggggcc cgcatgcgac tcctcggcc cgcgccgcgc gtcggggttc    360
gccagcctcc tggccgcgct cgccgtcgcg gtcaccgcgg tcaccgcgtc gtcgcccgcg    420
gggttcgtcg cgctgcgctt cgtggcgggc ctctcccctcg ccaacttcgt cgccaaccag    480
cactggatgt cgggcatctt cgcgccctcc gccgtggggc tcgccaacgc cgtcacggcc    540
ggctgggcca acgtcggcag cgccgcgcg cagctcgtca tgccgctcgc gtacgagctc    600
gtcctccgcc tcggcgtgcc catcaccgtc gcctggcgcg tcacctacct cctcccctgc    660
gcgctcctca tcaccacggg cctcgccgtc ctcgccttcc cytacgacct cccgcgcggc    720
gccggcgtcg gcggcggagc caagaccggc aagagcttgt ggaaggtggt gcgcggaggg    780
gtcagcaact accgcgcgtg ggtgctcgcg ctcacctacg gctactgcta cggcgtcgag    840
ctcatcatgg agaacgtggc cgccgacttc ttccggaaac gtttccacct cccatggag     900 gctgcgggcg ccgcggcggc gtgcttcggc gcgatgaacg cggtggcgcg ccccgcgggc    960
gggttggcgt cggacgcggt ggcgagactg ttcggcatgc gcgggaggct gtggcttctc   1020
tgggccgtgc agaccaccgg cgcggcactg tgccgtgctgg tcggcaggat gggcgcagcg   1080
gaagcgccgt cgctggcggc caccatggcg gtcatggtgc tgtgcgccgc gtttgtgcag   1140
gcctcgtcgg ggctcacctt cggcatcgtc ccgttcgtgt ccaagaggtc gttgggcgtg   1200
gtgtccggga tgacggcgag cggcggcgcg gtgggcgcga tcgtgacgaa ccggctcttc   1260
ttcagcgggt cgcggtacac cattgaggag gcyatctcgt tgaccggcgc cgccagcctc   1320
gtgtgcacgc tcccgctggc cctcgtccac ttcccgcgcc acggtggcat gctctgcggc   1380
ccaaccgccg tcgtcgatgg cgacgatgca ggatacgaca acgataatag tgctggagat   1440
tacacgctcc tcaaa                                                   1455

<210> SEQ ID NO 49
<211> LENGTH: 485
<212> TYPE: PRT
<213> ORGANISM: Zea mays

<400> SEQUENCE: 49

Met Val Ala Met Gly Lys Lys Gln Gln Leu Ala Asp Asp Glu Glu Asn
1               5                   10                  15

Cys Cys Tyr Gly Val Gly Ser Ser Glu Ala Glu Cys Gly Val Asp Ala
            20                  25                  30

Glu Phe Arg Ala Thr Asp Leu Arg Pro Leu Ser Leu Leu Ser Pro His
        35                  40                  45
```

-continued

```
Thr Gln Ala Phe His Leu Ala Trp Leu Ser Leu Phe Ala Cys Phe Phe
    50                  55                  60

Ala Ala Phe Ala Ala Pro Ile Leu Pro Ala Leu Arg Pro Ala Leu
65                  70                  75                  80

Val Leu Ala Pro Ser Asp Ala Pro Ala Ala Val Gly Ser Leu Ser
                85                  90                  95

Ala Thr Leu Val Gly Arg Leu Ala Met Gly Pro Ala Cys Asp Leu Leu
                100                 105                 110

Gly Pro Arg Arg Ala Ser Gly Phe Ala Ser Leu Leu Ala Ala Leu Ala
            115                 120                 125

Val Ala Val Thr Ala Val Thr Ala Ser Ser Pro Ala Gly Phe Val Ala
            130                 135                 140

Leu Arg Phe Val Ala Gly Leu Ser Leu Ala Asn Phe Val Ala Asn Gln
145                 150                 155                 160

His Trp Met Ser Gly Ile Phe Ala Pro Ser Ala Val Gly Leu Ala Asn
                165                 170                 175

Ala Val Thr Ala Gly Trp Ala Asn Val Gly Ser Ala Ala Gln Leu
                180                 185                 190

Val Met Pro Leu Ala Tyr Glu Leu Val Leu Arg Leu Gly Val Pro Ile
            195                 200                 205

Thr Val Ala Trp Arg Val Thr Tyr Leu Leu Pro Cys Ala Leu Leu Ile
            210                 215                 220

Thr Thr Gly Leu Ala Val Leu Ala Phe Pro Tyr Asp Leu Pro Arg Gly
225                 230                 235                 240

Ala Gly Val Gly Gly Ala Lys Thr Gly Lys Ser Leu Trp Lys Val
                245                 250                 255

Val Arg Gly Gly Val Ser Asn Tyr Arg Ala Trp Val Leu Ala Leu Thr
            260                 265                 270

Tyr Gly Tyr Cys Tyr Gly Val Glu Leu Ile Met Glu Asn Val Ala Ala
            275                 280                 285

Asp Phe Phe Arg Lys Arg Phe His Leu Pro Met Glu Ala Ala Gly Ala
            290                 295                 300

Ala Ala Ala Cys Phe Gly Ala Met Asn Ala Val Ala Arg Pro Ala Gly
305                 310                 315                 320

Gly Leu Ala Ser Asp Ala Val Ala Arg Leu Phe Gly Met Arg Gly Arg
                325                 330                 335

Leu Trp Leu Leu Trp Ala Val Gln Thr Thr Gly Ala Ala Leu Cys Val
                340                 345                 350

Leu Val Gly Arg Met Gly Ala Ala Glu Ala Pro Ser Leu Ala Ala Thr
            355                 360                 365

Met Ala Val Met Val Leu Cys Ala Ala Phe Val Gln Ala Ser Ser Gly
            370                 375                 380

Leu Thr Phe Gly Ile Val Pro Phe Val Ser Lys Arg Ser Leu Gly Val
385                 390                 395                 400

Val Ser Gly Met Thr Ala Ser Gly Gly Ala Val Gly Ala Ile Val Thr
                405                 410                 415

Asn Arg Leu Phe Phe Ser Gly Ser Arg Tyr Thr Ile Glu Glu Ala Ile
                420                 425                 430

Ser Leu Thr Gly Ala Ala Ser Leu Val Cys Thr Leu Pro Leu Ala Leu
            435                 440                 445

Val His Phe Pro Arg His Gly Gly Met Leu Cys Gly Pro Thr Ala Val
            450                 455                 460

Val Asp Gly Asp Asp Ala Gly Tyr Asp Asn Asp Asn Ser Ala Gly Asp
465                 470                 475                 480
```

Tyr Thr Leu Leu Lys
            485

<210> SEQ ID NO 50
<211> LENGTH: 14
<212> TYPE: PRT
<213> ORGANISM: Zea maize
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 50

Arg Leu Ala Met Gly Xaa Xaa Cys Asp Leu Leu Gly Pro Arg
1               5                   10

<210> SEQ ID NO 51
<211> LENGTH: 28
<212> TYPE: PRT
<213> ORGANISM: Zea maize
<220> FEATURE:
<221> NAME/KEY: DOMAIN
<222> LOCATION: (1)..(28)
<223> OTHER INFORMATION: Xaa=any amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 51

Thr Phe Gly Xaa Xaa Pro Phe Val Ser Xaa Arg Ser Leu Gly Val Xaa Ser Gly
1               5                   10                  15

Xaa Thr Xaa Xaa Gly Gly Xaa Val Gly Ala
        20                  25

<210> SEQ ID NO 52
<211> LENGTH: 11
<212> TYPE: PRT
<213> ORGANISM: Zea maize
<220> FEATURE:
<221> NAME/KEY: misc_feature
<222> LOCATION: (6)..(6)
<223> OTHER INFORMATION: Xaa can be any naturally occurring amino acid

<400> SEQUENCE: 52

Cys Thr Leu Pro Leu Xaa Leu Val His Phe Pro
1               5                   10

<210> SEQ ID NO 53
<211> LENGTH: 1561
<212> TYPE: DNA
<213> ORGANISM: Zea mays

<400> SEQUENCE: 53

```
tagctatata cacatgtctg gtctgacgac aatcaaaagg gatcgctagc tcgggctagc      60
cttcctatca ctgtcatgac atgtgctctg cctctgctgg ttgataagcc gtgcgccttc     120
tcgctaattc tttcttgtgc tagaggcgag tcaaacaaac gctgcacctc gtagccctta     180
atctgcgcta aggtcacat gaccctgttc cctatcgcta gttaccaacg acccattccc      240
cctgacagat acttacgacg cgtccgtacg cggcaggcct cggcagttcg gcatcaccag     300
caccggcgcc ggcattcgcc ccctgccagc cggttcgcag attcgcaggg cggagtcggc     360
cgcagttgcc gcatcccaaa cgcccgggaa cctttggggc ccctctacga gcaaatgaag     420
ttgctgcccc tggcttcgta aagctctgac ttttgatcac ttgattggca gtcgtactcc     480
tcgctcatag gccgacacgg ccgcaaagtc aactacccgc tccgccatcc ttcaaccccc     540
gccacgcgcc tatatatgtt cgcggccatg tccgtactag tcctccaacc cacaagccac     600
aaccccgagc tcagatccct cgcctcgtgt cgtgtctccg gtcgacgacg accaacagcc     660
agtgtgggcc agacggacac cgccgagcta tagcgcttgg tgatagcaag ggacgaccgg     720
cggccggacc ggagcacgta cgtacgtacc gcagcgatgg ctcggcagca aagcgtgcag     780
gccttgtgtg tgctggcggc gcttctcttc gccgcctccc tgccgtcgcc ggccgccgcg     840
ggggtgcacc tctcctcgct gcccaaagcg ctcgacgtca ccacctccgc caaacccggc     900
caagtcctgc acgccggcgt ggactcgctg acggtgacgt ggagcctgaa cgccacggag     960
ccggccggcg ccgacgccgg gtacaagggc gtgaaggtga agctgtgcta cgcgccggcg    1020
agccagaagg accgcgggtg gcgcaagtcc gaggacgaca tcagcaagga caaggcgtgc    1080
cagttcaagg tcaccgagca ggcgtacgcg gcggcggcgc ccggcagctt ccagtacgcc    1140
gtcgcccgcg acgtcccctc gggctcctac tacctgcgcg ccttcgccac ggacgcgtcg    1200
ggcgccgagg tggcctacgg ccagacgcgc cccaccgccg ccttcgacgt cgccggcatc    1260
accggcatcc acgcctctct caagatcgcc gccggcgtct tctcggcctt ctccgtcgtc    1320
gcgctcgcct tcttcttcgt catcgagacc cgcaagaaga acaagtagaa cgagttgcgg    1380
ctgcgcgcca tacatgcata catgtaaatc gtcggcggcg atgagtggct gtcgttgctg    1440
attcattggt gcgcgcgact attttggtgt atcatgtaag ttacttttct gcagtgtgtg    1500
cgtcaaaatt accaaataat aacttaagtt tctctgctaa aaaaaaaaa aaaaaaaaa     1560
a                                                                   1561
```

<210> SEQ ID NO 54
<211> LENGTH: 612
<212> TYPE: DNA
<213> ORGANISM: Zea mays

<400> SEQUENCE: 54

```
atggctcggc agcaaagcgt gcaggccttg tgtgtgctgg cggcgcttct cttcgccgcc      60
```

```
tccctgccgt cgccggccgc cgcggggggtg cacctctcct cgctgcccaa agcgctcgac    120
gtcaccacct ccgccaaacc cggccaagtc ctgcacgccg cgtggactc gctgacggtg      180 acgtggagcc tgaacgccac ggagccggcc ggcgccgacg ccgggtacaa gggcgtgaag     240
gtgaagctgt gctacgcgcc ggcgagccag aaggaccgcg gtggcgcaa gtccgaggac      300 gacatcagca aggacaaggc gtgccagttc aaggtcaccg agcaggcgta cgcggcggcg    360
gcgcccggca gcttccagta cgccgtcgcc cgcgacgtcc cctcgggctc ctactacctg    420
cgcgccttcg ccacggacgc gtcgggcgcc gaggtggcct acggccagac ggcgcccacc   480
gccgccttcg acgtcgccgg catcaccggc atccacgcct ctctcaagat cgccgccggc   540
gtcttctcgg ccttctccgt cgtcgcgctc gccttcttct tcgtcatcga gacccgcaag   600
aagaacaagt ag                                                        612

<210> SEQ ID NO 55
<211> LENGTH: 203
<212> TYPE: PRT
<213> ORGANISM: Zea mays

<400> SEQUENCE: 55

Met Ala Arg Gln Gln Ser Val Gln Ala Leu Cys Val Leu Ala Ala Leu
1               5                   10                  15

Leu Phe Ala Ala Ser Leu Pro Ser Pro Ala Ala Gly Val His Leu
            20                  25                  30

Ser Ser Leu Pro Lys Ala Leu Asp Val Thr Thr Ser Ala Lys Pro Gly
        35                  40                  45

Gln Val Leu His Ala Gly Val Asp Ser Leu Thr Val Thr Trp Ser Leu
    50                  55                  60

Asn Ala Thr Glu Pro Ala Gly Ala Asp Ala Gly Tyr Lys Gly Val Lys
65                  70                  75                  80

Val Lys Leu Cys Tyr Ala Pro Ala Ser Gln Lys Asp Arg Gly Trp Arg
                85                  90                  95

Lys Ser Glu Asp Asp Ile Ser Lys Asp Lys Ala Cys Gln Phe Lys Val
            100                 105                 110

Thr Glu Gln Ala Tyr Ala Ala Ala Pro Gly Ser Phe Gln Tyr Ala
        115                 120                 125

Val Ala Arg Asp Val Pro Ser Gly Ser Tyr Tyr Leu Arg Ala Phe Ala
    130                 135                 140

Thr Asp Ala Ser Gly Ala Glu Val Ala Tyr Gly Gln Thr Ala Pro Thr
145                 150                 155                 160

Ala Ala Phe Asp Val Ala Gly Ile Thr Gly Ile His Ala Ser Leu Lys
                165                 170                 175

Ile Ala Ala Gly Val Phe Ser Ala Phe Ser Val Val Ala Leu Ala Phe
            180                 185                 190

Phe Phe Val Ile Glu Thr Arg Lys Lys Asn Lys
        195                 200

<210> SEQ ID NO 56
<211> LENGTH: 756
<212> TYPE: DNA
<213> ORGANISM: Zea mays

<400> SEQUENCE: 56
tagctatata cacatgtctg gtctgacgac aatcaaaagg gatcgctagc tcgggctagc    60
cttcctatca ctgtcatgac atgtgctctg cctctgctgg ttgataagcc gtgcgccttc   120
tcgctaattc tttcttgtgc tagaggcgag tcaaacaaac gctgcacctc gtagccctta   180
```

```
atctgcgcta agggtcacat gaccctgttc cctatcgcta gttaccaacg acccattccc      240
cctgacagat acttacgacg cgtccgtacg cggcaggcct cggcagttcg gcatcaccag      300
caccggcgcc ggcattcgcc ccctgccagc cggttcgcag attcgcaggg cggagtcggc      360
cgcagttgcc gcatcccaaa cgcccgggaa cctttggggc ccctctacga gcaaatgaag      420
ttgctgcccc tggcttcgta aagtctgac ttttgatcac ttgattggca gtcgtactcc       480
tcgctcatag gccgacacgg ccgcaaagtc aactacccgc tccgccatcc ttcaaccccc      540
gccacgcgcc tatatatgtt cgcggccatg tccgtactag tcctccaacc cacaagccac      600
aaccccgagc tcagatccct cgcctcgtgt cgtgtctccg gtcgacgacg accaacagcc      660
agtgtgggcc agacggacac cgccgagcta tagcgcttgg tgatagcaag ggacgaccgg      720
cggccggacc ggagcacgta cgtacgtacc gcagcg                                756

<210> SEQ ID NO 57
<211> LENGTH: 594
<212> TYPE: DNA
<213> ORGANISM: Zea mays

<400> SEQUENCE: 57
atgacgatgg ctcgtcctgg ggcggctttg ccgctgctgc tggtcgtggt cggcgcttgc       60
tgcgcgcgcc tggcggcggc agtgcacctc tccgcgctcg gcaggacact catcgtcgag      120
gcgtcgccga aggccggaca gtcctgcac gccggcgagg acacgataac cgtgacatgg       180
cacctcaacg cgtcggcgtc cagcgtcggg tacaaggcgc tggaggtgac cctctgctac      240
gcgccggcga gccaggagga ccgcgggtgg cgcaaggcca acgacgactt gagcaaggac      300
aaggcgtgcc agttcaggat cgcccggcat gcatacgccg cggcagggg acgctccgg       360 tacagggtcg cccgcgacgt ccccaccgcg tcctaccacg tgcgcgccta cgcgctggac      420
gcgtccgggg cgccggtggg ctacggccag accgcgcccg cctactactt ccacgtcgcg      480
ggcgtctcgg gcgtccacgc gtccctccgg gtcgccgccg ccgtgctctc gcgttctcc       540 atcgccgcgc tcgccttctt tgtcgtcgtc gagaagagga ggaaggacga gtag            594

<210> SEQ ID NO 58
<211> LENGTH: 197
<212> TYPE: PRT
<213> ORGANISM: Zea mays

<400> SEQUENCE: 58

Met Thr Met Ala Arg Pro Gly Ala Ala Leu Pro Leu Leu Leu Val Val
1               5                   10                  15

Val Gly Ala Cys Cys Ala Arg Leu Ala Ala Ala Val His Leu Ser Ala
            20                  25                  30

Leu Gly Arg Thr Leu Ile Val Glu Ala Ser Pro Lys Ala Gly Gln Val
        35                  40                  45

Leu His Ala Gly Glu Asp Thr Ile Thr Val Thr Trp His Leu Asn Ala
    50                  55                  60

Ser Ala Ser Ser Val Gly Tyr Lys Ala Leu Glu Val Thr Leu Cys Tyr
65                  70                  75                  80

Ala Pro Ala Ser Gln Glu Asp Arg Gly Trp Arg Lys Ala Asn Asp Asp
                85                  90                  95

Leu Ser Lys Asp Lys Ala Cys Gln Phe Arg Ile Ala Arg His Ala Tyr
            100                 105                 110

Ala Gly Gly Gln Gly Thr Leu Arg Tyr Arg Val Ala Arg Asp Val Pro
        115                 120                 125
```

Thr Ala Ser Tyr His Val Arg Ala Tyr Ala Leu Asp Ala Ser Gly Ala
    130                 135                 140

Pro Val Gly Tyr Gly Gln Thr Ala Pro Ala Tyr Tyr Phe His Val Ala
145                 150                 155                 160

Gly Val Ser Gly Val His Ala Ser Leu Arg Val Ala Ala Ala Val Leu
                165                 170                 175

Ser Ala Phe Ser Ile Ala Ala Leu Ala Phe Phe Val Val Glu Lys
            180                 185                 190

Arg Arg Lys Asp Glu
        195

<210> SEQ ID NO 59
<211> LENGTH: 30
<212> TYPE: DNA
<213> ORGANISM: Artificial
<220> FEATURE:
<223> OTHER INFORMATION: Primer

<400> SEQUENCE: 59
ggtcgttggt aactagcgat agggaacagg                                    30

<210> SEQ ID NO 60
<211> LENGTH: 27
<212> TYPE: DNA
<213> ORGANISM: Artificial
<220> FEATURE:
<223> OTHER INFORMATION: Primer

<400> SEQUENCE: 60
gtgcagcgtt tgtttgactc gcctcta                                       27

<210> SEQ ID NO 61
<211> LENGTH: 18
<212> TYPE: DNA
<213> ORGANISM: Artificial
<220> FEATURE:
<223> OTHER INFORMATION: Primer

<400> SEQUENCE: 61
caacggacca gctcttgg                                                 18

<210> SEQ ID NO 62
<211> LENGTH: 20
<212> TYPE: DNA
<213> ORGANISM: Artificial
<220> FEATURE:
<223> OTHER INFORMATION: Primer

<400> SEQUENCE: 62
tctttgtggg ttgtggaagg                                               20

<210> SEQ ID NO 63
<211> LENGTH: 20
<212> TYPE: DNA
<213> ORGANISM: Artificial
<220> FEATURE:
<223> OTHER INFORMATION: Primer

<400> SEQUENCE: 63
cgagcagatc gtgcaaatag                                               20

<210> SEQ ID NO 64
<211> LENGTH: 22
<212> TYPE: DNA

<213> ORGANISM: Artificial
<220> FEATURE:
<223> OTHER INFORMATION: Primer

<400> SEQUENCE: 64
gggctttgat atgtttagtt gg　　　　　　　　　　　　　　　　　　　　　22

<210> SEQ ID NO 65
<211> LENGTH: 2917
<212> TYPE: DNA
<213> ORGANISM: Zea mays
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t

<400> SEQUENCE: 65

| | | | | | |
|---|---|---|---|---|---|
| ttactatagg | gcacgcgtgg | tcgacggccc | tggctggtcc | ttgtttgatt | tacttccagg | 60 |
| attacataat | ccagcttata | tcataatcta | ggtatctaga | ttacataatc | tatctaataa | 120 |
| tctgtgttgt | tgtttaccta | ctaacttatt | tataagctgg | gttatataat | cttgaggcca | 180 |
| aataaacggg | ttctaaaatg | gtctagggtc | cagtgttaag | ctaaatcgac | attatgtcta | 240 |
| gtagtgttaa | gctaaatcga | catttctttg | tgggatgggt | ccgatgtgtc | gtctagtagt | 300 |
| gttaagctaa | agcgacattt | ctttgtgggt | tgtggaaggt | gtccctgctc | tctaagttgt | 360 |
| tagtgttaag | ctaaatgtcg | ttcttttgtgg | gttgtggctg | ctccctaagt | tgttagtgtt | 420 |
| aagctaaatg | tcgttcttttg | tgggttgtgg | aaggtgttcc | ttttccttaa | attgttagtg | 480 |
| ttaagctaaa | tcgacatttc | tttgtgggtt | gtggaangtg | ttcctttttcc | ttaagttgtt | 540 |
| agttgtgcaa | ggtgttcctt | atagcatctc | ccacatgagc | cataatggan | tttattttga | 600 |
| aatataggac | tctaaccaac | aaaaacatac | tccaataggg | attctatttt | acaaaaaat | 660 |
| atcaaatgat | tataggggtcg | attcttcggg | tcctaaatat | agtatctaat | ataatggagc | 720 |
| tctatcctca | ttttatatat | tatttctaaa | tttttattta | ctaaataaca | tgtaacatga | 780 |
| tttatttcct | aatactatga | tatagggctc | aactgttgga | gctgcaaacg | ttttttggca | 840 |
| ataaatactt | taaattaggt | cctattttaa | tttgaaagac | tatatcatgc | tcttagcgag | 900 |
| tgtttgtgca | tgattgctat | ttaggtagtt | cagttgggggg | ctttgatatg | tttagttgga | 960 |
| attctagtat | ttttttttgg | ttctccgctc | ttttgactat | cacaacgatc | gctatgcgcg | 1020 |
| agcagactat | ttgatctatt | aaattatgat | ccaaccatgt | cacattaagc | acttaaactc | 1080 |
| tttcaccatc | agtccaagta | tctttataaa | aaaccctaac | aaaccacaat | tgcatatgtg | 1140 |
| gttagattat | aatttaacgt | atcagatggt | tcgcttgcac | tcttacacac | ctagaaactg | 1200 |
| cttgcataac | agtcgttctc | tttgttatat | aatgctttag | taatcatgag | ctaagggtaa | 1260 |
| acaaatggta | catacaagta | gtgaacacat | cctcgctacc | tatctatagg | ggtggaacta | 1320 |
| gacatcctat | ttttttagaac | aaatttcata | ttttaaaata | gatatgcttg | aaaatttatg | 1380 |
| ctaatttttt | tatagtatca | agcatgttat | tacacataag | aataaaattt | tgtataaatt | 1440 |
| tttatccatt | atttgctccc | tacaattaaa | aaggtgagaa | agcaaaaagg | tgaagaaaca | 1500 |
| accgaacccg | tatccgtttc | atattcaaat | ttttacatct | attatttgag | aatatatttg | 1560 |
| aaaaatttga | ggtttagttt | ttacaaatct | ttacaaggtt | aatgttaaat | tataagactg | 1620 |
| tggatttaca | tggtaaattc | tatgtcttat | ttgtctgcga | tcgaagaaaa | atgacaaaaa | 1680 |

```
atctgacatt cgaataaaca tttgtttcca ctcctaccta tctcacctcc tatttcaaac    1740
tccacttcgt aatacgatac aaaatcaccc cctatctatc tcacctccta tttcaaactc    1800
cactcagtaa acaatattgt ctatggtaca aaatcaagtg ttttgtacat ctatttgcac    1860
gatctgctcg attcaggcat ccttgacaca caacatactc cttagggcta taaatgtcca    1920
aatagagcag acctaatgga tggaccgtgg catgacacga cttatcccaa cacagcacag    1980
tccgcccgat tggtcatggg gtctgggttg gtctagcctg atcatcgggt cactcttggg    2040
ccacaggtgc gccacaacag gatagcccaa cctatcctat tttttcatgc atatatctat    2100
attatagtta gtataaagta aaaaaacaaa aagtatgtgt gttatgttgg ctagatgtgt    2160
ttaaataact cttaaagct  agcaactatg gtttaaatca tacatataca cattttagt     2220 tttttttatt taaacaatat gagccttata ggcacgtcga gtgtgacggg ccagtgagat    2280
gacacattat aattactgat ctagcaggcc gtatctaggt cttctcgcg  gacctttctc    2340 gcggaccaag agctggtccg ttggctaatc tatacggtac cgatactgtc ctaattcata    2400
ctgggcctag ccgtgtctgt gactgggcat ggctagcgaa gcccgcccat ttgaacacct    2460
gtacaagagg ggaatttata aatgaggagg aatgtactca tgcggtacac caggggaatt    2520
gttttgttgt gctcagcgat agatttcaac gcaacggtga gccagtttca ccaaaaaaaa    2580
gggggaaaag gccacatcaa aggcgaggtg cagacgagca aagatgcta  gcagtgcagc    2640 taagtccagc agctagcaat gaaagggtac tcaggattta acaatgccta gagacggcat    2700 catccctca  atgatccggt gctctctttt tgtttattca cccgttggcg taactatata    2760
cacatgtctg gtctgacgaa cgaatcaagg gatcgctagc tcgggcgagc cttcctatca    2820
ctgtcatgac atgtgctctg cctctgctgg ttgataagcc gtgcgccttc tcgctaattc    2880
tttcttgtgc tagaggcgag tcaaacaaac gctgcac                            2917
```

<210> SEQ ID NO 66
<211> LENGTH: 4498
<212> TYPE: DNA
<213> ORGANISM: Zea mays
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t

<400> SEQUENCE: 66

```
ttactatagg gcacgcgtgg tcgacggccc tggctggtcc ttgtttgatt tacttccagg      60
attacataat ccagcttata tcataatcta ggtatctaga ttacataatc tatctaataa     120
tctgtgttgt tgtttaccta ctaacttatt tataagctgg gttatataat cttgaggcca     180
aataaacggg ttctaaaatg gtctagggtc cagtgttaag ctaaatcgac attatgtcta     240
gtagtgttaa gctaaatcga catttctttg tgggatgggt ccgatgtgtc gtctagtagt     300
gttaagctaa agcgacattt cttttgtggg tgtggaaggt gtccctgctc tctaagttgt     360
tagtgttaag ctaaatgtcg ttctttgtgg gttgtggctg ctccctaagt tgttagtgtt     420
aagctaaatg tcgttctttg tgggttgtgg aaggtgttcc ttttccttaa attgttagtg     480
ttaagctaaa tcgacatttc tttgtgggtt gtggaangtg ttccttttcc ttaagttgtt     540
agttgtgcaa ggtgttcctt atagcatctc ccacatgagc cataatggan tttattttga     600
aatataggac tctaaccaac aaaaacatac tccaataggg attctatttt acaaaaaaat     660
```

```
atcaaatgat tatagggtcg attcttcggg tcctaaatat agtatctaat ataatggagc    720
tctatcctca ttttatatat tatttctaaa tttttattta ctaaataaca tgtaacatga    780
tttatttcct aatactatga tatagggctc aactgttgga gctgcaaacg ttttttggca    840
ataaatactt taaattaggt cctatttaa tttgaaagac tatatcatgc tcttagcgag    900
tgtttgtgca tgattgctat ttaggtagtt cagttggggg ctttgatatg tttagttgga    960
attctagtat ttttttttgg ttctccgctc ttttgactat cacaacgatc gctatgcgcg   1020
agcagactat ttgatctatt aaattatgat ccaaccatgt cacattaagc acttaaactc   1080
tttcaccatc agtccaagta tctttataaa aaaccctaac aaaccacaat tgcatatgtg   1140
gttagattat aatttaacgt atcagatggt tcgcttgcac tcttacacac ctagaaactg   1200
cttgcataac agtcgttctc tttgttatat aatgctttag taatcatgag ctaagggtaa   1260
acaaatggta catacaagta gtgaacacat cctcgctacc tatctatagg ggtggaacta   1320
gacatcctat tttttagaac aaatttcata ttttaaaata gatatgcttg aaaatttatg   1380 ctaattttt tatagtatca agcatgttat tacacataag aataaaattt tgtataaatt   1440
tttatccatt atttgctccc tacaattaaa aaggtgagaa agcaaaaagg tgaagaaaca   1500
accgaacccg tatccgtttc atattcaaat ttttacatct attatttgag aatatatttg   1560
aaaaatttga ggtttagttt ttacaaatct ttacaaggtt aatgttaaat tataagactg   1620
tggatttaca tggtaaattc tatgtcttat ttgtctgcga tcgaagaaaa atgacaaaaa   1680
atctgacatt cgaataaaca tttgtttcca ctcctaccta tctcacctcc tatttcaaac   1740
tccacttcgt aatacgatac aaaatcaccc cctatctatc tcacctccta tttcaaactc   1800
cactcagtaa acaatattgt ctatggtaca aaatcaagtg ttttgtacat ctatttgcac   1860
gatctgctcg attcaggcat ccttgacaca caacatactc cttagggcta taaatgtcca   1920
aatagagcag acctaatgga tggaccgtgg catgacacga cttatcccaa cacagcacag   1980
tccgcccgat tggtcatggg gtctggggttg gtctagcctg atcatcgggt cactcttggg   2040
ccacaggtgc gccacaacag gatagcccaa cctatcctat tttttcatgc atatatctat   2100
attatagtta gtataaagta aaaaaacaaa aagtatgtgt gttatgttgg ctagatgtgt   2160
ttaaataact ctttaaagct agcaactatg gtttaaatca tacatataca catttttagt   2220
tttttttatt taaacaatat gagccttata ggcacgtcga gtgtgacggg ccagtgagat   2280
gacacattat aattactgat ctagcaggcc gtatctaggt ctttctcgcg gacctttctc   2340
gcggaccaag agctggtccg ttggctaatc tatacgtac cgatactgtc ctaattcata   2400
ctgggcctag ccgtgtctgt gactgggcat ggctagcgaa gcccgcccat tgaacacct   2460 gtacaagagg ggaatttata atgaggagg aatgtactca tgcggtacac caggggaatt   2520
gttttgttgt gctcagcgat agatttcaac gcaacggtga gccagtttca ccaaaaaaaa   2580
gggggaaaag gccacatcaa aggcgaggtg cagacgagca gaagatgcta gcagtgcagc   2640
taagtccagc agctagcaat gaaagggtac tcaggattta acaatgccta gagacggcat   2700
catcccctca atgatccggt gctctctttt tgtttattca cccgttggcg taactatata   2760
cacatgtctg gtctgacgaa cgaatcaagg gatcgctagc tcgggcgagc cttcctatca   2820
ctgtcatgac atgtgctctg cctctgctgg ttgataagcc gtgcgccttc tcgctaattc   2880
tttcttgtgc tagaggcgag tcaaacaaac gctgcacctc gtagcccttta atctgcgcta   2940 agggtcacat gaccctgttc cctatcgcta gttaccaacg acccattccc cctgacagat   3000
acttacgacg cgtccgtacg cggcaggcct cggcagttcg gcatcaccag caccggcgcc   3060
```

```
ggcattcgcc ccctgccagc cggttcgcag attcgcaggg cggagtcggc cgcagttgcc    3120
gcatcccaaa cgcccgggaa cctttggggc ccctctacga gcaaatgaag ttgctgcccc    3180
tggcttcgta aagctctgac ttttgatcac ttgattggca gtcgtactcc tcgctcatag    3240
gccgacacgg ccgcaaagtc aactacccgc tccgccatcc ttcaaccccc gccacgcgcc    3300
tatatatgtt cgcggccatg tccgtactag tcctccaacc cacaagccac aaccccgagc    3360
tcagatccct cgcctcgtgt cgtgtctccg gtcgacgacg accaacagcc agtgtgggcc    3420
agacggacac cgccgagcta tagcgcttgg tgatagcaag ggacgaccgg cggccggacc    3480
ggagcacgta cgtacgtacc gcagcgatgg ctcggcagca aagcgtgcag gccttgtgtg    3540
tgctggcggc gcttctcttc gccgcctccc tgccgtcgcc ggccgccgcg ggggtgcacc    3600
tctcctcgct gccaaagcg ctcgacgtca ccacctccgc caaacccggc caaggtgcgc    3660
gcgcgttccg gcccggctca tagtcatagc caaaggatta gcactttgat tacttgctcg    3720
gttaattcat agtcctattc ttctctatgt ttgaaacccc cctttagatt tgttcattca    3780
caatcaagga gctagctgat taaaatacac acgattgcca taaaatatat gcttctcgca    3840
gtcctgcacg ccggcgtgga ctcgctgacg gtgacgtgga gcctgaacgc cacggagccg    3900
gccggcgccg acgccgggta caagggcgtg aaggtgaagc tgtgctacgc gccggcgagc    3960
cagaaggacc gcgggtggcg caagtccgag gacgacatca gcaaggacaa ggcgtgccag    4020
ttcaaggtca ccgagcaggc gtacgcggcg gcggcgcccg gcagcttcca gtacgccgtc    4080
gcccgcgacg tccctcggg ctcctactac ctgcgcgcct tcgccacgga cgcgtcgggc    4140
gccgaggtgg cctacggcca gacggcgccc accgccgcct tcgacgtcgc cggcatcacc    4200
ggcatccacg cctctctcaa gatcgccgcc ggcgtcttct cggccttctc cgtcgtcgcg    4260
ctcgccttct tcttcgtcat cgagacccgc aagaagaaca agtagaacga gttgcggctg    4320
cgcgccatac atgcatacat gtaaatcgtc ggcggcgatg agtggctgtc gttgctgatt    4380
cattggtgcg cgcgactatt ttggtgtatc atgtaagtta cttttctgca gtgtgtgcgt    4440
caaaattacc aaataataac ttaagtttct ctgctaaaaa aaaaaaaaaa aaaaaaa      4498
```

<210> SEQ ID NO 67  
<211> LENGTH: 3506  
<212> TYPE: DNA  
<213> ORGANISM: Zea mays  
<220> FEATURE:  
<221> NAME/KEY: misc_feature  
<222> LOCATION: (517)..(517)  
<223> OTHER INFORMATION: n is a, c, g, or t  
<220> FEATURE:  
<221> NAME/KEY: misc_feature  
<222> LOCATION: (590)..(590)  
<223> OTHER INFORMATION: n is a, c, g, or t

<400> SEQUENCE: 67

```
ttactatagg gcacgcgtgg tcgacggccc tggctggtcc ttgtttgatt tacttccagg     60
attacataat ccagcttata tcataatcta ggtatctaga ttacataatc tatctaataa    120
tctgtgttgt tgtttaccta ctaacttatt tataagctgg gttatataat cttgaggcca    180
aataaacggg ttctaaaatg gtctagggtc cagtgttaag ctaaatcgac attatgtcta    240
gtagtgttaa gctaaatcga catttctttg tgggatgggt ccgatgtgtc gtctagtagt    300
gttaagctaa agcgacattt ctttgtgggt tgtggaaggt gtccctgctc tctaagttgt    360
tagtgttaag ctaaatgtcg ttctttgtgg gttgtggctg ctccctaagt tgttagtgtt    420
aagctaaatg tcgttctttg tgggttgtgg aaggtgttcc ttttccttaa attgttagtg    480
```

```
ttaagctaaa tcgacatttc tttgtgggtt gtggaangtg ttccttttcc ttaagttgtt    540
agttgtgcaa ggtgttcctt atagcatctc ccacatgagc cataatggan tttattttga    600
aatataggac tctaaccaac aaaaacatac tccaataggg attctatttt acaaaaaaat    660
atcaaatgat tatagggtcg attcttcggg tcctaaatat agtatctaat ataatggagc    720
tctatcctca ttttatatat tatttctaaa ttttttattta ctaaataaca tgtaacatga    780
tttatttcct aatactatga tatagggctc aactgttgga gctgcaaacg ttttttggca    840
ataaatactt taaattaggt cctatttttaa tttgaaagac tatatcatgc tcttagcgag    900
tgtttgtgca tgattgctat ttaggtagtt cagttggggg ctttgatatg tttagttgga    960
attctagtat ttttttttgg ttctccgctc ttttgactat cacaacgatc gctatgcgcg   1020
agcagactat ttgatctatt aaattatgat ccaaccatgt cacattaagc acttaaactc   1080
tttcaccatc agtccaagta tctttataaa aaccctaac aaaccacaat tgcatatgtg    1140
gttagattat aatttaacgt atcagatggt tcgcttgcac tcttacacac ctagaaactg   1200
cttgcataac agtcgttctc tttgttatat aatgctttag taatcatgag ctaagggtaa   1260
acaaatggta catacaagta gtgaacacat cctcgctacc tatctatagg ggtgaaacta   1320
gacatcctat tttttagaac aaatttcata ttttaaaata gatatgcttg aaaatttatg   1380 ctaattttttt tatagtatca agcatgttat tacacataag aataaaattt tgtataaatt   1440
tttatccatt atttgctccc tacaattaaa aaggtgagaa agcaaaaagg tgaagaaaca   1500
accgaacccg tatccgtttc atattcaaat ttttacatct attatttgag aatatatttg   1560
aaaaatttga ggtttagttt ttacaaatct ttacaaggtt aatgttaaat tataagactg   1620
tggatttaca tggtaaattc tatgtcttat ttgtctgcga tcgaagaaaa atgacaaaaa   1680
atctgacatt cgaataaaca tttgtttcca ctcctaccta tctcacctcc tatttcaaac   1740
tccacttcgt aatacgatac aaaatcaccc cctatctatc tcacctccta tttcaaactc   1800
cactcagtaa acaatattgt ctatggtaca aaatcaagtg ttttgtacat ctatttgcac   1860
gatctgctcg attcaggcat ccttgacaca caacatactc cttagggcta taaatgtcca   1920
aatagagcag acctaatgga tggaccgtgg catgacacga cttatcccaa cacagcacag   1980
tccgcccgat tggtcatggg gtctgggttg gtctagcctg atcatcgggt cactcttggg   2040
ccacaggtgc gccacaacag gatagcccaa cctatcctat tttttcatgc atatatctat   2100
attatagtta gtataaagta aaaaaacaaa aagtatgtgt gttatgttgg ctagatgtgt   2160
ttaaataact ctttaaagct agcaactatg gtttaaatca tacatataca catttttagt   2220 ttttttttatt taaacaatat gagccttata ggcacgtcga gtgtgacggg ccagtgagat   2280
gacacattat aattactgat ctagcaggcc gtatctaggt cttctcgcg gacctttctc    2340 gcggaccaag agctggtccg ttggctaatc tatacggtac cgatactgtc ctaattcata   2400
ctgggcctag ccgtgtctgt gactgggcat ggctagcgaa gcccgcccat ttgaacacct   2460
gtacaagagg ggaatttata atgaggagg aatgtactca tgcggtacac caggggaatt    2520
gttttgttgt gctcagcgat agatttcaac gcaacggtga gccagtttca ccaaaaaaaa   2580
gggggaaaag gccacatcaa aggcgaggtg cagacgagca aagatgcta gcagtgcagc    2640 taagtccagc agctagcaat gaaagggtac tcaggattta acaatgccta gagacggcat   2700
catcccctca atgatccggt gctctctttt tgtttattca cccgttggcg taactatata   2760
cacatgtctg gtctgacgaa cgaatcaagg gatcgctagc tcgggcgagc cttcctatca   2820
ctgtcatgac atgtgctctg cctctgctgg ttgataagcc gtgcgccttc tcgctaattc   2880
```

```
tttcttgtgc tagaggcgag tcaaacaaac gctgcacctc gtagccctta atctgcgcta    2940
agggtcacat gaccctgttc cctatcgcta gttaccaacg acccattccc cctgacagat    3000
acttacgacg cgtccgtacg cggcaggcct cggcagttcg gcatcaccag caccggcgcc    3060
ggcattcgcc ccctgccagc cggttcgcag attcgcaggg cggagtcggc cgcagttgcc    3120
gcatcccaaa cgcccgggaa cctttggggc ccctctacga gcaaatgaag ttgctgcccc    3180
tggcttcgta agctctgac ttttgatcac ttgattggca gtcgtactcc tcgctcatag    3240
gccgacacgg ccgcaaagtc aactacccgc tccgccatcc ttcaacccccc gccacgcgcc    3300 tatatatgtt cgcggccatg tccgtactag tcctccaacc cacaagccac aaccccgagc    3360
tcagatccct cgcctcgtgt cgtgtctccg gtcgacgacg accaacagcc agtgtgggcc    3420
agacggacac cgccgagcta tagcgcttgg tgatagcaag ggacgaccgg cggccggacc    3480
ggagcacgta cgtacgtacc gcagcg                                          3506

<210> SEQ ID NO 68
<211> LENGTH: 1014
<212> TYPE: DNA
<213> ORGANISM: Zea mays

<400> SEQUENCE: 68
cacaacgatc gctatgcgcg agcagactat ttgatctatt aaattatgat ccaaccatgt      60
cacattaagc acttaaactc tttcaccatc agtccaagta tctttataaa aaaccctaac     120
aaaccacaat tgcatatgtg gttagattat aatttaacgt atcagatggt tcgcttgcac     180
tcttacacac ctagaaactg cttgcataac agtcgttctc tttgttatat aatgctttag     240
taatcatgag ctaagggtaa acaaatggta catacaagta gtgaacacat cctcgctacc     300
tatctatagg ggtggaacta gacatcctat tttttagaac aaatttcata ttttaaaata     360
gatatgcttg aaaatttatg ctaattttt tatagtatca agcatgttat tacacataag     420
aataaaattt tgtataaatt tttatccatt atttgctccc tacaattaaa aaggtgagaa     480
agcaaaaagg tgaagaaaca accgaacccg tatccgtttc atattcaaat ttttacatct     540
attatttgag aatatatttg aaaaatttga ggtttagttt ttacaaatct ttacaaggtt     600
aatgttaaat tataagactg tggatttaca tggtaaattc tatgtcttat ttgtctgcga     660
tcgaagaaaa atgacaaaaa atctgacatt cgaataaaca tttgtttcca ctcctaccta     720
tctcacctcc tatttcaaac tccacttcgt aatacgatac aaaatcaccc cctatctatc     780
tcacctccta tttcaaactc cactcagtaa acaatattgt ctatggtaca aaatcaagtg     840
ttttgtacat ctatttgcac gatctgctcg attcaggcat ccttgacaca caacatactc     900
cttagggcta taaatgtcca aatagagcag acctaatgga tggaccgtgg catgacacga     960
cttatcccaa cacagcacag tccgcccgat tggtcatggg gtctggggttg gtct           1014

<210> SEQ ID NO 69
<211> LENGTH: 1492
<212> TYPE: DNA
<213> ORGANISM: Zea mays

<400> SEQUENCE: 69
agcctgatca tcgggtcact cttgggccac aggtgcgcca caacaggata gcccaaccta      60
tcctattttt tcatgcatat atctatatta tagttagtat aaagtaaaaa aacaaaaagt     120
atgtgtgtta tgttggctag atgtgtttaa ataactcttt aaagctagca actatggttt     180
aaatcataca tatacacatt tttagttttt tttatttaaa caatatgagc cttataggca     240
```

```
cgtcgagtgt gacgggccag tgagatgaca cattataatt actgatctag caggccgtat      300
ctaggtcttt ctcgcggacc tttctcgcgg accaagagct ggtccgttgg ctaatctata      360
cggtaccgat actgtcctaa ttcatactgg gcctagccgt gtctgtgact gggcatggct      420
agcgaagccc gcccatttga acacctgtac aagaggggaa tttataaatg aggaggaatg      480
tactcatgcg gtacaccagg ggaattgttt tgttgtgctc agcgatagat ttcaacgcaa      540
cggtgagcca gtttcaccaa aaaaagggg gaaaaggcca catcaaaggc gaggtgcaga      600
cgagcagaag atgctagcag tgcagctaag tccagcagct agcaatgaaa gggtactcag      660
gatttaacaa tgcctagaga cggcatcatc ccctcaatga tccggtgctc tcttttttgtt    720 tattcacccg ttggcgtaac tatatacaca tgtctggtct gacgaacgaa tcaagggatc      780
gctagctcgg gcgagccttc ctatcactgt catgacatgt gctctgcctc tgctggttga      840
taagccgtgc gccttctcgc taattctttc ttgtgctaga ggcgagtcaa acaaacgctg      900
cacctcgtag cccttaatct gcgctaaggg tcacatgacc ctgttcccta tcgctagtta      960
ccaacgaccc attccccctg acagatactt acgacgcgtc cgtacgcggc aggcctcggc     1020
agttcggcat caccagcacc ggcgccggca ttcgcccccct gccagccggt tcgcagattc     1080
gcagggcgga gtcggccgca gttgccgcat cccaaacgcc cgggaacctt tggggcccct     1140
ctacgagcaa atgaagttgc tgcccctggc ttcgtaaagc tctgactttt gatcacttga     1200
ttggcagtcg tactcctcgc tcataggccg acacggccgc aaagtcaact acccgctccg     1260
ccatccttca acccccgcca cgcgcctata tatgttcgcg gccatgtccg tactagtcct     1320
ccaacccaca agccacaacc ccgagctcag atccctcgcc tcgtgtcgtg tctccggtcg     1380
acgacgacca acagccagtg tgggccgac ggacaccgcc gagctatagc gcttggtgat      1440
agcaagggac gaccggcggc cggaccggag cacgtacgta cgtaccgcag cg             1492

<210> SEQ ID NO 70
<211> LENGTH: 3621
<212> TYPE: DNA
<213> ORGANISM: Zea mays

<400> SEQUENCE: 70
tggtccttgt ttgatttact tccaggatta tataatccag cttatggatt atataagtac       60
ctattgacgt cacgtgctta tgtattataa taatctaggt atatagatta tataatctat      120
ctaataataa tctgtgttgt tgtttatct ctcaaaacaa acaggtccta aaatggtccc       180
gggcgtccaa tgtgtcgtca agtagtgtta agctaaatcg acatttcttt gtgggttgtg      240
tggaaggtgt tccttttcct taagttgtta gttgtgcaag gtgttcctta gagcatctcc      300
aataggacct ataatggatt ctattttgaa ttataagact ctaacaacaa aagcatactt      360
taatggggat tctatttttac aaaaaaatat caaatgatta tatggtcgat tcctcgggtc     420
ctaaatatag tatctcatat aatagagctc tatcctcatt ttatatacta ttttttaagtt    480 tttatttact aaataacatg atttattttc taatactatg aactcaacta ttagagctgt      540
aaacgttttt gtggtactaa acactttaaa tcaggtccta ttttaatttg aaggacttaa      600
atataagact tctggttaga gatgctctta gcgagtgttt gtgcatgatt gctatttagt      660
ctttgtggat tgtggaaggt gttacttttc ctcaagttgt tagttgtgca aggtgtttct      720
tagagcatct ctaacaggag ccttaacgga atctattttg aagtatagta ctttaacacc      780
aaaaacatac tttaataggg gtcctatttt acaaaaaaat tatcaaatga ttataaggtc      840
cactcctcgg gtcctaaata taatatctca tatactagag ctctatcctc attttatata      900
```

```
ctatccctag gttttattc cctaaataac atgatttatt tcctaatact aagatatagg      960
gctcaactat tggagttgca aatgttttt ggcactaaac actttatatc aggtcctat      1020 ttaattttaa tttgaaggac tcaaatatag gacttctcgt tagagatgct cttagcgagt     1080
gtttgtgcat gattgctatt tatgtctgta gtttagttgg gggctttaat atgtttagtt     1140
gaagttctag tatttttag gttctccact ctttggatta tgacaacgac cactatccaa     1200
gcagtctttg agtgcaaacg cgcgagcaaa ctatctgatc tattaaatta tgatccaacc    1260
gttatgtcat attgaagact taaacccttt caccaccagc ccaagtatct ttatgaaaaa    1320
ccctaacaaa ccacaattgc atctatggtt ggattataat ttaacgtatc agatggttcg    1380
cttgcatgct tacatatcta gaaactgttt gcataacagt cgttctcttt ggttatataa    1440
tgctttagta atcatcagcc aagtgtaaac aaatggtaca aactagtagt gaacacatcc    1500
tccctaccta tctctagggg tgtaactaga tatccgaatt cttagaacaa atttcatatt    1560
ttaaaataga tatgcttcaa aatttatgct aatcttttt atattatcaa gcatattatt     1620
acacataaga ataaaatttt gtatagaatt ttatccatta tttgttccct agaatttaaa    1680
aagtgaaaaa acattcgaat ctgtatcagt ttcgtattca aatttttaca tctattattt    1740
gagaatatat atgataaatt tgaggtttag ttttttatgaa tctttacaag gttaatgtta    1800
aatacatgac tatggattta catagtaaat tctatgtctt atttgtccgc gattgaagaa    1860
aaatgacaaa aagatctgac attcgaataa acatctgttt ccactcctac ctatctgacc    1920
tcctatttca aactccactt tgtaacacgg tacaaaatca ctccctacct atctgacctc    1980
ctatttcaaa ctccactcag taaacaatat tgtctatggt acaaaaccaa gtgttttata    2040
catctatttg cacgatctgc tcgagtcagg catccttgac acacaacata ctccttgtgg    2100
ctataaatgt ccaaatagag cagacctaat gggtggaccg ttgcatgaca cgacttatcc    2160
caagacgagc acagttcgcc ccattggtca tgggggtccg ggctagtcta gcctgatcat    2220
cgggtcacac ttaggccaca ggtgtgccac aacgggatag cccaacatgt ccctttttgt    2280
catgcatata tctatattat agttagtata atgtaaaaaa acaaaaggta tgtgtgttat    2340
gttggttaga tgtgtttaaa taactctta aagctagcaa ctatggttta aatcatacat     2400
atacacattt ttattttatt tttatttaaa cgatatgggc cttctaggca cgtcgagtgt    2460
gacgggccag tgagatgaca cattataatt actggtctag caggccgtac ctaggtcttt    2520
ctcgtgggcc aagactaagg gttggcccgt tggctaatct gtacggtacc gatactgtcc    2580
taattcattt gaacacctgt agaagagggg aatttataat tgaggaggaa tgtactcatg    2640
cggtacacca ggggaattgt tttgttgtgc tcagcgatag atttcaacgc aacggtgagc    2700
cagtttcact aaaaaaaggg ggggggggg ggggggggga aggccacatc aaaggcgagg    2760
tgctgacgag cagaagatgc tagcagtgac gccaagtcca gcagctagca atgaaagggt    2820
actcgggatt taacaatgcc tagagacggc atcatcccct caataatccg gtgctctctt    2880
tttgtttatt caccagttgg cgtagctata tacacatgtc tggtctgacg aacaaatcaa    2940
gggatcgcta gctcgggcta gccttcctat cactgtcatg acatgtgctc tgcctctgct    3000
ggttgataag ccgtgcgcct tctcgctaat tctttcttgt gctagaggcg agtcaaacaa    3060
acgctgcacc tcgtagccct taatctgcgc taagggtcac atgaccctgt tccctatcgc    3120
tagttaccaa cgacccattc ccctgacag atacttacga cgcgtccgta cgcggcaggc    3180
ctcggcagtt cggcatcacc agcaccggcg ccggcattcg ccccctgcca gccggttcgc    3240
agattcgcag ggcggagtcg gccgcagttg ccgcatccca aacgcccggg aacctttggg    3300
```

```
gcccctctac gagcaaatga agttgctgcc cctggcttcg taaagctctg acttttgatc    3360
acttgattgg cagtcgtact cctcgctcat aggccgacac ggccgcaaag tcaactaccc    3420
gctccgccat ccttcaaccc ccgccacgcg cctatatatg ttcgcggcca tgtccgtact    3480
agtcctccaa cccacaagcc acaacccgga gctcagatcc ctcgcctcgt gtcgtgtctc    3540
cggtcgacga cgaccaacag ccagtgtggg ccagacggac accgccgagc tatagcgctt    3600
ggtgatagca agggacgacc g                                              3621

<210> SEQ ID NO 71
<211> LENGTH: 3236
<212> TYPE: DNA
<213> ORGANISM: Zea mays

<400> SEQUENCE: 71
tggtccttgt ttgatttact tccaggatta tataatccag cttatggatt atataagtac      60
ctattgacgt cacgtgctta tgtattataa taatctaggt atatagatta tataatctat     120
ctaataataa tctgtgttgt tgtttatctc tcaaaacaa acaggtccta aaatggtccc     180
gggcgtccaa tgtgtcgtca agtagtgtta agctaaatcg acatttcttt gtgggttgtg     240
tggaaggtgt tccttttcct taagttgtta gttgtgcaag gtgttcctta gagcatctcc     300
aataggacct ataatggatt ctattttgaa ttataagact ctaacaacaa aagcatactt     360
taatggggat tctattttac aaaaaaatat caaatgatta tatggtcgat cctcgggtc     420 ctaaatatag tatctcatat aatagagctc tatcctcatt ttatatacta ttttttaagtt    480 tttatttact aaataacatg atttattttc taatactatg aactcaacta ttagagctgt     540
aaacgttttt gtggtactaa acactttaaa tcaggtccta tttttaatttg aaggacttaa    600 atataagact tctggttaga gatgctctta gcgagtgttt gtgcatgatt gctatttagt     660
ctttgtggat tgtggaaggt gttactttc ctcaagttgt tagttgtgca aggtgttctct     720 tagagcatct ctaacaggag ccttaacgga atctattttg aagtatagta ctttaacacc     780
aaaaacatac tttaataggg gtcctatttt acaaaaaaat tatcaaatga ttataaggtc     840
cactcctcgg gtcctaaata taatatctca tatactagag ctctatcctc attttatata     900
ctatccctag ttttttattc cctaaataac atgatttatt tcctaatact aagatatagg     960
gctcaactat tggagttgca aatgtttttt ggcactaaac actttatatc aggtcctatt    1020
ttaattttaa tttgaaggac tcaaatatag gacttctcgt tagagatgct cttagcgagt    1080
gtttgtgcat gattgctatt tatgtctgta gtttagttgg gggctttaat atgtttagtt    1140
gaagttctag tatttttag gttctccact ctttggatta tgacaacgac cactatccaa     1200
gcagtctttg agtgcaaacg cgcgagcaaa ctatctgatc tattaaatta tgatccaacc    1260
gttatgtcat attgaagact taaacccttt caccaccagc ccaagtatct ttatgaaaaa    1320
ccctaacaaa ccacaattgc atctatggtt ggattataat ttaacgtatc agatggttcg    1380
cttgcatgct tacatatcta gaaactgttt gcataacagt cgttctcttt ggttatataa    1440
tgctttagta atcatcagcc aagtgtaaac aaatggtaca aactagtagt gaacacatcc    1500
tccctaccta tctctagggg tgtaactaga tatccgaatt cttagaacaa atttcatatt    1560
ttaaaataga tatgcttcaa aatttatgct aatcttttt atattatcaa gcatattatt     1620
acacataaga ataaaatttt gtatagaatt ttatccatta tttgttccct agaatttaaa    1680
aagtgaaaaa acattcgaat ctgtatcagt ttcgtattca aatttttaca tctattattt    1740
gagaatatat atgataaatt tgaggtttag tttttatgaa tctttacaag gttaatgtta    1800
```

```
aatacatgac tatggattta catagtaaat tctatgtctt atttgtccgc gattgaagaa    1860
aaatgacaaa aagatctgac attcgaataa acatctgttt ccactcctac ctatctgacc    1920
tcctatttca aactccactt tgtaacacgg tacaaaatca ctccctacct atctgacctc    1980
ctatttcaaa ctccactcag taaacaatat tgtctatggt acaaaaccaa gtgttttata    2040
catctatttg cacgatctgc tcgagtcagg catccttgac acacaacata ctccttgtgg    2100
ctataaatgt ccaaatagag cagacctaat gggtggaccg ttgcatgaca cgacttatcc    2160
caagacgagc acagttcgcc ccattggtca tgggggtccg ggctagtcta gcctgatcat    2220
cgggtcacac ttaggccaca ggtgtgccac aacgggatag cccaacatgt ccctttttgt    2280
catgcatata tctatattat agttagtata atgtaaaaaa acaaaaggta tgtgtgttat    2340
gttggttaga tgtgtttaaa taactcttta aagctagcaa ctatggttta aatcatacat    2400
atacacattt ttattttatt tttatttaaa cgatatgggc cttctaggca cgtcgagtgt    2460
gacgggccag tgagatgaca cattataatt actggtctag caggccgtac ctaggtcttt    2520
ctcgtgggcc aagactaagg gttggcccgt tggctaatct gtacggtacc gatactgtcc    2580
taattcattt gaacacctgt agaagagggg aatttataat tgaggaggaa tgtactcatg    2640
cggtacacca ggggaattgt tttgttgtgc tcagcgatag atttcaacgc aacggtgagc    2700
cagtttcact aaaaaaaggg ggggggggg ggggggggga aggccacatc aaaggcgagg    2760
tgctgacgag cagaagatgc tagcagtgac gccaagtcca gcagctagca atgaaagggt    2820
actcgggatt taacaatgcc tagagacggc atcatcccct caataatccg gtgctctctt    2880
tttgtttatt caccagttgg cgtagctata tacacatgtc tggtctgacg aacaaatcaa    2940
gggatcgcta gctcgggcta gccttcctat cactgtcatg acatgtgctc tgcctctgct    3000
ggttgataag ccgtgcgcct tctcgctaat tctttcttgt gctagaggcg agtcaaacaa    3060
acgctgcacc tcgtagccct taatctgcgc taagggtcac atgaccctgt tcctatcgc    3120
tagttaccaa cgacccattc ccctgacag atacttacga cgcgtccgta cgcggcaggc    3180
ctcggcagtt cggcatcacc agcaccggcg ccggcattcg ccccctgcca gccggt       3236
```

<210> SEQ ID NO 72
<211> LENGTH: 1000
<212> TYPE: DNA
<213> ORGANISM: Zea mays

<400> SEQUENCE: 72

```
tggtccttgt ttgatttact tccaggatta tataatccag cttatggatt atataagtac      60
ctattgacgt cacgtgctta tgtattataa taatctaggt atatagatta tataatctat     120
ctaataataa tctgtgttgt ttgtttatct ctcaaaacaa acaggtccta aaatggtccc     180
gggcgtccaa tgtgtcgtca agtagtgtta agctaaatcg acatttcttt gtgggttgtg     240
tggaaggtgt tccttttcct taagttgtta gttgtgcaag gtgttcctta gagcatctcc     300
aataggacct ataatggatt ctattttgaa ttataagact ctaacaacaa aagcatactt     360
taatggggat tctattttac aaaaaaatat caaatgatta tatggtcgat tcctcgggtc     420
ctaaatatag tatctcatat aatagagctc tatcctcatt ttatatacta ttttttaagtt    480
tttatttact aaataacatg atttatttc taatactatg aactcaacta ttagagctgt     540
aaacgttttt gtggtactaa acactttaaa tcaggtccta ttttaatttg aaggacttaa     600
atataagact tctggttaga gatgctctta gcgagtgttt tgcatgatt gctatttagt     660
ctttgtggat tgtggaaggt gttacttttc ctcaagttgt tagttgtgca aggtgtttct     720
```

| | |
|---|---|
| tagagcatct ctaacaggag ccttaacgga atctattttg aagtatagta ctttaacacc | 780 |
| aaaaacatac tttaataggg gtcctatttt acaaaaaaat tatcaaatga ttataaggtc | 840 |
| cactcctcgg gtcctaaata taatatctca tatactagag ctctatcctc attttatata | 900 |
| ctatccctag gttttattc cctaaataac atgatttatt tcctaatact aagatatagg | 960 |
| gctcaactat tggagttgca aatgttttt ggcactaaac | 1000 |

<210> SEQ ID NO 73
<211> LENGTH: 2236
<212> TYPE: DNA
<213> ORGANISM: Zea mays

<400> SEQUENCE: 73

| | |
|---|---|
| actttatatc aggtcctatt ttaattttaa tttgaaggac tcaaatatag gacttctcgt | 60 |
| tagagatgct cttagcgagt gtttgtgcat gattgctatt tatgtctgta gtttagttgg | 120 |
| gggctttaat atgtttagtt gaagttctag tatttttag gttctccact ctttggatta | 180 |
| tgacaacgac cactatccaa gcagtctttg agtgcaaacg cgcgagcaaa ctatctgatc | 240 |
| tattaaatta tgatccaacc gttatgtcat attgaagact taaaccctt caccaccagc | 300 |
| ccaagtatct ttatgaaaaa ccctaacaaa ccacaattgc atctatggtt ggattataat | 360 |
| ttaacgtatc agatggttcg cttgcatgct tacatatcta gaaactgttt gcataacagt | 420 |
| cgttctcttt ggttatataa tgctttagta atcatcagcc aagtgtaaac aaatggtaca | 480 |
| aactagtagt gaacacatcc tccctaccta tctctagggg tgtaactaga tatccgaatt | 540 |
| cttagaacaa atttcatatt ttaaaataga tatgcttcaa aatttatgct aatcttttt | 600 |
| atattatcaa gcatattatt acacataaga ataaaatttt gtatagaatt ttatccatta | 660 |
| tttgttccct agaatttaaa aagtgaaaaa acattcgaat ctgtatcagt ttcgtattca | 720 |
| aattttaca tctattattt gagaatatat atgataaatt tgaggtttag tttttatgaa | 780 |
| tctttacaag gttaatgtta aatacatgac tatggattta catagtaaat tctatgtctt | 840 |
| atttgtccgc gattgaagaa aaatgacaaa aagatctgac attcgaataa acatctgttt | 900 |
| ccactcctac ctatctgacc tcctatttca aactccactt tgtaacacgg tacaaaatca | 960 |
| ctccctacct atctgacctc ctatttcaaa ctccactcag taaacaatat tgtctatggt | 1020 |
| acaaaaccaa gtgttttata catctatttg cacgatctgc tcgagtcagg catccttgac | 1080 |
| acacaacata ctccttgtgg ctataaatgt ccaaatagag cagacctaat gggtggaccg | 1140 |
| ttgcatgaca cgacttatcc caagacgagc acagttcgcc ccattggtca tgggggtccg | 1200 |
| ggctagtcta gcctgatcat cgggtcacac ttaggccaca ggtgtgccac aacgggatag | 1260 |
| cccaacatgt cccttttgt catgcatata tctatattat agttagtata atgtaaaaaa | 1320 |
| acaaaaggta tgtgtgttat gttggttaga tgtgtttaaa taactctta aagctagcaa | 1380 |
| ctatggttta aatcatacat atacacattt ttattttatt tttatttaaa cgatatgggc | 1440 |
| cttctaggca cgtcgagtgt gacgggccag tgagatgaca cattataatt actggtctag | 1500 |
| caggccgtac ctaggtcttt ctcgtgggcc aagactaagg gttggcccgt tggctaatct | 1560 |
| gtacggtacc gatactgtcc taattcattt gaacacctgt agaagagggg aatttataat | 1620 |
| tgaggaggaa tgtactcatg cggtacacca ggggaattgt tttgttgtgc tcagcgatag | 1680 |
| atttcaacgc aacggtgagc cagtttcact aaaaaaggg gggggggggg gggggggga | 1740 |
| aggccacatc aaaggcgagg tgctgacgag cagaagatgc tagcagtgac gccaagtcca | 1800 |
| gcagctagca atgaaagggt actcgggatt taacaatgcc tagagacggc atcatcccct | 1860 |

-continued

| | |
|---|---|
| caataatccg gtgctctctt tttgtttatt caccagttgg cgtagctata tacacatgtc | 1920 |
| tggtctgacg aacaaatcaa gggatcgcta gctcgggcta gccttcctat cactgtcatg | 1980 |
| acatgtgctc tgcctctgct ggttgataag ccgtgcgcct tctcgctaat tctttcttgt | 2040 |
| gctagaggcg agtcaaacaa acgctgcacc tcgtagccct taatctgcgc taagggtcac | 2100 |
| atgacccgt tccctatcgc tagttaccaa cgacccattc ccctgacag atacttacga | 2160 |
| cgcgtccgta cgcggcaggc ctcggcagtt cggcatcacc agcaccggcg ccggcattcg | 2220 |
| cccctgcca gccggt | 2236 |

<210> SEQ ID NO 74
<211> LENGTH: 1237
<212> TYPE: DNA
<213> ORGANISM: Zea Mays

<400> SEQUENCE: 74

| | |
|---|---|
| gtaaacaata ttgtctatgg tacaaaacca agtgttttat acatctatttt gcacgatctg | 60 |
| ctcgagtcag gcatccttga cacacaacat actccttgtg gctataaatg tccaaataga | 120 |
| gcagacctaa tgggtggacc gttgcatgac acgacttatc ccaagacgag cacagttcgc | 180 |
| cccattggtc atgggggtcc gggctagtct agcctgatca tcgggtcaca cttaggccac | 240 |
| aggtgtgcca caacgggata gcccaacatg tccctttttg tcatgcatat atctatatta | 300 |
| tagttagtat aatgtaaaaa aacaaaaggt atgtgtgtta tgttggttag atgtgtttaa | 360 |
| ataactcttt aaagctagca actatggttt aaatcataca tatacacatt tttattttat | 420 |
| ttttatttaa acgatatggg ccttctaggc acgtcgagtg tgacgggcca gtgagatgac | 480 |
| acattataat tactggtcta gcaggccgta cctaggtctt tctcgtgggc caagactaag | 540 |
| ggttggcccg ttggctaatc tgtacggtac cgatactgtc ctaattcatt tgaacacctg | 600 |
| tagaagaggg gaatttataa ttgaggagga atgtactcat gcggtacacc aggggaattg | 660 |
| ttttgttgtg ctcagcgata gatttcaacg caacggtgag ccagtttcac taaaaaaagg | 720 |
| ggggggggg gggggggggg aaggccacat caaaggcgag gtgctgacga gcagaagatg | 780 |
| ctagcagtga cgccaagtcc agcagctagc aatgaaaggg tactcgggat ttaacaatgc | 840 |
| ctagagacgg catcatcccc tcaataatcc ggtgctctct ttttgtttat tcaccagttg | 900 |
| gcgtagctat atacacatgt ctggtctgac gaacaaatca agggatcgct agctcgggct | 960 |
| agccttccta tcactgtcat gacatgtgct ctgcctctgc tggttgataa gccgtgcgcc | 1020 |
| ttctcgctaa ttctttcttg tgctagaggc gagtcaaaca aacgctgcac ctcgtagccc | 1080 |
| ttaatctgcg ctaagggtca catgacccctg ttccctatcg ctagttacca acgacccatt | 1140 |
| cccctgaca gatacttacg acgcgtccgt acgcggcagg cctcggcagt tcggcatcac | 1200 |
| cagcaccggc gccggcattc gcccctgcc agccggt | 1237 |

<210> SEQ ID NO 75
<211> LENGTH: 21
<212> TYPE: DNA
<213> ORGANISM: Artificial
<220> FEATURE:
<223> OTHER INFORMATION: Primer

<400> SEQUENCE: 75

| | |
|---|---|
| gccgtgcgcc ttctcgctaa t | 21 |

<210> SEQ ID NO 76
<211> LENGTH: 24
<212> TYPE: DNA

```
<213> ORGANISM: Artificial
<220> FEATURE:
<223> OTHER INFORMATION: Primer

<400> SEQUENCE: 76
gcgaggagta cgactgccaa tcaa                                          24

<210> SEQ ID NO 77
<211> LENGTH: 32
<212> TYPE: DNA
<213> ORGANISM: Artificial
<220> FEATURE:
<223> OTHER INFORMATION: Primer

<400> SEQUENCE: 77
ttcggatcct ggtccttgtt tgatttactt cc                                 32

<210> SEQ ID NO 78
<211> LENGTH: 27
<212> TYPE: DNA
<213> ORGANISM: Artificial
<220> FEATURE:
<223> OTHER INFORMATION: Primer

<400> SEQUENCE: 78
ggcaagcttc ggtcgtccct tgctatc                                       27

<210> SEQ ID NO 79
<211> LENGTH: 18
<212> TYPE: DNA
<213> ORGANISM: Artificial
<220> FEATURE:
<223> OTHER INFORMATION: Primer

<400> SEQUENCE: 79
tgtaaaacga cggccagt                                                 18

<210> SEQ ID NO 80
<211> LENGTH: 19
<212> TYPE: DNA
<213> ORGANISM: Artificial
<220> FEATURE:
<223> OTHER INFORMATION: Primer

<400> SEQUENCE: 80
ggaaacagct atgaccatg                                                19

<210> SEQ ID NO 81
<211> LENGTH: 24
<212> TYPE: DNA
<213> ORGANISM: Artificial
<220> FEATURE:
<223> OTHER INFORMATION: Primer

<400> SEQUENCE: 81
tcaaatgatt atatggtcga ttcc                                          24

<210> SEQ ID NO 82
<211> LENGTH: 20
<212> TYPE: DNA
<213> ORGANISM: Artificial
<220> FEATURE:
<223> OTHER INFORMATION: Primer

<400> SEQUENCE: 82
cgagcagatc gtgcaaatag                                               20
```

```
<210> SEQ ID NO 83
<211> LENGTH: 18
<212> TYPE: DNA
<213> ORGANISM: Artificial
<220> FEATURE:
<223> OTHER INFORMATION: Primer

<400> SEQUENCE: 83
tgctagctgc tggacttg                                                    18

<210> SEQ ID NO 84
<211> LENGTH: 24
<212> TYPE: DNA
<213> ORGANISM: Artificial
<220> FEATURE:
<223> OTHER INFORMATION: Primer

<400> SEQUENCE: 84
ttgattggca gtcgtactcc tcgc                                             24

<210> SEQ ID NO 85
<211> LENGTH: 2777
<212> TYPE: DNA
<213> ORGANISM: Artificial Seqeunce
<220> FEATURE:
<223> OTHER INFORMATION: Vector

<400> SEQUENCE: 85
gaaaggccca gtcttccgac tgagcctttc gttttatttg atgcctggca gttccctact      60
ctcgcgttaa cgctagcatg gatgttttcc cagtcacgac gttgtaaaac gacggccagt     120
cttaagctcg ggccccgcgtt aacgctacca tggagctcca ataatgatt ttattttgac     180 tgatagtgac ctgttcgttg caacaaattg ataagcaatg cttttttata atgccaactt     240
tgtatagaaa agttgggccg aattcgagct cggtacggcc agaatggccc ggaccgggtt     300
accgaattcg agctcggtac cctgggatcc gatatcgatg ggccctggcc gaagcttggt     360
cacccggtcc gggcctagaa ggccagcttc aagtttgtac aaaaaagttg aacgagaaac     420
gtaaaatgat ataaatatca atatattaaa ttagattttg cataaaaaac agactacata     480
atactgtaaa acacaacata tgcagtcact atgaatcaac tacttagatg gtattagtga     540
cctgtagaat tcgagctcta gagctgcagg gcggccgcga tatcccctat agtgagtcgt     600
attacatggt catagctgtt tcctggcagc tctggcccgt gtctcaaaat ctctgatgtt     660
acattgcaca agataaaaat atatcatcat gaacaataaa actgtctgct tacataaaca     720
gtaatacaag gggtgttatg agccatattc aacgggaaac gtcgaggccg cgattaaatt     780
ccaacatgga tgctgattta tgggtata aatgggctcg cgataatgtc gggcaatcag     840
gtgcgacaat ctatcgcttg tatgggaagc ccgatgcgcc agagttgttt ctgaaacatg     900
gcaaaggtag cgttgccaat gatgttacag atgagatggt cagactaaac tggctgacgg     960
aatttatgcc tcttccgacc atcaagcatt ttatccgtac tcctgatgat gcatggttac    1020
tcaccactgc gatccccgga aaaacagcat tccaggtatt agaagaatat cctgattcag    1080
gtgaaaatat tgttgatgcg ctggcagtgt tcctgcgccg gttgcattcg attcctgttt    1140
gtaattgtcc ttttaacagc gatcgcgtat ttcgtctcgc tcaggcgcaa tcacgaatga    1200
ataacggttt ggttgatgcg agtgattttg atgacgagcg taatggctgg cctgttgaac    1260
aagtctggaa agaaatgcat aaacttttgc cattctcacc ggattcagtc gtcactcatg    1320
gtgatttctc acttgataac cttatttttg acgaggggaa attaataggt tgtattgatg    1380
```

-continued

| | |
|---|---|
| ttggacgagt cggaatcgca gaccgatacc aggatcttgc catcctatgg aactgcctcg | 1440 |
| gtgagttttc tccttcatta cagaaacggc ttttcaaaa atatggtatt gataatcctg | 1500 |
| atatgaataa attgcagttt catttgatgc tcgatgagtt tttctaatca gaattggtta | 1560 |
| attggttgta acactggcag agcattacgc tgacttgacg ggacggcgca agctcatgac | 1620 |
| caaaatccct taacgtgagt tacgcgtcgt tccactgagc gtcagacccc gtagaaaaga | 1680 |
| tcaaaggatc ttcttgagat cctttttttc tgcgcgtaat ctgctgcttg caaacaaaaa | 1740 |
| aaccaccgct accagcggtg gtttgtttgc cggatcaaga gctaccaact cttttccga | 1800 |
| aggtaactgg cttcagcaga gcgcagatac caaatactgt ccttctagtg tagccgtagt | 1860 |
| taggccacca cttcaagaac tctgtagcac cgcctacata cctcgctctg ctaatcctgt | 1920 |
| taccagtggc tgctgccagt ggcgataagt cgtgtcttac cgggttggac tcaagacgat | 1980 |
| agttaccgga taaggcgcag cggtcgggct gaacggggggg ttcgtgcaca cagcccagct | 2040 |
| tggagcgaac gacctacacc gaactgagat acctacagcg tgagcattga aaagcgcca | 2100 |
| cgcttcccga agggagaaag gcggacaggt atccggtaag cggcagggtc ggaacaggag | 2160 |
| agcgcacgag ggagcttcca gggggaaacg cctggtatct ttatagtcct gtcgggtttc | 2220 |
| gccacctctg acttgagcgt cgatttttgt gatgctcgtc agggggggcgg agcctatgga | 2280 |
| aaaacgccag caacgcggcc ttttacggt tcctggcctt ttgctggcct tttgctcaca | 2340 |
| tgttctttcc tgcgttatcc cctgattctg tggataaccg tattaccgcc tttgagtgag | 2400 |
| ctgataccgc tcgccgcagc cgaacgaccg agcgcagcga gtcagtgagc gaggaagcgg | 2460 |
| aagagcgccc aatacgcaaa ccgcctctcc ccgcgcgttg gccgattcat taatgcagct | 2520 |
| ggcacgacag gtttcccgac tggaaagcgg gcagtgagcg caacgcaatt aatacgcgta | 2580 |
| ccgctagcca ggaagagttt gtagaaacgc aaaaaggcca tccgtcagga tggccttctg | 2640 |
| cttagtttga tgcctggcag tttatggcgg gcgtcctgcc cgccaccctc cgggccgttg | 2700 |
| cttcacaacg ttcaaatccg ctcccggcgg atttgtccta ctcaggagag cgttcaccga | 2760 |
| caaacaacag ataaaac | 2777 |

<210> SEQ ID NO 86
<211> LENGTH: 6377
<212> TYPE: DNA
<213> ORGANISM: Artificial Seqeunce
<220> FEATURE:
<223> OTHER INFORMATION: Vector

<400> SEQUENCE: 86

| | |
|---|---|
| gaaaggccca gtcttccgac tgagcctttc gttttatttg atgcctggca gttccctact | 60 |
| ctcgcgttaa cgctagcatg gatgttttcc cagtcacgac gttgtaaaac gacggccagt | 120 |
| cttaagctcg ggccccgcgtt aacgctacca tggagctcca ataatgatt ttattttgac | 180 |
| tgatagtgac ctgttcgttg caacaaattg ataagcaatg cttttttata atgccaactt | 240 |
| tgtatagaaa agttgggccg aattcgagct cggtacggcc agaatggccc ggaccgggtt | 300 |
| accgaattcg agctcggtac cctgggatcc gcaaggacg accgtggtcc ttgtttgatt | 360 |
| tacttccagg attatataat ccagcttatg gattatataa gtaccattg acgtcacgtg | 420 |
| cttatgtatt ataataatct aggtatatag attatataat ctatctaata ataatctgtg | 480 |
| ttgtttgttt atctctcaaa acaaacaggt cctaaaatgg tcccgggcgt ccaatgtgtc | 540 |
| gtcaagtagt gttaagctaa atcgacattt cttgtgggt tgtgtggaag gtgttccttt | 600 |
| tccttaagtt gttagttgtg caaggtgttc cttagagcat ctccaatagg acctataatg | 660 |

```
gattctattt tgaattataa gactctaaca acaaaagcat actttaatgg ggattctatt      720
ttacaaaaaa atatcaaatg attatatggt cgattcctcg ggtcctaaat atagtatctc      780
atataataga gctctatcct cattttatat actattttta agtttttatt tactaaataa      840
catgatttat tttctaatac tatgaactca actattagag ctgtaaacgt ttttgtggta      900
ctaaacactt taaatcaggt cctattttaa tttgaaggac ttaaatataa gacttctggt      960
tagagatgct cttagcgagt gtttgtgcat gattgctatt tagtctttgt ggattgtgga     1020
aggtgttact tttcctcaag ttgttagttg tgcaaggtgt ttcttagagc atctctaaca     1080
ggagccttaa cggaatctat tttgaagtat agtactttaa caccaaaaac atactttaat     1140
aggggtccta ttttacaaaa aaattatcaa atgattataa ggtccactcc tcgggtccta     1200 aatataaatat ctcatatact agagctctat cctcatttta tatactatcc ctaggttttt     1260
attccctaaa taacatgatt tatttcctaa tactaagata tagggctcaa ctattggagt     1320
tgcaaatgtt ttttggcact aaacacttta tatcaggtcc tattttaatt ttaatttgaa     1380
ggactcaaat ataggacttc tcgttagaga tgctcttagc gagtgtttgt gcatgattgc     1440
tatttatgtc tgtagtttag ttgggggctt taatatgttt agttgaagtt ctagtatttt     1500
ttaggttctc cactctttgg attatgacaa cgaccactat ccaagcagtc tttgagtgca     1560
aacgcgcgag caaactatct gatctattaa attatgatcc aaccgttatg tcatattgaa     1620
gacttaaacc ctttcaccac cagcccaagt atctttatga aaaccctaa caaaccacaa      1680 ttgcatctat ggttggatta taatttaacg tatcagatgg ttcgcttgca tgcttacata     1740
tctagaaact gtttgcataa cagtcgttct ctttggttat ataatgcttt agtaatcatc     1800
agccaagtgt aaacaaatgg tacaaactag tagtgaacac atcctcccta cctatctcta     1860
ggggtgtaac tagatatccg aattcttaga acaaatttca tattttaaaa tagatatgct     1920
tcaaaattta tgctaatctt ttttatatta tcaagcatat tattacacat aagaataaaa     1980
ttttgtatag aattttatcc attatttgtt ccctagaatt taaaaagtga aaaacattc     2040 gaatctgtat cagtttcgta ttcaaatttt tacatctatt atttgagaat atatatgata     2100
aatttgaggt ttagttttta tgaatcttta caaggttaat gttaaataca tgactatgga     2160
tttacatagt aaattctatg tcttatttgt ccgcgattga agaaaaatga caaaagatc      2220 tgacattcga ataaacatct gttttccactc ctacctatct gacctcctat ttcaaactcc     2280
actttgtaac acggtacaaa atcactcct acctatctga cctcctattt caaactccac     2340
tcagtaaaca atattgtcta tggtacaaaa ccaagtgttt tatacatcta tttgcacgat     2400
ctgctcgagt caggcatcct tgacacacaa catactcctt gtggctataa atgtccaaat     2460
agagcagacc taatgggtgg accgttgcat gacacgactt atcccaagac gagcacagtt     2520
cgccccattg gtcatggggg tccgggctag tctagcctga tcatcgggtc acacttaggc     2580
cacaggtgtg ccacaacggg atagcccaac atgtcccttt ttgtcatgca tatatctata     2640
ttatagttag tataatgtaa aaaaacaaaa ggtatgtgtg ttatgttggt tagatgtgtt     2700
taaataactc tttaaagcta gcaactatgg tttaaatcat acatatacac atttttattt     2760
tatttttatt taaacgatat gggccttcta ggcacgtcga gtgtgacggg ccagtgagat     2820
gacacattat aattactggt ctagcaggcc gtacctaggt cttctcgtg ggccaagact     2880 aagggttggc ccgttggcta atctgtacgg taccgatact gtcctaattc atttgaacac     2940
ctgtagaaga ggggaattta taattgagga ggaatgtact catgcggtac accagggaa      3000 ttgttttgtt gtgctcagcg atagatttca acgcaacggt gagccagttt cactaaaaaa     3060
```

```
agggggggggg gggggggggg gggaaggcca catcaaaggc gaggtgctga cgagcagaag    3120
atgctagcag tgacgccaag tccagcagct agcaatgaaa gggtactcgg gatttaacaa    3180
tgcctagaga cggcatcatc ccctcaataa tccggtgctc tcttttgtt tattcaccag     3240 ttggcgtagc tatatacaca tgtctggtct gacgaacaaa tcaagggatc gctagctcgg    3300
gctagccttc ctatcactgt catgacatgt gctctgcctc tgctggttga taagccgtgc    3360
gccttctcgc taattctttc ttgtgctaga ggcgagtcaa acaaacgctg cacctcgtag    3420
cccttaatct gcgctaaggg tcacatgacc ctgttcccta tcgctagtta ccaacgaccc    3480
attccccctg acagatactt acgacgcgtc cgtacgcggc aggcctcggc agttcggcat    3540
caccagcacc ggcgccggca ttcgccccct gccagccggt tcgcagattc gcagggcgga    3600
gtcggccgca gttgccgcat cccaaacgcc cgggaacctt tggggcccct ctacgagcaa    3660
atgaagttgc tgcccctggc ttcgtaaagc tctgacttt gatcacttga ttggcagtcg     3720
tactcctcgc tcataggccg acacggccgc aaagtcaact acccgctccg ccatccttca    3780 accccccgcca cgcgcctata tatgttcgcg gccatgtccg tactagtcct ccaacccaca    3840
agccacaacc ccgagctcag atccctgccc tcgtgtcgtg tctccggtcg acgacgacca    3900
acagccagtg tgggccagac ggacaccgcc gagctatagc gcttggtgat aaagcttggt    3960
cacccggtcc gggcctagaa ggccagcttc aagtttgtac aaaaaagttg aacgagaaac    4020
gtaaaatgat ataaatatca atatattaaa ttagattttg cataaaaaac agactacata    4080
atactgtaaa acacaacata tgcagtcact atgaatcaac tacttagatg gtattagtga    4140
cctgtagaat tcgagctcta gagctgcagg gcggccgcga tatcccctat agtgagtcgt    4200
attacatggt catagctgtt tcctggcagc tctggcccgt gtctcaaaat ctctgatgtt    4260
acattgcaca agataaaaat atatcatcat gaacaataaa actgtctgct tacataaaca    4320
gtaatacaag gggtgttatg agccatattc aacgggaaac gtcgaggccg cgattaaatt    4380
ccaacatgga tgctgattta tatgggtata atgggctcg cgataatgtc gggcaatcag     4440
gtgcgacaat ctatcgcttg tatgggaagc ccgatgcgcc agagttgttt ctgaaacatg    4500
gcaaaggtag cgttgccaat gatgttacag atgagatggt cagactaaac tggctgacgg    4560
aatttatgcc tcttccgacc atcaagcatt ttatccgtac tcctgatgat gcatggttac    4620
tcaccactgc gatccccgga aaaacagcat tccaggtatt agaagaatat cctgattcag    4680
gtgaaaatat tgttgatgcg ctggcagtgt tcctgcgccg gttgcattcg attcctgttt    4740
gtaattgtcc ttttaacagc gatcgcgtat ttcgtctcgc tcaggcgcaa tcacgaatga    4800
ataacggttt ggttgatgcg agtgattttg atgacgagcg taatggctgg cctgttgaac    4860
aagtctggaa agaaatgcat aaacttttgc cattctcacc ggattcagtc gtcactcatg    4920
gtgatttctc acttgataac cttatttttg acgaggggaa attaataggt tgtattgatg    4980
ttggacgagt cggaatcgca gaccgatacc aggatcttgc catcctatgg aactgcctcg    5040
gtgagttttc tccttcatta cagaaacggc ttttcaaaa atatggtatt gataatcctg    5100
atatgaataa attgcagttt catttgatgc tcgatgagtt tttctaatca gaattggtta    5160
attggttgta acactggcag agcattacgc tgacttgacg ggacggcgca agctcatgac    5220
caaaatccct taacgtgagt tacgcgtcgt tccactgagc gtcagacccc gtagaaaaga    5280
tcaaaggatc ttcttgagat ccttttttc tgcgcgtaat ctgctgcttg caaacaaaaa    5340
aaccaccgct accagcggtg gtttgtttgc cggatcaaga gctaccaact cttttttcga    5400
aggtaactgg cttcagcaga gcgcagatac caaatactgt ccttctagtg tagccgtagt    5460
```

-continued

| | |
|---|---|
| taggccacca cttcaagaac tctgtagcac cgcctacata cctcgctctg ctaatcctgt | 5520 |
| taccagtggc tgctgccagt ggcgataagt cgtgtcttac cgggttggac tcaagacgat | 5580 |
| agttaccgga taaggcgcag cggtcgggct gaacgggggg ttcgtgcaca cagcccagct | 5640 |
| tggagcgaac gacctacacc gaactgagat acctacagcg tgagcattga aaagcgcca | 5700 |
| cgcttcccga agggagaaag gcggacaggt atccggtaag cggcagggtc ggaacaggag | 5760 |
| agcgcacgag ggagcttcca gggggaaacg cctggtatct ttatagtcct gtcgggtttc | 5820 |
| gccacctctg acttgagcgt cgattttttgt gatgctcgtc agggggggcgg agcctatgga | 5880 |
| aaaacgccag caacgcggcc ttttttacggt tcctggcctt ttgctggcct tttgctcaca | 5940 |
| tgttctttcc tgcgttatcc cctgattctg tggataaccg tattaccgcc tttgagtgag | 6000 |
| ctgataccgc tcgccgcagc cgaacgaccg agcgcagcga gtcagtgagc gaggaagcgg | 6060 |
| aagagcgccc aatacgcaaa ccgcctctcc ccgcgcgttg gccgattcat taatgcagct | 6120 |
| ggcacgacag gtttcccgac tggaaagcgg gcagtgagcg caacgcaatt aatacgcgta | 6180 |
| ccgctagcca ggaagagttt gtagaaacgc aaaaaggcca tccgtcagga tggccttctg | 6240 |
| cttagtttga tgcctggcag tttatggcgg gcgtcctgcc cgccaccctc cgggccgttg | 6300 |
| cttcacaacg ttcaaatccg ctcccggcgg atttgtccta ctcaggagag cgttcaccga | 6360 |
| caaacaacag ataaaac | 6377 |

<210> SEQ ID NO 87
<211> LENGTH: 17777
<212> TYPE: DNA
<213> ORGANISM: Artificial Seqeunce
<220> FEATURE:
<223> OTHER INFORMATION: Vector

<400> SEQUENCE: 87

| | |
|---|---|
| attatacaaa gttgatagat atcggaccga ttaaacttta attcggtccg aagcttgcat | 60 |
| gcctgcagtg cagcgtgacc cggtcgtgcc cctctctaga gataatgagc attgcatgtc | 120 |
| taagttataa aaaattacca catatttttt ttgtcacact tgtttgaagt gcagtttatc | 180 |
| tatctttata catatattta aactttactc tacgaataat ataatctata gtactacaat | 240 |
| aatatcagtg ttttagagaa tcatataaat gaacagttag acatggtcta aaggacaatt | 300 |
| gagtattttg acaacaggac tctacagttt tatcttttta gtgtgcatgt gttctccttt | 360 |
| tttttttgcaa atagcttcac ctatataata cttcatccat tttattagta catccattta | 420 |
| gggtttaggg ttaatggttt ttatagacta attttttttag tacatctatt ttattctatt | 480 |
| ttagcctcta aattaagaaa actaaaactc tattttagtt tttttattta ataatttaga | 540 |
| tataaaatag aataaaataa agtgactaaa aattaaacaa ataccccttta agaaattaaa | 600 |
| aaaactaagg aaacatttt cttgtttcga gtagataatg ccagcctgtt aaacgccgtc | 660 |
| gacgagtcta acgacacca accagcgaac cagcagcgtc gcgtcgggcc aagcgaagca | 720 |
| gacggcacgg catctctgtc gctgcctctg gacccctctc gagagttccg ctccaccgtt | 780 |
| ggacttgctc cgctgtcggc atccagaaat tgcgtggcgg agcggcagac gtgagccggc | 840 |
| acggcaggcg gcctcctcct cctctcacgg caccggcagc tacgggggat tcctttccca | 900 |
| ccgctccttc gctttccctt cctcgcccgc cgtaataaat agacaccccc tccacaccct | 960 |
| ctttccccaa cctcgtgttg ttcggagcgc acacacacac aaccagatct cccccaaatc | 1020 |
| cacccgtcgg cacctccgct tcaaggtacg ccgtcgtcc tcccccccc ccctctctac | 1080 |
| cttctctaga tcggcgttcc ggtccatgca tggttagggc ccggtagttc tacttctgtt | 1140 |

```
catgtttgtg ttagatccgt gtttgtgtta gatccgtgct gctagcgttc gtacacggat    1200
gcgacctgta cgtcagacac gttctgattg ctaacttgcc agtgtttctc tttggggaat    1260
cctgggatgg ctctagccgt tccgcagacg ggatcgattt catgatttt tttgtttcgt     1320 tgcatagggt ttggtttgcc cttttccttt atttcaatat atgccgtgca cttgtttgtc    1380
gggtcatctt ttcatgcttt ttttgtctt ggttgtgatg atgtggtctg gttgggcggt     1440
cgttctagat cggagtagaa ttctgtttca aactacctgg tggatttatt aattttggat    1500
ctgtatgtgt gtgccataca tattcatagt tacgaattga agatgatgga tggaaatatc    1560
gatctaggat aggtatacat gttgatgcgg gttttactga tgcatataca gagatgcttt    1620
ttgttcgctt ggttgtgatg atgtggtgtg gttgggcggt cgttcattcg ttctagatcg    1680
gagtagaata ctgtttcaaa ctacctggtg tatttattaa ttttggaact gtatgtgtgt    1740
gtcatacatc ttcatagtta cgagtttaag atggatggaa atatcgatct aggataggta    1800
tacatgttga tgtgggtttt actgatgcat atacatgatg gcatatgcag catctattca    1860
tatgctctaa ccttgagtac ctatctatta taataaacaa gtatgtttta taattatttt    1920
gatcttgata tacttggatg atggcatatg cagcagctat atgtggattt ttttagccct    1980
gccttcatac gctatttatt tgcttggtac tgtttctttt gtcgatgctc accctgttgt    2040
ttggtgttac ttctgcaggt cgactttaac ttagcctagg atccacacga caccatgtcc    2100
cccgagcgcc gccccgtcga gatccgcccg gccaccgccg ccgacatggc cgccgtgtgc    2160
gacatcgtga accactacat cgagacctcc accgtgaact tccgcaccga gccgcagacc    2220
ccgcaggagt ggatcgacga cctggagcgc ctccaggacc gctacccgtg gctcgtggcc    2280
gaggtggagg gcgtggtggc cggcatcgcc tacgccggcc cgtggaaggc ccgcaacgcc    2340
tacgactgga ccgtggagtc caccgtgtac gtgtcccacc gccaccagcg cctcggcctc    2400
ggctccaccc tctacaccca cctcctcaag agcatggagg cccagggctt caagtccgtg    2460
gtggccgtga tcggcctccc gaacgacccg tccgtgcgcc tccacgaggc cctcggctac    2520
accgcccgcg gcaccctccg cgccgccggc tacaagcacg gcggctggca cgacgtcggc    2580
ttctggcagc gcgacttcga gctgccggcc ccgccgcgcc cggtgcgccc ggtgacgcag    2640
atctgagtcg aaacctagac ttgtccatct tctggattgg ccaacttaat taatgtatga    2700
aataaaagga tgcacacata gtgacatgct aatcactata atgtgggcat caaagttgtg    2760
tgttatgtgt aattactagt tatctgaata aagagaaag agatcatcca tatttcttat     2820
cctaaatgaa tgtcacgtgt ctttataatt ctttgatgaa ccagatgcat tcattaacc     2880 aaatccatat acatataaat attaatcata tataattaat atcaattggg ttagcaaaac    2940
aaatctagtc taggtgtgtt ttgcgaattg cggccgccac cgcggtggag ctcgaattca    3000
ttccgattaa tcgtggcctc ttgctcttca ggatgaagag ctatgtttaa acgtgcaagc    3060
gctactagac aattcagtac attaaaaacg tccgcaatgt gttattaagt tgtctaagcg    3120
tcaatttgtt tacaccacaa tatatcctgc caccagccag ccaacagctc cccgaccggc    3180
agctcggcac aaaatcacca ctcgatacag gcagcccatc agtccgggac ggcgtcagcg    3240
ggagagccgt tgtaaggcgg cagactttgc tcatgttacc gatgctattc ggaagaacgg    3300
caactaagct gccgggtttg aaacacggat gatctcgcgg agggtagcat gttgattgta    3360
acgatgacag agcgttgctg cctgtgatca aatatcatct ccctcgcaga gatccgaatt    3420
atcagccttc ttattcattt ctcgcttaac cgtgacaggc tgtcgatctt gagaactatg    3480
ccgacataat aggaaatcgc tggataaagc cgctgaggaa gctgagtggc gctatttctt    3540
```

```
tagaagtgaa cgttgacgat cgtcgaccgt accccgatga attaattcgg acgtacgttc   3600
tgaacacagc tggatactta cttgggcgat tgtcatacat gacatcaaca atgtacccgt   3660
ttgtgtaacc gtctcttgga ggttcgtatg acactagtgg ttcccctcag cttgcgacta   3720
gatgttgagg cctaacattt tattagagag caggctagtt gcttagatac atgatcttca   3780
ggccgttatc tgtcagggca agcgaaaatt ggccatttat gacgaccaat gccccgcaga   3840
agctcccatc tttgccgcca tagacgccgc gccccccttt tggggtgtag aacatccttt   3900
tgccagatgt ggaaaagaag ttcgttgtcc cattgttggc aatgacgtag tagccggcga   3960
aagtgcgaga cccatttgcg ctatatataa gcctacgatt ccgttgcgca ctattgtcgt   4020
aattggatga actattatcg tagttgctct cagagttgtc gtaatttgat ggactattgt   4080
cgtaattgct tatggagttg tcgtagttgc ttggagaaat gtcgtagttg gatggggagt   4140
agtcataggg aagacgagct tcatccacta aaacaattgg caggtcagca agtgcctgcc   4200
ccgatgccat cgcaagtacg aggcttagaa ccaccttcaa cagatcgcgc atagtcttcc   4260
ccagctctct aacgcttgag ttaagccgcg ccgcgaagcg gcgtcggctt gaacgaattg   4320
ttagacatta tttgccgact accttggtga tctcgccttt cacgtagtga acaaattctt   4380
ccaactgatc tgcgcgcgag gccaagcgat cttcttgtcc aagataagcc tgcctagctt   4440
caagtatgac gggctgatac tgggccggca ggcgctccat tgcccagtcg gcagcgacat   4500
ccttcggcgc gattttgccg gttactgcgc tgtaccaaat gcgggacaac gtaagcacta   4560
catttcgctc atcgccagcc cagtcgggcg gcgagttcca tagcgttaag gtttcattta   4620
gcgcctcaaa tagatcctgt tcaggaaccg gatcaaagag ttcctccgcc gctggaccta   4680
ccaaggcaac gctatgttct cttgcttttg tcagcaagat agccagatca atgtcgatcg   4740
tggctggctc gaagatacct gcaagaatgt cattgcgctg ccattctcca aattgcagtt   4800
cgcgcttagc tggataacgc cacggaatga tgtcgtcgtg cacaacaatg gtgacttcta   4860
cagcgcggag aatctcgctc tctccagggg aagccgaagt ttccaaaagg tcgttgatca   4920
aagctcgccg cgttgtttca tcaagcctta cagtcaccgt aaccagcaaa tcaatatcac   4980
tgtgtggctt caggccgcca tccactgcgg agccgtacaa atgtacgcc agcaacgtcg   5040 gttcgagatg gcgctcgatg acgccaacta cctctgatag ttgagtcgat acttcggcga   5100
tcaccgcttc cctcatgatg tttaactcct gaattaagcc gcgccgcgaa gcggtgtcgg   5160
cttgaatgaa ttgttaggcg tcatcctgtg ctcccgagaa ccagtaccag tacatcgctg   5220
tttcgttcga gacttgaggt ctagttttat acgtgaacag gtcaatgccg ccgagagtaa   5280
agccacattt tgcgtacaaa ttgcaggcag gtacattgtt cgtttgtgtc tctaatcgta   5340
tgccaaggag ctgtctgctt agtgccact ttttcgcaaa ttcgatgaga ctgtgcgcga   5400
ctcctttgcc tcggtgcgtg tgcgacacaa caatgtgttc gatagaggct agatcgttcc   5460
atgttgagtt gagttcaatc ttcccgacaa gctcttggtc gatgaatgcg ccatagcaag   5520
cagagtcttc atcagagtca tcatccgaga tgtaatcctt ccggtagggg ctcacacttc   5580
tggtagatag ttcaaagcct tggtcggata ggtgcacatc gaacacttca cgaacaatga   5640
aatggttctc agcatccaat gtttccgcca cctgctcagg gatcaccgaa atcttcatat   5700
gacgcctaac gcctggcaca gcggatcgca aacctggcgc ggcttttggc acaaaaggcg   5760
tgacaggttt gcgaatccgt tgctgccact tgttaaccct tttgccagat ttggtaacta   5820
taatttatgt tagaggcgaa gtcttgggta aaaactggcc taaaattgct ggggatttca   5880
ggaaagtaaa catcaccttc cggctcgatg tctattgtag atatatgtag tgtatctact   5940
```

```
tgatcggggg atctgctgcc tcgcgcgttt cggtgatgac ggtgaaaacc tctgacacat    6000
gcagctcccg gagacggtca cagcttgtct gtaagcggat gccgggagca gacaagcccg    6060
tcagggcgcg tcagcgggtg ttggcgggtg tcggggcgca gccatgaccc agtcacgtag    6120
cgatagcgga gtgtatactg gcttaactat gcggcatcag agcagattgt actgagagtg    6180
caccatatgc ggtgtgaaat accgcacaga tgcgtaagga gaaaataccg catcaggcgc    6240
tcttccgctt cctcgctcac tgactcgctg cgctcggtcg ttcggctgcg gcgagcggta    6300
tcagctcact caaaggcggt aatacggtta tccacagaat caggggataa cgcaggaaag    6360
aacatgtgag caaaaggcca gcaaaaggcc aggaaccgta aaaaggccgc gttgctggcg    6420 ttttccata ggctccgccc ccctgacgag catcacaaaa atcgacgctc aagtcagagg    6480
tggcgaaacc cgacaggact ataaagatac caggcgtttc ccctggaag ctccctcgtg    6540 cgctctcctg ttccgaccct gccgcttacc ggatacctgt ccgcctttct cccttcggga    6600
agcgtggcgc tttctcatag ctcacgctgt aggtatctca gttcggtgta ggtcgttcgc    6660
tccaagctgg gctgtgtgca cgaaccccc gttcagcccg accgctgcgc cttatccggt    6720
aactatcgtc ttgagtccaa cccggtaaga cacgacttat cgccactggc agcagccact    6780
ggtaacagga ttagcagagc gaggtatgta ggcggtgcta cagagttctt gaagtggtgg    6840
cctaactacg gctacactag aaggacagta tttggtatct gcgctctgct gaagccagtt    6900
accttcggaa aaagagttgg tagctcttga tccggcaaac aaaccaccgc tggtagcggt    6960
ggtttttttg tttgcaagca gcagattacg cgcagaaaaa aaggatctca agaagatcct    7020
ttgatctttt ctacggggtc tgacgctcag tggaacgaaa actcacgtta agggattttg    7080
gtcatgagat tatcaaaaag gatcttcacc tagatccttt taaattaaaa atgaagtttt    7140
aaatcaatct aaagtatata tgagtaaact tggtctgaca gttaccaatg cttaatcagt    7200
gaggcaccta tctcagcgat ctgtctattt cgttcatcca tagttgcctg actccccgtc    7260
gtgtagataa ctacgatacg ggagggctta ccatctggcc ccagtgctgc aatgataccg    7320
cgagacccac gctcaccggc tccagattta tcagcaataa accagccagc cggaagggcc    7380
gagcgcagaa gtggtcctgc aactttatcc gcctccatcc agtctattaa ttgttgccgg    7440
gaagctagag taagtagttc gccagttaat agtttgcgca acgttgttgc cattgctgca    7500 ggggggggg ggggggggga cttccattgt tcattccacg acaaaaaca gagaaaggaa    7560 acgacagagg ccaaaaagcc tcgctttcag cacctgtcgt ttcctttctt ttcagagggt    7620
attttaaata aaacattaa gttatgacga agaagaacgg aaacgcctta aaccggaaaa    7680
ttttcataaa tagcgaaaac ccgcgaggtc gccgccccgt aacctgtcgg atcaccggaa    7740
aggacccgta aagtgataat gattatcatc tacatatcac aacgtgcgtg gaggccatca    7800
aaccacgtca aataatcaat tatgacgcag gtatcgtatt aattgatctg catcaactta    7860
acgtaaaaac aacttcagac aatacaaatc agcgacactg aatacggggc aacctcatgt    7920 ccccccccc cccccccctg caggcatcgt ggtgtcacgc tcgtcgtttg gtatggcttc    7980
attcagctcc ggttcccaac gatcaaggcg agttacatga tccccatgt tgtgcaaaaa    8040 agcggttagc tccttcggtc ctccgatcgt tgtcagaagt aagttggccg cagtgttatc    8100
actcatggtt atggcagcac tgcataattc tcttactgtc atgccatccg taagatgctt    8160
ttctgtgact ggtgagtact caaccaagtc attctgagaa tagtgtatgc ggcgaccgag    8220
ttgctcttgc ccggcgtcaa cacgggataa taccgcgcca catagcagaa ctttaaaagt    8280
gctcatcatt ggaaaacgtt cttcggggcg aaaactctca aggatcttac cgctgttgag    8340
```

```
atccagttcg atgtaaccca ctcgtgcacc caactgatct tcagcatctt ttactttcac      8400
cagcgtttct gggtgagcaa aaacaggaag gcaaaatgcc gcaaaaaagg gaataagggc      8460
gacacggaaa tgttgaatac tcatactctt cctttttcaa tattattgaa gcatttatca      8520
gggttattgt ctcatgagcg gatacatatt tgaatgtatt tagaaaaata aacaaatagg      8580
ggttccgcgc acatttcccc gaaaagtgcc acctgacgtc taagaaacca ttattatcat      8640
gacattaacc tataaaaata ggcgtatcac gaggccctttt cgtcttcaag aattggtcga      8700
cgatcttgct gcgttcggat attttcgtgg agttcccgcc acagaccccgg attgaaggcg      8760 agatccagca actcgcgcca gatcatcctg tgacggaact tggcgcgtg atgactggcc       8820 aggacgtcgg ccgaaagagc gacaagcaga tcacgctttt cgacagcgtc ggatttgcga      8880
tcgaggattt tcggcgctg cgctacgtcc gcgaccgcgt tgagggatca agccacagca      8940
gcccactcga ccttctagcc gacccagacg agccaaggga tctttttgga atgctgctcc     9000
gtcgtcaggc tttccgacgt ttgggtggtt gaacagaagt cattatcgta cggaatgcca    9060
agcactcccg aggggaaccc tgtggttggc atgcacatac aaatggacga acggataaac    9120
cttttcacgc ccttttaaat atccgttatt ctaataaacg ctctttttctc ttaggtttac    9180 ccgccaatat atcctgtcaa acactgatag tttaaactga aggcgggaaa cgacaatctg    9240
atcatgagcg gagaattaag ggagtcacgt tatgaccccc gccgatgacg cgggacaagc    9300
cgttttacgt ttgaactga cagaaccgca acgttgaagg agccactcag caagctggta     9360
cgattgtaat acgactcact atagggcgaa ttgagcgctg tttaaacgct cttcaactgg    9420
aagagcggtt accagagctg gtcacctttg tccaccaaga tggaactgcg gccgctcatt    9480
aattaagtca ggcgcgcctc tagttgaaga cacgttcatg tcttcatcgt aagaagacac    9540
tcagtagtct tcggccagaa tggcccggac cgaagctggc cgctctagaa ctagtggatc    9600
tcgatgtgta gtctacgaga agggttaacc gtctcttcgt gagaataacc gtggcctaaa    9660
aataagccga tgaggataaa taaaatgtgg tggtacagta cttcaagagg tttactcatc    9720
aagaggatgc ttttccgatg agctctagta gtacatcgga cctcacatac ctccattgtg    9780
gtgaaatatt ttgtgctcat ttagtgatgg gtaaattttg tttatgtcac tctaggtttt    9840
gacatttcag ttttgccact cttaggtttt gacaaataat ttccattccg cggcaaaagc    9900
aaaacaattt tattttactt ttaccactct tagctttcac aatgtatcac aaatgccact    9960
ctagaaattc tgtttatgcc acagaatgtg aaaaaaaaca ctcacttatt tgaagccaag   10020
gtgttcatgg catggaaatg tgacataaag taacgttcgt gtataagaaa aaattgtact   10080
cctcgtaaca agagacggaa acatcatgag acaatcgcgt ttggaaggct ttgcatcacc   10140 tttgatgat gcgcatgaat ggagtcgtct gcttgctagc cttcgcctac cgcccactga    10200
gtccgggcgg caactaccat cggcgaacga cccagctgac ctctaccgac cggacttgaa   10260
tgcgctacct tcgtcagcga cgatggccgc gtacgctggc gacgtgcccc gcatgcatg    10320 gcggcacatg gcgagctcag accgtgcgtg gctggctaca aatacgtacc ccgtgagtgc   10380
cctagctaga aacttacacc tgcaactgcg agagcgagcg tgtgagtgta gccgagtaga   10440
tcccccggtc gccaccatgg cctcctccga gaacgtcatc accgagttca tgcgcttcaa   10500
ggtgcgcatg gagggcaccg tgaacggcca cgagttcgag atcgagggcg agggcgaggg   10560
ccgcccctac gagggccaca acaccgtgaa gctgaaggtg accaagggcg gccccctgcc   10620
cttcgcctgg gacatcctgt cccccccagtt ccagtacggc tccaaggtgt acgtgaagca   10680
ccccgccgac atccccgact acaagaagct gtccttcccc gagggcttca agtgggagcg   10740
```

```
cgtgatgaac ttcgaggacg gcggcgtggc gaccgtgacc caggactcct ccctgcagga    10800
cggctgcttc atctacaagg tgaagttcat cggcgtgaac ttcccctccg acggcccgt    10860 gatgcagaag aagaccatgg gctgggaggc ctccaccgag cgcctgtacc cccgcgacgg    10920
cgtgctgaag ggcgagaccc acaaggccct gaagctgaag gacggcggcc actacctggt    10980
ggagttcaag tccatctaca tggccaagaa gcccgtgcag ctgcccggct actactacgt    11040
ggacgccaag ctggacatca cctcccacaa cgaggactac accatcgtgg agcagtacga    11100
gcgcaccgag ggccgccacc acctgttcct gtagcggccc atggatattc gaacgcgtag    11160
gtaccacatg gttaacctag acttgtccat cttctggatt ggccaactta attaatgtat    11220
gaaataaaag gatgcacaca tagtgacatg ctaatcacta taatgtgggc atcaaagttg    11280
tgtgttatgt gtaattacta gttatctgaa taaaagagaa agatcatc catatttctt    11340 atcctaaatg aatgtcacgt gtctttataa ttctttgatg aaccagatgc atttcattaa    11400
ccaaatccat atacatataa atattaatca tatataatta atatcaattg ggttagcaaa    11460
acaaatctag tctaggtgtg ttttgcgaat gcggccgcca ccgcggtgga gctcgaattc    11520
cggtccgggc ctagaaggcc atttaaatcc tgaggatctg gtcttcctaa ggacccggga    11580
tatcgctatc aactttgtat agaaaagttg gccgaattc gagctcggta cggccagaat    11640
ggcccggacc gggttaccga attcgagctc ggtaccctgg gatccgcaag ggacgaccgt    11700
ggtccttgtt tgatttactt ccaggattat ataatccagc ttatggatta tataagtacc    11760
tattgacgtc acgtgcttat gtattataat aatctaggta tatagattat ataatctatc    11820
taataataat ctgtgttgtt tgtttatctc tcaaaacaaa caggtcctaa aatggtcccg    11880
ggcgtccaat gtgtcgtcaa gtagtgttaa gctaaatcga catttctttg tgggttgtgt    11940
ggaaggtgtt ccttttcctt aagttgttag ttgtgcaagg tgttccttag agcatctcca    12000
ataggaccta taatggattc tatttgaat tataagactc taacaacaaa agcatacttt    12060 aatgggatt ctattttaca aaaaatatc aaatgattat atggtcgatt cctcgggtcc    12120
taaatatagt atctcatata atagagctct atcctcattt tatatactat tttttaagttt    12180 ttatttacta aataacatga tttatttct aatactatga actcaactat tagagctgta    12240 aacgttttg tggtactaaa cacttttaaat caggtcctat tttaatttga aggacttaaa    12300
tataagactt ctggttagag atgctcttag cgagtgtttg tgcatgattg ctatttagtc    12360
tttgtggatt gtggaaggtg ttacttttcc tcaagttgtt agttgtgcaa ggtgtttctt    12420
agagcatctc taacaggagc cttaacggaa tctattttga agtatagtac tttaacacca    12480
aaaacatact ttaataggg tcctatttta caaaaaaatt atcaaatgat tataaggtcc    12540
actcctcggg tcctaaatat aatatctcat atactagagc tctatcctca ttttatatac    12600
tatccctagg tttttattcc ctaaataaca tgatttattt cctaatacta agatataggg    12660
ctcaactatt ggagttgcaa atgttttttg gcactaaaca cttatatca ggtcctattt    12720 taattttaat ttgaaggact caaatatagg acttctcgtt agagatgctc ttagcgagtg    12780
tttgtgcatg attgctattt atgtctgtag tttagttggg ggctttaata tgttttagttg    12840 aagttctagt attttttagg ttctccactc tttggattat gacaacgacc actatccaag    12900
cagtctttga gtgcaaacgc gcgagcaaac tatctgatct attaaattat gatccaaccg    12960
ttatgtcata ttgaagactt aaacccttc accaccagcc caagtatctt tatgaaaaac    13020
cctaacaaac cacaattgca tctatggttg gattataatt taacgtatca gatggttcgc    13080
ttgcatgctt acatatctag aaactgtttg cataacagtc gttctctttg gttatataat    13140
```

```
gctttagtaa tcatcagcca agtgtaaaca aatggtacaa actagtagtg aacacatcct    13200
ccctacctat ctctaggggt gtaactagat atccgaattc ttagaacaaa tttcatattt    13260
taaaatagat atgcttcaaa atttatgcta atctttttta tattatcaag catattatta    13320
cacataagaa taaaattttg tatagaattt tatccattat ttgttcccta gaatttaaaa    13380
agtgaaaaaa cattcgaatc tgtatcagtt tcgtattcaa attttacat ctattatttg     13440 agaatatata tgataaattt gaggtttagt ttttatgaat ctttacaagg ttaatgttaa    13500
atacatgact atggatttac atagtaaatt ctatgtctta tttgtccgcg attgaagaaa    13560
aatgacaaaa agatctgaca ttcgaataaa catctgtttc cactcctacc tatctgacct    13620
cctatttcaa actccacttt gtaacacggt acaaaatcac tccctaccta tctgacctcc    13680
tatttcaaac tccactcagt aaacaatatt gtctatggta caaaaccaag tgttttatac    13740
atctatttgc acgatctgct cgagtcaggc atccttgaca cacaacatac tccttgtggc    13800
tataaatgtc caaatagagc agacctaatg ggtggaccgt tgcatgacac gacttatccc    13860
aagacgagca cagttcgccc cattggtcat gggggtccgg gctagtctag cctgatcatc    13920
gggtcacact taggccacag gtgtgccaca acgggatagc ccaacatgtc ccttttgtc     13980 atgcatatat ctatattata gttagtataa tgtaaaaaaa caaaaggtat gtgtgttatg    14040
ttggttagat gtgtttaaat aactctttaa agctagcaac tatggtttaa atcatacata    14100
tacacatttt tattttattt ttatttaaac gatatgggcc ttctaggcac gtcgagtgtg    14160
acgggccagt gagatgacac attataatta ctggtctagc aggccgtacc taggtctttc    14220
tcgtgggcca agactaaggg ttggcccgtt ggctaatctg tacggtaccg atactgtcct    14280
aattcatttg aacacctgta gaagagggga atttataatt gaggaggaat gtactcatgc    14340
ggtacaccag gggaattgtt ttgttgtgct cagcgataga tttcaacgca acggtgagcc    14400
agtttcacta aaaaaagggg ggggggggg ggggggggaa ggccacatca aaggcgaggt     14460
gctgacgagc agaagatgct agcagtgacg ccaagtccag cagctagcaa tgaaagggta    14520
ctcgggattt aacaatgcct agagacggca tcatcccctc aataatccgg tgctctcttt    14580
ttgtttattc accagttggc gtagctatat acacatgtct ggtctgacga acaaatcaag    14640
ggatcgctag ctcgggctag ccttcctatc actgtcatga catgtgctct gcctctgctg    14700
gttgataagc cgtgcgcctt ctcgctaatt cttctgtg ctagaggcga gtcaaacaaa      14760
cgctgcacct cgtagccctt aatctgcgct aagggtcaca tgaccctgtt ccctatcgct    14820
agttaccaac gacccattcc ccctgacaga tacttacgac gcgtccgtac gcggcaggcc    14880
tcggcagttc ggcatcacca gcaccggcgc cggcattcgc cccctgccag ccggttcgca    14940
gattcgcagg gcggagtcgg ccgcagttgc cgcatcccaa acgcccggga accttgggg     15000 cccctctacg agcaaatgaa gttgctgccc ctggcttcgt aaagctctga cttttgatca    15060
cttgattggc agtcgtactc ctcgctcata ggccgacacg gccgcaaagt caactacccg    15120
ctccgccatc cttcaacccc cgccacgcgc ctatatatgt tcgcggccat gtccgtacta    15180
gtcctccaac ccacaagcca caaccccgag ctcagatccc tcgcctcgtg tcgtgtctcc    15240
ggtcgacgac gaccaacagc cagtgtgggc cagacggaca ccgccgagct atagcgcttg    15300
gtgataaagc ttggtcaccc ggtccgggcc tagaaggcca gcttcaagtt tgtacaaaaa    15360
agcaggctcc agcgctcacc atggtccgtc ctgtagaaac cccaacccgt gaaatcaaaa    15420
aactcgacgg cctgtgggca ttcagtctgg atcgcgaaaa ctgtggaatt gatcagcgtt    15480
ggtgggaaag cgcgttacaa gaaagccggg caattgctgt gccaggcagt tttaacgatc    15540
```

```
agttcgccga tgcagatatt cgtaattatg cgggcaacgt ctggtatcag cgcgaagtct   15600
ttataccgaa aggttgggca ggccagcgta tcgtgctgcg tttcgatgcg gtcactcatt   15660
acggcaaagt gtgggtcaat aatcaggaag tgatggagca tcagggcggc tatacgccat   15720
ttgaagccga tgtcacgccg tatgttattg ccgggaaaag tgtacgtaag tttctgcttc   15780
tacctttgat atatatataa taattatcat taattagtag taatataata tttcaaatat   15840
ttttttcaaa ataaaagaat gtagtatata gcaattgctt ttctgtagtt tataagtgtg   15900
tatattttaa tttataactt ttctaatata tgaccaaaat ttgttgatgt gcaggtatca   15960
ccgtttgtgt gaacaacgaa ctgaactggc agactatccc gccgggaatg gtgattaccg   16020
acgaaaacgg caagaaaaag cagtcttact tccatgattt ctttaactat gccggaatcc   16080
atcgcagcgt aatgctctac accacgccga cacctgggt ggacgatatc accgtggtga   16140
cgcatgtcgc gcaagactgt aaccacgcgt ctgttgactg gcaggtggtg gccaatggtg   16200
atgtcagcgt tgaactgcgt gatgcggatc aacaggtggt tgcaactgga caaggcacta   16260
gcgggacttt gcaagtggtg aatccgcacc tctggcaacc gggtgaaggt tatctctatg   16320
aactgtgcgt cacagccaaa agccagacag agtgtgatat ctacccgctt cgcgtcggca   16380
tccggtcagt ggcagtgaag ggcgaacagt tcctgattaa ccacaaaccg ttctacttta   16440
ctggctttgg tcgtcatgaa gatgcggact tgcgtggcaa aggattcgat aacgtgctga   16500
tggtgcacga ccacgcatta atggactgga ttggggccaa ctcctaccgt acctcgcatt   16560
acccttacgc tgaagagatg ctcgactggg cagatgaaca tggcatcgtg gtgattgatg   16620
aaactgctgc tgtcggcttt aacctctctt taggcattgg tttcgaagcg ggcaacaagc   16680
cgaaagaact gtacagcgaa gaggcagtca acggggaaac tcagcaagcg cacttacagg   16740
cgattaaaga gctgatagcg cgtgacaaaa accacccaag cgtggtgatg tggagtattg   16800
ccaacgaacc ggatacccgt ccgcaaggtg cacgggaata tttcgcgcca ctggcggaag   16860
caacgcgtaa actcgacccg acgcgtccga tcacctgcgt caatgtaatg ttctgcgacg   16920
ctcacaccga taccatcagc gatctctttg atgtgctgtg cctgaaccgt tattacggat   16980
ggtatgtcca aagcggcgat ttggaaacgg cagagaaggt actggaaaaa gaacttctgg   17040
cctggcagga gaaactgcat cagccgatta tcatcaccga atacggcgtg gatacgttag   17100
ccgggctgca ctcaatgtac accgacatgt ggagtgaaga gtatcagtgt gcatggctgg   17160
atatgtatca ccgcgtcttt gatcgcgtca gcgccgtcgt cggtgaacag gtatggaatt   17220
tcgccgattt tgcgacctcg caaggcatat tgcgcgttgg cggtaacaag aaagggatct   17280
tcactcgcga ccgcaaaccg aagtcggcgg cttttctgct gcaaaaacgc tggactggca   17340
tgaacttcgg tgaaaaaccg cagcaggag gcaaacaatg aagatctccc gggcacccag   17400
ctttcttgta caaagtggcc gttaacggat ccagacttgt ccatcttctg gattggccaa   17460
cttaattaat gtatgaaata aaaggatgca cacatagtga catgctaatc actataatgt   17520
gggcatcaaa gttgtgtgtt atgtgtaatt actagttatc tgaataaaag agaagagat   17580
catccatatt tcttatccta aatgaatgtc acgtgtcttt ataattcttt gatgaaccag   17640
atgcatttca ttaaccaaat ccatatacat ataaatatta atcatatata attaatatca   17700
attgggttag caaaacaaat ctagtctagg tgtgttttgc gaattgcggc aagcttgcgg   17760
ccgccccggg caacttt                                                  17777
```

<210> SEQ ID NO 88
<211> LENGTH: 54686
<212> TYPE: DNA

<213> ORGANISM: Artificial Seqeunce
<220> FEATURE:
<223> OTHER INFORMATION: Vector

<400> SEQUENCE: 88

```
tctagagctc gttcctcgag gcctcgaggc ctcgaggaac ggtacctgcg gggaagctta      60
caataatgtg tgttgttaag tcttgttgcc tgtcatcgtc tgactgactt tcgtcataaa     120
tcccggcctc cgtaacccag ctttgggcaa gctcacggat ttgatccggc ggaacgggaa     180
tatcgagatg ccgggctgaa cgctgcagtt ccagctttcc ctttcgggac aggtactcca     240
gctgattgat tatctgctga agggtcttgg ttccacctcc tggcacaatg cgaatgatta     300
cttgagcgcg atcgggcatc caattttctc ccgtcaggtg cgtggtcaag tgctacaagg     360
cacctttcag taacgagcga ccgtcgatcc gtcgccggga tacggacaaa atggagcgca     420
gtagtccatc gagggcggcg aaagcctcgc caaaagcaat acgttcatct cgcacagcct     480
ccagatccga tcgagggtct tcggcgtagg cagatagaag catggataca ttgcttgaga     540
gtattccgat ggactgaagt atggcttcca tcttttctcg tgtgtctgca tctatttcga     600
gaaagccccc gatgcggcgc accgcaacgc gaattgccat actatccgaa agtcccagca     660
ggcgcgcttg ataggaaaag gtttcatact cggccgatcg cagacgggca ctcacgacct     720
tgaacccttc aactttcagg gatcgatgct ggttgatggt agtctcactc gacgtggctc     780
tggtgtgttt tgacatagct tcctccaaag aaagcggaag gtctggatac tccagcacga     840
aatgtgcccg ggtagacgga tggaagtcta gccctgctca atatgaaatc aacagtacat     900
ttacagtcaa tactgaatat acttgctaca tttgcaattg tcttataacg aatgtgaaat     960
aaaaatagtg taacaacgct tttactcatc gataatcaca aaaacattta tacgaacaaa    1020
aatacaaatg cactccggtt tcacaggata ggcgggatca gaatatgcaa cttttgacgt    1080
tttgttcttt caaagggggt gctggcaaaa ccaccgcact catgggcctt tgcgctgctt    1140
tggcaaatga cggtaaacga gtggccctct ttgatgccga cgaaaaccgg cctctgacgc    1200
gatggagaga aaacgcctta caaagcagta ctgggatcct cgctgtgaag tctattccgc    1260
cgacgaaatg ccccttcttg aagcagccta tgaaaatgcc gagctcgaag gatttgatta    1320
tgcgttggcc gatacgcgtg gcggctcgag cgagctcaac aacacaatca tcgctagctc    1380
aaacctgctt ctgatcccca ccatgctaac gccgctcgac atcgatgagg cactatctac    1440
ctaccgctac gtcatcgagc tgctgttgag tgaaaatttg gcaattccta cagctgtttt    1500
gcgccaacgc gtcccggtcg gccgattgac aacatcgcaa cgcaggatgt cagagacgct    1560
agagagcctt ccagttgtac cgtctcccat gcatgaaaga gatgcatttg ccgcgatgaa    1620
agaacgcggc atgttgcatc ttacattact aaacacggga actgatccga cgatgcgcct    1680
catagagagg aatcttcgga ttgcgatgga ggaagtcgtg gtcatttcga aactgatcag    1740
caaaatcttg gaggcttgaa gatggcaatt cgcaagcccg cattgtcggt cggcgaagca    1800
cggcggcttg ctggtgctcg acccgagatc caccatccca acccgacact tgttccccag    1860
aagctggacc tccagcactt gcctgaaaaa gccgacgaga agaccagca acgtgagcct    1920
ctcgtcgccg atcacattta cagtcccgat cgacaactta agctaactgt ggatgccctt    1980
agtccacctc cgtccccgaa aaagctccag gttttctttt cagcgcgacc gcccgcgcct    2040
caagtgtcga aaacatatga caacctcgtt cggcaataca gtccctcgaa gtcgctacaa    2100
atgattttaa ggcgcgcgtt ggacgatttc gaaagcatgc tggcagatgg atcatttcgc    2160
gtggccccga aaagttatcc gatcccttca actacagaaa aatccgttct cgttcagacc    2220
```

```
tcacgcatgt tcccggttgc gttgctcgag gtcgctcgaa gtcatttga tccgttgggg    2280 ttggagaccg ctcgagcttt cggccacaag ctggctaccg ccgcgctcgc gtcattcttt    2340
gctggagaga agccatcgag caattggtga agagggacct atcggaaccc ctcaccaaat    2400
attgagtgta ggtttgaggc cgctggccgc gtcctcagtc accttttgag ccagataatt    2460
aagagccaaa tgcaattggc tcaggctgcc atcgtccccc cgtgcgaaac ctgcacgtcc    2520
gcgtcaaaga ataaccggc acctcttgct gttttatca gttgagggct tgacggatcc     2580
gcctcaagtt tgcggcgcag ccgcaaaatg agaacatcta tactcctgtc gtaaacctcc    2640
tcgtcgcgta ctcgactggc aatgagaagt tgctcgcgcg atagaacgtc gcggggtttc    2700
tctaaaaacg cgaggagaag attgaactca cctgccgtaa gtttcacctc accgccagct    2760
tcggacatca agcgacgttg cctgagatta agtgtccagt cagtaaaaca aaaagaccgt    2820
cggtctttgg agcggacaac gttggggcgc acgcgcaagg caacccgaat gcgtgcaaga    2880
aactctctcg tactaaacgg cttagcgata aaatcacttg ctcctagctc gagtgcaaca    2940
actttatccg tctcctcaag gcggtcgcca ctgataatta tgattggaat atcagacttt    3000
gccgccagat ttcgaacgat ctcaagccca tcttcacgac ctaaatttag atcaacaacc    3060
acgacatcga ccgtcgcgga agagagtact ctagtgaact gggtgctgtc ggctaccgcg    3120
gtcactttga aggcgtggat cgtaaggtat tcgataataa gatgccgcat agcgacatcg    3180
tcatcgataa gaagaacgtg tttcaacggc tcaccttca atctaaaatc tgaacccttg     3240 ttcacacgc ttgagaaatt ttcacgtgaa ggatgtacaa tcatctccag ctaaatgggc     3300
agttcgtcag aattgcggct gaccgcggat gacgaaaatg cgaaccaagt atttcaattt    3360
tatgacaaaa gttctcaatc gttgttacaa gtgaaacgct tcgaggttac agctactatt    3420
gattaaggag atcgcctatg gtctcgcccc ggcgtcgtgc gtccgccgcg agccagatct    3480
cgcctacttc ataaacgtcc tcataggcac ggaatggaat gatgacatcg atcgccgtag    3540
agagcatgtc aatcagtgtg cgatcttcca agctagcacc ttgggcgcta cttttgacaa    3600
gggaaaacag tttcttgaat ccttggattg gattcgcgcc gtgtattgtt gaaatcgatc    3660
ccggatgtcc cgagacgact tcactcagat aagcccatgc tgcatcgtcg cgcatctcgc    3720
caagcaatat ccggtccggc cgcatacgca gacttgcttg gagcaagtgc tcggcgctca    3780
cagcacccag cccagcaccg ttcttggagt agagtagtct aacatgatta tcgtgtggaa    3840
tgacgagttc gagcgtatct tctatggtga ttagcctttc ctgggggggg atggcgctga    3900
tcaaggtctt gctcattgtt gtcttgccgc ttccggtagg gccacatagc aacatcgtca    3960
gtcggctgac gacgcatgcg tgcagaaacg cttccaaatc cccgttgtca aaatgctgaa    4020
ggatagcttc atcatcctga ttttggcgtt tccttcgtgt ctgccactgg ttccacctcg    4080
aagcatcata acgggaggag acttctttaa gaccagaaac acgcgagctt ggccgtcgaa    4140
tggtcaagct gacggtgccc gagggaacgg tcggcggcag acagatttgt agtcgttcac    4200
caccaggaag ttcagtggcg cagaggggt tacgtggtcc gacatcctgc tttctcagcg     4260
cgcccgctaa aatagcgata tcttcaagat catcataaga gacgggcaaa ggcatcttgg    4320
taaaaatgcc ggcttggcgc acaaatgcct ctccaggtcg attgatcgca atttcttcag    4380
tcttcgggtc atcgagccat tccaaaatcg gcttcagaag aaagcgtagt tgcggatcca    4440 cttccatttta caatgtatcc tatctctaag cggaaatttg aattcattaa gagcggcggt    4500
tcctcccccg cgtggcgccg ccagtcaggc ggagctggta acaccaaag aaatcgaggt     4560 cccgtgctac gaaaatggaa acggtgtcac cctgattctt cttcagggtt ggcggtatgt    4620
```

```
tgatggttgc cttaagggct gtctcagttg tctgctcacc gttattttga aagctgttga    4680
agctcatccc gccaccccgag ctgccggcgt aggtgctagc tgcctggaag gcgccttgaa   4740
caacactcaa gagcatagct ccgctaaaac gctgccagaa gtggctgtcg accgagcccg   4800
gcaatcctga gcgaccgagt tcgtccgcgc ttggcgatgt taacgagatc atcgcatggt   4860
caggtgtctc ggcgcgatcc cacaacacaa aaacgcgccc atctccctgt tgcaagccac   4920
gctgtatttc gccaacaacg gtggtgccac gatcaagaag cacgatattg ttcgttgttc   4980
cacgaatatc ctgaggcaag acacacttta catagcctgc caaatttgtg tcgattgcgg   5040
tttgcaagat gcacggaatt attgtccctt gcgttaccat aaaatcgggg tgcggcaaga   5100
gcgtggcgct gctgggctgc agctcggtgg gtttcatacg tatcgacaaa tcgttctcgc   5160
cggacacttc gccattcggc aaggagttgt cgtcacgctt gccttcttgt cttcggcccg   5220
tgtcgccctg aatggcgcgt tgctgaccc cttgatcgcc gctgctatat gcaaaaatcg   5280
gtgtttcttc cggccgtggc tcatgccgct ccggttcgcc cctcggcggt agaggagcag   5340
caggctgaac agcctcttga accgctggag gatccggcgg cacctcaatc ggagctggat   5400
gaaatggctt ggtgttttgtt gcgatcaaag ttgacggcga tgcgttctca ttcaccttct   5460
tttgcgcccc acctagccaa atgaggctta atgataacgc gagaacgaca cctccgacga   5520
tcaatttctg agaccccgaa agacgccggc gatgtttgtc ggagaccagg gatccagatg   5580
catcaacctc atgtgccgct tgctgactat cgttattcat cccttcgccc ccttcaggac   5640
gcgtttcaca tcgggcctca ccgtgccgt ttgcggcctt tggccaacgg gatcgtaagc   5700
ggtgttccag atacatagta ctgtgtggcc atccctcaga cgccaacctc gggaaaccga   5760
agaaatctcg acatcgctcc ctttaactga atagttggca acagcttcct tgccatcagg   5820
attgatggtg tagatggagg gtatgcgtac attgcccgga aagtggaata ccgtcgtaaa   5880
tccattgtcg aagacttcga gtggcaacag cgaacgatcg ccttgggcga cgtagtgcca   5940
attactgtcc gccgcaccaa gggctgtgac aggctgatcc aataaattct cagctttccg   6000
ttgatattgt gcttccgcgt gtagtctgtc cacaacagcc ttctgttgtg cctcccttcg   6060
ccgagccgcc gcatcgtcgg cggggtaggc gaattggacg ctgtaataga gatcgggctg   6120
ctctttatcg aggtgggaca gagtcttgga acttatactg aaaacataac ggcgcatccc   6180
ggagtcgctt gcggttagca cgattactgg ctgaggcgtg aggacctggc ttgccttgaa   6240
aaatagataa tttccccgcg gtagggctgc tagatctttg ctatttgaaa cggcaaccgc   6300
tgtcaccgtt tcgttcgtgg cgaatgttac gaccaaagta gctccaaccg ccgtcgagag   6360
gcgcaccact tgatcgggat tgtaagccaa ataacgcatg cgcggatcta gcttgcccgc   6420
cattggagtc tcttcagcct ccgcaccagt cgcagcggca aataaacatg ctaaaatgaa   6480
aagtgctttt ctgatcatgg ttcgctgtgg cctacgtttg aaacggtatc ttccgatgtc   6540
tgataggagg tgacaaccag acctgccggg ttggttagtc tcaatctgcc gggcaagctg   6600
gtcaccttttt cgtagcgaac tgtcgcggtc cacgtactca ccacaggcat tttgccgtca   6660
acgacgaggg tcctttata gcgaatttgc tgcgtgcttg gagttacatc atttgaagcg   6720
atgtgctcga cctccaccct gccgcgtttg ccaagaatga cttgaggcga actgggattg   6780
ggatagttga agaattgctg gtaatcctgg cgcactgttg gggcactgaa gttcgatacc   6840
aggtcgtagg cgtactgagc ggtgtcggca tcataactct cgcgcaggcg aacgtactcc   6900
cacaatgagg cgttaacgac ggcctcctct tgagttgcag gcaatcgcga gacagacacc   6960
tcgctgtcaa cggtgccgtc cggccgtatc catagatata cgggcacaag cctgctcaac   7020
```

```
ggcaccattg tggctatagc gaacgcttga gcaacatttc ccaaaatcgc gatagctgcg    7080
acagctgcaa tgagtttgga gagacgtcgc gccgatttcg ctcgcgcggt ttgaaaggct    7140
tctacttcct tatagtgctc ggcaaggctt tcgcgcgcca ctagcatggc atattcaggc    7200
cccgtcatag cgtccacccg aattgccgag ctgaagatct gacggagtag gctgccatcg    7260
ccccacattc agcgggaaga tcgggccttt gcagctcgct aatgtgtcgt ttgtctggca    7320
gccgctcaaa gcgacaacta ggcacagcag gcaatacttc atagaattct ccattgaggc    7380 gaattttgc gcgacctagc ctcgctcaac ctgagcgaag cgacggtaca agctgctggc    7440
agattgggtt gcgccgctcc agtaactgcc tccaatgttg ccggcgatcg ccggcaaagc    7500
gacaatgagc gcatcccctg tcagaaaaaa catatcgagt tcgtaaagac caatgatctt    7560
ggccgcggtc gtaccggcga aggtgattac accaagcata agggtgagcg cagtcgcttc    7620
ggttaggatg acgatcgttg ccacgaggtt taagaggaga agcaagagac cgtaggtgat    7680
aagttgcccg atccacttag ctgcgatgtc ccgcgtgcga tcaaaaatat atccgacgag    7740
gatcagaggc ccgatcgcga aagcactttt cgtgagaatt ccaacggcgt cgtaaactcc    7800
gaaggcagac cagagcgtgc cgtaaaggac ccactgtgcc ccttggaaag caaggatgtc    7860
ctggtcgttc atcggaccga tttcggatgc gattttctga aaaacggcct gggtcacggc    7920
gaacattgta tccaactgtg ccggaacagt ctgcagaggc aagccggtta cactaaactg    7980
ctgaacaaag tttgggaccg tcttttcgaa gatggaaacc acatagtctt ggtagttagc    8040
ctgcccaaca attagagcaa caacgatggt gaccgtgatc acccgagtga taccgctacg    8100
ggtatcgact tcgccgcgta tgactaaaat accctgaaca ataatccaaa gagtgacaca    8160
ggcgatcaat ggcgcactca ccgcctcctg gatagtctca agcatcgagt ccaagcctgt    8220
cgtgaaggct acatcgaaga tcgtatgaat ggccgtaaac ggcgccggaa tcgtgaaatt    8280
catcgattgg acctgaactt gactggtttg tcgcataatg ttggataaaa tgagctcgca    8340
ttcggcgagg atgcgggcgg atgaacaaat cgcccagcct taggggaggg caccaaagat    8400
gacagcggtc ttttgatgct ccttgcgttg agcggccgcc tcttccgcct cgtgaaggcc    8460
ggcctgcgcg gtagtcatcg ttaataggct tgtcgcctgt acattttgaa tcattgcgtc    8520
atggatctgc ttgagaagca aaccattggt cacggttgcc tgcatgatat tgcgagatcg    8580
ggaaagctga gcagacgtat cagcattcgc cgtcaagcgt ttgtccatcg tttccagatt    8640
gtcagccgca atgccagcgc tgtttgcgga accggtgatc tgcgatcgca acaggtccgc    8700
ttcagcatca ctacccacga ctgcacgatc tgtatcgctg gtgatcgcac gtgccgtggc    8760
cgacattggc attcgcggcg aaaacatttc attgtctagg tccttcgtcg aaggatactg    8820 attttctgg ttgagcgaag tcagtagtcc agtaacgccg taggccgacg tcaacatcgt    8880
aaccatcgct atagtctgag tgagattctc cgcagtcgcg agcgcagtcg cgagcgtctc    8940
agcctccgtt gccgggtcgc taacaacaaa ctgcgcccgc gcgggctgaa tatatagaaa    9000
gctgcaggtc aaaactgttg caataagttg cgtcgtcttc atcgtttcct accttatcaa    9060
tcttctgcct cgtggtgacg ggccatgaat tcgctgagcc agccagatga gttgccttct    9120
tgtgcctcgc gtagtcgagt tgcaaagcgc accgtgttgg cacgccccga aagcacggcg    9180
acatattcac gcatatcccg cagatcaaat tcgcagatga cgcttccact ttctcgttta    9240
agaagaaact tacggctgcc gaccgtcatg tcttcacgga tcgcctgaaa ttcctttttcg    9300 gtacatttca gtccatcgac ataagccgat cgatctgcgg ttggtgatgg atagaaaatc    9360
ttcgtcatac attgcgcaac caagctggct cctagcggcg attccagaac atgctctggt    9420
```

```
tgctgcgttg ccagtattag catcccgttg ttttttcgaa cggtcaggag gaatttgtcg   9480
acgacagtcg aaaatttagg gtttaacaaa taggcgcgaa actcatcgca gctcatcaca   9540
aaacggcggc cgtcgatcat ggctccaatc cgatgcagga gatatgctgc agcgggagcg   9600
catacttcct cgtattcgag aagatgcgtc atgtcgaagc cggtaatcga cggatctaac   9660
tttacttcgt caacttcgcc gtcaaatgcc cagccaagcg catggccccg gcaccagcgt   9720
tggagccgcg ctcctgcgcc ttcggcgggc ccatgcaaca aaaattcacg taaccccgcg   9780
attgaacgca tttgtggatc aaacgagagc tgacgatgga taccacggac cagacggcgg   9840
ttctcttccg gagaaatccc accccgacca tcactctcga tgagagccac gatccattcg   9900
cgcagaaaat cgtgtgaggc tgctgtgttt tctaggccac gcaacggcgc caacccgctg   9960
ggtgtgcctc tgtgaagtgc caaatatgtt cctcctgtgg cgcgaaccag caattcgcca  10020
ccccggtcct tgtcaaagaa cacgaccgta cctgcacggt cgaccatgct ctgttcgagc  10080
atggctagaa caaacatcat gagcgtcgtc ttacccctcc cgataggccc gaatattgcc  10140
gtcatgccaa catcgtgctc atgcgggata tagtcgaaag gcgttccgcc attggtacga  10200
aatcgggcaa tcgcgttgcc ccagtggcct gagctggcgc cctctggaaa gttttcgaaa  10260
gagacaaacc ctgcgaaatt gcgtgaagtg attgcgccag ggcgtgtgcg ccacttaaaa  10320
ttccccggca attgggacca ataggccgct tccataccaa taccttcttg gacaaccacg  10380
gcacctgcat ccgccattcg tgtccgagcc cgcgcgcccc tgtccccaag actattgaga  10440
tcgtctgcat agacgcaaag gctcaaatga tgtgagccca taacgaattc gttgctcgca  10500
agtgcgtcct cagcctcgga taatttgccg atttgagtca cggctttatc gccggaactc  10560
agcatctggc tcgatttgag gctaagtttc gcgtgcgctt gcgggcgagt caggaacgaa  10620
aaactctgcg tgagaacaag tggaaaatcg agggatagca gcgcgttgag catgcccggc  10680 cgtgttttg cagggtattc gcgaaacgaa tagatggatc caacgtaact gtcttttggc  10740
gttctgatct cgagtcctcg cttgccgcaa atgactctgt cggtataaat cgaagcgccg  10800
agtgagccgc tgacgaccgg aaccggtgtg aaccgaccag tcatgatcaa ccgtagcgct  10860
tcgccaattt cggtgaagag cacaccctgc ttctcgcgga tgccaagacg atgcaggcca  10920
tacgctttaa gagagccagc gacaacatgc caaagatctt ccatgttcct gatctggccc  10980
gtgagatcgt tttccctttt tccgcttagc ttggtgaacc tcctctttac cttccctaaa  11040
gccgcctgtg ggtagacaat caacgtaagg aagtgttcat tgcggaggag ttggccggag  11100
agcacgcgct gttcaaaagc ttcgttcagg ctagcggcga aaacactacg gaagtgtcgc  11160
ggcgccgatg atggcacgtc ggcatgacgt acgaggtgag catatattga cacatgatca  11220
tcagcgatat tgcgcaacag cgtgttgaac gcacgacaac gcgcattgcg catttcagtt  11280
tcctcaagct cgaatgcaac gccatcaatt ctcgcaatgg tcatgatcga ccgtcttca   11340 agaaggacga tatggtcgct gaggtggcca atataaggga gatagatctc accggatctt  11400
tcggtcgttc cactcgcgcc gagcatcaca ccattcctct ccctcgtggg ggaaccctaa  11460
ttggatttgg gctaacagta gcgcccccccc aaactgcact atcaatgctt cttcccgcgg  11520
tccgcaaaaa tagcaggacg acgctcgccg cattgtagtc tcgctccacg atgagccggg  11580
ctgcaaacca taacggcacg agaacgactt cgtagagcgg gttctgaacg ataacgatga  11640
caaagccggc gaacatcatg aataaccctg ccaatgtcag tggcacccca agaaacaatg  11700
cgggccgtgt ggctgcgagg taagggtcg attcttccaa acgatcagcc atcaactacc   11760
gccagtgagc gtttggccga ggaagctcgc cccaaacatg ataacaatgc cgccgacgac  11820
```

```
gccggcaacc agcccaagcg aagcccgccc gaacatccag gagatcccga tagcgacaat   11880
gccgagaaca gcgagtgact ggccgaacgg accaaggata aacgtgcata tattgttaac   11940
cattgtggcg gggtcagtgc cgccacccgc agattgcgct gcggcgggtc cggatgagga   12000
aatgctccat gcaattgcac cgcacaagct tggggcgcag ctcgatatca cgcgcatcat   12060
cgcattcgag agcgagaggc gatttagatg taaacggtat ctctcaaagc atcgcatcaa   12120
tgcgcacctc cttagtataa gtcgaataag acttgattgt cgtctgcgga tttgccgttg   12180
tcctggtgtg gcggtggcgg agcgattaaa ccgccagcgc catcctcctg cgagcggcgc   12240
tgatatgacc cccaaacatc ccacgtctct tcggatttta gcgcctcgtg atcgtctttt   12300
ggaggctcga ttaacgcggg caccagcgat tgagcagctg tttcaacttt tcgcacgtag   12360
ccgtttgcaa aaccgccgat gaaattaccg gtgttgtaag cggagatcgc ccgacgaagc   12420
gcaaattgct tctcgtcaat cgtttcgccg cctgcataac gacttttcag catgtttgca   12480
gcggcagata atgatgtgca cgcctggagc gcaccgtcag gtgtcagacc gagcatagaa   12540
aaatttcgag agtttatttg catgaggcca acatccagcg aatgccgtgc atcgagacgg   12600
tgcctgacga cttgggttgc ttggctgtga tcttgccagt gaagcgtttc gccggtcgtg   12660
ttgtcatgaa tcgctaaagg atcaaagcga ctctccacct tagctatcgc cgcaagcgta   12720
gatgtcgcaa ctgatggggc acacttgcga gcaacatggt caaactcagc agatgagagt   12780
ggcgtggcaa ggctcgacga acagaaggag accatcaagg caagagaaag cgaccccgat   12840
ctcttaagca tacctatctc ccttagctcg caactaacac cgcctctccc gttggaagaa   12900
gtgcgttgtt ttatgttgaa gattatcggg agggtcggtt actcgaaaat tttcaattgc   12960 ttcttttatga tttcaattga agcgagaaac ctcgcccggc gtcttggaac gcaacatgga   13020
ccgagaaccg cgcatccatg actaagcaac cggatcgacc tattcaggcc gcagttggtc   13080
aggtcaggct cagaacgaaa atgctcggcg aggttacgct gtctgtaaac ccattcgatg   13140
aacgggaagc ttccttccga ttgctcttgg caggaatatt ggcccatgcc tgcttgcgct   13200
ttgcaaatgc tcttatcgcg ttggtatcat atgccttgtc cgccagcaga aacgcactct   13260
aagcgattat ttgtaaaaat gtttcggtca tgcggcggtc atgggcttga cccgctgtca   13320
gcgcaagacg gatcggtcaa ccgtcggcat cgacaacagc gtgaatcttg gtggtcaaac   13380
cgccacggga acgtcccata cagccatcgt cttgatcccg ctgtttcccg tcgccgcatg   13440
ttggtggacg cggacacagg aactgtcaat catgacgaca ttctatcgaa agccttggaa   13500
atcacactca gaatatgatc ccagacgtct gcctcacgcc atcgtacaaa gcgattgtag   13560
caggttgtac aggaaccgta tcgatcagga acgtctgccc agggcgggcc cgtccggaag   13620
cgccacaaga tgacattgat cacccgcgtc aacgcgcggc acgcgacgcg gcttatttgg   13680
gaacaaagga ctgaacaaca gtccattcga aatcggtgac atcaaagcgg ggacgggtta   13740
tcagtggcct ccaagtcaag cctcaatgaa tcaaaatcag accgatttgc aaacctgatt   13800
tatgagtgtg cggcctaaat gatgaaatcg tccttctaga tcgcctccgt ggtgtagcaa   13860
cacctcgcag tatcgccgtg ctgaccttgg ccagggaatt gactggcaag ggtgctttca   13920
catgaccgct cttttggccg cgatagatga tttcgttgct gctttgggca cgtagaagga   13980
gagaagtcat atcggagaaa ttcctcctgg cgcgagagcc tgctctatcg cgacggcatc   14040
ccactgtcgg gaacagaccg gatcattcac gaggcgaaag tcgtcaacac atgcgttata   14100
ggcatcttcc cttgaaggat gatcttgttg ctgccaatct ggaggtgcgg cagccgcagg   14160
cagatgcgat ctcagcgcaa cttgcggcaa aacatctcac tcacctgaaa accactagcg   14220
```

```
agtctcgcga tcagacgaag gccttttact taacgacaca atatccgatg tctgcatcac   14280
aggcgtcgct atcccagtca atactaaagc ggtgcaggaa ctaaagatta ctgatgactt   14340
aggcgtgcca cgaggcctga gacgacgcgc gtagacagtt ttttgaaatc attatcaaag   14400
tgatggcctc cgctgaagcc tatcacctct gcgccggtct gtcggagaga tgggcaagca   14460
ttattacggt cttcgcgccc gtacatgcat tggacgattg cagggtcaat ggatctgaga   14520
tcatccagag gattgccgcc cttaccttcc gtttcgagtt ggagccagcc cctaaatgag   14580
acgacatagt cgacttgatg tgacaatgcc aagagagaga tttgcttaac ccgattttt   14640 tgctcaagcg taagcctatt gaagcttgcc ggcatgacgt ccgcgccgaa agaatatcct   14700
acaagtaaaa cattctgcac accgaaatgc ttggtgtaga catcgattat gtgaccaaga   14760
tccttagcag tttcgcttgg ggaccgctcc gaccagaaat accgaagtga actgacgcca   14820
atgacaggaa tcccttccgt ctgcagatag gtaccatcga tagatctgct gcctcgcgcg   14880
tttcggtgat gacggtgaaa acctctgaca catgcagctc ccggagacgg tcacagcttg   14940
tctgtaagcg gatgccggga gcagacaagc ccgtcagggc gcgtcagcgg gtgttggcgg   15000
gtgtcggggc gcagccatga cccagtcacg tagcgatagc ggagtgtata ctggcttaac   15060
tatgcggcat cagagcagat tgtactgaga gtgcaccata tgcggtgtga aataccgcac   15120
agatgcgtaa ggagaaaata ccgcatcagg cgctcttccg cttcctcgct cactgactcg   15180
ctgcgctcgg tcgttcggct gcggcgagcg gtatcagctc actcaaaggc ggtaatacgg   15240
ttatccacag aatcagggga taacgcagga agaacatgt gagcaaaagg ccagcaaaag   15300
gccaggaacc gtaaaaaggc cgcgttgctg gcgttttcc ataggctccg ccccctgac   15360 gagcatcaca aaaatcgacg ctcaagtcag aggtggcgaa acccgacagg actataaaga   15420
taccaggcgt ttccccctgg aagctccctc gtgcgctctc ctgttccgac cctgccgctt   15480
accggatacc tgtccgcctt tctcccttcg ggaagcgtgg cgctttctca tagctcacgc   15540
tgtaggtatc tcagttcggt gtaggtcgtt cgctccaagc tgggctgtgt gcacgaaccc   15600
cccgttcagc ccgaccgctg cgccttatcc ggtaactatc gtcttgagtc aacccggta   15660 agacacgact tatcgccact ggcagcagcc actggtaaca ggattagcag agcgaggtat   15720
gtaggcggtg ctacagagtt cttgaagtgg tggcctaact acggctacac tagaaggaca   15780
gtatttggta tctgcgctct gctgaagcca gttaccttcg gaaaaagagt tggtagctct   15840
tgatccggca aacaaaccac cgctggtagc ggtggttttt ttgtttgcaa gcagcagatt   15900
acgcgcagaa aaaaggatc tcaagaagat cctttgatct tttctacggg gtctgacgct   15960
cagtggaacg aaaactcacg ttaagggatt ttggtcatga gattatcaaa aaggatcttc   16020
acctagatcc ttttaaatta aaaatgaagt tttaaatcaa tctaaagtat atatgagtaa   16080
acttggtctg acagttacca atgcttaatc agtgaggcac ctatctcagc gatctgtcta   16140
tttcgttcat ccatagttgc ctgactcccc gtcgtgtaga taactacgat acgggagggc   16200
ttaccatctg gccccagtgc tgcaatgata ccgcgagacc cacgctcacc ggctccagat   16260
ttatcagcaa taaccagcc agccggaagg gccgagcgca gaagtggtcc tgcaacttta   16320
tccgcctcca tccagtctat taattgttgc cgggaagcta gagtaagtag ttcgccagtt   16380
aatagtttgc gcaacgttgt tgccattgct gcaggggggg gggggggggg gttccattgt   16440
tcattccacg gacaaaaaca gagaaaggaa acgacagagg ccaaaaagct cgctttcagc   16500
acctgtcgtt tcctttcttt tcagggggta ttttaaataa aaacattaag ttatgacgaa   16560
gaagaacgga aacgccttaa accggaaaat tttcataaat agcgaaaacc cgcgaggtcg   16620
```

```
ccgccccgta acctgtcgga tcaccggaaa ggacccgtaa agtgataatg attatcatct    16680
acatatcaca acgtgcgtgg aggccatcaa accacgtcaa ataatcaatt atgacgcagg    16740
tatcgtatta attgatctgc atcaacttaa cgtaaaaaca acttcagaca atacaaatca    16800
gcgacactga atacggggca acctcatgtc cccccccccc ccccccctgc aggcatcgtg    16860
gtgtcacgct cgtcgtttgg tatggcttca ttcagctccg gttcccaacg atcaaggcga    16920
gttacatgat cccccatgtt gtgcaaaaaa gcggttagct ccttcggtcc tccgatcgtt    16980
gtcagaagta agttggccgc agtgttatca ctcatggtta tggcagcact gcataattct    17040
cttactgtca tgccatccgt aagatgcttt tctgtgactg gtgagtactc aaccaagtca    17100
ttctgagaat agtgtatgcg gcgaccgagt tgctcttgcc cggcgtcaac acgggataat    17160
accgcgccac atagcagaac tttaaaagtg ctcatcattg gaaaacgttc ttcggggcga    17220
aaactctcaa ggatcttacc gctgttgaga tccagttcga tgtaacccac tcgtgcaccc    17280
aactgatctt cagcatcttt tactttcacc agcgtttctg ggtgagcaaa aacaggaagg    17340
caaaatgccg caaaaaaggg aataagggcg acacggaaat gttgaatact catactcttc    17400
ctttttcaat attattgaag catttatcag ggttattgtc tcatgagcgg atacatattt    17460
gaatgtattt agaaaaataa acaaataggg gttccgcgca catttccccg aaaagtgcca    17520
cctgacgtct aagaaaccat tattatcatg acattaacct ataaaaatag gcgtatcacg    17580
aggccctttc gtcttcaaga attggtcgac gatcttgctg cgttcggata ttttcgtgga    17640
gttcccgcca cagacccgga ttgaaggcga gatccagcaa ctcgcgccag atcatcctgt    17700
gacggaactt tggcgcgtga tgactggcca ggacgtcggc cgaaagagcg acaagcagat    17760
cacgcttttc gacagcgtcg gatttgcgat cgaggatttt tcggcgctgc gctacgtccg    17820
cgaccgcgtt gagggatcaa gccacagcag cccactcgac cttctagccg acccagacga    17880
gccaagggat ctttttggaa tgctgctccg tcgtcaggct ttccgacgtt tgggtggttg    17940
aacagaagtc attatcgtac ggaatgccaa gcactcccga ggggaaccct gtggttggca    18000
tgcacataca aatggacgaa cggataaacc ttttcacgcc cttttaaata tccgttattc    18060
taataaacgc tcttttctct taggtttacc cgccaatata tcctgtcaaa cactgatagt    18120
ttaaactgaa ggcgggaaac gacaatctga tcatgagcgg agaattaagg gagtcacgtt    18180
atgaccccccg ccgatgacgc gggacaagcc gttttacgtt tggaactgac agaaccgcaa    18240
cgttgaagga gccactcagc aagctggtac gattgtaata cgactcacta tagggcgaat    18300
tgagcgctgt ttaaacgctc ttcaactgga agagcggtta ccagagctgg tcacctttgt    18360
ccaccaagat ggaactgcgg ccgctcatta attaagtcag gcgcgcctct agttgaagac    18420
acgttcatgt cttcatcgta agaagacact cagtagtctt cggccagaat ggcccggacc    18480
gaagctggcc gctctagaac tagtggatct cgatgtgtag tctacgagaa gggttaaccg    18540
tctcttcgtg agaataaccg tggcctaaaa ataagccgat gaggataaat aaaatgtggt    18600
ggtacagtac ttcaagaggt ttactcatca agaggatgct tttccgatga gctctagtag    18660
tacatcggac ctcacatacc tccattgtgg tgaaatattt tgtgctcatt tagtgatggg    18720
taaattttgt ttatgtcact ctaggttttg acatttcagt tttgccactc ttaggttttg    18780
acaaataatt tccattccgc ggcaaaagca aaacaatttt attttacttt taccactctt    18840
agctttcaca atgtatcaca aatgccactc tagaaattct gtttatgcca cagaatgtga    18900
aaaaaaacac tcacttattt gaagccaagg tgttcatggc atggaaatgt gacataaagt    18960
aacgttcgtg tataagaaaa aattgtactc ctcgtaacaa gagacggaaa catcatgaga    19020
```

```
caatcgcgtt tggaaggctt tgcatcacct ttggatgatg cgcatgaatg gagtcgtctg   19080
cttgctagcc ttcgcctacc gcccactgag tccgggcggc aactaccatc ggcgaacgac   19140
ccagctgacc tctaccgacc ggacttgaat gcgctacctt cgtcagcgac gatggccgcg   19200
tacgctggcg acgtgccccc gcatgcatgg cggcacatgg cgagctcaga ccgtgcgtgg   19260
ctggctacaa atacgtaccc cgtgagtgcc ctagctagaa acttacacct gcaactgcga   19320
gagcgagcgt gtgagtgtag ccgagtagat cccccggtcg ccaccatggc ctcctccgag   19380
aacgtcatca ccgagttcat gcgcttcaag gtgcgcatgg agggcaccgt gaacggccac   19440
gagttcgaga tcgagggcga gggcgagggc cgccccctacg agggccacaa caccgtgaag   19500
ctgaaggtga ccaagggcgg cccccctgccc ttcgcctggg acatcctgtc cccccagttc   19560
cagtacggct ccaaggtgta cgtgaagcac cccgccgaca tccccgacta caagaagctg   19620
tccttccccg agggcttcaa gtgggagcgc gtgatgaact tcgaggacgg cggcgtggcg   19680
accgtgaccc aggactcctc cctgcaggac ggctgcttca tctacaaggt gaagttcatc   19740
ggcgtgaact tcccctccga cggccccgtg atgcagaaga agaccatggg ctgggaggcc   19800
tccaccgagc gcctgtaccc ccgcgacggc gtgctgaagg gcgagaccca caaggccctg   19860
aagctgaagg acggcggcca ctacctggtg gagttcaagt ccatctacat ggccaagaag   19920
cccgtgcagc tgcccggcta ctactacgtg gacgccaagc tggacatcac ctcccacaac   19980
gaggactaca ccatcgtgga gcagtacgag cgcaccgagg ccgccacca cctgttcctg   20040 tagcggccca tggatattcg aacgcgtagg taccacatgg ttaacctaga cttgtccatc   20100
ttctggattg gccaacttaa ttaatgtatg aaataaaagg atgcacacat agtgacatgc   20160
taatcactat aatgtgggca tcaaagttgt gtgttatgtg taattactag ttatctgaat   20220
aaaagagaaa gagatcatcc atatttctta tcctaaatga atgtcacgtg tctttataat   20280
tctttgatga accagatgca tttcattaac caaatccata tacatataaa tattaatcat   20340
atataattaa tatcaattgg gttagcaaaa caaatctagt ctaggtgtgt tttgcgaatg   20400
cggccgccac cgcggtggag ctcgaattcc ggtccgggcc tagaaggcca tttaaatcct   20460
gaggatctgg tcttcctaag gacccgggat atcgctatca actttgtata gaaagttgg   20520 gccgaattcg agctcggtac ggccagaatg gcccggaccg ggttaccgaa ttcgagctcg   20580
gtaccctggg atccgcaagg gacgaccgtg gtccttgttt gatttacttc caggattata   20640
taatccagct tatggattat ataagtacct attgacgtca cgtgcttatg tattataata   20700
atctaggtat atagattata taatctatct aataataatc tgtgttgttt gtttatctct   20760
caaaacaaac aggtcctaaa atggtcccgg gcgtccaatg tgtcgtcaag tagtgttaag   20820
ctaaatcgac atttctttgt gggttgtgtg gaaggtgttc cttttcctta agttgttagt   20880
tgtgcaaggt gttccttaga gcatctccaa taggacctat aatggattct attttgaatt   20940
ataagactct aacaacaaaa gcatacttta atgggattc tattttacaa aaaaatatca   21000
aatgattata tggtcgattc ctcgggtcct aaatatagta tctcatataa tagagctcta   21060
tcctcatttt atatactatt tttaagtttt tatttactaa ataacatgat ttattttcta   21120
atactatgaa ctcaactatt agagctgtaa acgttttgt ggtactaaac actttaaatc   21180
aggtcctatt ttaatttgaa ggacttaaat ataagacttc tggttagaga tgctcttagc   21240
gagtgtttgt gcatgattgc tatttagtct ttgtggattg tggaaggtgt acttttcct   21300 caagttgtta gttgtgcaag gtgttttctta gagcatctct aacaggagcc ttaacggaat   21360
ctattttgaa gtatagtact ttaacaccaa aaacatactt taatagggggt cctatttttac   21420
```

```
aaaaaaatta tcaaatgatt ataaggtcca ctcctcgggt cctaaatata atatctcata   21480
tactagagct ctatcctcat ttatatact atccctaggt ttttattccc taaataacat   21540
gatttatttc ctaatactaa gatatagggc tcaactattg gagttgcaaa tgttttttgg   21600
cactaaacac tttatatcag gtcctatttt aattttaatt tgaaggactc aaatatagga   21660
cttctcgtta gagatgctct tagcgagtgt ttgtgcatga ttgctattta tgtctgtagt   21720
ttagttgggg gctttaatat gtttagttga agttctagta tttttaggt tctccactct    21780
ttggattatg acaacgacca ctatccaagc agtctttgag tgcaaacgcg cgagcaaact   21840
atctgatcta ttaaattatg atccaaccgt tatgtcatat tgaagactta aaccctttca   21900
ccaccagccc aagtatcttt atgaaaaacc ctaacaaacc acaattgcat ctatggttgg   21960
attataattt aacgtatcag atggttcgct tgcatgctta catatctaga aactgtttgc   22020
ataacagtcg ttctctttgg ttatataatg ctttagtaat catcagccaa gtgtaaacaa   22080
atggtacaaa ctagtagtga acacatcctc cctacctatc tctagggggtg taactagata   22140
tccgaattct tagaacaaat ttcatatttt aaaatagata tgcttcaaaa tttatgctaa   22200
tcttttttat attatcaagc atattattac acataagaat aaaattttgt atagaatttt   22260
atccattatt tgttccctag aatttaaaaa gtgaaaaaac attcgaatct gtatcagttt   22320
cgtattcaaa tttttacatc tattatttga gaatatatat gataaatttg aggtttagtt   22380
tttatgaatc tttacaaggt taatgttaaa tacatgacta tggatttaca tagtaaattc   22440
tatgtcttat ttgtccgcga ttgaagaaaa atgacaaaaa gatctgacat tcgaataaac   22500
atctgtttcc actcctacct atctgacctc ctatttcaaa ctccactttg taacacggta   22560
caaaatcact ccctacctat ctgacctcct atttcaaact ccactcagta aacaatattg   22620
tctatggtac aaaaccaagt gtttatatca tctatttgca cgatctgctc gagtcaggca   22680
tccttgacac acaacatact ccttgtggct ataaatgtcc aaatagagca gacctaatgg   22740
gtggaccgtt gcatgacacg acttatccca agacgagcac agttcgcccc attggtcatg   22800
ggggtccggg ctagtctagc ctgatcatcg ggtcacactt aggccacagg tgtgccacaa   22860
cgggatagcc caacatgtcc cttttttgtca tgcatatatc tatattatag ttagtataat   22920
gtaaaaaaac aaaaggtatg tgtgttatgt tggttagatg tgtttaaata actctttaaa   22980
gctagcaact atggtttaaa tcatacatat acacattttt atttattttt tatttaaacg   23040
atatgggcct tctaggcacg tcgagtgtga cgggccagtg agatgacaca ttataattac   23100
tggtctagca ggccgtacct aggtctttct cgtgggccaa gactaagggt tggcccgttg   23160
gctaatctgt acggtaccga tactgtccta attcatttga acacctgtag aagaggggaa   23220
tttataattg aggaggaatg tactcatgcg gtacaccagg ggaattgttt tgttgtgctc   23280
agcgatagat ttcaacgcaa cggtgagcca gtttcactaa aaaagggggg ggggggggg    23340
ggggggaag gccacatcaa aggcgaggtg ctgacgagca aagatgctca gcagtgacgc    23400
caagtccagc agctagcaat gaaagggtac tcgggattta acaatgccta gagacggcat   23460
catcccctca ataatccggt gctctctttt tgtttattca ccagttggcg tagctatata   23520
cacatgtctg gtctgacgaa caaatcaagg gatcgctagc tcgggctagc cttcctatca   23580
ctgtcatgac atgtgctctg cctctgctgg ttgataagcc gtgcgccttc tcgctaattc   23640
tttcttgtgc tagaggcgag tcaaacaaac gctgcacctc gtagccctta atctgcgcta   23700
agggtcacat gaccctgttc cctatcgcta gttaccaacg acccattccc cctgacagat   23760
acttacgacg cgtccgtacg cggcaggcct cggcagttcg gcatcaccag caccggcgcc   23820
```

```
ggcattcgcc ccctgccagc cggttcgcag attcgcaggg cggagtcggc cgcagttgcc    23880
gcatcccaaa cgcccgggaa cctttggggc ccctctacga gcaaatgaag ttgctgcccc    23940
tggcttcgta aagctctgac tttgatcac ttgattggca gtcgtactcc tcgctcatag     24000
gccgacacgg ccgcaaagtc aactacccgc tccgccatcc ttcaaccccc gccacgcgcc    24060
tatatatgtt cgcggccatg tccgtactag tcctccaacc cacaagccac aaccccgagc    24120
tcagatccct cgcctcgtgt cgtgtctccg gtcgacgacg accaacagcc agtgtgggcc    24180
agacggacac cgccgagcta tagcgcttgg tgataaagct tggtcacccg gtccgggcct    24240
agaaggccag cttcaagttt gtacaaaaaa gcaggctcca gcgctcacca tggtccgtcc    24300
tgtagaaacc ccaacccgtg aaatcaaaaa actcgacggc ctgtgggcat tcagtctgga    24360
tcgcgaaaac tgtggaattg atcagcgttg gtgggaaagc gcgttacaag aaagccgggc    24420
aattgctgtg ccaggcagtt ttaacgatca gttcgccgat gcagatattc gtaattatgc    24480
gggcaacgtc tggtatcagc gcgaagtctt tataccgaaa ggttgggcag ccagcgtat     24540
cgtgctgcgt ttcgatgcgg tcactcatta cggcaaagtg tgggtcaata atcaggaagt    24600
gatggagcat cagggcggct atacgccatt tgaagccgat gtcacgccgt atgttattgc    24660
cgggaaaagt gtacgtaagt ttctgcttct acctttgata tatatataat aattatcatt    24720
aattagtagt aatataatat ttcaaatatt tttttcaaaa taaaagaatg tagtatatag    24780
caattgcttt tctgtagttt ataagtgtgt atatttaat ttataacttt tctaatatat     24840
gaccaaaatt tgttgatgtg caggtatcac cgtttgtgtg aacaacgaac tgaactggca    24900
gactatcccg ccgggaatgg tgattaccga cgaaaacggc aagaaaaagc agtcttactt    24960
ccatgatttc tttaactatg ccggaatcca tcgcagcgta atgctctaca ccacgccgaa    25020
cacctgggtg gacgatatca ccgtggtgac gcatgtcgcg caagactgta accacgcgtc    25080
tgttgactgg caggtggtgg ccaatggtga tgtcagcgtt gaactgcgtg atgcggatca    25140
acaggtggtt gcaactggac aaggcactag cgggactttg caagtggtga atccgcacct    25200
ctggcaaccg ggtgaaggtt atctctatga actgtgcgtc acagccaaaa gccagacaga    25260
gtgtgatatc tacccgcttc gcgtcggcat ccggtcagtg gcagtgaagg gcgaacagtt    25320
cctgattaac cacaaaccgt tctactttac tggctttggt cgtcatgaag atgcggactt    25380
gcgtggcaaa ggattcgata cgtgctgat ggtgcacgac cacgcattaa tggactggat     25440
tggggccaac tcctaccgta cctcgcatta cccttacgct gaagagatgc tcgactgggc    25500
agatgaacat ggcatcgtgg tgattgatga aactgctgct gtcggcttta acctctcttt    25560
aggcattggt ttcgaagcgg gcaacaagcc gaaagaactg tacagcgaag aggcagtcaa    25620
cggggaaact cagcaagcgc acttacaggc gattaaagag ctgatagcgc gtgacaaaaa    25680
ccacccaagc gtggtgatgt ggagtattgc caacgaaccg gatacccgtc cgcaaggtgc    25740
acgggaatat ttcgcgccac tggcggaagc aacgcgtaaa ctcgacccga cgcgtccgat    25800
cacctgcgtc aatgtaatgt tctgcgacgc tcacaccgat accatcagcg atctctttga    25860
tgtgctgtgc ctgaaccgtt attacggatg gtatgtccaa agcggcgatt tggaaacggc    25920
agagaaggta ctggaaaaag aacttctggc ctggcaggag aaactgcatc agccgattat    25980
catcaccgaa tacggcgtgg atacgttagc cgggctgcac tcaatgtaca ccgacatgtg    26040
gagtgaagag tatcagtgtg catggctgga tatgtatcac cgcgtctttg atcgcgtcag    26100
cgccgtcgtc ggtgaacagg tatggaattt cgccgatttt gcgacctcgc aaggcatatt    26160
gcgcgttggc ggtaacaaga aagggatctt cactcgcgac cgcaaaccga gtcggcggc    26220
```

```
ttttctgctg caaaaacgct ggactggcat gaacttcggt gaaaaccgc agcagggagg   26280
caaacaatga agatctcccg ggcacccagc tttcttgtac aaagtggccg ttaacggatc   26340
cagacttgtc catcttctgg attggccaac ttaattaatg tatgaaataa aaggatgcac   26400
acatagtgac atgctaatca ctataatgtg ggcatcaaag ttgtgtgtta tgtgtaatta   26460
ctagttatct gaataaaaga gaaagagatc atccatattt cttatcctaa atgaatgtca   26520
cgtgtcttta taattctttg atgaaccaga tgcatttcat taaccaaatc catatacata   26580
taaatattaa tcatatataa ttaatatcaa ttgggttagc aaaacaaatc tagtctaggt   26640
gtgttttgcg aattgcggca agcttgcggc cgccccgggc aactttatta tacaaagttg   26700
atagatatcg gaccgattaa actttaattc ggtccgaagc ttgcatgcct gcagtgcagc   26760
gtgacccggt cgtgcccctc tctagagata atgagcattg catgtctaag ttataaaaaa   26820
ttaccacata ttttttttgt cacacttgtt tgaagtgcag tttatctatc tttatacata   26880
tatttaaact ttactctacg aataatataa tctatagtac tacaataata tcagtgtttt   26940
agagaatcat ataaatgaac agttagacat ggtctaaagg acaattgagt attttgacaa   27000
caggactcta cagttttatc ttttttagtgt gcatgtgttc tcctttttttt ttgcaaatag   27060
cttcacctat ataatacttc atccatttta ttagtacatc catttagggt ttagggttaa   27120
tggttttat agactaattt ttttagtaca tctattttat tctattttag cctctaaatt   27180
aagaaaacta aaactctatt ttagttttt tatttaataa tttagatata aaatagaata   27240
aaataaagtg actaaaaatt aaacaaatac cctttaagaa attaaaaaaa ctaaggaaac   27300
attttttcttg tttcgagtag ataatgccag cctgttaaac gccgtcgacg agtctaacgg   27360
acaccaacca gcgaaccagc agcgtcgcgt cgggccaagc gaagcagacg gcacggcatc   27420
tctgtcgctg cctctggacc cctctcgaga gttccgctcc accgttggac ttgctccgct   27480
gtcggcatcc agaaattgcg tggcggagcg gcagacgtga gccggcacgg caggcggcct   27540
cctcctcctc tcacggcacc ggcagctacg ggggattcct ttcccaccgc tccttcgctt   27600
tcccttcctc gcccgccgta ataaatagac accccctcca caccctcttt ccccaacctc   27660
gtgttgttcg gagcgcacac acacacaacc agatctcccc caaatccacc cgtcggcacc   27720
tccgcttcaa ggtacgccgc tcgtcctccc ccccccccct ctctaccttc tctagatcgg   27780
cgttccggtc catgcatggt tagggcccgg tagttctact tctgttcatg tttgtgttag   27840
atccgtgttt gtgttagatc cgtgctgcta gcgttcgtac acggatgcga cctgtacgtc   27900
agacacgttc tgattgctaa cttgccagtg tttctctttg gggaatcctg ggatggctct   27960
agccgttccg cagacgggat cgatttcatg atttttttttg tttcgttgca tagggtttgg   28020
tttgcccttt tccttattt caatatatgc cgtgcacttg tttgtcgggt catcttttca   28080
tgcttttttt tgtcttggtt gtgatgatgt ggtctggttg ggcggtcgtt ctagatcgga   28140
gtagaattct gtttcaaact acctggtgga tttattaatt ttggatctgt atgtgtgtgc   28200
catacatatt catagttacg aattgaagat gatggatgga aatatcgatc taggataggt   28260
atacatgttg atgcgggttt tactgatgca tatacagaga tgcttttttgt tcgcttggtt   28320
gtgatgatgt ggtgtggttg ggcggtcgtt cattcgttct agatcggagt agaatactgt   28380
ttcaaactac ctggtgtatt tattaatttt ggaactgtat gtgtgtgtca tacatcttca   28440
tagttacgag tttaagatgg atggaaatat cgatctagga taggtataca tgttgatgtg   28500
ggttttactg atgcatatac atgatggcat atgcagcatc tattcatatg ctctaacctt   28560
gagtacctat ctattataat aaacaagtat gttttataat tattttgatc ttgatatact   28620
```

```
tggatgatgg catatgcagc agctatatgt ggatttttt  agccctgcct tcatacgcta   28680
tttatttgct tggtactgtt tcttttgtcg atgctcaccc tgttgtttgg tgttacttct   28740
gcaggtcgac tttaacttag cctaggatcc acacgacacc atgtccccg  agcgccgccc   28800
cgtcgagatc cgcccggcca ccgccgccga catggccgcc gtgtgcgaca tcgtgaacca   28860
ctacatcgag acctccaccg tgaacttccg caccgagccg cagacccgc  aggagtggat   28920
cgacgacctg gagcgcctcc aggaccgcta cccgtggctc gtggccgagg tggagggcgt   28980
ggtggccggc atcgcctacg ccggcccgtg aaggcccgc  aacgcctacg actggaccgt   29040
ggagtccacc gtgtacgtgt cccaccgcca ccagcgcctc ggcctcggct ccaccctcta   29100
cacccacctc ctcaagagca tggaggccca gggcttcaag tccgtggtgg ccgtgatcgg   29160
cctcccgaac gacccgtccg tgcgcctcca cgaggccctc ggctacaccg cccgcggcac   29220
cctccgcgcc gccggctaca agcacggcgg ctggcacgac gtcggcttct ggcagcgcga   29280
cttcgagctg ccgccccgc  cgcgcccggt gcgcccggtg acgcagatct gagtcgaaac   29340
ctagacttgt ccatcttctg gattggccaa cttaattaat gtatgaaata aaaggatgca   29400
cacatagtga catgctaatc actataatgt gggcatcaaa gttgtgtgtt atgtgtaatt   29460
actagttatc tgaataaaag agaaagagat catccatatt tcttatccta aatgaatgtc   29520
acgtgtcttt ataattcttt gatgaaccag atgcatttca ttaaccaaat ccatatacat   29580
ataaatatta atcatatata attaatatca attgggttag caaaacaaat ctagtctagg   29640
tgtgttttgc gaattgcggc cgccaccgcg gtggagctcg aattcattcc gattaatcgt   29700
ggcctcttgc tcttcaggat gaagagctat gtttaaacgt gcaagcgcta ctagacaatt   29760
cagtacatta aaaacgtccg caatgtgtta ttaagttgtc taagcgtcaa tttgtttaca   29820
ccacaatata tcctgccacc agccagccaa cagctccccg accggcagct cggcacaaaa   29880
tcaccactcg atacaggcag cccatcagtc cgggacggcg tcagcgggag agccgttgta   29940
aggcggcaga ctttgctcat gttaccgatg ctattcggaa gaacggcaac taagctgccg   30000
ggtttgaaac acggatgatc tcgcggaggg tagcatgttg attgtaacga tgacagagcg   30060
ttgctgcctg tgatcaaata tcatctccct cgcagagatc cgaattatca gccttcttat   30120
tcatttctcg cttaaccgtg acaggctgtc gatcttgaga actatgccga cataatagga   30180
aatcgctgga taaagccgct gaggaagctg agtggcgcta tttctttaga agtgaacgtt   30240
gacgatcgtc gaccgtaccc cgatgaatta attcggacgt acgttctgaa cacagctgga   30300
tacttacttg ggcgattgtc atacatgaca tcaacaatgt acccgtttgt gtaaccgtct   30360
cttggaggtt cgtatgacac tagtggttcc cctcagcttg cgactagatg ttgaggccta   30420
acattttatt agagagcagg ctagttgctt agatacatga tcttcaggcc gttatctgtc   30480
agggcaagcg aaaattggcc atttatgacg accaatgccc cgcagaagct cccatctttg   30540
ccgccataga cgccgcgccc ccttttggg  gtgtagaaca tccttttgcc agatgtgaa   30600
aagaagttcg ttgtcccatt gttggcaatg acgtagtagc cggcgaaagt gcgagaccca   30660
tttgcgctat atataagcct acgatttccg ttgcgactat tgtcgtaatt ggatgaacta   30720
ttatcgtagt tgctctcaga gttgtcgtaa tttgatggac tattgtcgta attgcttatg   30780
gagttgtcgt agttgcttgg agaaatgtcg tagttggatg gggagtagtc atagggaaga   30840
cgagcttcat ccactaaaac aattggcagg tcagcaagtg cctgccccga tgccatcgca   30900
agtacgaggc ttagaaccac cttcaacaga tcgcgcatag tcttccccag ctctctaacg   30960
cttgagttaa gccgcgccgc gaagcggcgt cggcttgaac gaattgttag acattatttg   31020
```

```
ccgactacct tggtgatctc gcctttcacg tagtgaacaa attcttccaa ctgatctgcg    31080
cgcgaggcca agcgatcttc ttgtccaaga taagcctgcc tagcttcaag tatgacgggc    31140
tgatactggg ccggcaggcg ctccattgcc cagtcggcag cgacatcctt cggcgcgatt    31200
ttgccggtta ctgcgctgta ccaaatgcgg gacaacgtaa gcactacatt tcgctcatcg    31260
ccagcccagt cgggcggcga gttccatagc gttaaggttt catttagcgc ctcaaataga    31320
tcctgttcag gaaccggatc aaagagttcc tccgccgctg gacctaccaa ggcaacgcta    31380
tgttctcttg cttttgtcag caagatagcc agatcaatgt cgatcgtggc tggctcgaag    31440
atacctgcaa gaatgtcatt gcgctgccat tctccaaatt gcagttcgcg cttagctgga    31500
taacgccacg gaatgatgtc gtcgtgcaca acaatggtga cttctacagc gcggagaatc    31560
tcgctctctc caggggaagc cgaagtttcc aaaaggtcgt tgatcaaagc tcgccgcgtt    31620
gtttcatcaa gccttacagt caccgtaacc agcaaatcaa tatcactgtg tggcttcagg    31680
ccgccatcca ctgcggagcc gtacaaatgt acggccagca acgtcggttc gagatggcgc    31740
tcgatgacgc caactacctc tgatagttga gtcgatactt cggcgatcac cgcttccctc    31800
atgatgttta actcctgaat taagccgcgc gcgaagcgg tgtcggcttg aatgaattgt    31860
taggcgtcat cctgtgctcc cgagaaccag taccagtaca tcgctgtttc gttcgagact    31920
tgaggtctag ttttatacgt gaacaggtca atgccgccga gagtaaagcc acattttgcg    31980
tacaaattgc aggcaggtac attgttcgtt tgtgtctcta atcgtatgcc aaggagctgt    32040
ctgcttagtg cccactttt cgcaaattcg atgagactgt gcgcgactcc tttgcctcgg     32100
tgcgtgtgcg acacaacaat gtgttcgata gaggctagat cgttccatgt tgagttgagt    32160
tcaatcttcc cgacaagctc ttggtcgatg aatgcgccat agcaagcaga gtcttcatca    32220
gagtcatcat ccgagatgta atccttccgg taggggctca cacttctggt agatagttca    32280
aagccttggt cggataggtg cacatcgaac acttcacgaa caatgaaatg gttctcagca    32340
tccaatgttt ccgccacctg ctcagggatc accgaaatct tcatatgacg cctaacgcct    32400
ggcacagcgg atcgcaaacc tggcgcggct tttggcacaa aaggcgtgac aggtttgcga    32460
atccgttgct gccacttgtt aacccttttg ccagatttgg taactataat ttatgttaga    32520
ggcgaagtct tgggtaaaaa ctggcctaaa attgctgggg atttcaggaa agtaaacatc    32580
accttccggc tcgatgtcta ttgtagatat atgtagtgta tctacttgat cggggatct    32640
gctgcctcgc gcgtttcggt gatgacggtg aaaacctctg acacatgcag ctcccggaga    32700
cggtcacagc ttgtctgtaa gcggatgccg ggagcagaca agcccgtcag ggcgcgtcag    32760
cgggtgttgg cgggtgtcgg ggcgcagcca tgacccagtc acgtagcgat agcggagtgt    32820
atactggctt aactatgcgg catcagagca gattgtactg agagtgcacc atatgcggtg    32880
tgaaataccg cacagatgcg taaggagaaa ataccgcatc aggcgctctt ccgcttcctc    32940
gctcactgac tcgctgcgct cggtcgttcg gctgcggcga gcggtatcag ctcactcaaa    33000
ggcggtaata cggttatcca cagaatcagg ggataacgca ggaaagaaca tgtgagcaaa    33060
aggccagcaa aaggccagga accgtaaaaa ggccgcgttg ctggcgtttt tccataggct    33120
ccgcccccct gacgagcatc acaaaaatcg acgctcaagt cagaggtggc gaaacccgac    33180
aggactataa agataccagg cgtttccccc tggaagctcc ctcgtgcgct ctcctgttcc    33240
gaccctgccg cttaccggat acctgtccgc ctttctccct tcgggaagcg tggcgctttc    33300
tcatagctca cgctgtaggt atctcagttc ggtgtaggtc gttcgctcca agctgggctg    33360
tgtgcacgaa ccccccgttc agcccgaccg ctgcgcctta tccggtaact atcgtcttga    33420
```

```
gtccaacccg gtaagacacg acttatcgcc actggcagca gccactggta acaggattag    33480
cagagcgagg tatgtaggcg gtgctacaga gttcttgaag tggtggccta actacggcta    33540
cactagaagg acagtatttg gtatctgcgc tctgctgaag ccagttacct tcggaaaaag    33600
agttggtagc tcttgatccg gcaaacaaac caccgctggt agcggtggtt tttttgtttg    33660
caagcagcag attacgcgca gaaaaaagg atctcaagaa gatcctttga tcttttctac    33720
ggggtctgac gctcagtgga acgaaaactc acgttaaggg attttggtca tgagattatc    33780
aaaaaggatc ttcacctaga tccttttaaa ttaaaaatga agttttaaat caatctaaag    33840
tatatatgag taaacttggt ctgacagtta ccaatgctta atcagtgagg cacctatctc    33900
agcgatctgt ctatttcgtt catccatagt tgcctgactc cccgtcgtgt agataactac    33960
gatacgggag ggcttaccat ctggccccag tgctgcaatg ataccgcgag acccacgctc    34020
accggctcca gatttatcag caataaacca gccagccgga agggccgagc gcagaagtgg    34080
tcctgcaact ttatccgcct ccatccagtc tattaattgt tgccgggaag ctagagtaag    34140
tagttcgcca gttaatagtt tgcgcaacgt tgttgccatt gctgcagggg ggggggggg    34200 gggggacttc cattgttcat tccacggaca aaaacagaga aaggaaacga cagaggccaa    34260
aaagcctcgc tttcagcacc tgtcgtttcc tttcttttca gagggtattt taaataaaaa    34320
cattaagtta tgacgaagaa gaacggaaac gccttaaacc ggaaaatttt cataaatagc    34380
gaaaacccgc gaggtcgccg cccgtaacc tgtcggatca ccggaaagga cccgtaaagt    34440
gataatgatt atcatctaca tatcacaacg tgcgtggagg ccatcaaacc acgtcaaata    34500
atcaattatg acgcaggtat cgtattaatt gatctgcatc aacttaacgt aaaaacaact    34560
tcagacaata caaatcagcg acactgaata cggggcaacc tcatgtcccc cccccccc    34620 cccctgcagg catcgtggtg tcacgctcgt cgtttggtat ggcttcattc agctccggtt    34680
cccaacgatc aaggcgagtt acatgatccc ccatgttgtg caaaaaagcg gttagctcct    34740
tcggtcctcc gatcgttgtc agaagtaagt tggccgcagt gttatcactc atggttatgg    34800
cagcactgca taattctctt actgtcatgc catccgtaag atgcttttct gtgactggtg    34860
agtactcaac caagtcattc tgagaatagt gtatgcggcg accgagttgc tcttgcccgg    34920
cgtcaacacg ggataatacc gcgccacata gcagaacttt aaaagtgctc atcattggaa    34980
aacgttcttc ggggcgaaaa ctctcaagga tcttaccgct gttgagatcc agttcgatgt    35040
aacccactcg tgcacccaac tgatcttcag catcttttac tttcaccagc gtttctgggt    35100
gagcaaaaac aggaaggcaa aatgccgcaa aaaagggaat aagggcgaca cggaaatgtt    35160
gaatactcat actcttcctt tttcaatatt attgaagcat ttatcagggt tattgtctca    35220
tgagcggata catatttgaa tgtatttaga aaaataaaca aataggggtt ccgcgcacat    35280
ttccccgaaa agtgccacct gacgtctaag aaaccattat tatcatgaca ttaacctata    35340
aaaataggcg tatcacgagg ccctttcgtc ttcaagaatt cggagctttt gccattctca    35400
ccggattcag tcgtcactca tggtgatttc tcacttgata accttatttt tgacgagggg    35460
aaattaatag gttgtattga tgttggacga gtcggaatcg cagaccgata ccaggatctt    35520
gccatcctat ggaactgcct cggtgagttt tctccttcat tacagaaacg gcttttttcaa    35580 aaatatggta ttgataatcc tgatatgaat aaattgcagt ttcatttgat gctcgatgag    35640 ttttttctaat cagaattggt taattggttg taacactggc agagcattac gctgacttga    35700
cgggacggcg gctttgttga ataaatcgaa cttttgctga gttgaaggat cagatcacgc    35760
atcttcccga caacgcagac cgttccgtgg caaagcaaaa gttcaaaatc accaactggt    35820
```

-continued

```
ccacctacaa caaagctctc atcaaccgtg gctccctcac tttctggctg gatgatgggg    35880
cgattcaggc ctggtatgag tcagcaacac cttcttcacg aggcagacct cagcgccaga    35940
aggccgccag agaggccgag cgcggccgtg aggcttggac gctagggcag ggcatgaaaa    36000
agcccgtagc gggctgctac gggcgtctga cgcggtggaa aggggagggg gatgttgtct    36060
acatggctct gctgtagtga gtgggttgcg ctccggcagc ggtcctgatc aatcgtcacc    36120
cttctcggt ccttcaacgt tcctgacaac gagcctcctt ttcgccaatc catcgacaat    36180
caccgcgagt ccctgctcga acgctgcgtc cggaccggct tcgtcgaagg cgtctatcgc    36240
ggcccgcaac agcggcgaga gcggagcctg ttcaacggtg ccgccgcgct cgccggcatc    36300
gctgtcgccg gcctgctcct caagcacggc cccaacagtg aagtagctga ttgtcatcag    36360
cgcattgacg gcgtccccgg ccgaaaaacc cgcctcgcag aggaagcgaa gctgcgcgtc    36420
ggccgtttcc atctgcggtg cgcccggtcg cgtgccggca tggatgcgcg cgccatcgcg    36480
gtaggcgagc agcgcctgcc tgaagctgcg ggcattcccg atcagaaatg agcgccagtc    36540
gtcgtcggct ctcggcaccg aatgcgtatg attctccgcc agcatggctt cggccagtgc    36600
gtcgagcagc gcccgcttgt tcctgaagtg ccagtaaagc gccggctgct gaaccccaa    36660
ccgttccgcc agtttgcgtg tcgtcagacc gtctacgccg acctcgttca acaggtccag    36720
ggcggcacgg atcactgtat tcggctgcaa cttttgtcatg cttgacactt tatcactgat    36780
aaacataata tgtccaccaa cttatcagtg ataaagaatc cgcgcgttca atcggaccag    36840
cggaggctgg tccggaggcc agacgtgaaa cccaacatac ccctgatcgt aattctgagc    36900
actgtcgcgc tcgacgctgt cggcatcggc ctgattatgc cggtgctgcc gggcctcctg    36960
cgcgatctgg ttcactcgaa cgacgtcacc gcccactatg gcattctgct ggcgctgtat    37020
gcgttggtgc aatttgcctg cgcacctgtg ctgggcgcgc tgtcggatcg tttcgggcgg    37080
cggccaatct tgctcgtctc gctggccggc gccactgtcg actacgccat catggcgaca    37140
gcgcctttcc tttgggttct ctatatcggg cggatcgtgg ccggcatcac cggggcgact    37200
ggggcggtag ccggcgctta tattgccgat atcactgatg gcgatgagcg cgcgcggcac    37260
ttcggcttca tgagcgcctg tttcgggttc gggatggtcg cgggacctgt gctcggtggg    37320
ctgatgggcg gtttctcccc ccacgctccg ttcttcgccg cggcagcctt gaacggcctc    37380
aatttcctga cgggctgttt cctttttgccg gagtcgcaca aaggcgaacg ccggccgtta    37440
cgccgggagg ctctcaaccc gctcgcttcg ttccggtggg cccggggcat gaccgtcgtc    37500
gccgccctga tggcggtctt cttcatcatg caacttgtcg gacaggtgcc ggccgcgctt    37560
tgggtcattt tcggcgagga tcgctttcac tgggacgcga ccacgatcgg catttcgctt    37620
gccgcatttg gcattctgca ttcactcgcc caggcaatga tcaccggccc tgtagccgcc    37680
cggctcggcg aaaggcgggc actcatgctc ggaatgattg ccgacggcac aggctacatc    37740
ctgcttgcct tcgcgacacg gggatggatg gcgttcccga tcatggtcct gcttgcttcg    37800
ggtggcatcg gaatgccggc gctgcaagca atgttgtcca ggcaggtgga tgaggaacgt    37860
cagggggcagc tgcaaggctc actggcggcg ctcaccagcc tgacctcgat cgtcggaccc    37920
ctcctcttca cggcgatcta tgcggcttct ataacaacgt ggaacgggtg ggcatggatt    37980
gcaggcgctg ccctctactt gctctgcctg ccggcgctgc gtcgcgggct ttggagcggc    38040
gcagggcaac gagccgatcg ctgatcgtgg aaacgatagg cctatgccat gcgggtcaag    38100
gcgacttccg gcaagctata cgcgcccctag gagtgcggtt ggaacgttgg cccagccaga    38160
tactcccgat cacgagcagg acgccgatga tttgaagcgc actcagcgtc tgatccaaga    38220
```

```
acaaccatcc tagcaacacg gcggtccccg ggctgagaaa gcccagtaag gaaacaactg    38280
taggttcgag tcgcgagatc ccccggaacc aaaggaagta ggttaaaccc gctccgatca    38340
ggccgagcca cgccaggccg agaacattgg ttcctgtagg catcgggatt ggcggatcaa    38400
acactaaagc tactggaacg agcagaagtc ctccggccgc cagttgccag gcggtaaagg    38460
tgagcagagg cacgggaggt tgccacttgc gggtcagcac ggttccgaac gccatggaaa    38520
ccgcccccgc caggcccgct cgacgccga caggatctag cgctgcgttt ggtgtcaaca     38580
ccaacagcgc cacgcccgca gttccgcaaa tagcccccag gaccgccatc aatcgtatcg    38640
ggctacctag cagagcggca gagatgaaca cgaccatcag cggctgcaca cgcctaccg     38700
tcgccgcgac cccgcccggc aggcggtaga ccgaaataaa caacaagctc cagaatagcg    38760
aaatattaag tgcgccgagg atgaagatgc gcatccacca gattcccgtt ggaatctgtc    38820
ggacgatcat cacgagcaat aaacccgccg gcaacgcccg cagcagcata ccggcgaccc    38880
ctcggcctcg ctgttcgggc tccacgaaaa cgccggacag atgcgccttg tgagcgtcct    38940
tggggccgtc ctcctgtttg aagaccgaca gcccaatgat ctcgccgtcg atgtaggcgc    39000
cgaatgccac ggcatctcgc aaccgttcag cgaacgcctc catgggcttt ttctcctcgt    39060
gctcgtaaac ggacccgaac atctctggag ctttcttcag ggccgacaat cggatctcgc    39120
ggaaatcctg cacgtcggcc gctccaagcc gtcgaatctg agccttaatc acaattgtca    39180
attttaatcc tctgtttatc ggcagttcgt agagcgcgcc gtgcgtcccg agcgatactg    39240
agcgaagcaa gtgcgtcgag cagtgccgc ttgttcctga aatgccagta aagcgctggc     39300
tgctgaaccc ccagccggaa ctgaccccac aaggccctag cgtttgcaat gcaccaggtc    39360
atcattgacc caggcgtgtt ccaccaggcc gctgcctcgc aactcttcgc aggcttcgcc    39420
gacctgctcg cgccacttct tcacgcgggt ggaatccgat ccgcacatga ggcggaaggt    39480
ttccagcttg agcgggtacg gctcccggtg cgagctgaaa tagtcgaaca tccgtcgggc    39540
cgtcggcgac agcttgcggt acttctccca tatgaatttc gtgtagtggt cgccagcaaa    39600
cagcacgacg atttcctcgt cgatcaggac ctggcaacgg acgttttct tgccacggtc     39660
caggacgcgg aagcggtgca gcagcgacac cgattccagg tgcccaacgc ggtcggacgt    39720
gaagcccatc gccgtcgcct gtaggcgcga caggcattcc tcggccttcg tgtaataccg    39780
gccattgatc gaccagccca ggtcctggca aagctcgtag aacgtgaagg tgatcggctc    39840
gccgataggg gtgcgcttcg cgtactccaa cacctgctgc cacaccagtt cgtcatcgtc    39900
ggcccgcagc tcgacgccgg tgtaggtgat cttcacgtcc ttgttgacgt ggaaaatgac    39960
cttgttttgc agcgcctcgc gcgggatttt cttgttgcgc gtggtgaaca gggcagagcg    40020
ggccgtgtcg tttggcatcg ctcgcatcgt gtccggccac ggcgcaatat cgaacaagga    40080
aagctgcatt tccttgatct gctgcttcgt gtgtttcagc aacgcggcct gcttggcctc    40140
gctgacctgt tttgccaggt cctcgccggc ggttttcgc ttcttggtcg tcatagttcc     40200
tcgcgtgtcg atggtcatcg acttcgccaa acctgccgcc tcctgttcga gacgacgcga    40260
acgctccacg gcggccgatg gcgcgggcag ggcaggggga gccagttgca cgctgtcgcg    40320
ctcgatcttg gccgtagctt gctggaccat cgagccgacg gactggaagg tttcgcgggg    40380
cgcacgcatg acggtgcggc ttgcgatggt ttcggcatcc tcggcggaaa accccgcgtc    40440
gatcagttct tgcctgtatg ccttccggtc aaacgtccga ttcattcacc ctccttgcgg    40500
gattgccccg actcacgccg gggcaatgtg cccttattcc tgatttgacc cgcctggtgc    40560
cttggtgtcc agataatcca ccttatcggc aatgaagtcg gtcccgtaga ccgtctggcc    40620
```

```
gtccttctcg tacttggtat tccgaatctt gccctgcacg aataccagcg acccccttgcc   40680
caaatacttg ccgtgggcct cggcctgaga gccaaaacac ttgatgcgga agaagtcggt   40740
gcgctcctgc ttgtcgccgg catcgttgcg ccactcttca ttaaccgcta tatcgaaaat   40800
tgcttgcggc ttgttagaat tgccatgacg tacctcggtg tcacgggtaa gattaccgat   40860
aaactggaac tgattatggc tcatatcgaa agtctccttg agaaggaga ctctagttta    40920
gctaaacatt ggttccgctg tcaagaactt tagcggctaa aattttgcgg gccgcgacca   40980
aaggtgcgag gggcggcttc cgctgtgtac aaccagatat ttttcaccaa catccttcgt   41040
ctgctcgatg agcggggcat gacgaaacat gagctgtcgg agagggcagg ggtttcaatt   41100
tcgttttat cagacttaac caacggtaag gccaacccct cgttgaaggt gatggaggcc    41160
attgccgacg ccctggaaac tcccctacct cttctcctgg agtccaccga ccttgaccgc   41220
gaggcactcg cggagattgc gggtcatcct ttcaagagca gcgtgccgcc cggatacgaa   41280
cgcatcagtg tggttttgcc gtcacataag gcgtttatcg taaagaaatg gggcgacgac   41340
acccgaaaaa agctgcgtgg aaggctctga cgccaagggt tagggcttgc acttccttct   41400
ttagccgcta aaacgccccc ttctctgcgg gccgtcggct cgcgcatcat atcgacatcc   41460
tcaacggaag ccgtgccgcg aatggcatcg ggcgggtgcg ctttgacagt tgttttctat   41520
cagaacccct acgtcgtgcg gttcgattag ctgtttgtct tgcaggctaa acactttcgg   41580
tatatcgttt gcctgtgcga taatgttgct aatgatttgt tgcgtagggg ttactgaaaa   41640
gtgagcggga aagaagagtt tcagaccatc aaggagcggg ccaagcgcaa gctggaacgc   41700
gacatgggtg cggacctgtt ggccgcgctc aacgacccga aaaccgttga agtcatgctc   41760
aacgcggacg gcaaggtgtg gcacgaacgc cttggcgagc cgatgcggta catctgcgac   41820
atgcggccca gccagtcgca ggcgattata gaaacggtgg ccggattcca cggcaaagag   41880
gtcacgcggc attcgcccat cctggaaggc gagttcccct tggatggcag ccgctttgcc   41940
ggccaattgc cgccggtcgt ggccgcgcca acctttgcga tccgcaagcg cgcggtcgcc   42000
atcttcacgc tggaacagta cgtcgaggcg ggcatcatga cccgcgagca atacgaggtc   42060
attaaaagcg ccgtcgcggc gcatcgaaac atcctcgtca ttggcggtac tggctcgggc   42120
aagaccacgc tcgtcaacgc gatcatcaat gaaatggtcg ccttcaaccc gtctgagcgc   42180
gtcgtcatca tcgaggacac cggcgaaatc cagtgcgccg cagagaacgc cgtccaatac   42240
cacaccagca tcgacgtctc gatgacgctg ctgctcaaga caacgctgcg tatgcgcccc   42300
gaccgcatcc tggtcggtga ggtacgtggc cccgaagccc ttgatctgtt gatgcctgg    42360
aacaccgggc atgaaggagg tgccgccacc ctgcacgcaa acaacccaa agcgggcctg    42420
agccggctcg ccatgcttat cagcatgcac ccggattcac cgaaacccat tgagccgctg   42480
attggcgagg cggttcatgt ggtcgtccat atcgccagga cccctagcgg ccgtcgagtg   42540
caagaaattc tcgaagttct tggttacgag aacggccagt acatcaccaa aaccctgtaa   42600
ggagtatttc caatgacaac ggctgttccg ttccgtctga ccatgaatcg cggcattttg   42660
ttctaccttg ccgtgttctt cgttctcgct ctcgcgttat ccgcgcatcc ggcgatggcc   42720
tcggaaggca ccggcggcag cttgccatat gagagctggc tgacgaacct gcgcaactcc   42780
gtaaccggcc cggtggcctt cgcgctgtcc atcatcggca tcgtcgtcgc cggcggcgtg   42840
ctgatcttcg gcggcgaact caacgccttc ttccgaaccc tgatcttcct ggttctggtg   42900
atggcgctgc tggtcggcgc gcagaacgtg atgagcacct tcttcggtcg tggtgccgaa   42960
atcgcggccc tcggcaacgg ggcgctgcac caggtgcaag tcgcggcggc ggatgccgtg   43020
```

```
cgtgcggtag cggctggacg gctcgcctaa tcatggctct gcgcacgatc cccatccgtc   43080
gcgcaggcaa ccgagaaaac ctgttcatgg gtggtgatcg tgaactggtg atgttctcgg   43140
gcctgatggc gttttgcgct gattttcagcg cccaagagct gcgggccacc gtggtcggtc   43200
tgatcctgtg gttcggggcg ctctatgcgt tccgaatcat ggcgaaggcc gatccgaaga   43260
tgcggttcgt gtacctgcgt caccgccggt acaagccgta ttacccggcc cgctcgaccc   43320
cgttccgcga gaacaccaat agccaaggga agcaataccg atgatccaag caattgcgat   43380
tgcaatcgcg ggcctcggcg cgcttctgtt gttcatcctc tttgcccgca tccgcgcggt   43440
cgatgccgaa ctgaaactga aaaagcatcg ttccaaggac gccggcctgg ccgatctgct   43500
caactacgcc gctgtcgtcg atgacggcgt aatcgtgggc aagaacggca gctttatggc   43560
tgcctggctg tacaagggcg atgacaacgc aagcagcacc gaccagcagc gcgaagtagt   43620
gtccgcccgc atcaaccagg ccctcgcggg cctgggaagt gggtggatga tccatgtgga   43680
cgccgtgcgg cgtcctgctc cgaactacgc ggagcggggc ctgtcggcgt tccctgaccg   43740
tctgacggca gcgattgaag aagagcgctc ggtcttgcct tgctcgtcgg tgatgtactt   43800
caccagctcc gcgaagtcgc tcttcttgat ggagcgcatg gggacgtgct tggcaatcac   43860
gcgcaccccc cggccgtttt agcggctaaa aaagtcatgg ctctgccctc gggcggacca   43920
cgcccatcat gaccttgcca agctcgtcct gcttctcttc gatcttcgcc agcagggcga   43980
ggatcgtggc atcaccgaac cgcgccgtgc gcgggtcgtc ggtgagccag agtttcagca   44040
ggccgcccag gcggcccagg tcgccattga tgcgggccag ctcgcggacg tgctcatagt   44100
ccacgacgcc cgtgattttg tagccctggc cgacggccag caggtaggcc gacaggctca   44160
tgccggccgc cgccgccttt tcctcaatcg ctcttcgttc gtctggaagg cagtacacct   44220
tgataggtgg gctgcccttc ctggttggct tggtttcatc agccatccgc ttgccctcat   44280
ctgttacgcc ggcggtagcc ggccagcctc gcagagcagg attcccgttg agcaccgcca   44340
ggtgcgaata agggacagtg aagaaggaac acccgctcgc gggtgggcct acttcaccta   44400
tcctgcccgg ctgacgccgt tggatacacc aaggaaagtc tacacgaacc ctttggcaaa   44460
atcctgtata tcgtgcgaaa aaggatggat ataccgaaaa aatcgctata atgacccccga   44520 agcagggtta tgcagcggaa aagcgctgct tccctgctgt tttgtggaat atctaccgac   44580
tggaaacagg caaatgcagg aaattactga actgagggga caggcgagag acgatgccaa   44640
agagctacac cgacgagctg gccgagtggg ttgaatcccg cgcggccaag aagcgccggc   44700
gtgatgaggc tgcggttgcg ttcctggcgg tgagggcgga tgtcgaggcg gcgttagcgt   44760
ccggctatgc gctcgtcacc atttgggagc acatgcggga acgggggaag gtcaagttct   44820
cctacgagac gttccgctcg cacgccaggc ggcacatcaa ggccaagccc gccgatgtgc   44880
ccgcaccgca ggccaaggct gcggaacccg cgccggcacc caagacgccg gagccacggc   44940
ggccgaagca gggggggcaag gctgaaaagc cggcccccgc tgcggccccg accggcttca   45000
ccttcaaccc aacaccggac aaaaaggatc tactgtaatg gcgaaaattc acatggtttt   45060
gcagggcaag ggcggggtcg gcaagtcggc catcgccgcg atcattgcgc agtacaagat   45120
ggacaagggg cagacaccct tgtgcatcga caccgacccg gtgaacgcga cgttcgaggg   45180
ctacaaggcc ctgaacgtcc gccggctgaa catcatggcc ggcgacgaaa ttaactcgcg   45240
caacttcgac accctggtcg agctgattgc gccgaccaag gatgacgtgg tgatcgacaa   45300
cggtgccagc tcgttcgtgc ctctgtcgca ttacctcatc agcaaccagg tgccggctct   45360
gctgcaagaa atggggcatg agctggtcat ccataccgtc gtcaccggcg gccaggctct   45420
```

```
cctggacacg gtgagcggct tcgcccagct cgccagccag ttcccggccg aagcgctttt   45480
cgtggtctgg ctgaacccgt attggggggcc tatcgagcat gagggcaaga gctttgagca   45540
gatgaaggcg tacacggcca acaaggcccg cgtgtcgtcc atcatccaga ttccggccct   45600
caaggaagaa acctacggcc gcgatttcag cgacatgctg caagagcggc tgacgttcga   45660
ccaggcgctg gccgatgaat cgctcacgat catgacgcgg caacgcctca agatcgtgcg   45720
gcgcggcctg tttgaacagc tcgacgcggc ggccgtgcta tgagcgacca gattgaagag   45780
ctgatccggg agattgcggc caagcacggc atcgccgtcg gccgcgacga cccggtgctg   45840
atcctgcata ccatcaacgc ccggctcatg gccgacagtg cggccaagca agaggaaatc   45900
cttgccgcgt tcaaggaaga gctggaaggg atcgcccatc gttggggcga ggacgccaag   45960
gccaaagcgg agcggatgct gaacgcgcc ctggcggcca gcaaggacgc aatggcgaag   46020
gtaatgaagg acagcgccgc gcaggcggcc gaagcgatcc gcaggaaat cgacgacggc   46080 cttgccgcc agctcgcggc caaggtcgcg gacgcgcggc gcgtggcgat gatgaacatg   46140
atcgccggcg gcatggtgtt gttcgcggcc gccctggtgg tgtgggcctc gttatgaatc   46200
gcagaggcgc agatgaaaaa gcccggcgtt gccgggcttt gttttttgcgt tagctgggct   46260 tgtttgacag gcccaagctc tgactgcgcc cgcgctcgcg ctcctgggcc tgtttcttct   46320
cctgctcctg cttgcgcatc agggcctggt gccgtcgggc tgcttcacgc atcgaatccc   46380
agtcgccggc cagctcggga tgctccgcgc gcatcttgcg cgtcgccagt tcctcgatct   46440
tgggcgcgtg aatgcccatg ccttccttga tttcgcgcac catgtccagc cgcgtgtgca   46500
gggtctgcaa gcgggcttgc tgttgggcct gctgctgctg ccaggcggcc tttgtacgcg   46560
gcagggacag caagccgggg gcattggact gtagctgctg caaacgcgcc tgctgacggt   46620
ctacgagctg ttctaggcgg tcctcgatgc gctccacctg gtcatgcttt gcctgcacgt   46680
agagcgcaag ggtctgctgg taggtctgct cgatgggcgc ggattctaag agggcctgct   46740
gttccgtctc ggcctcctgg gccgcctgta gcaaatcctc gccgctgttg ccgctggact   46800
gctttactgc cggggactgc tgttgccctg ctcgcgccgt cgtcgcagtt cggcttgccc   46860
ccactcgatt gactgcttca tttcgagccg cagcgatgcg atctcggatt gcgtcaacgg   46920
acggggcagc gcggaggtgt ccggcttctc cttgggtgag tcggtcgatg ccatagccaa   46980
aggtttcctt ccaaaatgcg tccattgctg gaccgtgttt ctcattgatg cccgcaagca   47040
tcttcggctt gaccgccagg tcaagcgcgc cttcatgggc ggtcatgacg gacgccgcca   47100
tgaccttgcc gccgttgttc tcgatgtagc cgcgtaatga ggcaatggtg ccgcccatcg   47160
tcagcgtgtc atcgacaacg atgtacttct ggccggggat cacctccccc tcgaaagtcg   47220
ggttgaacgc caggcgatga tctgaaccgg ctccggttcg ggcgaccttc tcccgctgca   47280
caatgtccgt ttcgacctca aggccaaggc ggtcggccag aacgaccgcc atcatggccg   47340
gaatcttgtt gttccccgcc gcctcgacgg cgaggactgg aacgatgcgg ggcttgtcgt   47400
cgccgatcag cgtcttgagc tgggcaacag tgtcgtccga aatcaggcgc tcgaccaaat   47460
taagcgccgc ttccgcgtcg ccctgcttcg cagcctggta ttcaggctcg ttggtcaaag   47520
aaccaaggtc gccgttgcga accaccttcg ggaagtctcc ccacggtgcg cgctcggctc   47580
tgctgtagct gctcaagacg cctccctttt tagccgctaa aactctaacg agtgcgcccg   47640
cgactcaact tgacgctttc ggcacttacc tgtgccttgc cacttgcgtc ataggtgatg   47700
cttttcgcac tccgatttc aggtacttta tcgaaatctg accggcgtg cattacaaag   47760 ttcttcccca cctgttggta aatgctgccg ctatctgcgt ggacgatgct gccgtcgtgg   47820
```

```
cgctgcgact tatcggcctt tgggccata tagatgttgt aaatgccagg tttcagggcc    47880
ccggctttat ctaccttctg gttcgtccat gcgccttggt tctcggtctg gacaattctt    47940
tgcccattca tgaccaggag gcggtgtttc attgggtgac tcctgacggt tgcctctggt    48000
gttaaacgtg tcctggtcgc ttgccggcta aaaaaaagcc gacctcggca gttcgaggcc    48060
ggctttccct agagccgggc gcgtcaaggt tgttccatct attttagtga actgcgttcg    48120
atttatcagt tactttcctc ccgctttgtg tttcctccca ctcgtttccg cgtctagccg    48180 accccctcaac atagcggcct cttcttgggc tgcctttgcc tcttgccgcg cttcgtcacg    48240
ctcggcttgc accgtcgtaa agcgctcggc ctgcctggcc gcctcttgcg ccgccaactt    48300
cctttgctcc tggtgggcct cggcgtcggc ctgcgccttc gctttcaccg ctgccaactc    48360
cgtgcgcaaa ctctccgctt cgcgcctggt ggcgtcgcgc tcgccgcgaa gcgcctgcat    48420
ttcctggttg gccgcgtcca gggtcttgcg gctctcttct ttgaatgcgc gggcgtcctg    48480
gtgagcgtag tccagctcgg cgcgcagctc ctgcgctcga cgctccacct cgtcggcccg    48540
ctgcgtcgcc agcgcggccc gctgctcggc tcctgccagg gcggtgcgtg cttcggccag    48600
ggcttgccgc tggcgtgcgg ccagctcggc cgcctcggcg gcctgctgct ctagcaatgt    48660
aacgcgcgcc tgggcttctt ccagctcgcg ggcctgcgcc tcgaaggcgt cggccagctc    48720
cccgcgcacg gcttccaact cgttgcgctc acgatcccag ccggcttgcg ctgcctgcaa    48780
cgattcattg gcaagggcct gggcggcttg ccagagggcg gccacggcct ggttgccggc    48840
ctgctgcacc gcgtccggca cctggactgc cagcggggcg gcctgcgccg tgcgctggcg    48900
tcgccattcg cgcatgccgg cgctggcgtc gttcatgttg acgcgggcgg ccttacgcac    48960
tgcatccacg gtcgggaagt tctcccggtc gccttgctcg aacagctcgt ccgcagccgc    49020
aaaaatgcgg tcgcgcgtct cttttgttcag ttccatgttg gctccggtaa ttggtaagaa    49080
taataatact cttacctacc ttatcagcgc aagagtttag ctgaacagtt ctcgacttaa    49140
cggcaggttt tttagcggct gaagggcagg caaaaaaagc cccgcacggt cggcggggc    49200 aaagggtcag cgggaagggg attagcgggc gtcgggcttc ttcatgcgtc ggggccgcgc    49260
ttcttgggat ggagcacgac gaagcgcgca cgcgcatcgt cctcggccct atcggcccgc    49320
gtcgcggtca ggaacttgtc gcgcgctagg tcctccctgg tgggcaccag gggcatgaac    49380
tcggcctgct cgatgtaggt ccactccatg accgcatcgc agtcgaggcc gcgttccttc    49440
accgtctctt gcaggtcgcg gtacgcccgc tcgttgagcg gctggtaacg ggccaattgg    49500
tcgtaaatgg ctgtcggcca tgagcggcct ttcctgttga gccagcagcc gacgacgaag    49560
ccggcaatgc aggcccctgg cacaaccagg ccgacgccgg gggcagggga tggcagcagc    49620
tcgccaacca ggaaccccgc cgcgatgatg ccgatgccgg tcaaccagcc cttgaaacta    49680
tccggccccg aaacacccct gcgcattgcc tggatgctgc gccggatagc ttgcaacatc    49740
aggagccgtt tcttttgttc gtcagtcatg gtccgccctc accagttgtt cgtatcggtg    49800
tcggacgaac tgaaatcgca agagctgccg gtatcggtcc agccgctgtc cgtgtcgctg    49860
ctgccgaagc acgcgagggg gtccgcgaac gccgcagacg gcgtatccgg ccgcagcgca    49920
tcgcccagca tggccccggt cagcgagccg ccggccaggt agcccagcat ggtgctgttg    49980
gtcgccccgg ccaccagggc cgacgtgacg aaatcgccgt cattccctct ggattgttcg    50040
ctgctcggcg gggcagtgcg ccgcgccggc ggcgtcgtgg atggctcggg ttggctggcc    50100
tgcgacggcc ggcgaaaggt gcgcagcagc tcgttatcga ccggctgcgg cgtcgggccc    50160
gccgccttgc gctgcggtcg gtgttccttc ttcggctcgc gcagcttgaa cagcatgatc    50220
```

```
gcggaaacca gcagcaacgc cgcgcctacg cctcccgcga tgtagaacag catcggattc  50280
attcttcggt cctccttgta gcggaaccgt tgtctgtgcg gcgcgggtgg cccgcgccgc  50340
tgtctttggg gatcagccct cgatgagcgc gaccagtttc acgtcggcaa ggttcgcctc  50400
gaactcctgg ccgtcgtcct cgtacttcaa ccaggcatag ccttccgccg gcggccgacg  50460
gttgaggata aggcgggcag ggcgctcgtc gtgctcgacc tggacgatgg cctttttcag  50520
cttgtccggg tccggctcct tcgcgccctt ttccttggcg tccttaccgt cctggtcgcc  50580
gtcctcgccg tcctggccgt cgccggcctc cgcgtcacgc tcggcatcag tctggccgtt  50640
gaaggcatcg acggtgttgg gatcgcggcc cttctcgtcc aggaactcgc gcagcagctt  50700
gaccgtgccg cgcgtgattt cctgggtgtc gtcgtcaagc cacgcctcga cttcctccgg  50760
gcgcttcttg aaggccgtca ccagctcgtt caccacggtc acgtcgcgca cgcggccggt  50820
gttgaacgca tcggcgatct tctccggcag gtccagcagc gtgacgtgct gggtgatgaa  50880
cgccggcgac ttgccgattt ccttggcgat atcgcctttc ttcttgccct tcgccagctc  50940
gcggccaatg aagtcggcaa tttcgcgcgg ggtcagctcg ttgcgttgca ggttctcgat  51000
aacctggtcg gcttcgttgt agtcgttgtc gatgaacgcc gggatggact tcttgccggc  51060
ccacttcgag ccacggtagc ggcgggcgcc gtgattgatg atatagcggc ccggctgctc  51120
ctggttctcg cgcaccgaaa tgggtgactt caccccgcgc tctttgatcg tggcaccgat  51180
ttccgcgatg ctctccgggg aaaagccggg gttgtcggcc gtccgcggct gatgcggatc  51240
ttcgtcgatc aggtccaggt ccagctcgat agggccggaa ccgccctgag acgccgcagg  51300
agcgtccagg aggctcgaca ggtcgccgat gctatccaac cccaggccgg acggctgcgc  51360
cgcgcctgcg gcttcctgag cggccgcagc ggtgtttttc ttggtggtct tggcttgagc  51420
cgcagtcatt gggaaatctc catcttcgtg aacacgtaat cagccagggc gcgaacctct  51480
ttcgatgcct tgcgcgcggc cgttttcttg atcttccaga ccggcacacc ggatgcgagg  51540
gcatcggcga tgctgctgcg caggccaacg gtggccggaa tcatcatctt ggggtacgcg  51600
gccagcagct cggcttggtg gcgcgcgtgg cgcggattcc gcgcatcgac cttgctgggc  51660
accatgccaa ggaattgcag cttggcgttc ttctggcgca cgttcgcaat ggtcgtgacc  51720
atcttcttga tgccctggat gctgtacgcc tcaagctcga tgggggacag cacatagtcg  51780
gccgcgaaga gggcggccgc caggccgacg ccaagggtcg gggccgtgtc gatcaggcac  51840
acgtcgaagc cttggttcgc cagggccttg atgttcgccc cgaacagctc gcgggcgtcg  51900
tccagcgaca gccgttcggc gttcgccagt accgggttgg actcgatgag ggcgaggcgc  51960
gcggcctggc cgtcgccggc tgcgggtgcg gtttcggtcc agccgccggc agggacagcg  52020
ccgaacagct tgcttgcatg caggccggta gcaaagtcct tgagcgtgta ggacgcattg  52080
ccctgggggt ccaggtcgat cacggcaacc cgcaagccgc gctcgaaaaa gtcgaaggca  52140
agatgcacaa gggtcgaagt cttgccgacg ccgcctttct ggttggccgt gaccaaagtt  52200
ttcatcgttt ggtttcctgt ttttcttgg cgtccgcttc ccacttccgg acgatgtacg  52260
cctgatgttc cggcagaacc gccgttaccc gcgcgtaccc ctcgggcaag ttcttgtcct  52320
cgaacgcggc ccacacgcga tgcaccgctt gcgacactgc gcccctggtc agtcccagcg  52380
acgttgcgaa cgtcgcctgt ggcttcccat cgactaagac gccccgcgct atctcgatgg  52440
tctgctgccc cacttccagc ccctggatcg cctcctggaa ctggctttcg gtaagccgtt  52500
tcttcatgga taacacccat aatttgctcc gcgccttggt tgaacatagc ggtgacagcc  52560
gccagcacat gagagaagtt tagctaaaca tttctcgcac gtcaacacct ttagccgcta  52620
```

```
aaactcgtcc ttggcgtaac aaaacaaaag cccggaaacc gggctttcgt ctcttgccgc    52680
ttatggctct gcacccggct ccatcaccaa caggtcgcgc acgcgcttca ctcggttgcg    52740
gatcgacact gccagcccaa caaagccggt tgccgccgcc gccaggatcg cgccgatgat    52800
gccggccaca ccgccatcg cccaccaggt cgccgccttc cggttccatt cctgctggta     52860
ctgcttcgca atgctggacc tcggctcacc ataggctgac cgctcgatgg cgtatgccgc    52920
ttctcccctt ggcgtaaaac ccagcgccgc aggcggcatt gccatgctgc ccgccgcttt    52980
cccgaccacg acgcgcgcac caggcttgcg gtccagacct tcggcacgg cgagctgcgc     53040 aaggacataa tcagccgccg acttggctcc acgcgcctcg atcagctctt gcactcgcgc    53100
gaaatccttg gcctccacgg ccgccatgaa tcgcgcacgc ggcgaaggct ccgcagggcc    53160
ggcgtcgtga tcgccgccga gaatgcccctt caccaagttc gacgcacga aaatcatgct    53220 gacggctatc accatcatgc agacggatcg cacgaacccg ctgaattgaa cacgagcacg    53280
gcacccgcga ccactatgcc aagaatgccc aaggtaaaaa ttgccggccc cgccatgaag    53340
tccgtgaatg ccccgacggc cgaagtgaag ggcaggccgc acccaggcc gccgccctca     53400 ctgcccggca cctggtcgct gaatgtcgat gccagcacct gcggcacgtc aatgcttccg    53460
ggcgtcgcgc tcgggctgat cgcccatccc gttactgccc cgatcccggc aatggcaagg    53520
actgccagcg ctgccatttt tggggtgagg ccgttcgcgg ccgaggggcg cagcccctgg    53580
ggggatggga ggcccgcgtt agcgggccgg gagggttcga aaggggggg caccccctt      53640 cggcgtgcgc ggtcacgcgc acagggcgca gccctggtta aaaacaaggt ttataaatat    53700
tggtttaaaa gcaggttaaa agacaggtta gcggtggccg aaaaacgggc ggaaaccctt    53760
gcaaatgctg gattttctgc ctgtggacag ccctcaaat gtcaataggt gcgcccctca     53820
tctgtcagca ctctgcccct caagtgtcaa ggatcgcgcc cctcatctgt cagtagtcgc    53880
gcccctcaag tgtcaatacc gcagggcact tatccccagg cttgtccaca tcatctgtgg    53940
gaaactcgcg taaaatcagg cgttttcgcc gatttgcgag gctggccagc tccacgtcgc    54000
cggccgaaat cgagcctgcc cctcatctgt caacgccgcg ccgggtgagt cggcccctca    54060
agtgtcaacg tccgcccctc atctgtcagt gagggccaag ttttccgcga ggtatccaca    54120
acgccggcgg ccgcggtgtc tcgcacacgg cttcgacggc gtttctggcg cgtttgcagg    54180
gccatagacg gccgccagcc cagcggcgag ggcaaccagc ccggtgagcg tcggaaaggc    54240
gctggaagcc ccgtagcgac gcggagaggg gcgagacaag ccaagggcgc aggctcgatg    54300
cgcagcacga catagccggt tctcgcaagg acgagaattt ccctgcggtg ccctcaagt     54360 gtcaatgaaa gttccaacg cgagccattc gcgagagcct tgagtccacg ctagatgaga     54420
gctttgttgt aggtggacca gttggtgatt ttgaactttt gctttgccac ggaacgtct     54480 gcgttgtcgg gaagatgcgt gatctgatcc ttcaactcag caaaagttcg atttattcaa    54540
caaagccacg ttgtgtctca aaatctctga tgttacattg cacaagataa aaatatatca    54600
tcatgaacaa taaaactgtc tgcttacata aacagtaata caagggtgtg tatgagccat    54660
attcaacggg aaacgtcttg ctcgac                                        54686
```

<210> SEQ ID NO 89
<211> LENGTH: 3324
<212> TYPE: DNA
<213> ORGANISM: Zea mays

<400> SEQUENCE: 89

```
tggtccttgt ttgatttact tccaggatta tataatccag cttatggatt atataagtac    60
```

```
ctattgacgt cacgtgctta tgtattataa taatctaggt atatagatta tataatctat    120
ctaataataa tctgtgttgt ttgtttatct ctcaaaacaa acaggtccta aaatggtccc    180
gggcgtccaa tgtgtcgtca agtagtgtta agctaaatcg acatttcttt gtgggttgtg    240
tggaaggtgt tccttttcct taagttgtta gttgtgcaag gtgttcctta gagcatctcc    300
aataggacct ataatggatt ctattttgaa ttataagact ctaacaacaa aagcatactt    360
taatggggat tctattttac aaaaaaatat caaatgatta tatggtcgat tcctcgggtc    420
ctaaatatag tatctcatat aatagagctc tatcctcatt ttatatacta tttttaagtt    480
tttatttact aaataacatg atttatttc taatactatg aactcaacta ttagagctgt    540
aaacgttttt gtggtactaa acactttaaa tcaggtccta ttttaatttg aaggacttaa    600
atataagact tctggttaga gatgctctta gcgagtgttt gtgcatgatt gctatttagt    660 cttgtggat tgtggaaggt gttactttc ctcaagttgt tagttgtgca aggtgtttct    720
tagagcatct ctaacaggag ccttaacgga atctattttg aagtatagta ctttaacacc    780 aaaacatac tttaataggg gtcctatttt acaaaaaaat tatcaaatga ttataaggtc    840
cactcctcgg gtcctaaata taatatctca tatactagag ctctatcctc attttatata    900
ctatccctag gttttattc cctaaataac atgatttatt tcctaatact aagatatagg    960
gctcaactat tggagttgca aatgtttttt ggcactaaac actttatatc aggtcctatt   1020
ttaattttaa tttgaaggac tcaaatatag gacttctcgt tagagatgct cttagcgagt   1080
gtttgtgcat gattgctatt tatgtctgta gtttagttgg gggctttaat atgtttagtt   1140
gaagttctag tattttttag gttctccact ctttggatta tgacaacgac cactatccaa   1200
gcagtctttg agtgcaaacg cgcgagcaaa ctatctgatc tattaaatta tgatccaacc   1260
gttatgtcat attgaagact taaacccttt caccaccagc ccaagtatct ttatgaaaaa   1320
ccctaacaaa ccacaattgc atctatggtt ggattataat ttaacgtatc agatggttcg   1380
cttgcatgct tacatatcta gaaactgttt gcataacagt cgttctcttt ggttatataa   1440
tgctttagta atcatcagcc aagtgtaaac aaatggtaca aactagtagt gaacacatcc   1500
tccctaccta tctctagggg tgtcatagta aattctatgt cttatttgtc cgcgattgaa   1560
gaaaaatgac aaaagatct gacattcgaa taaacatctg tttccactcc tacctatctg   1620
acctcctatt tcaaactcca ctttgtaaca cggtacaaaa tcactcccta cctatctgac   1680
ctcctatttc aaactccact cagtaaacaa tattgtctat ggtacaaaac caagtgtttt   1740
atacatctat ttgcacgatc tgctcgagtc aggcatcctt gacacacaac atactccttg   1800
tggctataaa tgtccaaata gagcagacct aatgggtgga ccgttgcatg acacgactta   1860
tcccaagacg agcacagttc gccccattgg tcatgggggt ccgggctagt ctagcctgat   1920
catcgggtca cacttaggcc acaggtgtgc cacaacggga tagcccaaca tgtccctttt   1980
tgtcatgcat atatctatat tatagttagt ataatgtaaa aaaacaaaag gtatgtgtgt   2040
tatgttggtt agatgtgttt aaataactct ttaaagctag caactatggt ttaaatcata   2100
catatacaca tttttatttt atttttattt aaacgatatg ggccttctag gcacgtcgag   2160
tgtgacgggc cagtgagatg acacattata attactggtc tagcaggccg tacctaggtc   2220
tttctcgtgg gccaagacta agggttggcc cgttggctaa tctgtacggt accgatactg   2280
tcctaattca tttgaacacc tgtagaagag gggaatttat aattgaggag gaatgtactc   2340
atgcggtaca ccaggggaat tgttttgttg tgctcagcga tagatttcaa cgcaacggtg   2400
agccagtttc actaaaaaaa gggggggggg gggggggggg ggaaggccac atcaaaggcg   2460
```

| | |
|---|---:|
| aggtgctgac gagcagaaga tgctagcagt gacgccaagt ccagcagcta gcaatgaaag | 2520 |
| ggtactcggg atttaacaat gcctagagac ggcatcatcc cctcaataat ccggtgctct | 2580 |
| cttttgttt attcaccagt tggcgtagct atatacacat gtctggtctg acgaacaaat | 2640 |
| caagggatcg ctagctcggg ctagccttcc tatcactgtc atgacatgtg ctctgcctct | 2700 |
| gctggttgat aagccgtgcg ccttctcgct aattctttct tgtgctagag gcgagtcaaa | 2760 |
| caaacgctgc acctcgtagc ccttaatctg cgctaagggt cacatgaccc tgttccctat | 2820 |
| cgctagttac caacgaccca ttccccctga cagatactta cgacgcgtcc gtacgcggca | 2880 |
| ggcctcggca gttcggcatc accagcaccg gcgccggcat tcgcccctg ccagccggtt | 2940 |
| cgcagattcg cagggcggag tcggccgcag ttgccgcatc ccaaacgccc gggaaccttt | 3000 |
| ggggcccctc tacgagcaaa tgaagttgct gcccctggct tcgtaaagct ctgacttttg | 3060 |
| atcacttgat tggcagtcgt actcctcgct cataggccga cacggccgca aagtcaacta | 3120 |
| cccgctccgc catccttcaa cccccgccac gcgcctatat atgttcgcgg ccatgtccgt | 3180 |
| actagtcctc caacccacaa gccacaaccc cgagctcaga tccctcgcct cgtgtcgtgt | 3240 |
| ctccggtcga cgacgaccaa cagccagtgt gggccagacg acaccgccg agctatagcg | 3300 |
| cttggtgata gcaagggacg accg | 3324 |

<210> SEQ ID NO 90
<211> LENGTH: 500
<212> TYPE: DNA
<213> ORGANISM: Zea mays

<400> SEQUENCE: 90

| | |
|---|---:|
| agttaccaac gacccattcc ccctgacaga tacttacgac gcgtccgtac gcggcaggcc | 60 |
| tcggcagttc ggcatcacca gcaccggcgc cggcattcgc cccctgccag ccggttcgca | 120 |
| gattcgcagg gcggagtcgg ccgcagttgc cgcatcccaa acgcccggga acctttgggg | 180 |
| cccctctacg agcaaatgaa gttgctgccc ctggcttcgt aaagctctga cttttgatca | 240 |
| cttgattggc agtcgtactc ctcgctcata ggccgacacg gccgcaaagt caactacccg | 300 |
| ctccgccatc cttcaacccc cgccacgcgc ctatatatgt tcgcggccat gtccgtacta | 360 |
| gtcctccaac ccacaagcca caaccccgag ctcagatccc tcgcctcgtg tcgtgtctcc | 420 |
| ggtcgacgac gaccaacagc cagtgtgggc cagacggaca ccgccgagct atagcgcttg | 480 |
| gtgatagcaa gggacgaccg | 500 |

<210> SEQ ID NO 91
<211> LENGTH: 2025
<212> TYPE: DNA
<213> ORGANISM: Zea mays

<400> SEQUENCE: 91

| | |
|---|---:|
| gagcgctccg ctgccgtgcg cgcccccgcg ccggcctccc actggatcgc tccacctcat | 60 |
| gctccaaatc tttattggtt tccacgttgc cccctcgccg tccccaacca tcgaccgcgc | 120 |
| cgcgcccgct gccgcctccc agctcgctct atataaacac cacgtacgcg ccgaagcatc | 180 |
| agcacagcca cgtacgtacg accggcttcc ggcaggtgag agaacagtga aagcaggcg | 240 |
| agcggtgaca tggcggaggg ggagttcaag cccgcggcga tgcaggtgga ggctcctgcc | 300 |
| gaggcggcgg cggcgccgtc caagccgcgg ttcaggatgc ccgtcgactc cgacaacaag | 360 |
| gccaccgagt tctggctctt ctccttgcgc aggccgcaca tgagcgcctt ccacatgtcg | 420 |
| tggttctcct tcttctgctg cttcctctcc accttcgcgg cgccgccgct gctcccgctc | 480 |

-continued

```
atccgggaca cgctggggct cacggccacg gacatcggca acgccgggat cgcctccgtg    540
tccggcgcgg tcttcgcgcg cgtggccatg ggcacggcgt gcgacctggt gggcccgcgc    600
ctggcgtccg cggccatcat actcctcacc acgcccgccg tctactactc cgccgtcatc    660
gactccgcct cgtcctacct gctcgtgcgc ttcttcacgg gcttctcgct cgcgtccttc    720
gtgtccacgc agttctggat gagctccatg ttctcgccgc ccaaggtggg gctggccaac    780
ggcgtcgccg gggggtgggg caacctcggc ggcggcgccg tgcagctcat catgccgctc    840
gtgttcgagg ccatccgcaa ggccggggcc acgccgttca cggcgtggcg cgtcgccttc    900
ttcgtcccgg gcctgctgca gacgctgtcg gccgtcgccg tgctggcgtt cggccaggac    960
atgcccgacg gcaactaccg caagctgcac aggtccggcg acatgcacaa ggacagcttc   1020
ggcaacgtgc tccgccacgc cgtcaccaac taccgcgcct ggatcctggc gctcacctac   1080
ggatactgct cggcgtgga gctcgccgtg acaacatcg tcgcgcagta cttctacgac   1140
cgcttcggcg tcaagctcag caccgccggc ttcatcgccg ccagcttcgg gatggccaac   1200
atcgtctccc gccccggcgg cggcctcctg tcggactggc tctccagccg cttcggcatg   1260
cgcggcaggc tgtggggcct gtgggtggtg cagaccatcg ggggcgtcct ctgcgtcgtg   1320
ctcggcgccg tcgactactc cttcgccgcg tccgtggccg tcatgatact cttctccatg   1380
ttcgtgcagg cggcctgcgg gctcaccttt ggcatcgtcc cgttcgtctc ccgaaggtcg   1440
ctggggctca tctccggcat gaccggcggc ggcggcaacg tgggcgccgt gctcacgcag   1500
ctcatcttct ccacggatc caagtacaag acggagacgg ggatcaagta catgggggttc   1560 atgatcatcg cctgcacgtt gcccatcacg ctcatctact tcccgcagtg gggcggcatg   1620
ttcctggggc gcggcccgg ggcgacggcg gaggactact acaaccggga gtggacagcg    1680
cacgagtgcg acaagggttt caacaccgcg agcgtacgct ttgcggagaa cagcgtgcgg   1740 gaaggggac gctcgggcag ccagtccaag cacactactg tgcccgtcga gtcctcgccg   1800
gccgacgtgt gaaacacaca caagcatacg gtactgcccg tataatcagc ggtccctccc   1860
gtgtcagcaa atcatatgta gtgttcctaa gtcgtgatga ctccgtacgt gtggtaattt   1920
ctgtgtgaag gaaaaaccgg gggtgaattt cagcgaggag tgacattata agcagggctc   1980
gtttgcataa aaaaaaaaaa aaaaaaaaaa aaaaaaaaaa aaaaa               2025
```

<210> SEQ ID NO 92
<211> LENGTH: 520
<212> TYPE: PRT
<213> ORGANISM: Zea mays

<400> SEQUENCE: 92

```
Met Ala Glu Gly Glu Phe Lys Pro Ala Ala Met Gln Val Glu Ala Pro
1               5                   10                  15

Ala Glu Ala Ala Ala Ala Pro Ser Lys Pro Arg Phe Arg Met Pro Val
            20                  25                  30

Asp Ser Asp Asn Lys Ala Thr Glu Phe Trp Leu Phe Ser Phe Ala Arg
        35                  40                  45

Pro His Met Ser Ala Phe His Met Ser Trp Phe Ser Phe Phe Cys Cys
    50                  55                  60

Phe Leu Ser Thr Phe Ala Ala Pro Pro Leu Leu Pro Leu Ile Arg Asp
65                  70                  75                  80

Thr Leu Gly Leu Thr Ala Thr Asp Ile Gly Asn Ala Gly Ile Ala Ser
                85                  90                  95

Val Ser Gly Ala Val Phe Ala Arg Val Ala Met Gly Thr Ala Cys Asp
            100                 105                 110
```

```
Leu Val Gly Pro Arg Leu Ala Ser Ala Ala Ile Ile Leu Leu Thr Thr
            115                 120                 125
Pro Ala Val Tyr Tyr Ser Ala Val Ile Asp Ser Ala Ser Ser Tyr Leu
130                 135                 140
Leu Val Arg Phe Phe Thr Gly Phe Ser Leu Ala Ser Phe Val Ser Thr
145                 150                 155                 160
Gln Phe Trp Met Ser Ser Met Phe Ser Pro Pro Lys Val Gly Leu Ala
            165                 170                 175
Asn Gly Val Ala Gly Gly Trp Gly Asn Leu Gly Gly Gly Ala Val Gln
            180                 185                 190
Leu Ile Met Pro Leu Val Phe Glu Ala Ile Arg Lys Ala Gly Ala Thr
            195                 200                 205
Pro Phe Thr Ala Trp Arg Val Ala Phe Phe Val Pro Gly Leu Leu Gln
210                 215                 220
Thr Leu Ser Ala Val Ala Val Leu Ala Phe Gly Gln Asp Met Pro Asp
225                 230                 235                 240
Gly Asn Tyr Arg Lys Leu His Arg Ser Gly Asp Met His Lys Asp Ser
            245                 250                 255
Phe Gly Asn Val Leu Arg His Ala Val Thr Asn Tyr Arg Ala Trp Ile
            260                 265                 270
Leu Ala Leu Thr Tyr Gly Tyr Cys Phe Gly Val Glu Leu Ala Val Asp
            275                 280                 285
Asn Ile Val Ala Gln Tyr Phe Tyr Asp Arg Phe Gly Val Lys Leu Ser
            290                 295                 300
Thr Ala Gly Phe Ile Ala Ala Ser Phe Gly Met Ala Asn Ile Val Ser
305                 310                 315                 320
Arg Pro Gly Gly Gly Leu Leu Ser Asp Trp Leu Ser Arg Phe Gly
            325                 330                 335
Met Arg Gly Arg Leu Trp Gly Leu Trp Val Val Gln Thr Ile Gly Gly
            340                 345                 350
Val Leu Cys Val Val Leu Gly Ala Val Asp Tyr Ser Phe Ala Ala Ser
            355                 360                 365
Val Ala Val Met Ile Leu Phe Ser Met Phe Val Gln Ala Ala Cys Gly
            370                 375                 380
Leu Thr Phe Gly Ile Val Pro Phe Val Ser Arg Arg Ser Leu Gly Leu
385                 390                 395                 400
Ile Ser Gly Met Thr Gly Gly Gly Asn Val Gly Ala Val Leu Thr
            405                 410                 415
Gln Leu Ile Phe Phe His Gly Ser Lys Tyr Lys Thr Glu Thr Gly Ile
            420                 425                 430
Lys Tyr Met Gly Phe Met Ile Ile Ala Cys Thr Leu Pro Ile Thr Leu
            435                 440                 445
Ile Tyr Phe Pro Gln Trp Gly Gly Met Phe Leu Gly Pro Arg Pro Gly
450                 455                 460
Ala Thr Ala Glu Asp Tyr Tyr Asn Arg Glu Trp Thr Ala His Glu Cys
465                 470                 475                 480
Asp Lys Gly Phe Asn Thr Ala Ser Val Arg Phe Ala Glu Asn Ser Val
            485                 490                 495
Arg Glu Gly Gly Arg Ser Gly Ser Gln Ser Lys His Thr Thr Val Pro
            500                 505                 510
Val Glu Ser Ser Pro Ala Asp Val
            515                 520
```

-continued

```
<210> SEQ ID NO 93
<211> LENGTH: 49597
<212> TYPE: DNA
<213> ORGANISM: Artificial Sequnce
<220> FEATURE:
<223> OTHER INFORMATION: Vector

<400> SEQUENCE: 93
```

| | | | | | |
|---|---|---|---|---|---|
| gtcttgctcg | actctagagc | tcgttcctcg | aggcctcgag | gcctcgagga | acggtacctg | 60 |
| cggggaagct | tacaataatg | tgtgttgtta | agtcttgttg | cctgtcatcg | tctgactgac | 120 |
| tttcgtcata | aatcccggcc | tccgtaaccc | agctttgggc | aagctcacgg | atttgatccg | 180 |
| gcggaacggg | aatatcgaga | tgccgggctg | aacgctgcag | ttccagcttt | cccttttcggg | 240 |
| acaggtactc | cagctgattg | attatctgct | gaagggtctt | ggttccacct | cctggcacaa | 300 |
| tgcgaatgat | tacttgagcg | cgatcgggca | tccaattttc | tcccgtcagg | tgcgtggtca | 360 |
| agtgctacaa | ggcacctttc | agtaacgagc | gaccgtcgat | ccgtcgccgg | gatacggaca | 420 |
| aaatggagcg | cagtagtcca | tcgagggcgg | cgaaagcctc | gccaaaagca | atacgttcat | 480 |
| ctcgcacagc | ctccagatcc | gatcgagggt | cttcggcgta | ggcagataga | agcatggata | 540 |
| cattgcttga | gagtattccg | atggactgaa | gtatggcttc | catcttttct | cgtgtgtctg | 600 |
| catctatttc | gagaaagccc | ccgatgcggc | gcaccgcaac | gcgaattgcc | atactatccg | 660 |
| aaagtcccag | caggcgcgct | tgataggaaa | aggtttcata | tcggccgat | cgcagacggg | 720 |
| cactcacgac | cttgaaccct | tcaactttca | gggatcgatg | ctggttgatg | gtagtctcac | 780 |
| tcgacgtggc | tctggtgtgt | tttgacatag | cttcctccaa | agaaagcgga | aggtctggat | 840 |
| actccagcac | gaaatgtgcc | cgggtagacg | gatggaagtc | tagccctgct | caatatgaaa | 900 |
| tcaacagtac | atttacagtc | aatactgaat | atacttgcta | catttgcaat | tgtcttataa | 960 |
| cgaatgtgaa | ataaaaatag | tgtaacaacg | cttttactca | tcgataatca | caaaaacatt | 1020 |
| tatacgaaca | aaaatacaaa | tgcactccgg | tttcacagga | taggcgggat | cagaatatgc | 1080 |
| aacttttgac | gttttgttct | tcaaagggg | gtgctggcaa | aaccaccgca | ctcatgggcc | 1140 |
| tttgcgctgc | tttggcaaat | gacggtaaac | gagtggccct | ctttgatgcc | gacgaaaacc | 1200 |
| ggcctctgac | gcgatggaga | gaaaacgcct | tacaaagcag | tactgggatc | ctcgctgtga | 1260 |
| agtctattcc | gccgacgaaa | tgccccttct | tgaagcagcc | tatgaaaatg | ccagctcga | 1320 |
| aggatttgat | tatgcgttgg | ccgatacgcg | tggcggctcg | agcgagctca | acaacacaat | 1380 |
| catcgctagc | tcaaacctgc | ttctgatccc | caccatgcta | acgccgctcg | acatcgatga | 1440 |
| ggcactatct | acctaccgct | acgtcatcga | gctgctgttg | agtgaaaatt | tggcaattcc | 1500 |
| tacagctgtt | ttgcgccaac | gcgtcccggt | cggccgattg | acaacatcgc | aacgcaggat | 1560 |
| gtcagagacg | ctagagagcc | ttccagttgt | accgtctccc | atgcatgaaa | gagatgcatt | 1620 |
| tgccgcgatg | aaagaacgcg | gcatgttgca | tcttacatta | ctaaacacgg | gaactgatcc | 1680 |
| gacgatcgc | ctcatagaga | ggaatcttcg | gattgcgatg | gaggaagtcg | tggtcatttc | 1740 |
| gaaactgatc | agcaaaatct | tggaggcttg | aagatggcaa | ttcgcaagcc | cgcattgtcg | 1800 |
| gtcggcgaag | cacggcggct | tgctggtgct | cgacccgaga | tccaccatcc | caacccgaca | 1860 |
| cttgttcccc | agaagctgga | cctccagcac | ttgcctgaaa | agccgacga | gaaagaccag | 1920 |
| caacgtgagc | ctctcgtcgc | cgatcacatt | tacagtcccg | atcgacaact | taagctaact | 1980 |
| gtggatgccc | ttagtccacc | tccgtccccg | aaaaagctcc | aggtttttct | tcagcgcga | 2040 |
| ccgcccgcgc | ctcaagtgtc | gaaaacatat | gacaacctcg | ttcggcaata | cagtccctcg | 2100 |
| aagtcgctac | aaatgatttt | aaggcgcgcg | ttggacgatt | tcgaaagcat | gctggcagat | 2160 |

```
ggatcatttc gcgtggcccc gaaaagttat ccgatcccct caactacaga aaaatccgtt    2220
ctcgttcaga cctcacgcat gttccggtt gcgttgctcg aggtcgctcg aagtcatttt    2280
gatccgttgg ggttggagac cgctcgagct ttcggccaca agctggctac cgccgcgctc    2340
gcgtcattct ttgctggaga aagccatcg agcaattggt gaagagggac ctatcggaac    2400
ccctcaccaa atattgagtg taggtttgag gccgctggcc gcgtcctcag tcaccttttg    2460
agccagataa ttaagagcca aatgcaattg gctcaggctg ccatcgtccc cccgtgcgaa    2520
acctgcacgt ccgcgtcaaa gaaataaccg gcacctcttg ctgttttat cagttgaggg    2580 cttgacggat ccgcctcaag tttgcggcgc agccgcaaaa tgagaacatc tatactcctg    2640
tcgtaaacct cctcgtcgcg tactcgactg gcaatgagaa gttgctcgcg cgatagaacg    2700
tcgcggggtt tctctaaaaa cgcgaggaga agattgaact cacctgccgt aagtttcacc    2760
tcaccgccag cttcggacat caagcgacgt tgcctgagat taagtgtcca gtcagtaaaa    2820 caaaagacc gtcggtcttt ggagcggaca acgttgggc gcacgcgcaa ggcaacccga    2880
atgcgtgcaa gaaactctct cgtactaaac ggcttagcga taaaatcact tgctcctagc    2940
tcgagtgcaa caactttatc cgtctcctca aggcggtcgc cactgataat tatgattgga    3000
atatcagact ttgccgccag atttcgaacg atctcaagcc catcttcacg acctaaattt    3060
agatcaacaa ccacgacatc gaccgtcgcg gaagagagta ctctagtgaa ctgggtgctg    3120
tcggctaccg cggtcacttt gaaggcgtgg atcgtaaggt attcgataat aagatgccgc    3180
atagcgacat cgtcatcgat aagaagaacg tgtttcaacg gctcaccttt caatctaaaa    3240
tctgaaccct tgttcacagc gcttgagaaa ttttcacgtg aaggatgtac aatcatctcc    3300
agctaaatgg gcagttcgtc agaattgcgg ctgaccgcgg atgacgaaaa tgcgaaccaa    3360
gtatttcaat tttatgacaa aagttctcaa tcgttgttac aagtgaaacg cttcgaggtt    3420
acagctacta ttgattaagg gatcgcctca tggtctcgcc ccggcgtcgt gcgtccgccg    3480
cgagccagat ctcgcctact tcataaacgt cctcataggc acggaatgga atgatgacat    3540
cgatcgccgt agagagcatg tcaatcagtg tgcgatcttc caagctagca ccttgggcgc    3600
tacttttgac aagggaaaac agtttcttga atccttggat tggattcgcg ccgtgtattg    3660
ttgaaatcga tcccggatgt cccgagacga cttcactcag ataagcccat gctgcatcgt    3720
cgcgcatctc gccaagcaat atccggtccg gccgcatacg cagacttgct tggagcaagt    3780
gctcggcgct cacagcaccc agcccagcac cgttcttgga gtagagtagt ctaacatgat    3840
tatcgtgtgg aatgacgagt tcgagcgtat cttctatggt gattagcctt tcctgggggg    3900
ggatggcgct gatcaaggtc ttgctcattg ttgtcttgcc gcttccggta gggccacata    3960
gcaacatcgt cagtcggctg acgacgcatg cgtgcagaaa cgcttccaaa tccccgttgt    4020
caaaatgctg aaggatagct tcatcatcct gattttggcg tttccttcgt gtctgccact    4080
ggttccacct cgaagcatca taacgggagg agacttcttt aagaccagaa acacgcgagc    4140
ttggccgtcg aatggtcaag ctgacggtgc ccgagggaac ggtcggcggc agacagattt    4200
gtagtcgttc accaccagga agttcagtgg cgcagagggg gttacgtggt ccgacatcct    4260
gctttctcag cgcgcccgct aaaatagcga tatcttcaag atcatcataa gagacgggca    4320
aaggcatctt ggtaaaaatg ccggcttggc gcacaaatgc ctctccaggt cgattgatcg    4380
caatttcttc agtcttcggg tcatcgagcc attccaaaat cggcttcaga agaaagcgta    4440
gttgcggatc cacttccatt tacaatgtat cctatctcta agcggaaatt tgaattcatt    4500
aagagcggcg gttcctcccc cgcgtggcgc cgccagtcag gcggagctgg taaacaccaa    4560
```

```
agaaatcgag gtcccgtgct acgaaaatgg aaacggtgtc accctgattc ttcttcaggg    4620
ttggcggtat gttgatggtt gccttaaggg ctgtctcagt tgtctgctca ccgttatttt    4680
gaaagctgtt gaagctcatc ccgccacccg agctgccggc gtaggtgcta gctgcctgga    4740
aggcgccttg aacaacactc aagagcatag ctccgctaaa acgctgccag aagtggctgt    4800
cgaccgagcc cggcaatcct gagcgaccga gttcgtccgc gcttggcgat gttaacgaga    4860
tcatcgcatg gtcaggtgtc tcggcgcgat cccacaacac aaaaacgcgc ccatctccct    4920
gttgcaagcc acgctgtatt tcgccaacaa cggtggtgcc acgatcaaga agcacgatat    4980
tgttcgttgt tccacgaata tcctgaggca agacacactt tacatagcct gccaaatttg    5040
tgtcgattgc ggtttgcaag atgcacgaaa ttattgtccc ttgcgttacc ataaaatcgg    5100
ggtgcggcaa gagcgtggcg ctgctgggct gcagctcggt gggtttcata cgtatcgaca    5160
aatcgttctc gccggacact tcgccattcg gcaaggagtt gtcgtcacgc ttgccttctt    5220
gtcttcggcc cgtgtcgccc tgaatggcgc gtttgctgac cccttgatcg ccgctgctat    5280
atgcaaaaat cggtgtttct tccggccgtg gctcatgccg ctccggttcg cccctcggcg    5340
gtagaggagc agcaggctga acagcctctt gaaccgctgg aggatccggc ggcacctcaa    5400
tcggagctgg atgaaatggc ttggtgtttg ttgcgatcaa agttgacggc gatgcgttct    5460
cattcacctt cttttggcgc ccacctagcc aaatgaggct taatgataac gcgagaacga    5520
cacctccgac gatcaatttc tgagaccccg aaagacgccg gcgatgtttg tcggagacca    5580
gggatccaga tgcatcaacc tcatgtgccg cttgctgact atcgttattc atcccttcgc    5640 cccccttcagg acgcgtttca catcgggcct caccgtgccc gtttgcggcc tttggccaac    5700
gggatcgtaa gcggtgttcc agatacatag tactgtgtgg ccatccctca gacgccaacc    5760
tcgggaaacc gaagaaatct cgacatcgct cccctttaact gaatagttgg caacagcttc    5820
cttgccatca ggattgatgg tgtagatgga gggtatgcgt acattgcccg gaaagtggaa    5880
taccgtcgta aatccattgt cgaagacttc gagtggcaac agcgaacgat cgccttgggc    5940
gacgtagtgc caattactgt ccgccgcacc aagggctgtg acaggctgat ccaataaatt    6000
ctcagctttc cgttgatatt gtgcttccgc gtgtagtctg tccacaacag ccttctgttg    6060
tgcctccctt cgccgagccg ccgcatcgtc ggcggggtag gcgaattgga cgctgtaata    6120
gagatcgggc tgctctttat cgaggtggga cagagtcttg gaacttatac tgaaaacata    6180
acggcgcatc ccggagtcgc ttgcggttag cacgattact ggctgaggcg tgaggacctg    6240
gcttgccttg aaaaatagat aatttccccg cggtagggct gctagatctt tgctatttga    6300
aacggcaacc gctgtcaccg tttcgttcgt ggcgaatgtt acgaccaaag tagctccaac    6360
cgccgtcgag aggcgcacca cttgatcggg attgtaagcc aaataacgca tgcgcggatc    6420
tagcttgccc gccattggag tgtcttcagc ctccgcacca gtcgcagcgg caaataaaca    6480
tgctaaaatg aaaagtgctt ttctgatcat ggttcgctgt ggcctacgtt tgaaacggta    6540
tcttccgatg tctgatagga ggtgacaacc agacctgccg ggttggttag tctcaatctg    6600
ccgggcaagc tggtcacctt ttcgtagcga actgtcgcgg tccacgtact caccacaggc    6660
attttgccgt caacgacgag ggtccttttta tagcgaattt gctgcgtgct tggagttaca    6720
tcatttgaag cgatgtgctc gacctccacc ctgccgcgtt tgccaagaat gacttgaggc    6780
gaactgggat tgggatagtt gaagaattgc tggtaatcct ggcgcactgt tggggcactg    6840
aagttcgata ccaggtcgta ggcgtactga gcggtgtcgg catcataact ctcgcgcagg    6900
cgaacgtact cccacaatga ggcgttaacg acggcctcct cttgagttgc aggcaatcgc    6960
```

-continued

```
gagacagaca cctcgctgtc aacggtgccg tccggccgta tccatagata tacgggcaca    7020
agcctgctca acggcaccat tgtggctata gcgaacgctt gagcaacatt tcccaaaatc    7080
gcgatagctg cgacagctgc aatgagtttg gagagacgtc gcgccgattt cgctcgcgcg    7140
gtttgaaagg cttctacttc cttatagtgc tcggcaaggc tttcgcgcgc cactagcatg    7200
gcatattcag gccccgtcat agcgtccacc cgaattgccg agctgaagat ctgacggagt    7260
aggctgccat cgcccacat tcagcgggaa gatcgggcct ttgcagctcg ctaatgtgtc     7320
gtttgtctgg cagccgctca aagcgacaac taggcacagc aggcaatact tcatagaatt    7380
ctccattgag gcgaattttt gcgcgaccta gcctcgctca acctgagcga agcgacggta    7440
caagctgctg gcagattggg ttgcgccgct ccagtaactg cctccaatgt tgccggcgat    7500
cgccggcaaa gcgacaatga gcgcatcccc tgtcagaaaa acatatcga gttcgtaaag     7560 accaatgatc ttggccgcgg tcgtaccggc gaaggtgatt acaccaagca taagggtgag    7620
cgcagtcgct tcggttagga tgacgatcgt tgccacgagg tttaagagga gaagcaagag    7680
accgtaggtg ataagttgcc cgatccactt agctgcgatg tcccgcgtgc gatcaaaaat    7740
atatccgacg aggatcagag gcccgatcgc gagaagcact ttcgtgagaa ttccaacggc    7800
gtcgtaaact ccgaaggcag accagagcgt gccgtaaagg acccactgtg cccttggaa     7860 agcaaggatg tcctggtcgt tcatcggacc gatttcggat gcgattttct gaaaacggc     7920 ctgggtcacg gcgaacattg tatccaactg tgccggaaca gtctgcagag gcaagccggt    7980
tacactaaac tgctgaacaa agtttgggac cgtcttttcg aagatggaaa ccacatagtc    8040
ttggtagtta gcctgcccaa caattagagc aacaacgatg gtgaccgtga tcacccgagt    8100
gataccgcta cgggtatcga cttcgccgcg tatgactaaa ataccctgaa caataatcca    8160
aagagtgaca caggcgatca atggcgcact caccgcctcc tggatagtct caagcatcga    8220
gtccaagcct gtcgtgaagg ctacatcgaa gatcgtatga atggccgtaa acggcgccgg    8280
aatcgtgaaa ttcatcgatt ggacctgaac ttgactggtt tgtcgcataa tgttggataa    8340
aatgagctcg cattcggcga ggatgcgggc ggatgaacaa atcgcccagc cttaggggag    8400
ggcaccaaag atgacagcgg tcttttgatg ctccttgcgt tgagcggccg cctcttccgc    8460
ctcgtgaagg ccggcctgcg cggtagtcat cgttaatagg cttgtcgcct gtacattttg    8520
aatcattgcg tcatggatct gcttgagaag caaaccattg gtcacggttg cctgcatgat    8580
attgcgagat cgggaaagct gagcagacgt atcagcattc gccgtcaagc gtttgtccat    8640
cgtttccaga ttgtcagccg caatgccagc gctgtttgcg gaaccggtga tctgcgatcg    8700
caacaggtcc gcttcagcat cactacccac gactgcacga tctgtatcgc tggtgatcgc    8760
acgtgccgtg gtcgacattg gcattgcgg cgaaaacatt tcattgtcta ggtccttcgt     8820
cgaaggatac tgattttct ggttgagcga agtcagtagt ccagtaacgc cgtaggccga     8880
cgtcaacatc gtaaccatcg ctatagtctg agtgagattc tccgcagtcg cgagcgcagt    8940
cgcgagcgtc tcagcctccg ttgccgggtc gctaacaaca aactgcgccc gcgcgggctg    9000
aatatataga aagctgcagg tcaaaactgt tgcaataagt tgcgtcgtct tcatcgtttc    9060
ctaccttatc aatcttctgc ctcgtggtga cgggccatga attcgctgag ccagccagat    9120
gagttgcctt cttgtgcctc gcgtagtcga gttgcaaagc gcaccgtgtt ggcacgcccc    9180
gaaagcacgg cgacatattc acgcatatcc cgcagatcaa attcgcagat gacgcttcca    9240
cttttctcgt taagaagaaa cttacggctg ccgaccgtca tgtcttcacg gatcgcctga    9300 aattccttt cggtacattt cagtccatcg acataagccg atcgatctgc ggttggtgat     9360
```

-continued

```
ggatagaaaa tcttcgtcat acattgcgca accaagctgg ctcctagcgg cgattccaga    9420
acatgctctg gttgctgcgt tgccagtatt agcatcccgt tgttttttcg aacggtcagg    9480
aggaatttgt cgacgacagt cgaaaattta gggtttaaca aataggcgcg aaactcatcg    9540
cagctcatca caaaacggcg gccgtcgatc atggctccaa tccgatgcag gagatatgct    9600
gcagcgggag cgcatacttc ctcgtattcg agaagatgcg tcatgtcgaa gccggtaatc    9660
gacggatcta actttacttc gtcaacttcg ccgtcaaatg cccagccaag cgcatggccc    9720
cggcaccagc gttggagccg cgctcctgcg ccttcggcgg gcccatgcaa caaaaattca    9780
cgtaaccccg cgattgaacg catttgtgga tcaaacgaga gctgacgatg gataccacgg    9840
accagacggc ggttctcttc cggagaaatc ccaccccgac catcactctc gatgagagcc    9900
acgatccatt cgcgcagaaa atcgtgtgag gctgctgtgt tttctaggcc acgcaacggc    9960
gccaacccgc tgggtgtgcc tctgtgaagt gccaaatatg ttcctcctgt ggcgcgaacc   10020
agcaattcgc caccccggtc cttgtcaaag aacacgaccg tacctgcacg gtcgaccatg   10080
ctctgttcga gcatggctag aacaaacatc atgagcgtcg tcttacccct cccgataggc   10140
ccgaatattg ccgtcatgcc aacatcgtgc tcatgcggga tatagtcgaa aggcgttccg   10200
ccattggtac gaaatcgggc aatcgcgttg ccccagtggc ctgagctggc gccctctgga   10260
aagttttcga aagagacaaa ccctgcgaaa ttgcgtgaag tgattgcgcc agggcgtgtg   10320
cgccacttaa aattccccgg caattgggac caataggccg cttccatacc aataccttct   10380
tggacaacca cggcacctgc atccgccatt cgtgtccgag cccgcgcgcc cctgtcccca   10440
agactattga gatcgtctgc atagacgcaa aggctcaaat gatgtgagcc cataacgaat   10500
tcgttgctcg caagtgcgtc ctcagcctcg gataatttgc cgatttgagt cacggctttt   10560
cgccggaac tcagcatctg gctcgatttg aggctaagtt tcgcgtgcgc ttgcgggcga   10620
gtcaggaacg aaaaactctg cgtgagaaca agtggaaaat cgagggatag cagcgcgttg   10680
agcatgcccg gccgtgtttt tgcagggtat tcgcgaaacg aatagatgga tccaacgtaa   10740
ctgtcttttg gcgttctgat ctcgagtcct cgcttgccgc aaatgactct gtcggtataa   10800
atcgaagcgc cgagtgagcc gctgacgacc ggaaccggtg tgaaccgacc agtcatgatc   10860
aaccgtagcg cttcgccaat ttcggtgaag agcacaccct gcttctcgcg gatgccaaga   10920
cgatgcaggc catacgcttt aagagagcca gcgacaacat gccaaagatc ttccatgttc   10980
ctgatctggc ccgtgagatc gttttcccct ttttccgctta gcttggtgaa cctcctcttt   11040
accttcccta aagccgcctg tgggtagaca atcaacgtaa ggaagtgttc attgcggagg   11100
agttggccgg agagcacgcg ctgttcaaaa gcttcgttca ggctagcggc gaaaacacta   11160
cggaagtgtc gcggcgccga tgatggcacg tcggcatgac gtacgaggtg agcatatatt   11220
gacacatgat catcagcgat attgcgcaac agcgtgttga acgcacgaca acgcgcattg   11280
cgcatttcag tttcctcaag ctcgaatgca acgccatcaa ttctcgcaat ggtcatgatc   11340
gatccgtctt caagaaggac gatatggtcg ctgaggtggc caatataagg gagatagatc   11400
tcaccggatc tttcggtcgt tccactcgcg ccgagcatca caccattcct ctccctcgtg   11460
ggggaaccct aattggattt gggctaacag tagcgccccc ccaaactgca ctatcaatgc   11520
ttcttcccgc ggtccgcaaa aatagcagga cgacgctcgc cgcattgtag tctcgctcca   11580
cgatgagccg ggctgcaaac cataacggca cgagaacgac ttcgtagagc gggttctgaa   11640
cgataacgat gacaaagccg gcgaacatca tgaataaccc tgccaatgtc agtggcaccc   11700
caagaaacaa tgcgggccgt gtggctgcga ggtaaagggt cgattcttcc aaacgatcag   11760
```

```
ccatcaacta ccgccagtga gcgtttggcc gaggaagctc gccccaaaca tgataacaat    11820
gccgccgacg acgccggcaa ccagcccaag cgaagcccgc ccgaacatcc aggagatccc    11880
gatagcgaca atgccgagaa cagcgagtga ctggccgaac ggaccaagga taaacgtgca    11940
tatattgtta accattgtgg cggggtcagt gccgccaccc gcagattgcg ctgcggcggg    12000
tccggatgag gaaatgctcc atgcaattgc accgcacaag cttggggcgc agctcgatat    12060
cacgcgcatc atcgcattcg agagcgagag gcgatttaga tgtaaacggt atctctcaaa    12120
gcatcgcatc aatgcgcacc tccttagtat aagtcgaata agacttgatt gtcgtctgcg    12180
gatttgccgt tgtcctggtg tggcggtggc ggagcgatta aaccgccagc gccatcctcc    12240
tgcgagcggc gctgatatga cccccaaaca tcccacgtct cttcggattt tagcgcctcg    12300
tgatcgtctt ttggaggctc gattaacgcg ggcaccagcg attgagcagc tgtttcaact    12360
tttcgcacgt agccgtttgc aaaaccgccg atgaaattac cggtgttgta agcggagatc    12420
gcccgacgaa gcgcaaattg cttctcgtca atcgtttcgc cgcctgcata acgacttttc    12480
agcatgtttg cagcggcaga taatgatgtg cacgcctgga gcgcaccgtc aggtgtcaga    12540
ccgagcatag aaaaatttcg agagtttatt tgcatgaggc caacatccag cgaatgccgt    12600
gcatcgagac ggtgcctgac gacttgggtt gcttggctgt gatcttgcca gtgaagcgtt    12660
tcgccggtcg tgttgtcatg aatcgctaaa ggatcaaagc gactctccac cttagctatc    12720
gccgcaagcg tagatgtcgc aactgatggg gcacacttgc gagcaacatg gtcaaactca    12780
gcagatgaga gtggcgtggc aaggctcgac gaacagaagg agaccatcaa ggcaagagaa    12840
agcgaccccg atctcttaag cataccttat ctccttagct cgcaactaac accgcctctc    12900
ccgttggaag aagtgcgttg ttttatgttg aagattatcg ggagggtcgg ttactcgaaa    12960
attttcaatt gcttctttat gatttcaatt gaagcgagaa acctcgcccg gcgtcttgga    13020
acgcaacatg gaccgagaac cgcgcatcca tgactaagca accggatcga cctattcagg    13080
ccgcagttgg tcaggtcagg ctcagaacga aaatgctcgg cgaggttacg ctgtctgtaa    13140
acccattcga tgaacgggaa gcttccttcc gattgctctt ggcaggaata ttggcccatg    13200
cctgcttgcg ctttgcaaat gctcttatcg cgttggtatc atatgccttg tccgccagca    13260
gaaacgcact ctaagcgatt attgtaaaa atgtttcggt catgcggcgg tcatgggctt    13320
gacccgctgt cagcgcaaga cggatcggtc aaccgtcggc atcgacaaca gcgtgaatct    13380
tggtggtcaa accgccacgg gaacgtccca tacagccatc gtcttgatcc cgctgtttcc    13440
cgtcgccgca tgttggtgga cgcggacaca ggaactgtca atcatgacga cattctatcg    13500
aaagccttgg aaatcacact cagaatatga tcccagacgt ctgcctcacg ccatcgtaca    13560
aagcgattgt agcaggttgt acaggaaccg tatcgatcag gaacgtctgc ccagggcggg    13620
cccgtccgga agcgccacaa gatgacattg atcacccgcg tcaacgcgcg gcacgcgacg    13680
cggcttattt gggaacaaag gactgaacaa cagtccattc gaaatcggtg acatcaaagc    13740
ggggacgggt tatcagtggc ctccaagtca agcctcaatg aatcaaaatc agaccgattt    13800
gcaaacctga tttatgagtg tgcggcctaa atgatgaaat cgtccttcta gatcgcctcc    13860
gtggtgtagc aacacctcgc agtatcgccg tgctgacctt ggccagggaa ttgactggca    13920
agggtgcttt cacatgaccg ctcttttggc cgcgatagat gatttcgttg ctgctttggg    13980
cacgtagaag gagagaagtc atatcggaga aattcctcct ggcgcgagag cctgctctat    14040
cgcgacggca tcccactgtc gggaacagac cggatcattc acgaggcgaa agtcgtcaac    14100
acatgcgtta taggcatctt cccttgaagg atgatcttgt tgctgccaat ctggaggtgc    14160
```

```
ggcagccgca ggcagatgcg atctcagcgc aacttgcggc aaaacatctc actcacctga    14220
aaaccactag cgagtctcgc gatcagacga aggcctttta cttaacgaca caatatccga    14280
tgtctgcatc acaggcgtcg ctatcccagt caatactaaa gcggtgcagg aactaaagat    14340
tactgatgac ttaggcgtgc cacgaggcct gagacgacgc gcgtagacag tttttttgaaa   14400 tcattatcaa agtgatggcc tccgctgaag cctatcacct ctgcgccggt ctgtcggaga    14460
gatgggcaag cattattacg gtcttcgcgc ccgtacatgc attggacgat tgcagggtca    14520
atggatctga gatcatccag aggattgccg cccttacctt ccgtttcgag ttggagccag    14580
cccctaaatg agacgacata gtcgacttga tgtgacaatg ccaagagaga gatttgctta    14640
acccgatttt tttgctcaag cgtaagccta ttgaagcttg ccggcatgac gtccgcgccg    14700
aaagaatatc ctacaagtaa aacattctgc acaccgaaat gcttggtgta gacatcgatt    14760
atgtgaccaa gatccttagc agtttcgctt ggggaccgct ccgaccagaa ataccgaagt    14820
gaactgacgc caatgacagg aatcccttcc gtctgcagat aggtaccatc gatagatctg    14880
ctgcctcgcg cgtttcggtg atgacggtga aaacctctga cacatgcagc tcccggagac    14940
ggtcacagct tgtctgtaag cggatgccgg gagcagacaa gcccgtcagg gcgcgtcagc    15000
gggtgttggc gggtgtcggg gcgcagccat gacccagtca cgtagcgata gcggagtgta    15060
tactggctta actatgcggc atcagagcag attgtactga gagtgcacca tatgcggtgt    15120
gaaataccgc acagatgcgt aaggagaaaa taccgcatca ggcgctcttc cgcttcctcg    15180
ctcactgact cgctgcgctc ggtcgttcgg ctgcggcgag cggtatcagc tcactcaaag    15240
gcggtaatac ggttatccac agaatcaggg gataacgcag gaaagaacat gtgagcaaaa    15300
ggccagcaaa aggccaggaa ccgtaaaaag gccgcgttgc tggcgttttt ccataggctc    15360
cgcccccctg acgagcatca caaaaatcga cgctcaagtc agaggtggcg aaacccgaca    15420
ggactataaa gataccaggc gtttccccct ggaagctccc tcgtgcgctc tcctgttccg    15480
accctgccgc ttaccggata cctgtccgcc tttctccctt cgggaagcgt ggcgctttct    15540
catagctcac gctgtaggta tctcagttcg gtgtaggtcg ttcgctccaa gctgggctgt    15600
gtgcacgaac cccccgttca gcccgaccgc tgcgccttat ccggtaacta tcgtcttgag    15660
tccaacccgg taagacacga cttatcgcca ctggcagcag ccactggtaa caggattagc    15720
agagcgaggt atgtaggcgg tgctacagag ttcttgaagt ggtggcctaa ctacggctac    15780
actagaagga cagtatttgg tatctgcgct ctgctgaagc cagttacctt cggaaaaaga    15840
gttggtagct cttgatccgg caaacaaacc accgctggta gcggtggttt ttttgtttgc    15900
aagcagcaga ttacgcgcag aaaaaaagga tctcaagaag atcctttgat cttttctacg    15960
gggtctgacg ctcagtggaa cgaaaactca cgttaaggga ttttggtcat gagattatca    16020
aaaaggatct tcacctagat ccttttaaat taaaaatgaa gttttaaatc aatctaaagt    16080
atatatgagt aaacttggtc tgacagttac caatgcttaa tcagtgaggc acctatctca    16140
gcgatctgtc tatttcgttc atccatagtt gcctgactcc ccgtcgtgta gataactacg    16200
atacgggagg gcttaccatc tggccccagt gctgcaatga taccgcgaga cccacgctca    16260
ccggctccag atttatcagc aataaaccag ccagccggaa gggccgagcg cagaagtggt    16320
cctgcaactt tatccgcctc catccagtct attaattgtt gccgggaagc tagagtaagt    16380
agttcgccag ttaatagttt gcgcaacgtt gttgccattg ctgcagggggg gggggggggg   16440 gggttccatt gttcattcca cggacaaaaa cagagaaagg aaacgacaga gccaaaaag    16500 ctcgctttca gcacctgtcg tttcctttct tttcagaggg tatttttaaat aaaaacatta   16560
```

```
agttatgacg aagaagaacg gaaacgcctt aaaccggaaa atttccataa atagcgaaaa    16620
cccgcgaggt ccctgtcgga tcaccggaaa ggacccgtaa agtgataatg attatcatct    16680
acatatcaca acgtgcgtgg aggccatcaa accacgtcaa ataatcaatt atgacgcagg    16740
tatcgtatta attgatctgc atcaacttaa cgtaaaaaca acttcagaca atacaaatca    16800
gcgacactga atacgggggca acctcatgtc cccccccccc ccccccctgc aggcatcgtg    16860
gtgtcacgct cgtcgtttgg tatggcttca ttcagctccg gttcccaacg atcaaggcga    16920
gttacatgat cccccatgtt gtgcaaaaaa gcggttagct ccttcggtcc tccgatcgtt    16980
gtcagaagta agttggccgc agtgttatca ctcatggtta tggcagcact gcataattct    17040
cttactgtca tgccatccgt aagatgcttt tctgtgactg gtgagtactc aaccaagtca    17100
ttctgagaat agtgtatgcg gcgaccgagt tgctcttgcc cggcgtcaac acgggataat    17160
accgcgccac atagcagaac tttaaaagtg ctcatcattg gaaaacgttc ttcgggggcga    17220
aaactctcaa ggatcttacc gctgttgaga tccagttcga tgtaacccac tcgtgcaccc    17280
aactgatctt cagcatcttt tactttcacc agcgtttctg ggtgagcaaa aacaggaagg    17340
caaaatgccg caaaaaaggg aataagggcg acacggaaat gttgaatact catactcttc    17400
cttttcaat attattgaag catttatcag ggttattgtc tcatgagcgg atacatattt    17460
gaatgtattt agaaaaataa acaaataggg gttccgcgca catttccccg aaaagtgcca    17520
cctgacgtct aagaaaccat tattatcatg acattaacct ataaaaatag gcgtatcacg    17580
aggccctttc gtcttcaaga attggtcgac gatcttgctg cgttcggata ttttcgtgga    17640
gttcccgcca cagacccgga ttgaaggcga gatccagcaa ctcgcgccag atcatcctgt    17700
gacggaactt tggcgcgtga tgactggcca ggacgtcggc cgaaagagcg acaagcagat    17760
cacgcttttc gacagcgtcg gatttgcgat cgaggatttt tcggcgctgc gctacgtccg    17820
cgaccgcgtt gagggatcaa gccacagcag cccactcgac cttctagccg acccagacga    17880
gccaagggat cttttttggaa tgctgctccg tcgtcaggct ttccgacgtt tgggtggttg    17940
aacagaagtc attatcgtac ggaatgccaa gcactcccga ggggaaccct gtggttggca    18000
tgcacataca aatggacgaa cggataaacc ttttcacgcc cttttaaata tccgttattc    18060
taataaacgc tcttttctct taggtttacc cgccaatata tcctgtcaaa cactgatagt    18120
ttaaactgaa ggcgggaaac gacaatctga tcatgagcgg agaattaagg gagtcacgtt    18180
atgaccccccg ccgatgacgc gggacaagcc gttttacgtt tggaactgac agaaccgcaa    18240
cgttgaagga gccactcagc aagctggtac gattgtaata cgactcacta tagggcgaat    18300
tgagcgctgt ttaaacgctc ttcaactgga agagcggtta cccggaccga agcttgcatg    18360
cctgcagtgc agcgtgaccc ggtcgtgccc ctctctagag ataatgagca ttgcatgtct    18420
aagttataaa aaattaccac atattttttt tgtcacactt gtttgaagtg cagtttatct    18480
atctttatac atatatttaa actttactct acgaataata taatctatag tactacaata    18540
atatcagtgt tttagagaat catataaatg aacagttaga catggtctaa aggacaattg    18600
agtattttga caacaggact ctacagtttt atctttttag tgtgcatgtg ttctcctttt    18660
ttttgcaaa tagcttcacc tatataatac ttcatccatt ttattagtac atccatttag    18720
ggtttagggt taatggtttt tatagactaa ttttttttagt acatctattt tattctattt    18780
tagcctctaa attaagaaaa ctaaaactct atttttagttt tttattttaa taatttagat    18840
ataaaataga ataaaataaa gtgactaaaa attaaacaaa taccctttaa gaaattaaaa    18900
aaactaagga aacattttc ttgtttcgag tagataatgc cagcctgtta aacgccgtcg    18960
```

```
acgagtctaa cggacaccaa ccagcgaacc agcagcgtcg cgtcgggcca agcgaagcag    19020
acggcacggc atctctgtcg ctgcctctgg acccctctcg agagttccgc tccaccgttg    19080
gacttgctcc gctgtcggca tccagaaatt gcgtggcgga gcggcagacg tgagccggca    19140
cggcaggcgg cctcctcctc ctctcacggc acggcagcta cggggattc ctttcccacc     19200
gctccttcgc tttcccttcc tcgcccgccg taataaatag acaccccctc cacaccctct    19260
ttccccaacc tcgtgttgtt cggagcgcac acacacacaa ccagatctcc cccaaatcca    19320
cccgtcggca cctccgcttc aaggtacgcc gtcgtcctc ccccccccc cctctctacc      19380
ttctctagat cggcgttccg gtccatggtt agggcccggt agttctactt ctgttcatgt    19440
ttgtgttaga tccgtgtttg tgttagatcc gtgctgctag cgttcgtaca cggatgcgac    19500
ctgtacgtca gacacgttct gattgctaac ttgccagtgt ttctctttgg ggaatcctgg    19560
gatggctcta gccgttccgc agacgggatc gatttcatga ttttttttgt ttcgttgcat    19620
agggtttggt ttgcccttt ccttattc aatatatgcc gtgcacttgt ttgtcgggtc       19680
atcttttcat gcttttttt gtcttggttg tgatgatgtg gtctggttgg gcggtcgttc     19740
tagatcggag tagaattctg tttcaaacta cctggtggat ttattaattt tggatctgta    19800
tgtgtgtgcc atacatattc atagttacga attgaagatg atggatggaa atatcgatct    19860
aggataggta tacatgttga tgcgggtttt actgatgcat atacagagat gcttttttgtt  19920
cgcttggttg tgatgatgtg gtgtggttgg gcggtcgttc attcgttcta gatcggagta    19980
gaatactgtt tcaaactacc tggtgtattt attaattttg gaactgtatg tgtgtgtcat    20040
acatcttcat agttacgagt ttaagatgga tggaaatatc gatctaggat aggtatacat    20100
gttgatgtgg gttttactga tgcatataca tgatggcata tgcagcatct attcatatgc    20160
tctaaccttg agtacctatc tattataata aacaagtatg ttttataatt attttgatct    20220
tgatatactt ggatgatggc atatgcagca gctatatgtg gatttttta gccctgcctt     20280
catacgctat ttatttgctt ggtactgttt cttttgtcga tgctcaccct gttgtttggt    20340
gttacttctg caggtcgact ctagaggatc tacaagtttg tacaaaaaag caggctccgc    20400
ggccgccccc ttcaccatgg ctcggcagca aagcgtgcag gccttgtgtg tgctggcggc    20460
gcttctcttc gccgcctccc tgccgtcgcc ggccgccgcg ggggtgcacc tctcctcgct    20520
gcccaaagcg ctcgacgtca ccacctccgc caaacccggc caagtcctgc acgccggcgt    20580
ggactcgctg acggtgacgt ggagcctgaa cgccacggag ccggccggcg ccgacgccgg    20640
gtacaagggc gtgaaggtga agctgtgcta cgcgccggcg agccagaagg accgcgggtg    20700
gcgcaagtcc gaggacgaca tcagcaagga caaggcgtgc cagttcaagg tcaccgagca    20760
ggcgtacgcg gcggcggcgc ccggcagctt ccagtacgcc gtcgcccgcg acgtcccctc    20820
gggctcctac tacctgcgcg ccttcgccac ggacgcgtcg ggcgccgagg tggcctacgg    20880
ccagacggcg cccaccgccg ccttcgacgt cgccggcatc accggcatcc acgcctctct    20940
caagatcgcc gccggcgtct tctcggcctt ctccgtcgtc gcgctcgcct tcttcttcgt    21000
catcgagacc cgcaagaaga acaagtagaa gggtgggcgc gccgacccag ctttcttgta    21060
caaagtggtg ttaacctaga cttgtccatc ttctggattg ccaacttaa ttaatgtatg     21120
aaataaaagg atgcacacat agtgacatgc taatcactat aatgtgggca tcaaagttgt    21180
gtgttatgtg taattactag ttatctgaat aaaagagaaa gagatcatcc atatttctta    21240
tcctaaatga atgtcacgtg tctttataat tctttgatga accagatgca tttcattaac    21300
caaatccata tacatataaa tattaatcat atataattaa tatcaattgg gttagcaaaa    21360
```

```
caaatctagt ctaggtgtgt tttgcgaatt gcggccgcca ccgcggtgga gctcgaattc    21420
cggtccgggt cacctttgtc caccaagatg gaactgcggc cgctcattaa ttaagtcagg    21480
cgcgcctcta gttgaagaca cgttcatgtc ttcatcgtaa gaagacactc agtagtcttc    21540
ggccagaatg gccatctgga ttcagcaggc ctagaaggcc atttaaatcc tgaggatctg    21600
gtcttcctaa ggacccgggc ggtccgatta aactttaatt cggaccgaag cttgcatgcc    21660
tgcagtgcag cgtgacccgg tcgtgcccct ctctagagat aatgagcatt gcatgtctaa    21720
gttataaaaa attaccacat atttttttg tcacacttgt ttgaagtgca gtttatctat    21780
ctttatacat atatttaaac tttactctac gaataatata atctatagta ctacaataat    21840
atcagtgttt tagagaatca tataaatgaa cagttagaca tggtctaaag gacaattgag    21900
tattttgaca acaggactct acagttttat cttttttagtg tgcatgtgtt ctccttttt    21960
tttgcaaata gcttcaccta tataatactt catccatttt attagtacat ccatttaggg    22020
tttagggtta atggttttta tagactaatt ttttagtac atctattta ttctattta     22080
gcctctaaat taagaaaact aaaactctat tttagttttt ttatttaata atttagatat    22140
aaaatagaat aaaataaagt gactaaaaat taaacaaata ccctttaaga aattaaaaaa    22200
actaaggaaa cattttctt gtttcgagta gataatgcca gcctgttaaa cgccgtcgac    22260
gagtctaacg gacaccaacc agcgaaccag cagcgtcgcg tcgggccaag cgaagcagac    22320
ggcacggcat ctctgtcgct gcctctggac ccctctcgag agttccgctc caccgttgga    22380
cttgctccgc tgtcggcatc cagaaattgc gtggcggagc ggcagacgtg agccggcacg    22440
gcaggcggcc tcctcctcct ctcacggcac cggcagctac gggggattcc tttcccaccg    22500
ctccttcgct ttcccttcct cgcccgccgt aataaataga caccccctcc acccctctt    22560
tccccaacct cgtgttgttc ggagcgcaca cacacacaac cagatctccc ccaaatccac    22620
ccgtcggcac ctccgcttca aggtacgccg ctcgtcctcc ccccccccc tctctacctt    22680
ctctagatcg gcgttccggt ccatgcatgg ttagggcccg gtagttctac ttctgttcat    22740
gtttgtgtta gatccgtgtt tgtgttagat ccgtgctgct agcgttcgta cacgatgcg    22800
acctgtacgt cagacacgtt ctgattgcta acttgccagt gtttctcttt ggggaatcct    22860
gggatggctc tagccgttcc gcagacggga tcgatttcat gattttttt gtttcgttgc    22920
atagggtttg gtttgccctt ttcctttatt tcaatatatg ccgtgcactt gtttgtcggg    22980
tcatcttttc atgcttttt ttgtcttggt tgtgatgatg tggtctggtt gggcggtcgt    23040
tctagatcgg agtagaattc tgtttcaaac tacctggtgg atttattaat tttggatctg    23100
tatgtgtgtg ccatacatat tcatagttac gaattgaaga tgatggatgg aaatatcgat    23160
ctaggatagg tatacatgtt gatgcgggtt ttactgatgc atatacagag atgctttttg    23220
ttcgcttggt tgtgatgatg tggtgtggtt gggcggtcgt tcattcgttc tagatcggag    23280
tagaatactg tttcaaacta cctggtgtat ttattaattt tggaactgta tgtgtgtgtc    23340
atacatcttc atagttacga gtttaagatg gatggaaata tcgatctagg ataggtatac    23400
atgttgatgt gggttttact gatgcatata catgatggca tatgcagcat ctattcatat    23460
gctctaacct tgagtaccta tctattataa taaacaagta tgttttataa ttattttgat    23520
cttgatatac ttggatgatg gcatatgcag cagctatatg tggatttttt tagccctgcc    23580
ttcatacgct atttatttgc ttggtactgt ttcttttgtc gatgctcacc ctgttgtttg    23640
gtgttacttc tgcaggtcga ctttaactta gcctaggatc cacacgacac catgtccccc    23700
gagcgccgcc ccgtcgagat ccgcccggcc accgccgccg acatggccgc cgtgtgcgac    23760
```

```
atcgtgaacc actacatcga gacctccacc gtgaacttcc gcaccgagcc gcagacccccg   23820 caggagtgga tcgacgacct ggagcgcctc caggaccgct acccgtggct cgtggccgag   23880
gtggagggcg tggtggccgg catcgcctac gccggcccgt ggaaggcccg caacgcctac   23940
gactggaccg tggagtccac cgtgtacgtg tcccaccgcc accagcgcct cggcctcggc   24000
tccaccctct acacccacct cctcaagagc atggaggccc agggcttcaa gtccgtggtg   24060
gccgtgatcg gcctcccgaa cgacccgtcc gtgcgcctcc acgaggccct cggctacacc   24120
gcccgcggca ccctccgcgc cgccggctac aagcacggcg gctggcacga cgtcggcttc   24180
tggcagcgcg acttcgagct gccggcccccg ccgcgccccgg tgcgcccggt gacgcagatc   24240
tgagtcgaaa cctagacttg tccatcttct ggattggcca acttaattaa tgtatgaaat   24300
aaaaggatgc acacatagtg acatgctaat cactataatg tgggcatcaa agttgtgtgt   24360
tatgtgtaat tactagttat ctgaataaaa gagaaagaga tcatccatat ttcttatcct   24420
aaatgaatgt cacgtgtctt tataattctt tgatgaacca gatgcatttc attaaccaaa   24480
tccatataca tataaatatt aatcatatat aattaatatc aattgggtta gcaaaacaaa   24540
tctagtctag gtgtgttttg cgaattgcgg ccgccaccgc ggtggagctc gaattcattc   24600
cgattaatcg tggcctcttg ctcttcagga tgaagagcta tgtttaaacg tgcaagcgct   24660
actagacaat tcagtacatt aaaaacgtcc gcaatgtgtt attaagttgt ctaagcgtca   24720
atttgtttac accacaatat atcctgccac cagccagcca acagctcccc gaccggcagc   24780
tcggcacaaa atcaccactc gatacaggca gcccatcagt ccgggacggc gtcagcggga   24840
gagccgttgt aaggcggcag actttgctca tgttaccgat gctattcgga agaacggcaa   24900
ctaagctgcc gggtttgaaa cacgatgat ctcgcgagg gtagcatgtt gattgtaacg   24960
atgacagagc gttgctgcct gtgatcaaat atcatctccc tcgcagagat ccgaattatc   25020
agccttctta ttcatttctc gcttaaccgt gacaggctgt cgatcttgag aactatgccg   25080
acataatagg aaatcgctgg ataaagccgc tgaggaagct gagtggcgct atttctttag   25140
aagtgaacgt tgacgatcgt cgaccgtacc ccgatgaatt aattcggacg tacgttctga   25200
acacagctgg atacttactt gggcgattgt catacatgac atcaacaatg tacccgtttg   25260
tgtaaccgtc tcttggaggt tcgtatgaca ctagtggttc ccctcagctt gcgactagat   25320
gttgaggcct aacattttat tagagagcag gctagttgct tagatacatg atcttcaggc   25380
cgttatctgt cagggcaagc gaaaattggc catttatgac gaccaatgcc ccgcagaagc   25440
tcccatcttt gccgccatag acgccgcgcc cccctttgg ggtgtagaac atccttttgc   25500
cagatgtgga aaagaagttc gttgtcccat tgttggcaat gacgtagtag ccggcgaaag   25560
tgcgagaccc atttgcgcta tatataagcc tacgatttcc gttgcgacta ttgtcgtaat   25620
tggatgaact attatcgtag ttgctctcag agttgtcgta atttgatgga ctattgtcgt   25680
aattgcttat ggagttgtcg tagttgcttg gagaaatgtc gtagttggat ggggagtagt   25740
catagggaag acgagcttca tccactaaaa caattggcag gtcagcaagt gcctgccccg   25800
atgccatcgc aagtacgagg cttagaacca ccttcaacag atcgcgcata gtcttcccca   25860
gctctctaac gcttgagtta agccgcgccg cgaagcggcg tcggcttgaa cgaattgtta   25920
gacattattt gccgactacc ttggtgatct cgcctttcac gtagtgaaca aattcttcca   25980
actgatctgc gcgcgaggcc aagcgatctt cttgtccaag ataagcctgc ctagcttcaa   26040
gtatgacggg ctgatactgg gccggcaggc gctccattgc ccagtcggca gcgacatcct   26100
tcggcgcgat tttgccggtt actgcgctgt accaaatgcg ggacaacgta agcactacat   26160
```

```
ttcgctcatc gccagcccag tcgggcggcg agttccatag cgttaaggtt tcatttagcg   26220
cctcaaatag atcctgttca ggaaccggat caaagagttc ctccgccgct ggacctacca   26280
aggcaacgct atgttctctt gcttttgtca gcaagatagc cagatcaatg tcgatcgtgg   26340
ctggctcgaa gatacctgca agaatgtcat tgcgctgcca ttctccaaat tgcagttcgc   26400
gcttagctgg ataacgccac ggaatgatgt cgtcgtgcac aacaatggtg acttctacag   26460
cgcggagaat ctcgctctct ccaggggaag ccgaagtttc caaaaggtcg ttgatcaaag   26520
ctcgccgcgt tgtttcatca agccttacag tcaccgtaac cagcaaatca atatcactgt   26580
gtggcttcag gccgccatcc actgcggagc cgtacaaatg tacggccagc aacgtcggtt   26640
cgagatggcg ctcgatgacg ccaactacct ctgatagttg agtcgatact tcggcgatca   26700
ccgcttccct catgatgttt aactcctgaa ttaagccgcg ccgcgaagcg gtgtcggctt   26760
gaatgaattg ttaggcgtca tcctgtgctc ccgagaacca gtaccagtac atcgctgttt   26820
cgttcgagac ttgaggtcta gttttatacg tgaacaggtc aatgccgccg agagtaaagc   26880
cacattttgc gtacaaattg caggcaggta cattgttcgt ttgtgtctct aatcgtatgc   26940
caaggagctg tctgcttagt gcccactttt tcgcaaattc gatgagactg tgcgcgactc   27000
ctttgcctcg gtgcgtgtgc gacacaacaa tgtgttcgat agaggctaga tcgttccatg   27060
ttgagttgag ttcaatcttc ccgacaagct cttggtcgat gaatgcgcca tagcaagcag   27120
agtcttcatc agagtcatca tccgagatgt aatccttccg gtaggggctc acacttctgg   27180
tagatagttc aaagccttgg tcggataggt gcacatcgaa cacttcacga acaatgaaat   27240
ggttctcagc atccaatgtt tccgccacct gctcagggat caccgaaatc ttcatatgac   27300
gcctaacgcc tggcacagcg gatcgcaaac ctggcgcggc ttttggcaca aaaggcgtga   27360
caggtttgcg aatccgttgc tgccacttgt taacccttt gccagatttg gtaactataa   27420
tttatgttag aggcgaagtc ttgggtaaaa actggcctaa aattgctggg gatttcagga   27480
aagtaaacat caccttccgg ctcgatgtct attgtagata tatgtagtgt atctacttga   27540 tcggggatc tgctgcctcg cgcgtttcgg tgatgacggt gaaaacctct gacacatgca   27600
gctcccggag acggtcacag cttgtctgta agcggatgcc gggagcagac aagcccgtca   27660
gggcgcgtca gcgggtgttg gcgggtgtcg gggcgcagcc atgacccagt cacgtagcga   27720
tagcggagtg tatactggct taactatgcg gcatcagagc agattgtact gagagtgcac   27780
catatgcggt gtgaaatacc gcacagatgc gtaaggagaa ataccgcat caggcgctct   27840 tccgcttcct cgctcactga ctcgctgcgc tcggtcgttc ggctgcggcg agcggtatca   27900
gctcactcaa aggcggtaat acggttatcc acagaatcag gggataacgc aggaaagaac   27960
atgtgagcaa aaggccagca aaaggccagg aaccgtaaaa aggccgcgtt gctggcgttt   28020
ttccataggc tccgcccccc tgacgagcat cacaaaaatc gacgctcaag tcagaggtgg   28080
cgaaacccga caggactata aagataccag gcgtttcccc ctggaagctc cctcgtgcgc   28140
tctcctgttc cgaccctgcc gcttaccgga tacctgtccg cctttctccc ttcgggaagc   28200
gtggcgcttt ctcatagctc acgctgtagg tatctcagtt cggtgtaggt cgttcgctcc   28260
aagctgggct gtgtgcacga accccccgtt cagcccgacc gctgcgcctt atccggtaac   28320
tatcgtcttg agtccaaccc ggtaagacac gacttatcgc cactggcagc agccactggt   28380
aacaggatta gcagagcgag gtatgtaggc ggtgctacag agttcttgaa gtggtggcct   28440
aactacggct acactagaag gacagtattt ggtatctgcg ctctgctgaa gccagttacc   28500
ttcggaaaaa gagttggtag ctcttgatcc ggcaaacaaa ccaccgctgg tagcggtggt   28560
```

```
tttttttgttt gcaagcagca gattacgcgc agaaaaaaag gatctcaaga agatcctttg  28620
atcttttcta cggggtctga cgctcagtgg aacgaaaact cacgttaagg gattttggtc  28680
atgagattat caaaaaggat cttcacctag atccttttaa attaaaaatg aagttttaaa  28740
tcaatctaaa gtatatatga gtaaacttgg tctgacagtt accaatgctt aatcagtgag  28800
gcacctatct cagcgatctg tctatttcgt tcatccatag ttgcctgact ccccgtcgtg  28860
tagataacta cgatacggga gggcttacca tctggcccca gtgctgcaat gataccgcga  28920
gacccacgct caccggctcc agatttatca gcaataaacc agccagccgg aagggccgag  28980
cgcagaagtg gtcctgcaac tttatccgcc tccatccagt ctattaattg ttgccgggaa  29040
gctagagtaa gtagttcgcc agttaatagt ttgcgcaacg ttgttgccat tgctgcaggg  29100 ggggggggg gggggactt ccattgttca ttccacggac aaaaacagag aaaggaaacg  29160
acagaggcca aaaagcctcg ctttcagcac ctgtcgtttc ctttcttttc agagggtatt  29220
ttaaataaaa acattaagtt atgacgaaga agaacgaaaa cgccttaaac cggaaaattt  29280
tcataaatag cgaaaacccg cgaggtcgcc gccccgtaag ccgccccgta acctgtcgga  29340
tcaccggaaa ggaccgtaa agtgataatg attatcatct acatatcaca acgtgcgtgg  29400
aggccatcaa accacgtcaa ataatcaatt atgacgcagg tatcgtatta attgatctgc  29460
atcaacttaa cgtaaaaaca acttcagaca atacaaatca gcgacactga atacggggca  29520
acctcatgtc cccccccccc ccccccctgc aggcatcgtg gtgtcacgct cgtcgtttgg  29580
tatggcttca ttcagctccg gttcccaacg atcaaggcga gttacatgat ccccatgtt  29640 gtgcaaaaaa gcggttagct ccttcggtcc tccgatcgtt gtcagaagta agttggccgc  29700
agtgttatca ctcatggtta tggcagcact gcataattct cttactgtca tgccatccgt  29760
aagatgcttt tctgtgactg gtgagtactc aaccaagtca ttctgagaat agtgtatgcg  29820
gcgaccgagt tgctcttgcc cggcgtcaac acgggataat accgcgccac atagcagaac  29880
tttaaaagtg ctcatcattg gaaaacgttc ttcggggcga aaactctcaa ggatcttacc  29940
gctgttgaga tccagttcga tgtaacccac tcgtgcaccc aactgatctt cagcatcttt  30000
tactttcacc agcgtttctg ggtgagcaaa aacaggaagg caaaatgccg caaaaaaggg  30060
aataagggcg acacggaaat gttgaatact catactcttc ctttttcaat attattgaag  30120
catttatcag ggttattgtc tcatgagcgg atacatattt gaatgtattt agaaaaataa  30180
acaaataggg gttccgcgca catttccccg aaaagtgcca cctgacgtct aagaaaccat  30240
tattatcatg acattaacct ataaaaatag gcgtatcacg aggccctttc gtcttcaaga  30300
attcggagct tttgccattc tcaccggatt cagtcgtcac tcatggtgat ttctcacttg  30360
ataaccttat ttttgacgag gggaaattaa taggttgtat tgatgttgga cgagtcggaa  30420
tcgcagaccg ataccaggat cttgccatcc tatggaactg cctcggtgag ttttctcctt  30480
cattacagaa acggctttt caaaaatatg gtattgataa tcctgatatg aataaattgc  30540
agtttcattt gatgctcgat gagttttctt aatcagaatt ggttaattgg ttgtaacact  30600
ggcagagcat tacgctgact tgacgggacg gcggctttgt tgaataaatc gaacttttgc  30660
tgagttgaag gatcagatca cgcatcttcc cgacaacgca gaccgttccg tggcaaagca  30720
aaagttcaaa atcaccaact ggtccaccta caacaaagct ctcatcaacc gtggctccct  30780
cactttctgg ctggatgatg gggcgattca ggcctggtat gagtcagcaa caccttcttc  30840
acgaggcaga cctcagcgcc agaaggccgc cagagaggcc gagcgcggcc gtgaggcttc  30900
gacgctaggg cagggcatga aaagcccgt agcgggctgc tacgggcgtc tgacgcggtg  30960
```

```
gaaaggggga ggggatgttg tctacatggc tctgctgtag tgagtgggtt gcgctccggc   31020
agcggtcctg atcaatcgtc acccctttctc ggtccttcaa cgttcctgac aacgagcctc   31080
cttttcgcca atccatcgac aatcaccgcg agtccctgct cgaacgctgc gtccggaccg   31140
gcttcgtcga aggcgtctat cgcggcccgc aacagcggcg agagcggagc ctgttcaacg   31200
gtgccgccgc gctcgccggc atcgctgtcg ccggcctgct cctcaagcac ggccccaaca   31260
gtgaagtagc tgattgtcat cagcgcattg acggcgtccc cggccgaaaa acccgcctcg   31320
cagaggaagc gaagctgcgc gtcggccgtt tccatctgcg gtgcgcccgg tcgcgtgccg   31380
gcatggatgc gcgcgccatc gcggtaggcg agcagcgcct gcctgaagct gcgggcattc   31440
ccgatcagaa atgagcgcca gtcgtcgtcg gctctcggca ccgaatgcgt atgattctcc   31500
gccagcatgg cttcggccag tgcgtcgagc agcgcccgct tgttcctgaa gtgccagtaa   31560
agcgccggct gctgaacccc caaccgttcc gccagtttgc gtgtcgtcag accgtctacg   31620
ccgacctcgt tcaacaggtc cagggcggca cggatcactg tattcggctg caactttgtc   31680
atgcttgaca ctttatcact gataaacata atatgtccac caacttatca gtgataaaga   31740
atccgcgcgt tcaatcggac cagcggaggc tggtccggag gccagacgtg aaacccaaca   31800 taccccctgat cgtaattctg agcactgtcg cgctcgacgc tgtcggcatc ggcctgatta   31860
tgccggtgct gccgggcctc ctgcgcgatc tggttcactc gaacgacgtc accgcccact   31920
atggcattct gctggcgctg tatgcgttgg tgcaatttgc ctgcgcacct gtgctgggcg   31980
cgctgtcgga tcgtttcggg cggcggccaa tcttgctcgt ctcgctggcc ggcgccactg   32040
tcgactacgc catcatggcg acagcgcctt tcctttgggt tctctatatc gggcggatcg   32100
tggccggcat caccggggcg actggggcgg tagccggcgc ttatattgcc gatatcactg   32160
atggcgatga gcgcgcgcgg cacttcggct tcatgagcgc ctgtttcggg ttcgggatgg   32220
tcgcgggacc tgtgctcggt gggctgatgg gcggtttctc ccccacgct ccgttcttcg   32280 ccgcggcagc cttgaacggc ctcaatttcc tgacgggctg ttttccttttg ccggagtcgc   32340 acaaaggcga acgccggccg ttacgccggg aggctctcaa cccgctcgct tcgttccggt   32400
gggcccgggg catgaccgtc gtcgccgccc tgatggcggt cttcttcatc atgcaacttg   32460
tcggacaggt gccggccgcg cttttgggtca ttttcggcga ggatcgcttt cactgggacg   32520
cgaccacgat cggcatttcg cttgccgcat ttggcattct gcattcactc gcccaggcaa   32580
tgatcaccgg ccctgtagcc gcccggctcg gcgaaaggcg ggcactcatg ctcggaatga   32640
ttgccgacgg cacaggctac atcctgcttg ccttcgcgac acggggatgg atggcgttcc   32700
cgatcatggt cctgcttgct tcgggtggca tcggaatgcc ggcgctgcaa gcaatgttgt   32760
ccaggcaggt ggatgaggaa cgtcagggggc agctgcaagg ctcactggcg gcgctcacca   32820
gcctgacctc gatcgtcgga cccctcctct tcacggcgat ctatgcggct tctataacaa   32880
cgtggaacgg gtgggcatgg attgcaggcg ctgccctcta cttgctctgc ctgccggcgc   32940
tgcgtcgcgg gctttggagc ggcgcagggc aacgagccga tcgctgatcg tggaaacgat   33000
aggcctatgc catgcgggtc aaggcgactt ccggcaagct atacgcgccc taggagtgcg   33060
gttggaacgt tggcccagcc agatactccc gatcacgagc aggacgccga tgatttgaag   33120
cgcactcagc gtctgatcca agaacaacca tcctagcaac acggcggtcc ccgggctgag   33180
aaagcccagt aaggaaacaa ctgtaggttc gagtcgcgag atccccggga accaaaggaa   33240
gtaggttaaa cccgctccga tcaggccgag ccacgccagg ccgagaacat tggttcctgt   33300
aggcatcggg attggcggat caaacactaa agctactgga acgagcagaa gtcctccggc   33360
```

```
cgccagttgc caggcggtaa aggtgagcag aggcacggga ggttgccact tgcgggtcag   33420
cacggttccg aacgccatgg aaaccgcccc cgccaggccc gctgcgacgc cgacaggatc   33480
tagcgctgcg tttggtgtca acaccaacag cgccacgccc gcagttccgc aaatagcccc   33540
caggaccgcc atcaatcgta tcgggctacc tagcagagcg gcagagatga acacgaccat   33600
cagcggctgc acagcgccta ccgtcgccgc gaccccgccc ggcaggcggt agaccgaaat   33660
aaacaacaag ctccagaata gcgaaatatt aagtgcgccg aggatgaaga tgcgcatcca   33720
ccagattccc gttggaatct gtcggacgat catcacgagc aataaacccg ccggcaacgc   33780
ccgcagcagc ataccggcga cccctcggcc tcgctgttcg ggctccacga aaacgccgga   33840
cagatgcgcc ttgtgagcgt ccttggggcc gtcctcctgt ttgaagaccg acagcccaat   33900
gatctcgccg tcgatgtagg cgccgaatgc cacggcatct cgcaaccgtt cagcgaacgc   33960
ctccatgggc ttttctcct cgtgctcgta aacggacccg aacatctctg gagctttctt   34020
cagggccgac aatcggatct cgcggaaatc ctgcacgtcg gccgctccaa gccgtcgaat   34080
ctgagcctta atcacaattg tcaattttaa tcctctgttt atcggcagtt cgtagagcgc   34140
gccgtgcgtc ccgagcgata ctgagcgaag caagtgcgtc gagcagtgcc cgcttgttcc   34200
tgaaatgcca gtaaagcgct ggctgctgaa cccccagccg gaactgaccc cacaaggccc   34260
tagcgtttgc aatgcaccag gtcatcattg acccaggcgt gttccaccag gccgctgcct   34320
cgcaactctt cgcaggcttc gccgacctgc tcgcgccact tcttcacgcg ggtggaatcc   34380
gatccgcaca tgaggcggaa ggtttccagc ttgagcgggt acggctcccg gtgcgagctg   34440
aaatagtcga acatccgtcg ggccgtcggc gacagcttgc ggtacttctc ccatatgaat   34500
ttcgtgtagt ggtcgccagc aaacagcacg acgatttcct cgtcgatcag gacctggcaa   34560
cgggacgttt tcttgccacg gtccaggacg cggaagcggt gcagcagcga caccgattcc   34620
aggtgcccaa cgcggtcgga cgtgaagccc atcgccgtcg cctgtaggcg cgacaggcat   34680
tcctcggcct tcgtgtaata ccggccattg atcgaccagc ccaggtcctg gcaaagctcg   34740
tagaacgtga aggtgatcgg ctcgccgata ggggtgcgct tcgcgtactc caacacctgc   34800
tgccacacca gttcgtcatc gtcggcccgc agctcgacgc cggtgtaggt gatcttcacg   34860
tccttgttga cgtggaaaat gaccttgttt tgcagcgcct cgcgcgggat tttcttgttg   34920
cgcgtggtga acagggcaga gcgggccgtg tcgtttggca tcgctcgcat cgtgtccggc   34980
cacggcgcaa tatcgaacaa ggaaagctgc atttccttga tctgctgctt cgtgtgtttc   35040
agcaacgcgg cctgcttggc ctcgctgacc tgttttgcca ggtcctcgcc ggcggttttt   35100
cgcttcttgg tcgtcatagt tcctcgcgtg tcgatggtca tcgacttcgc caaacctgcc   35160
gcctcctgtt cgagacgacg cgaacgctcc acggcggccg atggcgcggg cagggcaggg   35220
ggagccagtt gcacgctgtc gcgctcgatc ttggccgtag cttgctggac catcgagccg   35280
acggactgga aggtttcgcg gggcgcacgc atgacggtgc ggcttgcgat ggtttcggca   35340
tcctcggcgg aaaaccccgc gtcgatcagt tcttgcctgt atgccttccg gtcaaacgtc   35400
cgattcattc accctccttg cgggattgcc ccgactcacg ccggggcaat gtgcccttat   35460
tcctgatttg acccgcctgg tgccttggtg tccagataat ccaccttatc ggcaatgaag   35520
tcggtcccgt agaccgtctg gccgtccttc tcgtacttgg tattccgaat cttgcccctgc   35580 acgaatacca gcgacccctt gcccaaatac ttgccgtggg cctcggcctg agagccaaaa   35640
cacttgatcg ggaagaagtc ggtgcgctcc tgcttgtcgc cggcatcgtt gcgccactct   35700
tcattaaccg ctatatcgaa aattgcttgc ggcttgttag aattgccatg acgtacctcg   35760
```

```
gtgtcacggg taagattacc gataaactgg aactgattat ggctcatatc gaaagtctcc    35820
ttgagaaagg agactctagt ttagctaaac attggttccg ctgtcaagaa ctttagcggc    35880
taaaattttg cgggccgcga ccaaaggtgc gaggggcggc ttccgctgtg tacaaccaga    35940 tattttcac caacatcctt cgtctgctcg atgagcgggg catgacgaaa catgagctgt    36000
cggagagggc aggggtttca atttcgtttt tatcagactt aaccaacggt aaggccaacc    36060
cctcgttgaa ggtgatggag gccattgccg acgccctgga aactcccta cctcttctcc    36120 tggagtccac cgaccttgac cgcgaggcac tcgcggagat tgcgggtcat cctttcaaga    36180
gcagcgtgcc gcccggatac gaacgcatca gtgtggtttt gccgtcacat aaggcgttta    36240
tcgtaaagaa atggggcgac gacacccgaa aaaagctgcg tggaaggctc tgacgccaag    36300
ggttagggct tgcacttcct tctttagccg ctaaaacggc cccttctctg cgggccgtcg    36360
gctcgcgcat catatcgaca tcctcaacgg aagccgtgcc gcgaatggca tcgggcgggt    36420
gcgctttgac agttgttttc tatcagaacc cctacgtcgt gcggttcgat tagctgtttg    36480
tcttgcaggc taaacacttt cggtatatcg tttgcctgtg cgataatgtt gctaatgatt    36540
tgttgcgtag gggttactga aaagtgagcg ggaaagaaga gtttcagacc atcaaggagc    36600
gggccaagcg caagctggaa cgcgacatgg gtgcggacct gttggccgcg ctcaacgacc    36660
cgaaaaccgt tgaagtcatg ctcaacgcgg acggcaaggt gtggcacgaa cgccttggcg    36720
agccgatgcg gtacatctgc gacatgcggc ccagccagtc gcaggcgatt atagaaacgg    36780
tggccggatt ccacggcaaa gaggtcacgc ggcattcgcc catcctggaa ggcgagttcc    36840
ccttggatgg cagccgcttt gccggccaat tgccgccggt cgtggccgcg ccaacctttg    36900
cgatccgcaa gcgcgcggtc gccatcttca cgctggaaca gtacgtcgag gcgggcatca    36960
tgacccgcga gcaatacgag gtcattaaaa gcgccgtcgc ggcgcatcga aacatcctcg    37020
tcattggcgg tactggctcg ggcaagacca cgctcgtcaa cgcgatcatc aatgaaatgg    37080
tcgccttcaa cccgtctgag cgcgtcgtca tcatcgagga caccggcgaa atccagtgcg    37140
ccgcagagaa cgccgtccaa taccacacca gcatcgacgt ctcgatgacg ctgctgctca    37200
agacaacgct gcgtatgcgc cccgaccgca tcctggtcgg tgaggtacgt ggccccgaag    37260
cccttgatct gttgatggcc tggaacaccg ggcatgaagg aggtgccgcc acctgcacg    37320 caaacaaccc caaagcgggc ctgagccggc tcgccatgct tatcagcatg cacccggatt    37380
caccgaaacc cattgagccg ctgattggcg aggcggttca tgtggtcgtc catatcgcca    37440 ggaccctag cggccgtcga gtgcaagaaa ttctcgaagt tcttggttac gagaacggcc    37500
agtacatcac caaaaccctg taaggagtat ttccaatgac aacggctgtt ccgttccgtc    37560
tgaccatgaa tcgcggcatt tgttctacc ttgccgtgtt cttcgttctc gctctcgcgt    37620
tatccgcgca tccggcgatg gcctcggaag gcaccgcgg cagcttgcca tatgagagct    37680
ggctgacgaa cctgcgcaac tccgtaaccg gcccggtggc cttcgcgctg tccatcatcg    37740
gcatcgtcgt cgccggcggc gtgctgatct tcggcggcga actcaacgcc ttcttccgaa    37800
ccctgatctt cctggttctg gtgatggcgc tgctggtcgg cgcgcagaac gtgatgagca    37860
ccttcttcgg tcgtggtgcc gaaatcgcgg ccctcggcaa cggggcgctg caccaggtgc    37920
aagtcgcggc ggcggatgcc gtgcgtgcgg tagcggctgg acggctcgcc taatcatggc    37980
tctgcgcacg atccccatcc gtcgcgcagg caaccgagaa aacctgttca tgggtggtga    38040
tcgtgaactg gtgatgttct cgggcctgat ggcgtttgcg ctgattttca gcgcccaaga    38100
gctgcgggcc accgtggtcg gtctgatcct gtggttcggg gcgctctatg cgttccgaat    38160
```

```
catggcgaag gccgatccga agatgcggtt cgtgtacctg cgtcaccgcc ggtacaagcc      38220
gtattacccg gcccgctcga ccccgttccg cgagaacacc aatagccaag ggaagcaata      38280
ccgatgatcc aagcaattgc gattgcaatc gcgggcctcg gcgcgcttct gttgttcatc      38340
ctctttgccc gcatccgcgc ggtcgatgcc gaactgaaac tgaaaaagca tcgttccaag      38400
gacgccggcc tggccgatct gctcaactac gccgctgtcg tcgatgacgg cgtaatcgtg      38460
ggcaagaacg gcagctttat ggctgcctgg ctgtacaagg gcgatgacaa cgcaagcagc      38520
accgaccagc agcgcgaagt agtgtccgcc cgcatcaacc aggccctcgc gggcctggga      38580
agtgggtgga tgatccatgt ggacgccgtg cggcgtcctg ctccgaacta cgcggagcgg      38640
ggcctgtcgg cgttccctga ccgtctgacg gcagcgattg aagaagacg ctcggtcttg       38700 ccttgctcgt cggtgatgta cttcaccagc tccgcgaagt cgctcttctt gatggagcgc      38760
atggggacgt gcttggcaat cacgcgcacc ccccggccgt tttagcggct aaaaaagtca      38820
tggctctgcc ctcgggcgga ccacgccat catgaccttg ccaagctcgt cctgcttctc       38880
ttcgatcttc gccagcaggg cgaggatcgt ggcatcaccg aaccgcgccg tgcgcgggtc      38940
gtcggtgagc cagagtttca gcaggccgcc caggcggccc aggtcgccat tgatgcgggc      39000
cagctcgcgg acgtgctcat agtccacgac gcccgtgatt ttgtagcccct ggccgacggc     39060 cagcaggtag gccgacaggc tcatgccggc cgccgccgcc ttttcctcaa tcgctcttcg      39120
ttcgtctgga aggcagtaca ccttgatagg tgggctgccc ttcctggttg gcttggtttc      39180
atcagccatc cgcttgccct catctgttac gccggcggta ccggccagc ctcgcagagc       39240 aggattcccg ttgagcaccg ccaggtgcga ataagggaca gtgaagaagg aacacccgct      39300
cgcgggtggg cctacttcac ctatcctgcc cggctgacgc cgttggatac accaaggaaa      39360
gtctacacga acccttggc aaaatcctgt atatcgtgcg aaaaaggatg gatataccga       39420
aaaaatcgct ataatgaccc cgaagcaggg ttatgcagcg gaaaagcgct gcttccctgc      39480
tgttttgtgg aatatctacc gactggaaac aggcaaatgc aggaaattac tgaactgagg      39540
ggacaggcga gagacgatgc caaagagcta caccgacgag ctggccgagt gggttgaatc      39600
ccgcgcggcc aagaagcgcc ggcgtgatga ggctgcggtt gcgttcctgg cggtgagggc      39660
ggatgtcgag gcggcgttag cgtccggcta tgcgctcgtc accatttggg agcacatgcg      39720
ggaaacgggg aaggtcaagt tctcctacga gacgttccgc tcgcacgcca ggcggcacat      39780
caaggccaag cccgccgatg tgcccgcacc gcaggccaag gctgcggaac ccgcgccggc      39840
acccaagacg ccggagccac ggcggccgaa gcagggggc aaggctgaaa agccggcccc       39900
cgctgcggcc ccgaccggct tcaccttcaa cccaacaccg gacaaaaagg atctactgta      39960
atggcgaaaa ttcacatggt tttgcagggc aagggcgggg tcggcaagtc ggccatcgcc      40020
gcgatcattg cgcagtacaa gatggacaag gggcagacac ccttgtgcat cgacaccgac      40080
ccggtgaacg cgacgttcga gggctacaag gccctgaacg tccgccggct gaacatcatg      40140
gccggcgacg aaattaactc gcgcaacttc gacaccctgg tcgagctgat tgcgccgacc      40200
aaggatgacg tggtgatcga caacggtgcc agctcgttcg tgcctctgtc gcattacctc      40260
atcagcaacc aggtgccggc tctgctgcaa gaaatggggc atgagctggt catccatacc      40320
gtcgtcaccg cggccaggc tctcctggac acggtgagcg gcttcgccca gctcgccagc       40380
cagttcccgg ccgaagcgct tttcgtggtc tggctgaacc cgtattgggg gcctatcgag      40440
catgagggca gagctttga gcagatgaag gcgtacacgg ccaacaaggc ccgcgtgtcg       40500
tccatcatcc agattccggc cctcaaggaa gaaacctacg gccgcgattt cagcgacatg      40560
```

```
ctgcaagagc ggctgacgtt cgaccaggcg ctggccgatg aatcgctcac gatcatgacg    40620
cggcaacgcc tcaagatcgt gcggcgcggc ctgtttgaac agctcgacgc ggcggccgtg    40680
ctatgagcga ccagattgaa gagctgatcc gggagattgc ggccaagcac ggcatcgccg    40740
tcggccgcga cgacccggtg ctgatcctgc ataccatcaa cgcccggctc atggccgaca    40800
gtgcggccaa gcaagaggaa atccttgccg cgttcaagga agagctggaa gggatcgccc    40860
atcgttgggg cgaggacgcc aaggccaaag cggagcggat gctgaacgcg ccctggcgg    40920 ccagcaagga cgcaatggcg aaggtaatga aggacagcgc cgcgcaggcg ccgaagcga    40980 tccgcaggga aatcgacgac ggccttggcc gccagctcgc ggccaaggtc gcggacgcgc    41040
ggcgcgtggc gatgatgaac atgatcgccg gcggcatggt gttgttcgcg gccgccctgg    41100
tggtgtgggc ctcgttatga atcgcagagg cgcagatgaa aaagcccggc gttgccgggc    41160 tttgttttg cgttagctgg gcttgtttga caggcccaag ctctgactgc gcccgcgctc    41220
gcgctcctgg gcctgtttct tctcctgctc ctgcttgcgc atcagggcct ggtgccgtcg    41280
ggctgcttca cgcatcgaat cccagtcgcc ggccagctcg ggatgctccg cgcgcatctt    41340
gcgcgtcgcc agttcctcga tcttgggcgc gtgaatgccc atgccttcct tgatttcgcg    41400
caccatgtcc agccgcgtgt gcagggtctg caagcgggct tgctgttggg cctgctgctg    41460
ctgccaggcg gcctttgtac gcggcaggga cagcaagccg ggggcattgg actgtagctg    41520
ctgcaaacgc gcctgctgac ggtctacgag ctgttctagg cggtcctcga tgcgctccac    41580
ctggtcatgc tttgcctgca cgtagagcgc aagggtctgc tggtaggtct gctcgatggg    41640
cgcggattct aagagggcct gctgttccgt ctcggcctcc tgggccgcct gtagcaaatc    41700
ctcgccgctg ttgccgctgg actgctttac tgccggggac tgctgttgcc ctgctcgcgc    41760
cgtcgtcgca gttcggcttg ccccactcg attgactgct tcatttcgag ccgcagcgat    41820
gcgatctcgg attgcgtcaa cggacggggc agcgcggagg tgtccggctt ctccttgggt    41880
gagtcggtcg atgccatagc caaaggtttc cttccaaaat gcgtccattg ctggaccgtg    41940
tttctcattg atgcccgcaa gcatcttcgg cttgaccgcc aggtcaagcg cgccttcatg    42000
ggcggtcatg acggacgccg ccatgacctt gccgccgttg ttctcgatgt agccgcgtaa    42060
tgaggcaatg gtgccgccca tcgtcagcgt gtcatcgaca acgatgtact ctgtgccggg    42120
gatcacctcc ccctcgaaag tcgggttgaa cgccaggcga tgatctgaac cggctccggt    42180
tcgggcgacc ttctcccgct gcacaatgtc cgtttcgacc tcaaggccaa ggcggtcggc    42240
cagaacgacc gccatcatgg ccggaatctt gttgttcccc gccgcctcga cggcgaggac    42300
tggaacgatg cggggcttgt cgtcgccgat cagcgtcttg agctgggcaa cagtgtcgtc    42360
cgaaatcagg cgctcgacca aattaagcgc cgcttccgcg tcgccctgct tcgcagcctg    42420
gtattcaggc tcgttggtca aagaaccaag gtcgccgttg cgaaccacct tcgggaagtc    42480
tccccacggt gcgcgctcgg ctctgctgta gctgctcaag acgcctccct ttttagccgc    42540
taaaactcta acgagtgcgc ccgcgactca acttgacgct ttcggcactt acctgtgcct    42600
tgccacttgc gtcataggtg atgcttttcg cactcccgat ttcaggtact ttatcgaaat    42660
ctgaccgggc gtgcattaca aagttcttcc ccacctgttg gtaaatgctg ccgctatctg    42720
cgtggacgat gctgccgtcg tggcgctgcg acttatcggc cttttgggcc atatagatgt    42780
tgtaaatgcc aggtttcagg gccccggctt tatctacctt ctggttcgtc catgcgcctt    42840
ggttctcggc ctggacaatt ctttgcccat tcatgaccag gaggcggtgt tcattgggt    42900 gactcctgac ggttgcctct ggtgttaaac gtgtcctggt cgcttgccgg ctaaaaaaaa    42960
```

```
gccgacctcg gcagttcgag gccggctttc cctagagccg ggcgcgtcaa ggttgttcca    43020 tctatttag tgaactgcgt tcgatttatc agttactttc ctcccgcttt gtgtttcctc    43080
ccactcgttt ccgcgtctag ccgacccctc aacatagcgg cctcttcttg ggctgccttt    43140
gcctcttgcc gcgcttcgtc acgctcggct tgcaccgtcg taaagcgctc ggcctgcctg    43200
gccgcctctt gcgccgccaa cttcctttgc tcctggtggg cctcggcgtc ggcctgcgcc    43260
ttcgctttca ccgctgccaa ctccgtgcgc aaactctccg cttcgcgcct ggtggcgtcg    43320
cgctcgccgc gaagcgcctg catttcctgg ttggccgcgt ccagggtctt gcggctctct    43380
tctttgaatg cgcgggcgtc ctggtgagcg tagtccagct cggcgcgcag ctcctgcgct    43440
cgacgctcca cctcgtcggc ccgctgcgtc gccagcgcgg cccgctgctc ggctcctgcc    43500
agggcggtgc gtgcttcggc cagggcttgc cgctggcgtg cggccagctc ggccgcctcg    43560
gcggcctgct gctctagcaa tgtaacgcgc gcctgggctt cttccagctc gcgggcctgc    43620
gcctcgaagg cgtcggccag ctccccgcgc acggcttcca actcgttgcg ctcacgatcc    43680
cagccggctt gcgctgcctg caacgattca ttggcaaggg cctgggcggc ttgccagagg    43740
gcggccacgc cctggttgcc ggcctgctgc accgcgtccg gcacctggac tgccagcggg    43800
gcggcctgcg ccgtgcgctg gcgtcgccat tcgcgcatgc cggcgctggc gtcgttcatg    43860
ttgacgcggg cggccttacg cactgcatcc acggtcggga agttctcccg gtcgccttgc    43920
tcgaacagct cgtccgcagc cgcaaaaatg cggtcgcgcg tctctttgtt cagttccatg    43980
ttggctccgg taattggtaa gaataataat actcttacct accttatcag cgcaagagtt    44040
tagctgaaca gttctcgact taacggcagg ttttttagcg gctgaagggc aggcaaaaaa    44100
agccccgcac ggtcggcggg ggcaaagggt cagcgggaag gggattagcg ggcgtcgggc    44160
ttcttcatgc gtcggggccg cgcttcttgg gatggagcac gacgaagcgc gcacgcgcat    44220
cgtcctcggc cctatcggcc cgcgtcgcgg tcaggaactt gtcgcgcgct aggtcctccc    44280
tggtgggcac caggggcatg aactcggcct gctcgatgta ggtccactcc atgaccgcat    44340
cgcagtcgag gccgcgttcc ttcaccgtct cttgcaggtc gcggtacgcc cgctcgttga    44400
gcggctggta acgggccaat tggtcgtaaa tggctgtcgg ccatgagcgg cctttcctgt    44460
tgagccagca gccgacgacg aagccggcaa tgcaggcccc tggcacaacc aggccgacgc    44520 cggggggcagg ggatggcagc agctcgccaa ccaggaaccc cgccgcgatg atgccgatgc    44580
cggtcaacca gcccttgaaa ctatccggcc ccgaaacacc cctgcgcatt gcctggatgc    44640
tgcgccggat agcttgcaac atcaggagcc gtttcttttg ttcgtcagtc atggtccgcc    44700
ctcaccagtt gttcgtatcg gtgtcggacg aactgaaatc gcaagagctg ccggtatcgg    44760
tccagccgct gtccgtgtcg ctgctgccga agcacggcga ggggtccgcg aacgccgcag    44820
acggcgtatc cggccgcagc gcatcgccca gcatggcccc ggtcagcgag ccgcggcca    44880 ggtagcccag catggtgctg ttggtcgccc cggccaccag ggccgacgtg acgaaatcgc    44940
cgtcattccc tctggattgt tcgctgctcg gcggggcagt gcgccgcgcc ggcggcgtcg    45000
tggatggctc gggttggctg gcctgcgacg gccggcgaaa ggtgcgcagc agctcgttat    45060
cgaccggctg cggcgtcggg gccgccgcct tgcgctgcgg tcggtgttcc ttcttcggct    45120
cgcgcagctt gaacagcatg atcgcggaaa ccagcagcaa cgccgcgcct acgcctcccg    45180
cgatgtagaa cagcatcgga ttcattcttc ggtcctcctt gtagcggaac cgttgtctgt    45240
gcggcgcggg tggcccgcgc cgctgtcttt ggggatcagc cctcgatgag cgcgaccagt    45300
ttcacgtcgg caaggttcgc ctcgaactcc tggccgtcgt cctcgtactt caaccaggca    45360
```

```
tagccttccg ccggcggccg acggttgagg ataaggcggg cagggcgctc gtcgtgctcg   45420
acctggacga tggccttttt cagcttgtcc gggtccggct ccttcgcgcc cttttccttg   45480
gcgtccttac cgtcctggtc gccgtcctcg ccgtcctggc cgtcgccggc ctccgcgtca   45540
cgctcggcat cagtctggcc gttgaaggca tcgacggtgt tgggatcgcg gcccttctcg   45600
tccaggaact cgcgcagcag cttgaccgtg ccgcgcgtga tttcctgggt gtcgtcgtca   45660
agccacgcct cgacttcctc cgggcgcttc ttgaaggccg tcaccagctc gttcaccacg   45720
gtcacgtcgc gcacgcggcc ggtgttgaac gcatcggcga tcttctccgg caggtccagc   45780
agcgtgacgt gctgggtgat gaacgccggc gacttgccga tttccttggc gatatcgcct   45840
ttcttcttgc ccttcgccag ctcgcggcca atgaagtcgg caatttcgcg cggggtcagc   45900
tcgttgcgtt gcaggttctc gataacctgg tcggcttcgt tgtagtcgtt gtcgatgaac   45960
gccgggatgg acttcttgcc ggcccacttc gagccacggt agcggcgggc gccgtgattg   46020
atgatatagc ggcccggctg ctcctggttc tcgcgcaccg aaatgggtga cttcaccccg   46080
cgctctttga tcgtggcacc gatttccgcg atgctctccg gggaaaagcc ggggttgtcg   46140
gccgtccgcg gctgatgcgg atcttcgtcg atcaggtcca ggtccagctc gatagggccg   46200
gaaccgccct gagacgccgc aggagcgtcc aggaggctcg acaggtcgcc gatgctatcc   46260
aaccccaggc cggacggctg cgccgcgcct gcggcttcct gagcggccgc agcggtgttt   46320
ttcttggtgg tcttggcttg agccgcagtc attgggaaat ctccatcttc gtgaacacgt   46380
aatcagccag ggcgcgaacc tctttcgatg ccttgcgcgc ggccgttttc ttgatcttcc   46440
agaccggcac accggatgcg agggcatcgg cgatgctgct gcgcaggcca acggtggccg   46500
gaatcatcat cttggggtac gcggccagca gctcggcttg gtggcgcgcg tggcgcggat   46560
tccgcgcatc gaccttgctg ggcaccatgc caaggaattg cagcttggcg ttcttctggc   46620
gcacgttcgc aatggtcgtg accatcttct tgatgccctg gatgctgtac gcctcaagct   46680
cgatggggga cagcacatag tcggccgcga agagggcggc cgccaggccg acgccaaggg   46740
tcggggccgt gtcgatcagg cacacgtcga agccttggtt cgccagggcc ttgatgttcg   46800
ccccgaacag ctcgcgggcg tcgtccagcg acagccgttc ggcgttcgcc agtaccgggt   46860
tggactcgat gagggcgagg cgcgcggcct ggccgtcgcc ggctgcgggt gcggtttcgg   46920
tccagccgcc ggcagggaca gcgccgaaca gcttgcttgc atgcaggccg gtagcaaagt   46980
ccttgagcgt gtaggacgca ttgccctggg ggtccaggtc gatcacggca acccgcaagc   47040
cgcgctcgaa aaagtcgaag gcaagatgca caagggtcga agtcttgccg acgccgcctt   47100
tctggttggc cgtgaccaaa gttttcatcg tttggtttcc tgtttttttct tggcgtccgc   47160 ttcccacttc cggacgatgt acgcctgatg ttccggcaga accgccgtta cccgcgcgta   47220
cccctcgggc aagttcttgt cctcgaacgc ggcccacacg cgatgcaccg cttgcgacac   47280
tgcgcccctg gtcagtccca gcgacgttgc gaacgtcgcc tgtggcttcc catcgactaa   47340
gacgccccgc gctatctcga tggtctgctg ccccacttcc agccctgga tcgcctcctg   47400 gaactggctt tcggtaagcc gttctttcat ggataacacc cataatttgc tccgcgcctt   47460
ggttgaacat agcggtgaca gccgccagca catgagagaa gtttagctaa acatttctcg   47520
cacgtcaaca cctttagccg ctaaaactcg tccttggcgt aacaaaacaa agcccggaa    47580 accgggctttt cgtctcttgc cgcttatggc tctgcacccg gctccatcac caacaggtcg   47640
cgcacgcgct tcactcggtt gcggatcgac actgccagcc caacaaagcc ggttgccgc    47700 gccgccagga tcgcgccgat gatgccggcc acaccggcca tcgcccacca ggtcgccgcc   47760
```

```
ttccggttcc attcctgctg gtactgcttc gcaatgctgg acctcggctc accataggct    47820
gaccgctcga tggcgtatgc cgcttctccc cttggcgtaa acccagcgc cgcaggcggc     47880 attgccatgc tgcccgccgc tttcccgacc acgacgcgcg caccaggctt gcggtccaga    47940
ccttcggcca cggcgagctg cgcaaggaca taatcagccg ccgacttggc tccacgcgcc    48000
tcgatcagct cttgcactcg cgcgaaatcc ttggcctcca cggccgccat gaatcgcgca    48060
cgcggcgaag gctccgcagg gccggcgtcg tgatcgccgc cgagaatgcc cttcaccaag    48120
ttcgacgaca cgaaaatcat gctgacggct atcaccatca tgcagacgga tcgcacgaac    48180
ccgctgaatt gaacacgagc acggcacccg cgaccactat gccaagaatg cccaaggtaa    48240
aaattgccgg ccccgccatg aagtccgtga atgccccgac ggccgaagtg aagggcaggc    48300
cgccacccag gccgccgccc tcactgcccg gcacctggtc gctgaatgtc gatgccagca    48360
cctgcggcac gtcaatgctt ccgggcgtcg cgctcgggct gatcgcccat cccgttactg    48420
ccccgatccc ggcaatggca aggactgcca gcgctgccat ttttgggtg aggccgttcg     48480 cggccgaggg gcgcagcccc tggggggatg ggaggcccgc gttagcgggc cgggagggtt    48540
cgagaagggg gggcacccc cttcggcgtg cgcggtcacg cgcacagggc gcagccctgg     48600
ttaaaaacaa ggtttataaa tattggttta aaagcaggtt aaaagacagg ttagcggtgg    48660
ccgaaaaacg ggcggaaacc cttgcaaatg ctggattttc tgcctgtgga cagcccctca    48720
aatgtcaata ggtgcgcccc tcatctgtca gcactctgcc cctcaagtgt caaggatcgc    48780 gccctcatc tgtcagtagt cgcgcccctc aagtgtcaat accgcagggc acttatcccc     48840
aggcttgtcc acatcatctg tgggaaactc gcgtaaaatc aggcgttttc gccgatttgc    48900
gaggctggcc agctccacgt cgccggccga atcgagcct gccctcatc tgtcaacgcc      48960 gcgccgggtg agtcggcccc tcaagtgtca acgtccgccc ctcatctgtc agtgagggcc    49020
aagttttccg cgaggtatcc acaacgccgg cggccgcgt gtctcgcaca cggcttcgac     49080
ggcgtttctg gcgcgtttgc agggccatag acggccgcca gcccagcggc gagggcaacc    49140
agcccggtga gcgtcggaaa ggcgctggaa gccccgtagc gacgcggaga ggggcgagac    49200
aagccaaggg cgcaggctcg atgcgcagca cgacatagcc ggttctcgca aggacgagaa    49260
tttccctgcg gtgccctca agtgtcaatg aaagtttcca acgcgagcca ttcgcgagag     49320
ccttgagtcc acgctagatg agagctttgt tgtaggtgga ccagttggtg attttgaact    49380
tttgctttgc cacggaacgg tctgcgttgt cgggaagatg cgtgatctga tccttcaact    49440
cagcaaaagt tcgatttatt caacaaagcc acgttgtgtc tcaaaatctc tgatgttaca    49500
ttgcacaaga taaaaatata tcatcatgaa caataaaact gtctgcttac ataaacagta    49560
atacaagggg tgttatgagc catattcaac gggaaac                              49597
```

<210> SEQ ID NO 94
<211> LENGTH: 49579
<212> TYPE: DNA
<213> ORGANISM: Artificial Seqeunce
<220> FEATURE:
<223> OTHER INFORMATION: Vector

<400> SEQUENCE: 94

```
gtcttgctcg actctagagc tcgttcctcg aggcctcgag gcctcgagga acggtacctg      60
cggggaagct tacaataatg tgtgttgtta agtcttgttg cctgtcatcg tctgactgac     120
tttcgtcata aatcccggcc tccgtaaccc agctttgggc aagctcacgg atttgatccg    180
gcggaacggg aatatcgaga tgccgggctg aacgctgcag ttccagcttt cccttttcggg   240
```

```
acaggtactc cagctgattg attatctgct gaagggtctt ggttccacct cctggcacaa    300
tgcgaatgat tacttgagcg cgatcgggca tccaattttc tcccgtcagg tgcgtggtca    360
agtgctacaa ggcacctttc agtaacgagc gaccgtcgat ccgtcgccgg gatacggaca    420
aaatggagcg cagtagtcca tcgagggcgg cgaaagcctc gccaaaagca atacgttcat    480
ctcgcacagc ctccagatcc gatcgagggt cttcggcgta ggcagataga agcatggata    540
cattgcttga gagtattccg atggactgaa gtatggcttc catctttct cgtgtgtctg     600
catctatttc gagaaagccc ccgatgcggc gcaccgcaac gcgaattgcc atactatccg    660
aaagtcccag caggcgcgct tgataggaaa aggtttcata ctcggccgat cgcagacggg    720
cactcacgac cttgaaccct tcaactttca gggatcgatg ctggttgatg gtagtctcac    780
tcgacgtggc tctggtgtgt tttgacatag cttcctccaa agaaagcgga aggtctggat    840
actccagcac gaaatgtgcc cgggtagacg gatggaagtc tagccctgct caatatgaaa    900
tcaacagtac atttacagtc aatactgaat atacttgcta catttgcaat tgtcttataa    960
cgaatgtgaa ataaaaatag tgtaacaacg cttttactca tcgataatca caaaaacatt   1020
tatacgaaca aaaatacaaa tgcactccgg tttcacagga taggcgggat cagaatatgc   1080
aacttttgac gttttgttct ttcaaagggg gtgctggcaa aaccaccgca ctcatgggcc   1140
tttgcgctgc tttggcaaat gacggtaaac gagtggccct cttttgatgcc gacgaaaacc   1200
ggcctctgac gcgatggaga gaaaacgcct tacaaagcag tactgggatc ctcgctgtga   1260
agtctattcc gccgacgaaa tgccccttct tgaagcagcc tatgaaaatg ccagagctcga   1320
aggatttgat tatgcgttgg ccgatacgcg tggcggctcg agcgagctca acaacacaat   1380
catcgctagc tcaaacctgc ttctgatccc caccatgcta acgccgctcg acatcgatga   1440
ggcactatct acctaccgct acgtcatcga gctgctgttg agtgaaaatt tggcaattcc   1500
tacagctgtt ttgcgccaac gcgtcccggt cggccgattg acaacatcgc aacgcaggat   1560
gtcagagacg ctagagagcc ttccagttgt accgtctccc atgcatgaaa gagatgcatt   1620
tgccgcgatg aaagaacgcg gcatgttgca tcttacatta ctaaacacgg gaactgatcc   1680
gacgatgcgc ctcatagaga ggaatcttcg gattgcgatg gaggaagtcg tggtcatttc   1740
gaaactgatc agcaaaatct tggaggcttg aagatggcaa ttcgcaagcc cgcattgtcg   1800
gtcggcgaag cacggcggct tgctggtgct cgacccgaga tccaccatcc caacccgaca   1860
cttgttcccc agaagctgga cctccagcac ttgcctgaaa aagccgacga gaaagaccag   1920
caacgtgagc ctctcgtcgc cgatcacatt tacagtcccg atcgacaact taagctaact   1980
gtggatgccc ttagtccacc tccgtccccg aaaaagctcc aggttttct ttcagcgcga    2040
ccgcccgcgc ctcaagtgtc gaaaacatat gacaacctcg ttcggcaata cagtccctcg   2100
aagtcgctac aaatgatttt aaggcgcgcg ttggacgatt tcgaaagcat gctggcagat   2160
ggatcatttc gcgtggcccc gaaaagttat ccgatcccttt caactacaga aaaatccgtt   2220
ctcgttcaga cctcacgcat gttcccggtt gcgttgctcg aggtcgctcg aagtcatttt   2280
gatccgttgg ggttggagac cgctcgagct ttcggccaca agctggctac cgccgcgctc   2340
gcgtcattct ttgctggaga gaagccatcg agcaattggt gaagagggac ctatcggaac   2400
ccctcaccaa atattgagtg tagggtttgag gccgctggcc gcgtcctcag tcaccttttg   2460
agccagataa ttaagagcca aatgcaattg gctcaggctg ccatcgtccc cccgtgcgaa   2520
acctgcacgt ccgcgtcaaa gaaataaccg gcacctcttg ctgttttat cagttgaggg    2580
cttgacggat ccgcctcaag tttgcggcgc agccgcaaaa tgagaacatc tatactcctg   2640
```

```
tcgtaaacct cctcgtcgcg tactcgactg gcaatgagaa gttgctcgcg cgatagaacg    2700
tcgcggggtt tctctaaaaa cgcgaggaga agattgaact cacctgccgt aagtttcacc    2760
tcaccgccag cttcggacat caagcgacgt tgcctgagat taagtgtcca gtcagtaaaa    2820
caaaaagacc gtcggtcttt ggagcggaca acgttgggggc gcacgcgcaa ggcaacccga    2880
atgcgtgcaa gaaactctct cgtactaaac ggcttagcga taaaatcact tgctcctagc    2940
tcgagtgcaa caactttatc cgtctcctca aggcggtcgc cactgataat tatgattgga    3000
atatcagact ttgccgccag atttcgaacg atctcaagcc catcttcacg acctaaattt    3060
agatcaacaa ccacgacatc gaccgtcgcg gaagagagta ctctagtgaa ctgggtgctg    3120
tcggctaccg cggtcacttt gaaggcgtgg atcgtaaggt attcgataat aagatgccgc    3180
atagcgacat cgtcatcgat aagaagaacg tgtttcaacg gctcaccttt caatctaaaa    3240
tctgaaccct tgttcacagc gcttgagaaa ttttcacgtg aaggatgtac aatcatctcc    3300
agctaaatgg gcagttcgtc agaattgcgg ctgaccgcgg atgacgaaaa tgcgaaccaa    3360
gtatttcaat tttatgacaa aagttctcaa tcgttgttac aagtgaaacg cttcgaggtt    3420
acagctacta ttgattaagg agatcgccta tggtctcgcc ccggcgtcgt gcgtccgccg    3480
cgagccagat ctcgcctact tcataaacgt cctcataggc acggaatgga atgatgacat    3540
cgatcgccgt agagagcatg tcaatcagtg tgcgatcttc caagctagca ccttgggcgc    3600
tacttttgac aagggaaaac agtttcttga atccttggat tggattcgcg ccgtgtattg    3660
ttgaaatcga tcccggatgt cccgagacga cttcactcag ataagcccat gctgcatcgt    3720
cgcgcatctc gccaagcaat atccggtccg gccgcatacg cagacttgct tggagcaagt    3780
gctcggcgct cacagcaccc agcccagcac cgttcttgga gtagagtagt ctaacatgat    3840
tatcgtgtgg aatgacgagt tcgagcgtat cttctatggt gattagcctt tcctgggggg    3900
ggatggcgct gatcaaggtc ttgctcattg ttgtcttgcc gcttccggta gggccacata    3960
gcaacatcgt cagtcggctg acgacgcatg cgtgcagaaa cgcttccaaa tccccgttgt    4020
caaaatgctg aaggatagct tcatcatcct gattttggcg tttccttcgt gtctgccact    4080
ggttccacct cgaagcatca taacgggagg agacttcttt aagaccagaa acacgcgagc    4140
ttggccgtcg aatggtcaag ctgacggtgc ccgagggaac ggtcggcggc agacagattt    4200
gtagtcgttc accaccagga agttcagtgg cgcagagggg gttacgtggt ccgacatcct    4260
gctttctcag cgcgcccgct aaaatagcga tatcttcaag atcatcataa gagacgggca    4320
aaggcatctt ggtaaaaatg ccggcttggc gcacaaatgc ctctccaggt cgattgatcg    4380
caatttcttc agtcttcggg tcatcgagcc attccaaaat cggcttcaga agaaagcgta    4440
gttgcggatc cacttccatt tacaatgtat cctatctcta agcggaaatt tgaattcatt    4500
aagagcggcg gttcctcccc cgcgtggcgc cgccagtcag gcggagctgg taaacaccaa    4560
agaaatcgag gtcccgtgct acgaaaatgg aaacggtgtc accctgattc ttcttcaggg    4620
ttggcggtat gttgatggtt gccttaaggg ctgtctcagt tgtctgctca ccgttatttt    4680
gaaagctgtt gaagctcatc ccgccacccg agctgccggc gtaggtgcta gctgcctgga    4740
aggcgccttg aacaacactc aagagcatag ctccgctaaa acgctgccag aagtggctgt    4800
cgaccgagcc cggcaatcct gagcgaccga gttcgtccgc gcttggcgat gttaacgaga    4860
tcatcgcatg gtcaggtgtc tcggcgcgat cccacaacac aaaaacgcgc ccatctccct    4920
gttgcaagcc acgctgtatt tcgccaacaa cggtggtgcc acgatcaaga agcacgatat    4980
tgttcgttgt tccacgaata tcctgaggca agacacactt tacatagcct gccaaatttg    5040
```

```
tgtcgattgc ggtttgcaag atgcacggaa ttattgtccc ttgcgttacc ataaaatcgg   5100
ggtgcggcaa gagcgtggcg ctgctgggct gcagctcggt gggtttcata cgtatcgaca   5160
aatcgttctc gccggacact tcgccattcg gcaaggagtt gtcgtcacgc ttgccttctt   5220
gtcttcggcc cgtgtcgccc tgaatggcgc gtttgctgac cccttgatcg ccgctgctat   5280
atgcaaaaat cggtgtttct tccggccgtg gctcatgccg ctccggttcg ccctcggcg    5340 gtagaggagc agcaggctga acagcctctt gaaccgctgg aggatccggc ggcacctcaa   5400
tcggagctgg atgaaatggc ttggtgtttg ttgcgatcaa agttgacggc gatgcgttct   5460
cattcacctt cttttggcgc ccacctagcc aaatgaggct taatgataac gcgagaacga   5520
cacctccgac gatcaatttc tgagaccccg aaagacgccg gcgatgtttg tcggagacca   5580
gggatccaga tgcatcaacc tcatgtgccg cttgctgact atcgttattc atcccttcgc   5640 cccttcagg acgcgtttca catcgggcct caccgtgccc gtttgcggcc tttggccaac    5700
gggatcgtaa gcggtgttcc agatacatag tactgtgtgg ccatccctca gacgccaacc   5760
tcgggaaacc gaagaaatct cgacatcgct ccctttaact gaatagttgg caacagcttc   5820
cttgccatca ggattgatgg tgtagatgga gggtatgcgt acattgcccg gaaagtggaa   5880
taccgtcgta aatccattgt cgaagacttc gagtggcaac agcgaacgat cgccttgggc   5940
gacgtagtgc caattactgt ccgccgcacc aagggctgtg acaggctgat ccaataaatt   6000
ctcagctttc cgttgatatt gtgcttccgc gtgtagtctg tccacaacag ccttctgttg   6060
tgcctccctt cgccgagccg ccgcatcgtc ggcggggtag gcgaattgga cgctgtaata   6120
gagatcgggc tgctctttat cgaggtggga cagagtcttg gaacttatac tgaaaacata   6180
acggcgcatc ccggagtcgc ttgcggttag cacgattact ggctgaggcg tgaggacctg   6240
gcttgccttg aaaaatagat aatttccccg cggtagggct gctagatctt tgctatttga   6300
aacggcaacc gctgtcaccg tttcgttcgt ggcgaatgtt acgaccaaag tagctccaac   6360
cgccgtcgag aggcgcacca cttgatcggg attgtaagcc aaataacgca tgcgcggatc   6420
tagcttgccc gccattggag tgtcttcagc ctccgcacca gtcgcagcgg caaataaaca   6480
tgctaaaatg aaaagtgctt ttctgatcat ggttcgctgt ggcctacgtt tgaaacggta   6540
tcttccgatg tctgatagga ggtgacaacc agacctgccg ggttggttag tctcaatctg   6600
ccgggcaagc tggtcacctt ttcgtagcga actgtcgcgg tccacgtact caccacaggc   6660
attttgccgt caacgacgag ggtccttta tagcgaattt gctgcgtgct tggagttaca    6720
tcatttgaag cgatgtgctc gacctccacc ctgccgcgtt tgccaagaat gacttgaggc   6780
gaactgggat tgggatagtt gaagaattgc tggtaatcct ggcgcactgt tgggcactg    6840 aagttcgata ccaggtcgta ggcgtactga gcggtgtcgg catcataact ctcgcgcagg   6900
cgaacgtact cccacaatga ggcgttaacg acggcctcct cttgagttgc aggcaatcgc   6960
gagacagaca cctcgctgtc aacggtgccg tccggccgta ccatagata tacgggcaca    7020 agcctgctca acggcaccat tgtggctata gcaacgcttt gagcaacatt tcccaaaatc   7080
gcgatagctg cgacagctgc aatgagtttg gagagacgtc gcgccgattt cgctcgcgcg   7140
gtttgaaagg cttctacttc cttatagtgc tcggcaaggc tttcgcgcgc cactagcatg   7200
gcatattcag gccccgtcat agcgtccacc cgaattgccg agctgaagat ctgacggagt   7260
aggctgccat cgcccacat tcagcgggaa gatcgggcct ttgcagctcg ctaatgtgtc    7320
gtttgtctgg cagccgctca aagcgacaac taggcacagc aggcaatact tcatagaatt   7380
ctccattgag gcgaatttt gcgcgaccta gcctcgctca acctgagcga agcgacggta    7440
```

```
caagctgctg gcagattggg ttgcgccgct ccagtaactg cctccaatgt tgccggcgat   7500
cgccggcaaa gcgacaatga gcgcatcccc tgtcagaaaa aacatatcga gttcgtaaag   7560
accaatgatc ttggccgcgg tcgtaccggc gaaggtgatt acaccaagca taagggtgag   7620
cgcagtcgct tcggttagga tgacgatcgt tgccacgagg tttaagagga gaagcaagag   7680
accgtaggtg ataagttgcc cgatccactt agctgcgatg tcccgcgtgc gatcaaaaat   7740
atatccgacg aggatcagag gcccgatcgc gagaagcact tcgtgagaa ttccaacggc    7800 gtcgtaaact ccgaaggcag accagagcgt gccgtaaagg ccccactgtg cccccttggaa  7860 agcaaggatg tcctggtcgt tcatcggacc gatttcggat gcgattttct gaaaaacggc   7920
ctgggtcacg gcgaacattg tatccaactg tgccggaaca gtctgcagag gcaagccggt   7980
tacactaaac tgctgaacaa agtttgggac cgtcttttcg aagatggaaa ccacatagtc   8040
ttggtagtta gcctgcccaa caattagagc aacaacgatg gtgaccgtga tcacccgagt   8100
gataccgcta cgggtatcga cttcgccgcg tatgactaaa ataccctgaa caataatcca   8160
aagagtgaca caggcgatca atggcgcact caccgcctcc tggatagtct caagcatcga   8220
gtccaagcct gtcgtgaagg ctacatcgaa gatcgtatga atggccgtaa acggcgccgg   8280
aatcgtgaaa ttcatcgatt ggacctgaac ttgactggtt tgtcgcataa tgttggataa   8340
aatgagctcg cattcggcga ggatgcgggc ggatgaacaa atcgcccagc cttaggggag   8400
ggcaccaaag atgacagcgg tcttttgatg ctccttgcgt tgagcggccg cctcttccgc   8460
ctcgtgaagg ccgccctgcg cggtagtcat cgttaatagg cttgtcgcct gtacattttg   8520
aatcattgcg tcatggatct gcttgagaag caaaccattg gtcacggttg cctgcatgat   8580
attgcgagat cgggaaagct gagcagacgt atcagcattc gccgtcaagc gtttgtccat   8640
cgtttccaga ttgtcagccg caatgccagc gctgtttgcg gaaccggtga tctgcgatcg   8700
caacaggtcc gcttcagcat cactacccac gactgcacga tctgtatcgc tggtgatcgc   8760
acgtgccgtg gtcgacattg gcattcgcgg cgaaaacatt tcattgtcta ggtccttcgt   8820
cgaaggatac tgattttct ggttgagcga agtcagtagt ccagtaacgc cgtaggccga    8880
cgtcaacatc gtaaccatcg ctatagtctg agtgagattc tccgcagtcg cgagcgcagt   8940
cgcgagcgtc tcagcctccg ttgccgggtc gctaacaaca aactgcgccc gcgcgggctg   9000
aatatataga aagctgcagg tcaaaactgt tgcaataagt tgcgtcgtct tcatcgtttc   9060
ctaccttatc aatcttctgc ctcgtggtga cgggccatga attcgctgag ccagccagat   9120
gagttgccct tcttgtgcctc gcgtagtcga gttgcaaagc gcaccgtgtt ggcacgcccc   9180
gaaagcacgg cgacatattc acgcatatcc cgcagatcaa attcgcagat gacgcttcca   9240 cttctcgtt taagaagaaa cttacggctg ccgaccgtca tgtcttcacg gatcgcctga    9300
aattcctttt cggtacattt cagtccatcg acataagccg atcgatctgc ggttggtgat   9360
ggatagaaaa tcttcgtcat acattgcgca accaagctgg ctcctagcgg cgattccaga   9420
acatgctctg gttgctgcgt tgccagtatt agcatcccgt tgtttttcg aacggtcagg    9480 aggaatttgt cgacgacagt cgaaaattta gggtttaaca aataggcgcg aaactcatcg   9540
cagctcatca caaacggcg gccgtcgatc atggctccaa tccgatgcag gagatatgct    9600
gcagcgggag cgcatacttc ctcgtattcg agaagatgcg tcatgtcgaa gccggtaatc   9660
gacggatcta actttacttc gtcaacttcg ccgtcaaatg cccagccaag cgcatggccc   9720
cggcaccagc gttggagccg cgctcctgcg ccttcggcgg gccatgcaa caaaaattca    9780 cgtaacccg cgattgaacg catttgtgga tcaaacgaga gctgacgatg gataccacgg    9840
```

```
accagacggc ggttctcttc cggagaaatc ccaccccgac catcactctc gatgagagcc    9900
acgatccatt cgcgcagaaa atcgtgtgag gctgctgtgt tttctaggcc acgcaacggc    9960
gccaacccgc tgggtgtgcc tctgtgaagt gccaaatatg ttcctcctgt ggcgcgaacc   10020
agcaattcgc caccccggtc cttgtcaaag aacacgaccg tacctgcacg gtcgaccatg   10080
ctctgttcga gcatggctag aacaaacatc atgagcgtcg tcttacccct cccgataggc   10140
ccgaatattg ccgtcatgcc aacatcgtgc tcatgcggga tatagtcgaa aggcgttccg   10200
ccattggtac gaaatcgggc aatcgcgttg ccccagtggc ctgagctggc gccctctgga   10260
aagttttcga aagagacaaa ccctgcgaaa ttgcgtgaag tgattgcgcc agggcgtgtg   10320
cgccacttaa aattccccgg caattgggac caataggccg cttccatacc aataccttct   10380
tggacaacca cggcacctgc atccgccatt cgtgtccgag cccgcgcgcc cctgtcccca   10440
agactattga gatcgtctgc atagacgcaa aggctcaaat gatgtgagcc cataacgaat   10500
tcgttgctcg caagtgcgtc ctcagcctcg gataatttgc cgatttgagt cacggcttta   10560
tcgccggaac tcagcatctg gctcgatttg aggctaagtt tcgcgtgcgc ttgcgggcga   10620
gtcaggaacg aaaaactctg cgtgagaaca agtggaaaat cgagggatag cagcgcgttg   10680
agcatgcccg gccgtgtttt tgcagggtat tcgcgaaacg aatagatgga tccaacgtaa   10740
ctgtcttttg gcgttctgat ctcgagtcct cgcttgccgc aaatgactct gtcggtataa   10800
atcgaagcgc cgagtgagcc gctgacgacc ggaaccggtg tgaaccgacc agtcatgatc   10860
aaccgtagcg cttcgccaat ttcggtgaag agcacaccct gcttctcgcg gatgccaaga   10920
cgatgcaggc catacgcttt aagagagcca gcgacaacat gccaaagatc ttccatgttc   10980
ctgatctggc ccgtgagatc gttttccctt tttccgctta gcttggtgaa cctcctcttt   11040
accttcccta aagccgcctg tgggtagaca atcaacgtaa ggaagtgttc attgcggagg   11100
agttggccgg agagcacgcg ctgttcaaaa gcttcgttca ggctagcggc gaaaacacta   11160
cggaagtgtc gcggcgccga tgatggcacg tcggcatgac gtacgaggtg agcatatatt   11220
gacacatgat catcagcgat attgcgcaac agcgtgttga acgcacgaca acgcgcattg   11280
cgcatttcag tttcctcaag ctcgaatgca acgccatcaa ttctcgcaat ggtcatgatc   11340
gatccgtctt caagaaggac gatatggtcg ctgaggtggc caatataagg gagatagatc   11400
tcaccggatc tttcggtcgt tccactcgcg ccgagcatca caccattcct ctccctcgtg   11460
ggggaaccct aattggattt gggctaacag tagcgccccc ccaaactgca ctatcaatgc   11520
ttcttcccgc ggtccgcaaa aatagcagga cgacgctcgc cgcattgtag tctcgctcca   11580
cgatgagccg ggctgcaaac cataacggca cgagaacgac ttcgtagagc gggttctgaa   11640
cgataacgat gacaaagccg gcgaacatca tgaataaccc tgccaatgtc agtggcaccc   11700
caagaaacaa tgcgggccgt gtggctgcga ggtaaagggt cgattcttcc aaacgatcag   11760
ccatcaacta ccgccagtga gcgtttggcc gaggaagctc gccccaaaca tgataacaat   11820
gccgccgacg acgccggcaa ccagcccaag cgaagcccgc ccgaacatcc aggagatccc   11880
gatagcgaca atgccgagaa cagcgagtga ctggccgaac ggaccaagga taaacgtgca   11940
tatattgtta accattgtgg cggggtcagt gccgccaccc gcagattgcg ctgcggcggg   12000 tccgatgag gaaatgctcc atgcaattgc accgcacaag cttggggcgc agctcgatat   12060
cacgcgcatc atcgcattcg agagcgagag gcgatttaga tgtaaacggt atctctcaaa   12120
gcatcgcatc aatgcgcacc tccttagtat aagtcgaata agacttgatt gtcgtctgcg   12180
gatttgccgt tgtcctggtg tggcggtggc ggagcgatta aaccgccagc gccatcctcc   12240
```

```
tgcgagcggc gctgatatga cccccaaaca tcccacgtct cttcggattt tagcgcctcg   12300
tgatcgtctt ttggaggctc gattaacgcg ggcaccagcg attgagcagc tgtttcaact   12360
tttcgcacgt agccgtttgc aaaaccgccg atgaaattac cggtgttgta agcggagatc   12420
gcccgacgaa gcgcaaattg cttctcgtca atcgtttcgc cgcctgcata acgacttttc   12480
agcatgtttg cagcggcaga taatgatgtg cacgcctgga gcgcaccgtc aggtgtcaga   12540
ccgagcatag aaaaatttcg agagtttatt tgcatgaggc caacatccag cgaatgccgt   12600
gcatcgagac ggtgcctgac gacttgggtt gcttggctgt gatcttgcca gtgaagcgtt   12660
tcgccggtcg tgttgtcatg aatcgctaaa ggatcaaagc gactctccac cttagctatc   12720
gccgcaagcg tagatgtcgc aactgatggg gcacacttgc gagcaacatg gtcaaactca   12780
gcagatgaga gtggcgtggc aaggctcgac gaacagaagg agaccatcaa ggcaagagaa   12840
agcgaccccg atctcttaag catacccttat ctccttagct cgcaactaac accgcctctc   12900
ccgttggaag aagtgcgttg ttttatgttg aagattatcg ggagggtcgg ttactcgaaa   12960
attttcaatt gcttctttat gatttcaatt gaagcgagaa acctcgcccg gcgtcttgga   13020
acgcaacatg gaccgagaac cgcgcatcca tgactaagca accggatcga cctattcagg   13080
ccgcagttgg tcaggtcagg ctcagaacga aaatgctcgg cgaggttacg ctgtctgtaa   13140
acccattcga tgaacgggaa gcttccttcc gattgctctt ggcaggaata ttggcccatg   13200
cctgcttgcg ctttgcaaat gctcttatcg cgttggtatc atatgccttg tccgccagca   13260
gaaacgcact ctaagcgatt atttgtaaaa atgtttcggt catgcggcgg tcatgggctt   13320
gacccgctgt cagcgcaaga cggatcggtc aaccgtcggc atcgacaaca gcgtgaatct   13380
tggtggtcaa accgccacgg gaacgtccca tacagccatc gtcttgatcc cgctgtttcc   13440
cgtcgccgca tgttggtgga cgcggacaca ggaactgtca atcatgacga cattctatcg   13500
aaagccttgg aaatcacact cagaatatga tcccagacgt ctgcctcacg ccatcgtaca   13560
aagcgattgt agcaggttgt acaggaaccg tatcgatcag gaacgtctgc ccagggcggg   13620
cccgtccgga agcgccacaa gatgacattg atcacccgcg tcaacgcgcg gcacgcgacg   13680
cggcttattt gggaacaaag gactgaacaa cagtccattc gaaatcggtg acatcaaagc   13740
ggggacgggt tatcagtggc ctccaagtca agcctcaatg aatcaaaatc agaccgattt   13800
gcaaacctga tttatgagtg tgcggcctaa atgatgaaat cgtccttcta gatcgcctcc   13860
gtggtgtagc aacacctcgc agtatcgccg tgctgacctt ggccagggaa ttgactggca   13920
agggtgcttt cacatgaccg ctcttttggc cgcgatagat gatttcgttg ctgctttggg   13980
cacgtagaag gagagaagtc atatcggaga aattcctcct ggcgcgagag cctgctctat   14040
cgcgacggca tcccactgtc gggaacagac cggatcattc acgaggcgaa agtcgtcaac   14100
acatgcgtta taggcatctt cccttgaagg atgatcttgt tgctgccaat ctggaggtgc   14160
ggcagccgca ggcagatgcg atctcagcgc aacttgcggc aaaacatctc actcacctga   14220
aaaccactag cgagtctcgc gatcagacga aggccttta cttaacgaca caatatccga   14280
tgtctgcatc acaggcgtcg ctatcccagt caatactaaa gcggtgcagg aactaaagat   14340
tactgatgac ttaggcgtgc cacgaggcct gagacgacgc gcgtagacag ttttttgaaa   14400
tcattatcaa agtgatggcc tccgctgaag cctatcacct ctgcgccggt ctgtcggaga   14460
gatgggcaag cattattacg gtcttcgcgc ccgtacatgc attggacgat tgcagggtca   14520
atggatctga gatcatccag aggattgccg cccttacctt ccgtttcgag ttggagccag   14580
cccctaaatg agacgacata gtcgacttga tgtgacaatg ccaagagaga gatttgctta   14640
```

```
acccgatttt tttgctcaag cgtaagccta ttgaagcttg ccggcatgac gtccgcgccg   14700
aaagaatatc ctacaagtaa aacattctgc acaccgaaat gcttggtgta gacatcgatt   14760
atgtgaccaa gatccttagc agtttcgctt ggggaccgct ccgaccagaa ataccgaagt   14820
gaactgacgc caatgacagg aatcccttcc gtctgcagat aggtaccatc gatagatctg   14880
ctgcctcgcg cgtttcggtg atgacggtga aaacctctga cacatgcagc tcccggagac   14940
ggtcacagct tgtctgtaag cggatgccgg gagcagacaa gcccgtcagg gcgcgtcagc   15000
gggtgttggc gggtgtcggg gcgcagccat gacccagtca cgtagcgata gcggagtgta   15060
tactggctta actatgcggc atcagagcag attgtactga gagtgcacca tatgcggtgt   15120
gaaataccgc acagatgcgt aaggagaaaa taccgcatca ggcgctcttc cgcttcctcg   15180
ctcactgact cgctgcgctc ggtcgttcgg ctgcggcgag cggtatcagc tcactcaaag   15240
gcggtaatac ggttatccac agaatcaggg gataacgcag gaaagaacat gtgagcaaaa   15300
ggccagcaaa aggccaggaa ccgtaaaaag gccgcgttgc tggcgttttt ccataggctc   15360
cgcccccctg acgagcatca caaaaatcga cgctcaagtc agaggtggcg aaacccgaca   15420
ggactataaa gataccaggc gtttccccct ggaagctccc tcgtgcgctc tcctgttccg   15480
accctgccgc ttaccggata cctgtccgcc tttctccctt cgggaagcgt ggcgctttct   15540
catagctcac gctgtaggta tctcagttcg gtgtaggtcg ttcgctccaa gctgggctgt   15600
gtgcacgaac cccccgttca gcccgaccgc tgcgccttat ccggtaacta tcgtcttgag   15660
tccaacccgg taagacacga cttatcgcca ctggcagcag ccactggtaa caggattagc   15720
agagcgaggt atgtaggcgg tgctacagag ttcttgaagt ggtggcctaa ctacggctac   15780
actagaagga cagtatttgg tatctgcgct ctgctgaagc cagttacctt cggaaaaaga   15840
gttggtagct cttgatccgg caaacaaacc accgctggta gcggtggttt ttttgtttgc   15900
aagcagcaga ttacgcgcag aaaaaaagga tctcaagaag atcctttgat cttttctacg   15960
gggtctgacg ctcagtggaa cgaaaactca cgttaaggga ttttggtcat gagattatca   16020
aaaaggatct tcacctagat ccttttaaat taaaaatgaa gttttaaatc aatctaaagt   16080
atatatgagt aaacttggtc tgacagttac caatgcttaa tcagtgaggc acctatctca   16140
gcgatctgtc tatttcgttc atccatagtt gcctgactcc ccgtcgtgta gataactacg   16200
atacgggagg gcttaccatc tggccccagt gctgcaatga taccgcgaga cccacgctca   16260
ccggctccag atttatcagc aataaaccag ccagccggaa gggccgagcg cagaagtggt   16320
cctgcaactt tatccgcctc catccagtct attaattgtt gccgggaagc tagagtaagt   16380
agttcgccag ttaatagttt gcgcaacgtt gttgccattg ctgcagggggg ggggggggg   16440 gggttccatt gttcattcca cggacaaaaa cagagaaagg aaacgacaga gccaaaaag   16500 ctcgctttca gcacctgtcg tttcctttct tttcagaggg tatttttaaat aaaaacatta   16560 agttatgacg aagaagaacg gaaacgcctt aaaccggaaa attttcataa atagcgaaaa   16620
cccgcgaggt ccctgtcgga tcaccggaaa ggacccgtaa agtgataatg attatcatct   16680
acatatcaca acgtgcgtgg aggccatcaa accacgtcaa ataatcaatt atgacgcagg   16740
tatcgtatta attgatctgc atcaacttaa cgtaaaaaca acttcagaca atacaaatca   16800
gcgacactga atacgtggca acctcatgtc ccccccccccc ccccccctgc aggcatcgtg   16860
gtgtcacgct cgtcgtttgg tatggcttca ttcagctccg gttcccaacg atcaaggcga   16920
gttacatgat cccccatgtt gtgcaaaaaa gcggttagct ccttcggtcc tccgatcgtt   16980
gtcagaagta agttggccgc agtgttatca ctcatggtta tggcagcact gcataattct   17040
```

```
cttactgtca tgccatccgt aagatgcttt tctgtgactg gtgagtactc aaccaagtca   17100
ttctgagaat agtgtatgcg gcgaccgagt tgctcttgcc cggcgtcaac acgggataat   17160
accgcgccac atagcagaac tttaaaagtg ctcatcattg gaaaacgttc ttcggggcga   17220
aaactctcaa ggatcttacc gctgttgaga tccagttcga tgtaacccac tcgtgcaccc   17280
aactgatctt cagcatcttt tactttcacc agcgtttctg ggtgagcaaa acaggaagg    17340
caaaatgccg caaaaaggg aataagggcg acacggaaat gttgaatact catactcttc    17400
ctttttcaat attattgaag catttatcag ggttattgtc tcatgagcgg atacatattt   17460
gaatgtattt agaaaaataa acaaataggg gttccgcgca catttccccg aaaagtgcca   17520
cctgacgtct aagaaaccat tattatcatg acattaacct ataaaaatag gcgtatcacg   17580
aggccctttc gtcttcaaga attggtcgac gatcttgctg cgttcggata ttttcgtgga   17640
gttcccgcca cagacccgga ttgaaggcga gatccagcaa ctcgcgccag atcatcctgt   17700
gacggaactt tggcgcgtga tgactggcca ggacgtcggc cgaaagagcg acaagcagat   17760
cacgcttttc gacagcgtcg gatttgcgat cgaggatttt tcggcgctgc gctacgtccg   17820
cgaccgcgtt gagggatcaa gccacagcag cccactcgac cttctagccg acccagacga   17880
gccaagggat cttttggaa tgctgctccg tcgtcaggct ttccgacgtt gggtggttg    17940
aacagaagtc attatcgtac ggaatgccaa gcactcccga ggggaaccct gtggttggca   18000
tgcacataca aatggacgaa cggataaacc ttttcacgcc cttttaaata tccgttattc   18060
taataaacgc tcttttctct taggtttacc cgccaatata tcctgtcaaa cactgatagt   18120
ttaaactgaa ggcgggaaac gacaatctga tcatgagcgg agaattaagg gagtcacgtt   18180
atgacccccg ccgatgacgc gggacaagcc gttttacgtt tggaactgac agaaccgcaa   18240
cgttgaagga gccactcagc aagctggtac gattgtaata cgactcacta tagggcgaat   18300
tgagcgctgt ttaaacgctc ttcaactgga agagcggtta cccggaccga agcttgcatg   18360
cctgcagtgc agcgtgaccc ggtcgtgccc ctctctagag ataatgagca ttgcatgtct   18420
aagttataaa aaattaccac atatttttt tgtcacactt gtttgaagtg cagtttatct    18480
atctttatac atatatttaa actttactct acgaataata taatctatag tactacaata   18540
atatcagtgt tttagagaat catataaatg aacagttaga catggtctaa aggacaattg   18600
agtattttga caacaggact ctacagttt atcttttag tgtgcatgtg ttctccttt     18660
ttttgcaaa tagcttcacc tatataatac ttcatccatt ttattagtac atccatttag    18720
ggtttagggt taatggtttt tatagactaa ttttttttagt acatctattt tattctattt   18780
tagcctctaa attaagaaaa ctaaaactct attttagttt ttttatttaa taatttagat    18840
ataaaataga ataaaataaa gtgactaaaa attaaacaaa tacccttta gaaattaaaa    18900
aaactaagga aacattttc ttgtttcgag tagataatgc cagcctgtta aacgccgtcg    18960
acgagtctaa cggacaccaa ccagcgaacc agcagcgtcg cgtcgggcca gcgaagcag    19020
acggcacggc atctctgtcg ctgcctctgg accctctcg agagttccgc tccaccgttg   19080
gacttgctcc gctgtcggca tccagaaatt gcgtggcgga gcgcagacg tgagccggca    19140
cggcaggcgg cctcctcctc ctctcacggc acggcagcta cggggattc ctttcccacc    19200
gctccttcgc tttcccttcc tcgcccgccg taataaatag acaccccctc cacccctct    19260
ttccccaacc tcgtgttgtt cggagcgcac acacacacaa ccagatctcc cccaaatcca   19320
cccgtcggca cctccgcttc aaggtacgcc gctcgtcctc ccccccccc cctctctacc    19380
ttctctagat cggcgttccg gtccatggtt agggcccggt agttctactt ctgttcatgt   19440
```

```
ttgtgttaga tccgtgtttg tgttagatcc gtgctgctag cgttcgtaca cggatgcgac    19500
ctgtacgtca gacacgttct gattgctaac ttgccagtgt ttctctttgg ggaatcctgg    19560
gatggctcta gccgttccgc agacgggatc gatttcatga ttttttttgt ttcgttgcat    19620
agggtttggt ttgcccttt cctttatttc aatatatgcc gtgcacttgt ttgtcgggtc     19680
atcttttcat gcttttttt gtcttggttg tgatgatgtg gtctggttgg gcggtcgttc     19740
tagatcggag tagaattctg tttcaaacta cctggtggat ttattaattt tggatctgta    19800
tgtgtgtgcc atacatattc atagttacga attgaagatg atggatggaa atatcgatct    19860
aggataggta tacatgttga tgcgggtttt actgatgcat atacagagat gcttttgtt     19920 cgcttggttg tgatgatgtg gtgtggttgg gcggtcgttc attcgttcta gatcggagta    19980
gaatactgtt tcaaactacc tggtgtattt attaattttg gaactgtatg tgtgtgtcat    20040
acatcttcat agttacgagt ttaagatgga tggaaatatc gatctaggat aggtatacat    20100
gttgatgtgg gttttactga tgcatataca tgatggcata tgcagcatct attcatatgc    20160
tctaaccttg agtacctatc tattataata aacaagtatg ttttataatt attttgatct    20220
tgatatactt ggatgatggc atatgcagca gctatatgtg gatttttta gccctgcctt     20280 catacgctat ttatttgctt ggtactgttt cttttgtcga tgctcaccct gttgtttggt    20340
gttacttctg caggtcgact ctagaggatc tacaagtttg tacaaaaaag caggctccgc    20400
ggccgccccc ttcaccatga cgatggctcg tcctggggcg gctttgccgc tgctgctggt    20460
cgtggtcggc gcttgctgcg cgcgcctggc ggcggcagtg cacctctccg cgctcggcag    20520
gacactcatc gtcgaggcgt cgccgaaggc cggacaagtc ctgcacgccg gcgaggacac    20580
gataaccgtg acatggcacc tcaacgcgtc ggcgtccagc gtcgggtaca aggcgctgga    20640
ggtgaccctc tgctacgcgc cggcgagcca ggaggaccgc gggtggcgca aggccaacga    20700
cgacttgagc aaggacaagg cgtgccagtt caggatcgcc cggcatgcat acgccggcgg    20760
ccaggggacg ctccggtaca gggtcgcccg cgacgtcccc accgcgtcct accacgtgcg    20820
cgcctacgcg ctgacgcgt ccggggcgcc ggtgggctac ggccagaccg cgcccgccta     20880
ctacttccac gtcgcgggcg tctcgggcgt ccacgcgtcc ctccgggtcg ccgccgccgt    20940
gctctccgcg ttctccatcg ccgcgctcgc cttctttgtc gtcgtcgaga agaggaggaa    21000
ggacgagtag aagggtgggc gcgccgaccc agctttcttg tacaaagtgg tgttaaccta    21060
gacttgtcca tcttctggat tggccaactt aattaatgta tgaaataaaa ggatgcacac    21120
atagtgacat gctaatcact ataatgtggg catcaaagtt gtgtgttatg tgtaattact    21180
agttatctga ataaaagaga aagagatcat ccatatttct tatcctaaat gaatgtcacg    21240
tgtctttata attctttgat gaaccagatg catttcatta accaaatcca tatacatata    21300
aatattaatc atatataatt aatatcaatt gggttagcaa aacaaatcta gtctaggtgt    21360
gttttgcgaa ttgcggccgc caccgcggtg gagctcgaat tccggtccgg gtcacctttg    21420
tccaccaaga tggaactgcg gccgctcatt aattaagtca ggcgcgcctc tagttgaaga    21480
cacgttcatg tcttcatcgt aagaagacac tcagtagtct tcggcagaa tggccatctg     21540 gattcagcag gcctagaagg ccatttaaat cctgaggatc tggtcttcct aaggacccgg    21600
gcggtccgat taaactttaa ttcggaccga agcttgcatg cctgcagtgc agcgtgaccc    21660
ggtcgtgccc ctctctagag ataatgagca ttgcatgtct aagttataaa aaattaccac    21720 atatttttt tgtcacactt gtttgaagtg cagtttatct atcttataac atatatttaa     21780
actttactct acgaataata taatctatag tactacaata atatcagtgt tttagagaat    21840
```

```
catataaatg aacagttaga catggtctaa aggacaattg agtattttga caacaggact   21900
ctacagtttt atctttttag tgtgcatgtg ttctccttt tttttgcaaa tagcttcacc   21960
tatataatac ttcatccatt ttattagtac atccatttag ggtttagggt taatggtttt   22020
tatagactaa ttttttagt acatctattt tattctattt tagcctctaa attaagaaaa   22080
ctaaaactct attttagttt tttatttaa taatttagat ataaatagaa ataaataaa    22140
gtgactaaaa attaaacaaa tacctttaa gaaattaaaa aaactaagga aacatttttc   22200
ttgtttcgag tagataatgc cagcctgtta aacgccgtcg acgagtctaa cggacaccaa   22260
ccagcgaacc agcagcgtcg cgtcgggcca agcgaagcag acggcacggc atctctgtcg   22320
ctgcctctgg acccctctcg agagttccgc tccaccgttg gacttgctcc gctgtcggca   22380
tccagaaatt gcgtggcgga gcggcagacg tgagccggca cggcaggcgg cctcctcctc   22440
ctctcacggc accggcagct acggggatt ccttccac cgctccttcg ctttcccttc     22500
ctcgcccgcc gtaataaata gacaccccct ccacaccctc ttccccaac ctcgtgttgt   22560
tcggagcgca cacacacaca accagatctc ccccaaatcc acccgtcggc acctccgctt   22620
caaggtacgc cgctcgtcct cccccccccc cctctctacc ttctctagat cggcgttccg   22680
gtccatgcat ggttagggcc cggtagttct acttctgttc atgtttgtgt tagatccgtg   22740
tttgtgttag atccgtgctg ctagcgttcg tacacggatg cgacctgtac gtcagacacg   22800
ttctgattgc taacttgcca gtgtttctct ttggggaatc ctgggatggc tctagccgtt   22860
ccgcagacgg gatcgatttc atgattttt ttgtttcgtt gcatagggtt tggttttgccc  22920
ttttccttta tttcaatata tgccgtgcac ttgtttgtcg ggtcatcttt tcatgctttt   22980
ttttgtcttg gttgtgatga tgtggtctgg ttgggcggtc gttctagatc ggagtagaat   23040
tctgtttcaa actacctggt ggatttatta attttggatc tgtatgtgtg tgccatacat   23100
attcatagtt acgaattgaa gatgatggat ggaaatatcg atctaggata ggtatacatg   23160
ttgatgcggg ttttactgat gcatatacag agatgctttt tgttcgcttg gttgtgatga   23220
tgtggtgtgg ttgggcggtc gttcattcgt tctagatcgg agtagaatac tgtttcaaac   23280
tacctggtgt atttattaat tttggaactg tatgtgtgtg tcatacatct tcatagttac   23340
gagtttaaga tggatggaaa tatcgatcta ggataggtat acatgttgat gtgggtttta   23400
ctgatgcata tacatgatgg catatgcagc atctattcat atgctctaac cttgagtacc   23460
tatctattat aataaacaag tatgttttat aattattttg atcttgatat acttggatga   23520
tggcatatgc agcagctata tgtggatttt tttagccctg ccttcatacg ctatttattt   23580
gcttggtact gtttctttg tcgatgctca ccctgttgtt tggtgttact tctgcaggtc   23640
gactttaact tagcctagga tccacacgac accatgtccc ccgagcgccg ccccgtcgag   23700
atccgcccgg ccaccgccgc cgacatggcc gccgtgtgcg acatcgtgaa ccactacatc   23760
gagacctcca ccgtgaactt ccgcaccgag ccgcagaccc gcaggagtg gatcgacgac   23820
ctggagcgcc tccaggaccg ctaccgtgg ctcgtggccg aggtggaggg cgtggtggcc   23880
ggcatcgcct acgccggccc gtggaaggcc cgcaacgcct acgactggac cgtggagtcc   23940
accgtgtacg tgtcccaccg ccaccagcgc ctcggcctcg gctccaccct ctacacccac   24000
ctcctcaaga gcatggaggc ccagggcttc aagtccgtgg tggccgtgat cggcctcccg   24060
aacgacccgt ccgtgcgcct ccacgaggcc ctcggctaca ccgccgcgcg caccctccgc   24120
gccgccggct acaagcacgg cggctggcac gacgtcggct tctggcagcg cgacttcgag   24180
ctgccggccc cgccgcgccc ggtgcgcccg gtgacgcaga tctgagtcga aacctagact   24240
```

```
tgtccatctt ctggattggc caacttaatt aatgtatgaa ataaaaggat gcacacatag    24300
tgacatgcta atcactataa tgtgggcatc aaagttgtgt gttatgtgta attactagtt    24360
atctgaataa aagagaaaga gatcatccat atttcttatc ctaaatgaat gtcacgtgtc    24420
tttataattc tttgatgaac cagatgcatt tcattaacca aatccatata catataaata    24480
ttaatcatat ataattaata tcaattgggt tagcaaaaca aatctagtct aggtgtgttt    24540
tgcgaattgc ggccgccacc gcggtggagc tcgaattcat tccgattaat cgtggcctct    24600
tgctcttcag gatgaagagc tatgtttaaa cgtgcaagcg ctactagaca attcagtaca    24660
ttaaaaacgt ccgcaatgtg ttattaagtt gtctaagcgt caatttgttt acaccacaat    24720
atatcctgcc accagccagc caacagctcc ccgaccggca gctcggcaca aaatcaccac    24780
tcgatacagg cagcccatca gtccgggacg gcgtcagcgg gagagccgtt gtaaggcggc    24840
agactttgct catgttaccg atgctattcg gaagaacggc aactaagctg ccgggtttga    24900
aacacggatg atctcgcgga gggtagcatg ttgattgtaa cgatgacaga gcgttgctgc    24960
ctgtgatcaa atatcatctc cctcgcagag atccgaatta tcagccttct tattcatttc    25020
tcgcttaacc gtgacaggct gtcgatcttg agaactatgc cgacataata ggaaatcgct    25080
ggataaagcc gctgaggaag ctgagtggcg ctatttcttt agaagtgaac gttgacgatc    25140
gtcgaccgta ccccgatgaa ttaattcgga cgtacgttct gaacacagct ggatacttac    25200
ttgggcgatt gtcatacatg acatcaacaa tgtacccgtt tgtgtaaccg tctcttggag    25260
gttcgtatga cactagtggt tcccctcagc ttgcgactag atgttgaggc ctaacatttt    25320
attagagagc aggctagttg cttagataca tgatcttcag gccgttatct gtcagggcaa    25380
gcgaaaattg gccattatg acgaccaatg ccccgcagaa gctcccatct ttgccgccat    25440
agacgccgcg ccccccttt ggggtgtaga acatccttt gccagatgtg gaaaagaagt    25500
tcgttgtccc attgttggca atgacgtagt agccggcgaa agtgcgagac ccatttgcgc    25560
tatatataag cctacgattt ccgttgcgac tattgtcgta attggatgaa ctattatcgt    25620
agttgctctc agagttgtcg taatttgatg gactattgtc gtaattgctt atggagttgt    25680
cgtagttgct tggagaaatg tcgtagttgg atggggagta gtcatagga agacgagctt    25740 catccactaa aacaattggc aggtcagcaa gtgcctgccc cgatgccatc gcaagtacga    25800
ggcttagaac caccttcaac agatcgcgca tagtcttccc cagctctcta acgcttgagt    25860
taagccgcgc cgcgaagcgg cgtcggcttg aacgaattgt tagacattat ttgccgacta    25920
ccttggtgat ctcgcctttc acgtagtgaa caaattcttc caactgatct gcgcgcgagg    25980
ccaagcgatc ttcttgtcca agataagcct gcctagcttc aagtatgacg ggctgatact    26040
gggccggcag gcgctccatt gcccagtcgg cagcgacatc cttcggcgcg attttgccgg    26100
ttactgcgct gtaccaaatg cgggacaacg taagcactac atttcgctca tcgccagccc    26160
agtcgggcgg cgagttccat agcgttaagg tttcatttag cgcctcaaat agatcctgtt    26220
caggaaccgg atcaaagagt tcctccgccg ctggacctac caaggcaacg ctatgttctc    26280
ttgcttttgt cagcaagata gccagatcaa tgtcgatcgt ggctggctcg aagatacctg    26340
caagaatgtc attgcgctgc cattctccaa attgcagttc gcgcttagct ggataacgcc    26400
acggaatgat gtcgtcgtgc acaacaatgg tgacttctac agcgcggaga atctcgctct    26460
ctccagggga agccgaagtt tccaaaaggt cgttgatcaa agctcgccgc gttgtttcat    26520
caagccttac agtcaccgta accagcaaat caatatcact gtgtggcttc aggccgccat    26580
ccactgcgga gccgtacaaa tgtacggcca gcaacgtcgg ttcgagatgg cgctcgatga    26640
```

```
cgccaactac ctctgatagt tgagtcgata cttcggcgat caccgcttcc ctcatgatgt   26700
ttaactcctg aattaagccg cgccgcgaag cggtgtcggc ttgaatgaat tgttaggcgt   26760
catcctgtgc tcccgagaac cagtaccagt acatcgctgt ttcgttcgag acttgaggtc   26820
tagttttata cgtgaacagg tcaatgccgc cgagagtaaa gccacatttt gcgtacaaat   26880
tgcaggcagg tacattgttc gtttgtgtct ctaatcgtat gccaaggagc tgtctgctta   26940
gtgcccactt tttcgcaaat tcgatgagac tgtgcgcgac tcctttgcct cggtgcgtgt   27000
gcgacacaac aatgtgttcg atagaggcta gatcgttcca tgttgagttg agttcaatct   27060
tcccgacaag ctcttggtcg atgaatgcgc catagcaagc agagtcttca tcagagtcat   27120
catccgagat gtaatccttc cggtaggggc tcacacttct ggtagatagt tcaaagcctt   27180
ggtcggatag gtgcacatcg aacacttcac gaacaatgaa atggttctca gcatccaatg   27240
tttccgccac ctgctcaggg atcaccgaaa tcttcatatg acgcctaacg cctggcacag   27300
cggatcgcaa acctggcgcg gcttttggca caaaaggcgt gacaggtttg cgaatccgtt   27360
gctgccactt gttaaccctt ttgccagatt tggtaactat aatttatgtt agaggcgaag   27420
tcttgggtaa aaactggcct aaaattgctg gggatttcag gaaagtaaac atcaccttcc   27480
ggctcgatgt ctattgtaga tatatgtagt gtatctactt gatcggggga tctgctgcct   27540
cgcgcgtttc ggtgatgacg gtgaaaacct ctgacacatg cagctcccgg agacggtcac   27600
agcttgtctg taagcggatg ccgggagcag acaagcccgt cagggcgcgt cagcgggtgt   27660
tggcgggtgt cggggcgcag ccatgaccca gtcacgtagc gatagcggag tgtatactgg   27720
cttaactatg cggcatcaga gcagattgta ctgagagtgc accatatgcg gtgtgaaata   27780
ccgcacagat gcgtaaggag aaaataccgc atcaggcgct cttccgcttc ctcgctcact   27840
gactcgctgc gctcggtcgt tcggctgcgg cgagcggtat cagctcactc aaaggcggta   27900
atacggttat ccacagaatc aggggataac gcaggaaaga acatgtgagc aaaaggccag   27960
caaaaggcca ggaaccgtaa aaaggccgcg ttgctggcgt ttttccatag gctccgcccc   28020
cctgacgagc atcacaaaaa tcgacgctca agtcagaggt ggcgaaaccc gacaggacta   28080
taaagatacc aggcgtttcc ccctggaagc tccctcgtgc gctctcctgt tccgaccctg   28140
ccgcttaccg gatacctgtc cgcctttctc ccttcgggaa gcgtggcgct ttctcatagc   28200
tcacgctgta ggtatctcag ttcggtgtag tcgttcgct ccaagctggg ctgtgtgcac   28260
gaaccccccg ttcagcccga ccgctgcgcc ttatccggta actatcgtct tgagtccaac   28320
ccggtaagac acgacttatc gccactggca gcagccactg gtaacaggat tagcagagcg   28380
aggtatgtag gcggtgctac agagttcttg aagtggtggc ctaactacgg ctacactaga   28440
aggacagtat ttggtatctg cgctctgctg aagccagtta ccttcggaaa aagagttggt   28500
agctcttgat ccggcaaaca aaccaccgct ggtagcggtg ttttttgt ttgcaagcag   28560 cagattacgc gcagaaaaaa aggatctcaa gaagatcctt tgatcttttc tacggggtct   28620
gacgctcagt ggaacgaaaa ctcacgttaa gggattttgg tcatgagatt atcaaaaagg   28680
atcttcacct agatcctttt aaattaaaaa tgaagtttta atcaatcta aagtatatat   28740 gagtaaactt ggtctgacag ttaccaatgc ttaatcagtg aggcacctat ctcagcgatc   28800
tgtctatttc gttcatccat agttgcctga ctccccgtcg tgtagataac tacgatacgg   28860
gagggcttac catctggccc cagtgctgca atgataccgc gagacccacg ctcaccggct   28920
ccagatttat cagcaataaa ccagccagcc ggaagggccg agcgcagaag tggtcctgca   28980
actttatccg cctccatcca gtctattaat tgttgccggg aagctagagt aagtagttcg   29040
```

```
ccagttaata gtttgcgcaa cgttgttgcc attgctgcag ggggggggggg ggggggggac   29100
ttccattgtt cattccacgg acaaaaacag agaaaggaaa cgacagaggc caaaaagcct   29160
cgcttttcagc acctgtcgtt tcctttcttt tcagagggta ttttaaataa aaacattaag   29220
ttatgacgaa gaagaacgga aacgccttaa accggaaaat tttcataaat agcgaaaacc   29280
cgcgaggtcg ccgccccgta agccgccccg taacctgtcg gatcaccgga aaggacccgt   29340
aaagtgataa tgattatcat ctacatatca caacgtgcgt ggaggccatc aaaccacgtc   29400
aaataatcaa ttatgacgca ggtatcgtat taattgatct gcatcaactt aacgtaaaaa   29460
caacttcaga caatacaaat cagcgacact gaatacgggg caacctcatg tcccccccc   29520
ccccccccct gcaggcatcg tggtgtcacg ctcgtcgttt ggtatggctt cattcagctc   29580
cggttcccaa cgatcaaggc gagttacatg atccccatg ttgtgcaaaa aagcggttag   29640
ctccttcggt cctccgatcg ttgtcagaag taagttggcc gcagtgttat cactcatggt   29700
tatggcagca ctgcataatt ctcttactgt catgccatcc gtaagatgct tttctgtgac   29760
tggtgagtac tcaaccaagt cattctgaga atagtgtatg cggcgaccga gttgctcttg   29820
cccggcgtca acacgggata ataccgcgcc acatagcaga actttaaaag tgctcatcat   29880
tggaaaacgt tcttcggggc gaaaactctc aaggatctta ccgctgttga gatccagttc   29940
gatgtaaccc actcgtgcac ccaactgatc ttcagcatct tttactttca ccagcgtttc   30000
tgggtgagca aaaacaggaa ggcaaaatgc cgcaaaaaag ggaataaggg cgacacggaa   30060
atgttgaata ctcatactct tcctttttca atattattga agcatttatc agggttattg   30120
tctcatgagc ggatacatat ttgaatgtat ttagaaaaat aaacaaatag gggttccgcg   30180
cacatttccc cgaaaagtgc cacctgacgt ctaagaaacc attattatca tgacattaac   30240
ctataaaaat aggcgtatca cgaggccctt tcgtcttcaa gaattcggag cttttgccat   30300
tctcaccgga ttcagtcgtc actcatggtg atttctcact tgataacctt attttttgacg   30360
aggggaaatt aataggttgt attgatgttg gacgagtcgg aatcgcagac cgataccagg   30420
atcttgccat cctatggaac tgcctcggtg agttttctcc ttcattacag aaacggcttt   30480
ttcaaaaata tggtattgat aatcctgata tgaataaatt gcagtttcat ttgatgctcg   30540
atgagttttt ctaatcagaa ttggttaatt ggttgtaaca ctggcagagc attacgctga   30600
cttgacggga cggcggcttt gttgaataaa tcgaacttt gctgagttga aggatcagat   30660
cacgcatctt cccgacaacg cagaccgttc cgtggcaaag caaaagttca aaatcaccaa   30720
ctggtccacc tacaacaaag ctctcatcaa ccgtggctcc ctcactttct ggctggatga   30780
tggggcgatt caggcctggt atgagtcagc aacaccttct tcacgaggca gacctcagcg   30840
ccagaaggcc gccagagagg ccgagcgcgg ccgtgaggct tggacgctag gcagggcat   30900
gaaaaagccc gtagcgggct gctacgggcg tctgacgcgg tggaaagggg gagggggatgt   30960
tgtctacatg gctctgctgt agtgagtggg ttgcgctccg gcagcggtcc tgatcaatcg   31020
tcacccttc tcggtccttc aacgttcctg acaacgagcc tccttttcgc caatccatcg   31080
acaatcaccg cgagtccctg ctcgaacgct gcgtccggac cggcttcgtc gaaggcgtct   31140
atcgcggccc gcaacagcgg cgagagcgga gcctgttcaa cggtgccgcc gcgctcgccg   31200
gcatcgctgt cgccggcctg ctcctcaagc acggccccaa cagtgaagta gctgattgtc   31260
atcagcgcat tgacgcgtc cccggccgaa aaacccgcct cgcagaggaa gcgaagctgc   31320
gcgtcggccg tttccatctg cggtgcgccc ggtcgcgtgc cggcatggat gcgcgcgcca   31380
tcgcggtagg cgagcagcgc ctgcctgaag ctgcgggcat tcccgatcag aaatgagcgc   31440
```

-continued

```
cagtcgtcgt cggctctcgg caccgaatgc gtatgattct ccgccagcat ggcttcggcc   31500
agtgcgtcga gcagcgcccg cttgttcctg aagtgccagt aaagcgccgg ctgctgaacc   31560
cccaaccgtt ccgccagttt gcgtgtcgtc agaccgtcta cgccgacctc gttcaacagg   31620
tccagggcgg cacggatcac tgtattcggc tgcaactttg tcatgcttga cactttatca   31680
ctgataaaca taatatgtcc accaacttat cagtgataaa gaatccgcgc gttcaatcgg   31740
accagcggag gctggtccgg aggccagacg tgaaacccaa catacccctg atcgtaattc   31800
tgagcactgt cgcgctcgac gctgtcggca tcggcctgat tatgccggtg ctgccgggcc   31860
tcctgcgcga tctggttcac tcgaacgacg tcaccgccca ctatggcatt ctgctggcgc   31920
tgtatgcgtt ggtgcaattt gcctgcgcac ctgtgctggg cgcgctgtcg gatcgtttcg   31980
ggcggcggcc aatcttgctc gtctcgctgg ccggcgccac tgtcgactac gccatcatgg   32040
cgacagcgcc tttcctttgg gttctctata tcgggcggat cgtggccggc atcaccgggg   32100
cgactggggc ggtagccggc gcttatattg ccgatatcac tgatgcgat gagcgcgcgc   32160 ggcacttcgg cttcatgagc gcctgtttcg ggttcgggat ggtcgcggga cctgtgctcg   32220
gtgggctgat gggcggtttc tccccccacg ctccgttctt cgccgcggca gccttgaacg   32280
gcctcaattt cctgacgggc tgtttccttt tgccggagtc gcacaaaggc gaacgccggc   32340
cgttacgccg ggaggctctc aacccgctcg cttcgttccg gtgggcccgg ggcatgaccg   32400
tcgtcgccgc cctgatggcg gtcttcttca tcatgcaact tgtcggacag gtgccggccg   32460
cgctttgggt cattttcggc gaggatcgct ttcactggga cgcgaccacg atcggcattt   32520
cgcttgccgc atttggcatt ctgcattcac tcgcccaggc aatgatcacc ggccctgtag   32580
ccgcccggct cggcgaaagg cgggcactca tgctcggaat gattgccgac ggcacaggct   32640
acatcctgct tgccttcgcg acacggggat ggatggcgtt cccgatcatg gtcctgcttg   32700
cttcgggtgg catcggaatg ccggcgctgc aagcaatgtt gtccaggcag gtggatgagg   32760
aacgtcaggg gcagctgcaa ggctcactgg cggcgctcac cagcctgacc tcgatcgtcg   32820
gacccctcct cttcacggcg atctatgcgg cttctataac aacgtggaac gggtgggcat   32880
ggattgcagg cgctgccctc tacttgctct gcctgccggc gctgcgtcgc gggctttgga   32940
gcggcgcagg gcaacgagcc gatcgctgat cgtggaaacg ataggcctat gccatgcggg   33000
tcaaggcgac ttccggcaag ctatacgcgc cctaggagtg cggttggaac gttggcccag   33060
ccagatactc ccgatcacga gcaggacgcc gatgatttga agcgcactca gcgtctgatc   33120
caagaacaac catcctagca acacggcggt ccccgggctg agaaagccca gtaaggaaac   33180
aactgtaggt tcgagtcgcg agatccccg gaaccaaagg aagtaggtta aacccgctcc   33240
gatcaggccg agccacgcca ggccgagaac attggttcct gtaggcatcg ggattggcgg   33300
atcaaacact aaagctactg gaacgagcag aagtcctccg gccgccagtt gccaggcggt   33360
aaaggtgagc agaggcacgg gaggttgcca cttgcgggtc agcacggttc cgaacgccat   33420
ggaaaccgcc cccgccaggc ccgctgcgac gccgacagga tctagcgctg cgtttggtgt   33480
caacaccaac agcgccacgc ccgcagttcc gcaaatagcc cccaggaccg ccatcaatcg   33540
tatcgggcta cctagcagag cggcagagat gaacacgacc atcagcggct gcacagcgcc   33600
taccgtcgcc gcgaccccgc ccggcaggcg gtagaccgaa ataaacaaca agctccagaa   33660
tagcgaaata ttaagtgcgc cgaggatgaa gatgcgcatc caccagattc ccgttggaat   33720
ctgtcggacg atcatcacga gcaataaacc cgccggcaac gcccgcagca gcataccggc   33780 gaccccctcgg cctcgctgtt cgggctccac gaaaacgccg gacagatgcg ccttgtgagc   33840
```

```
gtccttgggg ccgtcctcct gtttgaagac cgacagccca atgatctcgc cgtcgatgta   33900
ggcgccgaat gccacggcat ctcgcaaccg ttcagcgaac gcctccatgg gcttttctc    33960 ctcgtgctcg taaacggacc cgaacatctc tggagctttc ttcagggccg acaatcggat   34020
ctcgcggaaa tcctgcacgt cggccgctcc aagccgtcga atctgagcct taatcacaat   34080
tgtcaatttt aatcctctgt ttatcggcag ttcgtagagc gcgccgtgcg tcccgagcga   34140
tactgagcga agcaagtgcg tcgagcagtg cccgcttgtt cctgaaatgc cagtaaagcg   34200
ctggctgctg aacccccagc cggaactgac cccacaaggc cctagcgttt gcaatgcacc   34260
aggtcatcat tgacccaggc gtgttccacc aggccgctgc ctcgcaactc ttcgcaggct   34320
tcgccgacct gctcgcgcca cttcttcacg cgggtggaat ccgatccgca catgaggcgg   34380
aaggtttcca gcttgagcgg gtacggctcc cggtgcgagc tgaaatagtc gaacatccgt   34440
cgggccgtcg gcgacagctt gcggtacttc tcccatatga atttcgtgta gtggtcgcca   34500
gcaaacagca cgacgatttc ctcgtcgatc aggacctggc aacgggacgt tttcttgcca   34560
cggtccagga cgcggaagcg gtgcagcagc gacaccgatt ccaggtgccc aacgcggtcg   34620
gacgtgaagc ccatcgccgt cgcctgtagg cgcgacaggc attcctcggc cttcgtgtaa   34680
taccggccat tgatcgacca gcccaggtcc tggcaaagct cgtagaacgt gaaggtgatc   34740
ggctcgccga taggggtgcg cttcgcgtac tccaacacct gctgccacac cagttcgtca   34800
tcgtcggccc gcagctcgac gccggtgtag gtgatcttca cgtccttgtt gacgtggaaa   34860
atgaccttgt tttgcagcgc ctcgcgcggg attttcttgt tgcgcgtggt gaacagggca   34920
gagcgggccg tgtcgtttgg catcgctcgc atcgtgtccg gccacggcgc aatatcgaac   34980
aaggaaagct gcatttcctt gatctgctgc ttcgtgtgtt tcagcaacgc ggcctgcttg   35040
gcctcgctga cctgttttgc caggtcctcg ccggcggttt ttcgcttctt ggtcgtcata   35100
gttcctcgcg tgtcgatggt catcgacttc gccaaacctg ccgcctcctg ttcgagacga   35160
cgcgaacgct ccacggcggc cgatggcgcg ggcagggcag ggggagccag ttgcacgctg   35220
tcgcgctcga tcttggccgt agcttgctgg accatcgagc cgacggactg gaaggtttcg   35280
cggggcgcac gcatgacggt gcggcttgcg atggtttcgg catcctcggc ggaaaacccc   35340
gcgtcgatca gttcttgcct gtatgccttc cggtcaaacg tccgattcat tcaccctcct   35400
tgcgggattg ccccgactca cgccggggca atgtgcccct attcctgatt tgacccgcct   35460
ggtgccttgg tgtccagata atccaccta tcggcaatga agtcggtccc gtagaccgtc   35520
tggccgtcct tctcgtactt ggtattccga atcttgccct gcacgaatac cagcgacccc   35580
ttgcccaaat acttgccgtg ggcctcggcc tgagagccaa acacttgat gcggaagaag    35640 tcggtgcgct cctgcttgtc gccggcatcg ttgcgccact cttcattaac cgctatatcg   35700
aaaattgctt gcggcttgtt agaattgcca tgacgtacct cggtgtcacg ggtaagatta   35760
ccgataaact ggaactgatt atggctcata tcgaaagtct ccttgagaaa ggagactcta   35820
gtttagctaa acattggttc cgctgtcaag aactttagcg gctaaaattt tgcgggccgc   35880
gaccaaaggt gcgaggggcg gcttccgctg tgtacaacca gatattttc accaacatcc    35940 ttcgtctgct cgatgagcgg ggcatgacga acatgagct gtcggagagg gcagggggttt   36000 caatttcgtt tttatcagac ttaaccaacg gtaaggccaa cccctcgttg aaggtgatgg   36060
aggccattgc cgacgccctg gaaactcccc tacctcttct cctggagtcc accgaccttg   36120
accgcgaggc actcgcggag attgcgggtc atcctttcaa gagcagcgtg ccgcccggat   36180
acgaacgcat cagtgtggtt ttgccgtcac ataaggcgtt tatcgtaaag aaatggggcg   36240
```

```
acgacacccg aaaaaagctg cgtggaaggc tctgacgcca agggttaggg cttgcacttc   36300
cttctttagc cgctaaaacg gccccttctc tgcgggccgt cggctcgcgc atcatatcga   36360
catcctcaac ggaagccgtg ccgcgaatgg catcgggcgg gtgcgctttg acagttgttt   36420
tctatcagaa cccctacgtc gtgcggttcg attagctgtt tgtcttgcag gctaaacact   36480
ttcggtatat cgtttgcctg tgcgataatg ttgctaatga tttgttgcgt aggggttact   36540
gaaaagtgag cgggaaagaa gagtttcaga ccatcaagga gcgggccaag cgcaagctgg   36600
aacgcgacat gggtgcggac ctgttggccg cgctcaacga cccgaaaacc gttgaagtca   36660
tgctcaacgc ggacggcaag gtgtggcacg aacgccttgg cgagccgatg cggtacatct   36720
gcgacatgcg gcccagccag tcgcaggcga ttatagaaac ggtggccgga ttccacggca   36780
aagaggtcac gcggcattcg cccatcctgg aaggcgagtt ccccttggat ggcagccgct   36840
ttgccggcca attgccgccg gtcgtggccg cgccaacctt tgcgatccgc aagcgcgcgg   36900
tcgccatctt cacgctggaa cagtacgtcg aggcgggcat catgacccgc gagcaatacg   36960
aggtcattaa aagcgccgtc gcggcgcatc gaaacatcct cgtcattggc ggtactggct   37020
cgggcaagac cacgctcgtc aacgcgatca tcaatgaaat ggtcgccttc aacccgtctg   37080
agcgcgtcgt catcatcgag gacaccggcg aaatccagtg cgccgcagag aacgccgtcc   37140
aataccacac cagcatcgac gtctcgatga cgctgctgct caagacaacg ctgcgtatgc   37200
gccccgaccg catcctggtc ggtgaggtac gtggccccga agcccttgat ctgttgatgg   37260
cctggaacac cgggcatgaa ggaggtgccg ccaccctgca cgcaaacaac cccaaagcgg   37320
gcctgagccg gctcgccatg cttatcagca tgcacccgga ttcaccgaaa cccattgagc   37380
cgctgattgg cgaggcggtt catgtggtcg tccatatcgc caggacccct agcggccgtc   37440
gagtgcaaga aattctcgaa gttcttggtt acgagaacgg ccagtacatc accaaaaccc   37500
tgtaaggagt atttccaatg acaacggctg ttccgttccg tctgaccatg aatcgcggca   37560
ttttgttcta ccttgccgtg ttcttcgttc tcgctctcgc gttatccgcg catccggcga   37620
tggcctcgga aggcaccggc ggcagcttgc catatgagag ctggctgacg aacctgcgca   37680
actccgtaac cggcccggtg gccttcgcgc tgtccatcat cggcatcgtc gtcgccggcg   37740
gcgtgctgat cttcggcggc gaactcaacg ccttcttccg aaccctgatc ttcctggttc   37800
tggtgatggc gctgctggtc ggcgcgcaga acgtgatgag caccttcttc ggtcgtggtg   37860
ccgaaatcgc ggccctcggc aacgggcgc tgcaccaggt gcaagtcgcg gcggcggatg   37920
ccgtgcgtgc ggtagcggct ggacggctcg cctaatcatg gctctgcgca cgatccccat   37980
ccgtcgcgca ggcaaccgag aaaacctgtt catgggtggt gatcgtgaac tggtgatgtt   38040
ctcgggcctg atggcgtttg cgctgatttt cagcgcccaa gagctgcggg ccaccgtggt   38100
cggtctgatc ctgtggttcg gggcgctcta tgcgttccga atcatggcga aggccgatcc   38160
gaagatgcgg ttcgtgtacc tgcgtcaccg ccggtacaag ccgtattacc cggcccgctc   38220
gaccccgttc cgcgagaaca ccaatagcca agggaagcaa taccgatgat ccaagcaatt   38280
gcgattgcaa tcgcgggcct cggcgcgctt ctgttgttca tcctctttgc ccgcatccgc   38340
gcggtcgatg ccgaactgaa actgaaaaag catcgttcca aggacgccgg cctggccgat   38400
ctgctcaact acgccgctgt cgtcgatgac ggcgtaatcg tgggcaagaa cggcagcttt   38460
atggctgcct ggctgtacaa gggcgatgac aacgcaagca gcaccgacca gcagcgcgaa   38520
gtagtgtccg cccgcatcaa ccaggccctc gcgggcctgg gaagtgggtg gatgatccat   38580
gtggacgccg tgcggcgtcc tgctccgaac tacgcggagc ggggcctgtc ggcgttccct   38640
```

-continued

```
gaccgtctga cggcagcgat tgaagaagag cgctcggtct tgccttgctc gtcggtgatg    38700
tacttcacca gctccgcgaa gtcgctcttc ttgatggagc gcatggggac gtgcttggca    38760
atcacgcgca ccccccggcc gttttagcgg ctaaaaaagt catggctctg ccctcgggcg    38820
gaccacgccc atcatgacct tgccaagctc gtcctgcttc tcttcgatct tcgccagcag    38880
ggcgaggatc gtggcatcac cgaaccgcgc cgtgcgcggg tcgtcggtga ccagagttt     38940 cagcaggccg cccaggcggc ccaggtcgcc attgatgcgg gccagctcgc ggacgtgctc    39000
atagtccacg acgcccgtga ttttgtagcc ctggccgacg gccagcaggt aggccgacag    39060
gctcatgccg gccgccgccg ccttttcctc aatcgctctt cgttcgtctg gaaggcagta    39120
caccttgata ggtgggctgc ccttcctggt tggcttggtt tcatcagcca tccgcttgcc    39180
ctcatctgtt acgccggcgg tagccggcca gcctcgcaga gcaggattcc cgttgagcac    39240
cgccaggtgc gaataaggga cagtgaagaa ggaacacccg ctcgcgggtg ggcctacttc    39300
acctatcctg cccggctgac gccgttggat acaccaagga aagtctacac gaacccttg     39360 gcaaaatcct gtatatcgtg cgaaaaagga tggatatacc gaaaaaatcg ctaatgac      39420 cccgaagcag ggttatgcag cggaaaagcg ctgcttccct gctgttttgt ggaatatcta    39480
ccgactggaa acaggcaaat gcaggaaatt actgaactga ggggacaggc gagagacgat    39540 gccaagagc taccgacg agctggccga gtgggttgaa tcccgcgcgg ccaagaagcg        39600
ccggcgtgat gaggctgcgg ttgcgttcct ggcggtgagg gcggatgtcg aggcggcgtt    39660
agcgtccggc tatgcgctcg tcaccatttg ggagcacatg cgggaaacgg ggaaggtcaa    39720
gttctcctac gagacgttcc gctcgcacgc caggcggcac atcaaggcca gcccgccga    39780 tgtgcccgca ccgcaggcca aggctgcgga acccgcgccg gcacccaaga cgccggagcc   39840
acggcggccg aagcaggggg gcaaggctga aaagccggcc cccgctgcgg ccccgaccgg    39900
cttcaccttc aacccaacac cggacaaaaa ggatctactg taatggcgaa aattcacatg    39960
gttttgcagg gcaagggcgg ggtcggcaag tcggccatcg ccgcgatcat tgcgcagtac    40020
aagatggaca aggggcagac acccttgtgc atcgacaccg accggtgaa cgcgacgttc     40080 gagggctaca aggccctgaa cgtccgccgg ctgaacatca tggccggcga cgaaattaac    40140
tcgcgcaact tcgacaccct ggtcgagctg attgcgccga ccaaggatga cgtggtgatc    40200
gacaacggtg ccagctcgtt cgtgcctctg tcgcattacc tcatcagcaa ccaggtgccg    40260
gctctgctgc aagaaatggg gcatgagctg gtcatccata ccgtcgtcac cggcggccag    40320
gctctcctgg acacggtgag cggcttcgcc cagctcgcca gccagttccc ggccgaagcg    40380
cttttcgtgg tctggctgaa cccgtattgg gggcctatcg agcatgaggg caagagcttt    40440
gagcagatga aggcgtacac ggccaacaag gcccgcgtgt cgtccatcat ccagattccg    40500
gccctcaagg aagaaaccta cggccgcgat ttcagcgaca tgctgcaaga gcggctgacg    40560
ttcgaccagg cgctggccga tgaatcgctc acgatcatga cgcggcaacg cctcaagatc    40620
gtgcggcgcg gcctgtttga acagctcgac gcggcggccg tgctatgagc gaccagattg    40680
aagagctgat ccgggagatt gcggccaagc acggcatcgc cgtcggccgc gacgacccgg    40740
tgctgatcct gcataccatc aacgcccggc tcatggccga cagtgcgcc aagcaagagg      40800 aaatccttgc cgcgttcaag gaagagctgg aagggatcgc ccatcgttgg ggcgaggacg    40860
ccaaggccaa agcggagcgg atgctgaacg cggccctggc ggccagcaag gacgcaatgg    40920
cgaaggtaat gaaggacagc gccgcgcagg cggccgaagc gatccgcagg gaaatcgacg    40980
acggccttgg ccgccagctc gcggccaagg tcgcggacgc gcggcgcgtg gcgatgatga    41040
```

```
acatgatcgc cggcggcatg gtgttgttcg cggccgccct ggtggtgtgg gcctcgttat   41100
gaatcgcaga ggcgcagatg aaaaagcccg gcgttgccgg gctttgtttt tgcgttagct   41160
gggcttgttt gacaggccca agctctgact gcgcccgcgc tcgcgctcct gggcctgttt   41220
cttctcctgc tcctgcttgc gcatcagggc ctggtgccgt cgggctgctt cacgcatcga   41280
atcccagtcg ccggccagct cgggatgctc gcgcgcatc ttgcgcgtcg ccagttcctc    41340
gatcttgggc gcgtgaatgc ccatgccttc cttgatttcg cgcaccatgt ccagccgcgt   41400
gtgcagggtc tgcaagcggg cttgctgttg ggcctgctgc tgctgccagg cggccttttgt  41460 acgcggcagg gacagcaagc cgggggcatt ggactgtagc tgctgcaaac gcgcctgctg   41520
acggtctacg agctgttcta ggcggtcctc gatgcgctcc acctggtcat gctttgcctg   41580
cacgtagagc gcaagggtct gctggtaggt ctgctcgatg ggcgcggatt ctaagagggc   41640
ctgctgttcc gtctcggcct cctgggccgc ctgtagcaaa tcctcgccgc tgttgccgct   41700
ggactgcttt actgccgggg actgctgttg ccctgctcgc gccgtcgtcg cagttcggct   41760
tgcccccact cgattgactg cttcatttcg agccgcagcg atgcgatctc ggattgcgtc   41820 aacgacggg gcagcgcgga ggtgtccggc ttctccttgg gtgagtcggt cgatgccata    41880
gccaaaggtt tccttccaaa atgcgtccat tgctggaccg tgtttctcat tgatgcccgc   41940
aagcatcttc ggcttgaccg ccaggtcaag cgcgccttca tgggcggtca tgacggacgc   42000
cgccatgacc ttgccgccgt tgttctcgat gtagccgcgt aatgaggcaa tggtgccgcc   42060
catcgtcagc gtgtcatcga caacgatgta cttctggccg gggatcacct ccccctcgaa   42120
agtcgggttg aacgccaggc gatgatctga accggctccg gttcgggcga ccttctcccg   42180
ctgcacaatg tccgtttcga cctcaaggcc aaggcggtcg gccagaacga ccgccatcat   42240
ggccggaatc ttgttgttcc ccgccgcctc gacggcgagg actggaacga tgcggggctt   42300
gtcgtcgccg atcagcgtct tgagctgggc aacagtgtcg tccgaaatca ggcgctcgac   42360
caaattaagc gccgcttccg cgtcgccctg cttcgcagcc tggtattcag gctcgttggt   42420
caaagaacca aggtcgccgt tgcgaaccac cttcgggaag tctccccacg gtgcgcgctc   42480
ggctctgctg tagctgctca agacgcctcc cttttagcc gctaaaactc taacgagtgc    42540
gcccgcgact caacttgacg cttttcggcac ttacctgtgc cttgccactt gcgtcatagg   42600
tgatgctttt cgcactcccg atttcaggta ctttatcgaa atctgaccgg gcgtgcatta   42660
caaagttctt ccccacctgt tggtaaatgc tgccgctatc tgcgtggacg atgctgccgt   42720
cgtggcgctg cgacttatcg gccttttggg ccatatagat gttgtaaatg ccaggtttca   42780
gggccccggc tttatctacc ttctggttcg tccatgcgcc ttggttctcg gtctggacaa   42840
ttctttgccc attcatgacc aggaggcggt gtttcattgg gtgactcctg acggttgcct   42900
ctggtgttaa acgtgtcctg gtcgcttgcc ggctaaaaaa aagccgacct cggcagttcg   42960
aggccggctt tccctagagc cgggcgcgtc aaggttgttc catctatttt agtgaactgc   43020
gttcgattta tcagttactt tcctcccgct ttgtgtttcc tcccactcgt ttccgcgtct   43080
agccgacccc tcaacatagc ggcctcttct tgggctgcct ttgcctcttg ccgcgcttcg   43140
tcacgctcgg cttgcaccgt cgtaaagcgc tcggcctgcc tggccgcctc ttgcgccgcc   43200
aacttccttt gctcctggtg ggcctcggcg tcggcctgcg ccttcgcttt caccgctgcc   43260
aactccgtgc gcaaactctc cgcttcgcgc ctggtggcgt cgcgctcgcc gcgaagcgcc   43320
tgcatttcct ggttggccgc gtccagggtc ttgcggctct cttctttgaa tgcgcgggcg   43380
tcctggtgag cgtagtccag ctcggcgcgc agctcctgcg ctcgacgctc cacctcgtcg   43440
```

```
gcccgctgcg tcgccagcgc ggcccgctgc tcggctcctg ccagggcggt gcgtgcttcg   43500
gccagggctt gccgctggcg tgcggccagc tcggccgcct cggcggcctg ctgctctagc   43560
aatgtaacgc gcgcctgggc ttcttccagc tcgcgggcct gcgcctcgaa ggcgtcggcc   43620
agctccccgc gcacggcttc caactcgttg cgctcacgat cccagccggc ttgcgctgcc   43680
tgcaacgatt cattggcaag ggcctgggcg gcttgccaga gggcggccac ggcctggttg   43740
ccggcctgct gcaccgcgtc cggcacctgg actgccagcg gggcggcctg cgccgtgcgc   43800
tggcgtcgcc attcgcgcat gccggcgctg gcgtcgttca tgttgacgcg ggcggcctta   43860
cgcactgcat ccacggtcgg gaagttctcc cggtcgcctt gctcgaacag ctcgtccgca   43920
gccgcaaaaa tgcggtcgcg cgtctctttg ttcagttcca tgttggctcc ggtaattggt   43980
aagaataata atactcttac ctaccttatc agcgcaagag tttagctgaa cagttctcga   44040
cttaacggca ggtttttag cggctgaagg gcaggcaaaa aaagccccgc acggtcggcg   44100
ggggcaaagg gtcagcggga aggggattag cgggcgtcgg gcttcttcat gcgtcggggc   44160
cgcgcttctt gggatggagc acgacgaagc gcgcacgcgc atcgtcctcg gccctatcgg   44220
cccgcgtcgc ggtcaggaac ttgtcgcgcg ctaggtcctc cctggtgggc accaggggca   44280
tgaactcggc ctgctcgatg taggtccact ccatgaccgc atcgcagtcg aggccgcgtt   44340
ccttcaccgt ctcttgcagg tcgcggtacg cccgctcgtt gagcggctgg taacgggcca   44400
attggtcgta aatggctgtc ggccatgagc ggccttcct gttgagccag cagccgacga   44460
cgaagccggc aatgcaggcc cctggcacaa ccaggccgac gccgggggca ggggatggca   44520
gcagctcgcc aaccaggaac cccgccgcga tgatgccgat gccggtcaac cagcccttga   44580
aactatccgg ccccgaaaca cccctgcgca ttgcctggat gctgcgccgg atagcttgca   44640
acatcaggag ccgtttcttt tgttcgtcag tcatggtccg ccctcaccag ttgttcgtat   44700
cggtgtcgga cgaactgaaa tcgcaagagc tgccggtatc ggtccagccg ctgtccgtgt   44760
cgctgctgcc gaagcacggc gagggtccg cgaacgccgc agacggcgta tccggccgca   44820
gcgcatcgcc cagcatggcc ccggtcagcg agccgccggc caggtagccc agcatggtgc   44880
tgttggtcgc cccggccacc agggccgacg tgacgaaatc gccgtcattc cctctggatt   44940
gttcgctgct cggcggggca gtgcgccgcg ccggcggcgt cgtggatggc tcgggttggc   45000
tggcctgcga cggccggcga aaggtgcgca gcagctcgtt atcgaccggc tgcggcgtcg   45060
gggccgccgc cttgcgctgc ggtcggtgtt ccttcttcgg ctcgcgcagc ttgaacagca   45120
tgatcgcgga aaccagcagc aacgccgcgc ctacgcctcc cgcgatgtag aacagcatcg   45180
gattcattct tcggtcctcc ttgtagcgga accgttgtct gtgcggcgcg ggtgcccgc   45240 gccgctgtct ttggggatca gccctcgatg agcgcgacca gtttcacgtc ggcaaggttc   45300
gcctcgaact cctggccgtc gtcctcgtac ttcaaccagg catagccttc cgccggcggc   45360
cgacggttga ggataaggcg ggcagggcgc tcgtcgtgct cgacctggac gatggcctt   45420 ttcagcttgt ccgggtccgg ctccttcgcg cccttttcct tggcgtcctt accgtcctgg   45480
tcgccgtcct cgccgtcctg gccgtcgccg gcctccgcgt cacgctcggc atcagtctgg   45540
ccgttgaagg catcgacggt gttgggatcg cggcccttct cgtccaggaa ctcgcgcagc   45600
agcttgaccg tgccgcgcgt gatttcctgg gtgtcgtcgt caagccacgc ctcgacttcc   45660
tccgggcgct tcttgaaggc cgtcaccagc tcgttcacca cggtcacgtc gcgcacgcgg   45720
ccggtgttga acgcatcggc gatcttctcc ggcaggtcca gcagcgtgac gtgctgggtg   45780
atgaacgccg gcgacttgcc gatttccttg gcgatatcgc cttcttcct gcccttcgcc   45840
```

```
agctcgcggc caatgaagtc ggcaatttcg cgcggggtca gctcgttgcg ttgcaggttc   45900
tcgataacct ggtcggcttc gttgtagtcg ttgtcgatga acgccgggat ggacttcttg   45960
ccggcccact tcgagccacg gtagcggcgg gcgccgtgat tgatgatata gcggcccggc   46020
tgctcctggt tctcgcgcac cgaaatgggt gacttcaccc cgcgctcttt gatcgtggca   46080
ccgatttccg cgatgctctc cggggaaaag ccggggttgt cggccgtccg cggctgatgc   46140
ggatcttcgt cgatcaggtc caggtccagc tcgatagggc cggaaccgcc ctgagacgcc   46200
gcaggagcgt ccaggaggct cgacaggtcg ccgatgctat ccaacccag gccgacggc    46260 tgcgccgcgc ctgcggcttc ctgagcggcc gcagcggtgt ttttcttggt ggtcttggct   46320
tgagccgcag tcattgggaa atctccatct tcgtgaacac gtaatcagcc agggcgcgaa   46380
cctctttcga tgccttgcgc gcggccgttt tcttgatctt ccagaccggc acaccggatg   46440
cgagggcatc ggcgatgctg ctgcgcaggc caacggtggc cggaatcatc atcttggggt   46500
acgcggccag cagctcggct tggtggcgcg cgtggcgcgg attccgcgca tcgaccttgc   46560
tgggcaccat gccaaggaat tgcagcttgg cgttcttctg gcgcacgttc gcaatggtcg   46620
tgaccatctt cttgatgccc tggatgctgt acgcctcaag ctcgatgggg gacagcacat   46680
agtcggccgc gaagagggcg gccgccaggc cgacgccaag ggtcggggcc gtgtcgatca   46740
ggcacacgtc gaagccttgg ttcgccaggg ccttgatgtt cgccccgaac agctcgcggg   46800
cgtcgtccag cgacagccgt tcggcgttcg ccagtaccgg gttggactcg atgagggcga   46860
ggcgcgcggc ctgccgtcg ccggctgcgg gtgcggtttc ggtccagccg ccggcaggga   46920
cagcgccgaa cagcttgctt gcatgcaggc cggtagcaaa gtccttgagc gtgtaggacg   46980
cattgccctg ggggtccagg tcgatcacgg caacccgcaa gccgcgctcg aaaaagtcga   47040
aggcaagatg cacaagggtc gaagtcttgc cgacgccgcc tttctggttg gccgtgacca   47100
aagttttcat cgtttggttt cctgtttttt cttggcgtcc gcttcccact tccgacgat    47160 gtacgcctga tgttccggca gaaccgccgt tacccgcgcg taccctcgg gcaagttctt    47220 gtcctcgaac gcggcccaca cgcgatgcac cgcttgcgac actgcgcccc tggtcagtcc   47280
cagcgacgtt gcgaacgtcg cctgtggctt cccatcgact aagacgcccc gcgctatctc   47340
gatggtctgc tgccccactt ccagcccctg gatcgcctcc tggaactggc tttcggtaag   47400
ccgtttcttc atggataaca cccataattt gctccgcgcc ttggttgaac atagcggtga   47460
cagccgccag cacatgagag aagtttagct aaacatttct cgcacgtcaa caccttagc    47520 cgctaaaact cgtccttggc gtaacaaaac aaaagcccgg aaaccgggct ttcgtctctt   47580
gccgcttatg gctctgcacc cggctccatc accaacaggt cgcgcacgcg cttcactcgg   47640
ttgcggatcg acactgccag cccaacaaag ccggttgccg ccgccgccag gatcgcgccg   47700
atgatgccgg ccacaccggc catcgcccac caggtcgccg ccttccggtt ccattcctgc   47760
tggtactgct tcgcaatgct ggacctcggc tcaccatagg ctgaccgctc gatggcgtat   47820
gccgcttctc cccttggcgt aaacccagc gccgcaggcg gcattgccat gctgcccgcc    47880
gctttcccga ccacgacgcg cgcaccaggc ttgcggtcca gccttcggc cacggcgagc    47940 tgcgcaagga cataatcagc cgccgacttg gctccacgcg cctcgatcag ctcttgcact   48000
cgcgcgaaat ccttggcctc cacggccgcc atgaatcgcg cacgcggcga aggctccgca   48060
gggccggcgt cgtgatcgcc gccgagaatg ccccttcacca agttcgacga cacgaaaatc   48120
atgctgacgg ctatcaccat catgcagacg gatcgcacga acccgctgaa ttgaacacga   48180
gcacggcacc cgcgaccact atgccaagaa tgcccaaggt aaaaattgcc ggccccgcca   48240
```

```
tgaagtccgt gaatgccccg acggccgaag tgaagggcag gccgccaccc aggccgccgc   48300
cctcactgcc cggcacctgg tcgctgaatg tcgatgccag cacctgcggc acgtcaatgc   48360
ttccgggcgt cgcgctcggg ctgatcgccc atcccgttac tgccccgatc ccggcaatgg   48420
caaggactgc cagcgctgcc attttgggg tgaggccgtt cgcggccgag gggcgcagcc   48480
cctgggggga tgggaggccc gcgttagcgg gccgggaggg ttcgagaagg ggggcaccc   48540 cccttcggcg tgcgcggtca cgcgcacagg gcgcagccct ggttaaaaac aaggtttata   48600
aatattggtt taaaagcagg ttaaaagaca ggttagcgt ggccgaaaaa cgggcggaaa   48660
cccttgcaaa tgctggattt tctgcctgtg gacagcccct caaatgtcaa taggtgcgcc   48720
cctcatctgt cagcactctg cccctcaagt gtcaaggatc gcgcccctca tctgtcagta   48780
gtcgcgcccc tcaagtgtca ataccgcagg gcacttatcc ccaggcttgt ccacatcatc   48840
tgtgggaaac tcgcgtaaaa tcaggcgttt tcgccgattt gcgaggctgg ccagctccac   48900
gtcgccggcc gaaatcgagc ctgccctca tctgtcaacg ccgcgccggg tgagtcggcc   48960
cctcaagtgt caacgtccgc ccctcatctg tcagtgaggg ccaagttttc cgcgaggtat   49020
ccacaacgcc ggcggccgcg tgtctcgca cacggcttcg acggcgtttc tggcgcgttt   49080
gcagggccat agacggccgc cagcccagcg gcgagggcaa ccagcccggt gagcgtcgga   49140
aaggcgctgg aagcccgta gcgacgcgga gaggggcgag acaagccaag ggcgcaggct   49200
cgatgcgcag cacgacatag ccggttctcg caaggacgag aatttccctg cggtgccct   49260 caagtgtcaa tgaaagtttc caacgcgagc cattcgcgag agccttgagt ccacgctaga   49320
tgagagcttt gttgtaggtg gaccagttgg tgattttgaa cttttgcttt gccacggaac   49380
ggtctgcgtt gtcgggaaga tgcgtgatct gatccttcaa ctcagcaaaa gttcgattta   49440
ttcaacaaag ccacgttgtg tctcaaaatc tctgatgtta cattgcacaa gataaaaata   49500
tatcatcatg aacaataaaa ctgtctgctt acataaacag taatacaagg ggtgttatga   49560
gccatattca acgggaaac                                                 49579
```

<210> SEQ ID NO 95
<211> LENGTH: 49015
<212> TYPE: DNA
<213> ORGANISM: Artificial Sequence
<220> FEATURE:
<223> OTHER INFORMATION: Vector

<400> SEQUENCE: 95

```
gtcttgctcg actctagagc tcgttcctcg aggcctcgag gcctcgagga acggtacctg     60
cggggaagct acaataatg tgtgttgtta agtcttgttg cctgtcatcg tctgactgac    120
tttcgtcata aatcccggcc tccgtaaccc agctttgggc aagctcacgg atttgatccg    180
gcggaacggg aatatcgaga tgccgggctg aacgctgcag ttccagcttt cccttcggg    240 acaggtactc cagctgattg attatctgct gaagggtctt ggttccacct cctggcacaa    300
tgcgaatgat tacttgagcg cgatcgggca tccaattttc tcccgtcagg tgcgtggtca    360
agtgctacaa ggcacctttc agtaacgagc gaccgtcgat ccgtcgccgg gatacggaca    420
aaatggagcg cagtagtcca tcgagggcgg cgaaagcctc gccaaaagca atacgttcat    480
ctcgcacagc ctccagatcc gatcgagggt cttcggcgta ggcagataga agcatggata    540
cattgcttga gagtattccg atggactgaa gtatggcttc catctttct cgtgtgtctg    600 catctatttc gagaaagccc ccgatgcggc gcaccgcaac gcgaattgcc atactatccg    660
aaagtcccag caggcgcgct tgataggaaa aggtttcata ctcggccgat cgcagacggg    720
```

```
cactcacgac cttgaaccct tcaactttca gggatcgatg ctggttgatg gtagtctcac    780
tcgacgtggc tctggtgtgt tttgacatag cttcctccaa agaaagcgga aggtctggat    840
actccagcac gaaatgtgcc cgggtagacg gatggaagtc tagccctgct caatatgaaa    900
tcaacagtac atttacagtc aatactgaat atacttgcta catttgcaat tgtcttataa    960
cgaatgtgaa ataaaaatag tgtaacaacg cttttactca tcgataatca caaaaacatt   1020
tatacgaaca aaaatacaaa tgcactccgg tttcacagga taggcgggat cagaatatgc   1080
aactttgac gttttgttct ttcaaagggg gtgctggcaa aaccaccgca ctcatgggcc    1140
tttgcgctgc tttggcaaat gacggtaaac gagtggccct ctttgatgcc gacgaaaacc   1200
ggcctctgac gcgatggaga gaaaacgcct acaaagcag tactgggatc ctcgctgtga    1260
agtctattcc gccgacgaaa tgccccttct tgaagcagcc tatgaaaatg ccgagctcga   1320
aggatttgat tatgcgttgg ccgatacgcg tggcggctcg agcgagctca caacacaat    1380
catcgctagc tcaaacctgc ttctgatccc caccatgcta acgccgctcg acatcgatga   1440
ggcactatct acctaccgct acgtcatcga gctgctgttg agtgaaaatt tggcaattcc   1500
tacagctgtt ttgcgccaac gcgtcccggt cggccgattg acaacatcgc aacgcaggat   1560
gtcagagacg ctagagagcc ttccagttgt accgtctccc atgcatgaaa gagatgcatt   1620
tgccgcgatg aaagaacgcg gcatgttgca tcttacatta ctaaacacgg gaactgatcc   1680
gacgatgcgc ctcatagaga ggaatcttcg gattgcgatg gaggaagtcg tggtcatttc   1740
gaaactgatc agcaaaatct tggaggcttg aagatggcaa ttcgcaagcc cgcattgtcg   1800
gtcggcgaag cacggcggct tgctggtgct cgacccgaga tccaccatcc caacccgaca   1860
cttgttcccc agaagctgga cctccagcac ttgcctgaaa aagccgacga gaaagaccag   1920
caacgtgagc ctctcgtcgc cgatcacatt tacagtcccg atcgacaact taagctaact   1980
gtggatgccc ttagtccacc tccgtccccg aaaaagctcc aggttttct ttcagcgcga    2040
ccgcccgcgc ctcaagtgtc gaaaacatat gacaacctcg ttcggcaata cagtccctcg   2100
aagtcgctac aaatgatttt aaggcgcgcg ttggacgatt tcgaaagcat gctggcagat   2160
ggatcatttc gcgtggcccc gaaaagttat ccgatcccctt caactacaga aaaatccgtt   2220
ctcgttcaga cctcacgcat gttcccggtt gcgttgctcg aggtcgctcg aagtcatttt   2280
gatccgttgg ggttggagac cgctcgagct ttcggccaca agctggctac cgccgcgctc   2340
gcgtcattct ttgctggaga gaagccatcg agcaattggt gaagagggac ctatcggaac   2400
ccctcaccaa atattgagtg taggtttgag gccgctggcc gcgtcctcag tcaccttttg   2460
agccagataa ttaagagcca aatgcaattg gctcaggctg ccatcgtccc ccgtgcgaa    2520
acctgcacgt ccgcgtcaaa gaaataaccg gcacctcttg ctgttttat cagttgaggg    2580
cttgacggat ccgcctcaag tttgcggcgc agccgcaaaa tgagaacatc tatactcctg   2640
tcgtaaacct cctcgtcgcg tactcgactg gcaatgagaa gttgctcgcg cgatagaacg   2700
tcgcgggtt tctctaaaaa cgcgaggaga agattgaact cacctgccgt aagtttcacc    2760
tcaccgccag cttcggacat caagcgacgt tgcctgagat taagtgtcca gtcagtaaaa   2820
caaaaagacc gtcggtcttt ggagcggaca acgttggggc gcacgcgcaa ggcaacccga   2880
atgcgtgcaa gaaactctct cgtactaaac ggcttagcga taaatcact tgctcctagc    2940
tcgagtgcaa caactttatc cgtctcctca aggcggtcgc cactgataat tatgattgga   3000
atatcagact ttgccgccag atttcgaacg atctcaagcc catcttcacg acctaaattt   3060
agatcaacaa ccacgacatc gaccgtcgcg gaagagagta ctctagtgaa ctgggtgctg   3120
```

```
tcggctaccg cggtcacttt gaaggcgtgg atcgtaaggt attcgataat aagatgccgc    3180
atagcgacat cgtcatcgat aagaagaacg tgtttcaacg gctcaccttt caatctaaaa    3240
tctgaaccct tgttcacagc gcttgagaaa ttttcacgtg aaggatgtac aatcatctcc    3300
agctaaatgg gcagttcgtc agaattgcgg ctgaccgcgg atgacgaaaa tgcgaaccaa    3360
gtatttcaat tttatgacaa aagttctcaa tcgttgttac aagtgaaacg cttcgaggtt    3420
acagctacta ttgattaagg agatcgccta tggtctcgcc ccggcgtcgt gcgtccgccg    3480
cgagccagat ctcgcctact tcataaacgt cctcataggc acggaatgga atgatgacat    3540
cgatcgccgt agagagcatg tcaatcagtg tgcgatcttc caagctagca ccttgggcgc    3600
tacttttgac aagggaaaac agtttcttga atccttggat tggattcgcg ccgtgtattg    3660
ttgaaatcga tcccggatgt cccgagacga cttcactcag ataagcccat gctgcatcgt    3720
cgcgcatctc gccaagcaat atccggtccg gccgcatacg cagacttgct tggagcaagt    3780
gctcggcgct cacagcaccc agcccagcac cgttcttgga gtagagtagt ctaacatgat    3840
tatcgtgtgg aatgacgagt tcgagcgtat cttctatggt gattagcctt tcctggggg    3900
ggatggcgct gatcaaggtc ttgctcattg ttgtcttgcc gcttccggta gggccacata    3960
gcaacatcgt cagtcggctg acgacgcatg cgtgcagaaa cgcttccaaa tccccgttgt    4020
caaaatgctg aaggatagct tcatcatcct gattttggcg tttccttcgt gtctgccact    4080
ggttccacct cgaagcatca taacgggagg agacttcttt aagaccagaa acacgcgagc    4140
ttggccgtcg aatggtcaag ctgacggtgc ccgagggaac ggtcggcggc agacagattt    4200
gtagtcgttc accaccagga agttcagtgg cgcagagggg gttacgtggt ccgacatcct    4260
gctttctcag cgcgcccgct aaaatagcga tatcttcaag atcatcataa gagacgggca    4320
aaggcatctt ggtaaaaatg ccggcttggc gcacaaatgc ctctccaggt cgattgatcg    4380
caatttcttc agtcttcggg tcatcgagcc attccaaaat cggcttcaga agaaagcgta    4440
gttgcggatc cacttccatt tacaatgtat cctatctcta agcggaaatt tgaattcatt    4500
aagagcggcg ttcctccccc cgcgtggcgc cgccagtcag gcggagctgg taaacaccaa    4560
agaaatcgag gtcccgtgct acgaaaatgg aaacggtgtc accctgattc ttcttcaggg    4620
ttggcggtat gttgatggtt gccttaaggg ctgtctcagt tgtctgctca ccgttatttt    4680
gaaagctgtt gaagctcatc ccgccacccg agctgccggc gtaggtgcta gctgcctgga    4740
aggcgccttg aacaacactc aagagcatag ctccgctaaa acgctgccag aagtggctgt    4800
cgaccgagcc cggcaatcct gagcgaccga gttcgtccgc gcttggcgat gttaacgaga    4860
tcatcgcatg gtcaggtgtc tcggcgcgat cccacaacac aaaaacgcgc ccatctccct    4920
gttgcaagcc acgctgtatt tcgccaacaa cggtggtgcc acgatcaaga agcacgatat    4980
tgttcgttgt tccacgaata tcctgaggca agacacactt tacatagcct gccaaatttg    5040
tgtcgattgc ggtttgcaag atgcacggaa ttattgtccc ttgcgttacc ataaaatcgg    5100
ggtgcggcaa gagcgtggcg ctgctgggct gcagctcggt gggtttcata cgtatcgaca    5160
aatcgttctc gccggacact tcgccattcg gcaaggagtt gtcgtcacgc ttgccttctt    5220
gtcttcggcc cgtgtcgccc tgaatggcgc gtttgctgac cccttgatcg ccgctgctat    5280
atgcaaaaat cggtgtttct tccggccgtg gctcatgccg ctccggttcg cccctcggcg    5340
gtagaggagc agcaggctga acagcctctt gaaccgctgg aggatccggc ggcacctcaa    5400
tcggagctga tgaaatggc ttggtgtttg ttgcgatcaa agttgacggc gatgcgttct    5460
cattcacctt cttttggcgc ccacctagcc aaatgaggct taatgataac gcgagaacga    5520
```

| | |
|---|---|
| cacctccgac gatcaatttc tgagaccccg aaagacgccg gcgatgtttg tcggagacca | 5580 |
| gggatccaga tgcatcaacc tcatgtgccg cttgctgact atcgttattc atcccttcgc | 5640 |
| cccccttcagg acgcgtttca catcgggcct caccgtgccc gtttgcggcc tttggccaac | 5700 |
| gggatcgtaa gcggtgttcc agatacatag tactgtgtgg ccatccctca gacgccaacc | 5760 |
| tcgggaaacc gaagaaatct cgacatcgct ccctttaact gaatagttgg caacagcttc | 5820 |
| cttgccatca ggattgatgg tgtagatgga gggtatgcgt acattgcccg gaaagtggaa | 5880 |
| taccgtcgta aatccattgt cgaagacttc gagtggcaac agcgaacgat cgccttgggc | 5940 |
| gacgtagtgc caattactgt ccgccgcacc aagggctgtg acaggctgat ccaataaatt | 6000 |
| ctcagctttc cgttgatatt gtgcttccgc gtgtagtctg tccacaacag ccttctgttg | 6060 |
| tgcctcccctt cgccgagccg ccgcatcgtc ggcggggtag gcgaattgga cgctgtaata | 6120 |
| gagatcgggc tgctctttat cgaggtggga cagagtcttg gaacttatac tgaaaacata | 6180 |
| acggcgcatc ccgagtcgc ttgcggttag cacgattact ggctgaggcg tgaggacctg | 6240 |
| gcttgccttg aaaaatagat aatttccccg cggtagggct gctagatctt gctatttga | 6300 |
| aacggcaacc gctgtcaccg tttcgttcgt ggcgaatgtt acgaccaaag tagctccaac | 6360 |
| cgccgtcgag aggcgcacca cttgatcggg attgtaagcc aaataacgca tgcgcggatc | 6420 |
| tagcttgccc gccattggag tgtcttcagc ctccgcacca gtcgcagcgg caaataaaca | 6480 |
| tgctaaaatg aaaagtgctt ttctgatcat ggttcgctgt ggcctacgtt gaaacggta | 6540 |
| tcttccgatg tctgatagga ggtgacaacc agacctgccg ggttggttag tctcaatctg | 6600 |
| ccgggcaagc tggtcacctt ttcgtagcga actgtcgcgg tccacgtact caccacaggc | 6660 |
| attttgccgt caacgacgag ggtccttta tagcgaattt gctgcgtgct tggagttaca | 6720 |
| tcatttgaag cgatgtgctc gacctccacc ctgccgcgtt tgccaagaat gacttgaggc | 6780 |
| gaactgggat tgggatagtt gaagaattgc tggtaatcct ggcgcactgt tggggcactg | 6840 |
| aagttcgata ccaggtcgta ggcgtactga gcggtgtcgg catcataact ctcgcgcagg | 6900 |
| cgaacgtact cccacaatga ggcgttaacg acggcctcct cttgagttgc aggcaatcgc | 6960 |
| gagacagaca cctcgctgtc aacggtgccg tccggccgta tccatagata tacgggcaca | 7020 |
| agcctgctca acggcaccat tgtggctata gcgaacgctt gagcaacatt tcccaaaatc | 7080 |
| gcgatagctg cgacagctgc aatgagtttg gagagacgtc gcgccgattt cgctcgcgcg | 7140 |
| gtttgaaagg cttctacttc cttatagtgc tcggcaaggc tttcgcgcgc cactagcatg | 7200 |
| gcatattcag gccccgtcat agcgtccacc cgaattgccg agctgaagat ctgacggagt | 7260 |
| aggctgccat cgccccacat tcagcgggaa gatcgggcct ttgcagctcg ctaatgtgtc | 7320 |
| gtttgtctgg cagccgctca aagcgacaac taggcacagc aggcaatact tcatagaatt | 7380 |
| ctccattgag gcgaatttt gcgcgaccta gcctcgctca acctgagcga agcgacggta | 7440 |
| caagctgctg gcagattggg ttgcgccgct ccagtaactg cctccaatgt tgccggcgat | 7500 |
| cgccggcaaa gcgacaatga gcgcatcccc tgtcagaaaa aacatatcga gttcgtaaag | 7560 |
| accaatgatc ttggccgcgg tcgtaccggc gaaggtgatt acaccaagca taagggtgag | 7620 |
| cgcagtcgct tcggttagga tgacgatcgt tgccacgagg tttaagagga gaagcaagag | 7680 |
| accgtaggtg ataagttgcc cgatccactt agctgcgatg tcccgcgtgc gatcaaaaat | 7740 |
| atatccgacg aggatcagag gcccgatcgc gagaagcact ttcgtgagaa ttccaacggc | 7800 |
| gtcgtaaact ccgaaggcag accagagcgt gccgtaaagg acccactgtg cccccttgaa | 7860 |
| agcaaggatg tcctggtcgt tcatcggacc gatttcggat gcgattttct gaaaaacggc | 7920 |

```
ctgggtcacg gcgaacattg tatccaactg tgccggaaca gtctgcagag gcaagccggt    7980
tacactaaac tgctgaacaa agtttgggac cgtcttttcg aagatggaaa ccacatagtc    8040
ttggtagtta gcctgcccaa caattagagc aacaacgatg gtgaccgtga tcacccgagt    8100
gataccgcta cgggtatcga cttcgccgcg tatgactaaa ataccctgaa caataatcca    8160
aagagtgaca caggcgatca atggcgcact caccgcctcc tggatagtct caagcatcga    8220
gtccaagcct gtcgtgaagg ctacatcgaa gatcgtatga atggccgtaa acggcgccgg    8280
aatcgtgaaa ttcatcgatt ggacctgaac ttgactggtt tgtcgcataa tgttggataa    8340
aatgagctcg cattcggcga ggatgcgggc ggatgaacaa atcgcccagc cttaggggag    8400
ggcaccaaag atgacagcgg tcttttgatg ctccttgcgt tgagcggccg cctcttccgc    8460
ctcgtgaagg ccggcctgcg cggtagtcat cgttaatagg cttgtcgcct gtacattttg    8520
aatcattgcg tcatggatct gcttgagaag caaaccattg gtcacggttg cctgcatgat    8580
attgcgagat cgggaaagct gagcagacgt atcagcattc gccgtcaagc gtttgtccat    8640
cgtttccaga ttgtcagccg caatgccagc gctgtttgcg gaaccggtga tctgcgatcg    8700
caacaggtcc gcttcagcat cactacccac gactgcacga tctgtatcgc tggtgatcgc    8760
acgtgccgtg gtcgacattg gcattcgcgg cgaaaacatt tcattgtcta ggtccttcgt    8820
cgaaggatac tgattttcct ggttgagcga agtcagtagt ccagtaacgc cgtaggccga    8880
cgtcaacatc gtaaccatcg ctatagtctg agtgagattc tccgcagtcg cgagcgcagt    8940
cgcgagcgtc tcagcctccg ttgccgggtc gctaacaaca aactgcgccc gcgcgggctg    9000
aatatataga aagctgcagg tcaaaactgt tgcaataagt tgcgtcgtct tcatcgtttc    9060
ctaccttatc aatcttctgc ctcgtggtga cgggccatga attcgctgag ccagccagat    9120
gagttgcctt cttgtgcctc gcgtagtcga gttgcaaagc gcaccgtgtt ggcacgcccc    9180
gaaagcacgg cgacatattc acgcatatcc cgcagatcaa attcgcagat gacgcttcca    9240
ctttctcgtt taagaagaaa cttacggctg ccgaccgtca tgtcttcacg gatcgcctga    9300
aattcctttt cggtacattt cagtccatcg acataagccg atcgatctgc ggttggtgat    9360
ggatagaaaa tcttcgtcat acattgcgca accaagctgg ctcctagcgg cgattccaga    9420
acatgctctg gttgctgcgt tgccagtatt agcatcccgt tgttttttcg aacggtcagg    9480
aggaatttgt cgacgacagt cgaaaattta gggtttaaca aataggcgcg aaactcatcg    9540
cagctcatca caaacggcg gccgtcgatc atggctccaa tccgatgcag gagatatgct    9600
gcagcgggag cgcatacttc ctcgtattcg agaagatgcg tcatgtcgaa gccggtaatc    9660
gacggatcta actttacttc gtcaacttcg ccgtcaaatg cccagccaag cgcatggccc    9720
cggcaccagc gttggagccg cgctcctgcg ccttcggcgg gcccatgcaa caaaaattca    9780
cgtaaccccg cgattgaacg catttgtgga tcaaacgaga gctgacgatg gataccacgg    9840
accagacggc ggttctcttc cggagaaatc ccaccccgac catcactctc gatgagagcc    9900
acgatccatt cgcgcagaaa atcgtgtgag gctgctgtgt tttctaggcc acgcaacggc    9960
gccaacccgc tgggtgtgcc tctgtgaagt gccaaatatg ttcctcctgt ggcgcgaacc   10020
agcaattcgc caccccggtc cttgtcaaag aacacgaccg tacctgcacg gtcgaccatg   10080
ctctgttcga gcatggctag aacaaacatc atgagcgtcg tcttaccccct cccgataggc   10140
ccgaatattg ccgtcatgcc aacatcgtgc tcatgcggga tatagtcgaa aggcgttccg   10200
ccattggtac gaaatcgggc aatcgcgttg ccccagtggc ctgagctggc gccctctgga   10260
aagttttcga aagagacaaa ccctgcgaaa ttgcgtgaag tgattgcgcc agggcgtgtg   10320
```

```
cgccacttaa aattcccggg caattgggac caataggccg cttccatacc aataccttct    10380
tggacaacca cggcacctgc atccgccatt cgtgtccgag cccgcgcgcc cctgtcccca    10440
agactattga gatcgtctgc atagacgcaa aggctcaaat gatgtgagcc cataacgaat    10500
tcgttgctcg caagtgcgtc ctcagcctcg gataatttgc cgatttgagt cacggcttta    10560
tcgccggaac tcagcatctg gctcgatttg aggctaagtt tcgcgtgcgc ttgcgggcga    10620
gtcaggaacg aaaaactctg cgtgagaaca agtggaaaat cgagggatag cagcgcgttg    10680
agcatgcccg gccgtgtttt tgcagggtat tcgcgaaacg aatagatgga tccaacgtaa    10740
ctgtcttttg gcgttctgat ctcgagtcct cgcttgccgc aaatgactct gtcggtataa    10800
atcgaagcgc cgagtgagcc gctgacgacc ggaaccggtg tgaaccgacc agtcatgatc    10860
aaccgtagcg cttcgccaat ttcggtgaag agcacaccct gcttctcgcg gatgccaaga    10920
cgatgcaggc catacgcttt aagagagcca gcgacaacat gccaaagatc ttccatgttc    10980
ctgatctggc ccgtgagatc gttttccctt tttccgctta gcttggtgaa cctcctcttt    11040
accttcccta agccgcctg tgggtagaca atcaacgtaa ggaagtgttc attgcggagg    11100
agttggccga gagcacgcg ctgttcaaaa gcttcgttca ggctagcggc gaaaacacta    11160
cggaagtgtc gcggcgccga tgatggcacg tcggcatgac gtacgaggtg agcatatatt    11220
gacacatgat catcagcgat attgcgcaac agcgtgttga acgcacgaca acgcgcattg    11280
cgcatttcag tttcctcaag ctcgaatgca acgccatcaa ttctcgcaat ggtcatgatc    11340
gatccgtctt caagaaggac gatatggtcg ctgaggtggc caatataagg gagatagatc    11400
tcaccggatc tttcggtcgt tccactcgcg ccgagcatca caccattcct ctccctcgtg    11460
ggggaaccct aattggattt gggctaacag tagcgccccc ccaaactgca ctatcaatgc    11520
ttcttcccgc ggtccgcaaa aatagcagga cgacgctcgc cgcattgtag tctcgctcca    11580
cgatgagccg ggctgcaaac cataacggca cgagaacgac ttcgtagagc gggttctgaa    11640
cgataacgat gacaaagccg gcgaacatca tgaataaccc tgccaatgtc agtggcaccc    11700
caagaaacaa tgcgggccgt gtggctgcga ggtaaagggt cgattcttcc aaacgatcag    11760
ccatcaacta ccgccagtga gcgtttggcc gaggaagctc gccccaaaca tgataacaat    11820
gccgccgacg acgccggcaa ccagcccaag cgaagcccgc ccgaacatcc aggagatccc    11880
gatagcgaca atgccgagaa cagcgagtga ctggccgaac ggaccaagga taaacgtgca    11940
tatattgtta accattgtgg cggggtcagt gccgccaccc gcagattgcg ctgcggcggg    12000
tccggatgag gaaatgctcc atgcaattgc accgcacaag cttggggcgc agctcgatat    12060
cacgcgcatc atcgcattcg agagcgagag gcgatttaga tgtaaacggt atctctcaaa    12120
gcatcgcatc aatgcgcacc tccttagtat aagtcgaata agacttgatt gtcgtctgcg    12180
gatttgccgt tgtcctggtg tggcggtggc ggagcgatta aaccgccagc gccatcctcc    12240
tgcgagcggc gctgatatga cccccaaaca tcccacgtct cttcggattt tagcgcctcg    12300
tgatcgtctt ttggaggctc gattaacgcg ggcaccagcg attgagcagc tgtttcaact    12360
tttcgcacgt agccgtttgc aaaaccgccg atgaaattac cggtgttgta agcggagatc    12420
gcccgacgaa gcgcaaattg cttctcgtca atcgtttcgc cgcctgcata acgactttc    12480
agcatgtttg cagcggcaga taatgatgtg cacgcctgga gcgcaccgtc aggtgtcaga    12540
ccgagcatag aaaaatttcg agagtttatt tgcatgaggc caacatccag cgaatgccgt    12600
gcatcgagac ggtgcctgac gacttgggtt gcttggctgt gatcttgcca gtgaagcgtt    12660
tcgccggtcg tgttgtcatg aatcgctaaa ggatcaaagc gactctccac cttagctatc    12720
```

```
gccgcaagcg tagatgtcgc aactgatggg gcacacttgc gagcaacatg gtcaaactca   12780
gcagatgaga gtggcgtggc aaggctcgac gaacagaagg agaccatcaa ggcaagagaa   12840
agcgaccccg atctcttaag catacctttat ctccttagct cgcaactaac accgcctctc  12900
ccgttggaag aagtgcgttg ttttatgttg aagattatcg ggagggtcgg ttactcgaaa   12960
attttcaatt gcttctttat gatttcaatt gaagcgagaa acctcgcccg gcgtcttgga   13020
acgcaacatg gaccgagaac cgcgcatcca tgactaagca accggatcga cctattcagg   13080
ccgcagttgg tcaggtcagg ctcagaacga aaatgctcgg cgaggttacg ctgtctgtaa   13140
acccattcga tgaacgggaa gcttccttcc gattgctctt ggcaggaata ttggcccatg   13200
cctgcttgcg ctttgcaaat gctcttatcg cgttggtatc atatgccttg tccgccagca   13260
gaaacgcact ctaagcgatt atttgtaaaa atgtttcggt catgcggcgg tcatgggctt   13320
gacccgctgt cagcgcaaga cggatcggtc aaccgtcggc atcgacaaca gcgtgaatct   13380
tggtggtcaa accgccacgg gaacgtccca tacagccatc gtcttgatcc cgctgtttcc   13440
cgtcgccgca tgttggtgga cgcggacaca ggaactgtca atcatgacga cattctatcg   13500
aaagccttgg aaatcacact cagaatatga tcccagacgt ctgcctcacg ccatcgtaca   13560
aagcgattgt agcaggttgt acaggaaccg tatcgatcag gaacgtctgc ccagggcggg   13620
cccgtccgga agcgccacaa gatgacattg atcacccgcg tcaacgcgcg gcacgcgacg   13680
cggcttattt gggaacaaag gactgaacaa cagtccattc gaaatcggtg acatcaaagc   13740
ggggacgggt tatcagtggc ctccaagtca agcctcaatg aatcaaaatc agaccgattt   13800
gcaaacctga tttatgagtg tgcggcctaa atgatgaaat cgtccttcta gatcgcctcc   13860
gtggtgtagc aacacctcgc agtatcgccg tgctgacctt ggccagggaa ttgactggca   13920
agggtgcttt cacatgaccg ctcttttggc cgcgatagat gatttcgttg ctgctttggg   13980
cacgtagaag gagagaagtc atatcggaga aattcctcct ggcgcgagag cctgctctat   14040
cgcgacggca tcccactgtc gggaacagac cggatcattc acgaggcgaa agtcgtcaac   14100
acatgcgtta taggcatctt cccttgaagg atgatcttgt tgctgccaat ctggaggtgc   14160
ggcagccgca ggcagatgcg atctcagcgc aacttgcggc aaaacatctc actcacctga   14220
aaaccactag cgagtctcgc gatcagacga aggcctttta cttaacgaca caatatccga   14280
tgtctgcatc acaggcgtcg ctatcccagt caatactaaa gcggtgcagg aactaaagat   14340
tactgatgac ttaggcgtgc cacgaggcct gagacgacgc gcgtagacag ttttttgaaa   14400
tcattatcaa agtgatggcc tccgctgaag cctatcacct ctgcgccggt ctgtcggaga   14460
gatgggcaag cattattacg gtcttcgcgc ccgtacatgc attggacgat tgcagggtca   14520
atggatctga gatcatccag aggattgccg cccttacctt ccgtttcgag ttggagccag   14580
cccctaaatg agacgacata gtcgacttga tgtgacaatg ccaagagaga gatttgctta   14640
acccgatttt tttgctcaag cgtaagccta ttgaagcttg ccggcatgac gtccgcgccg   14700
aaagaatatc ctacaagtaa acattctgc acaccgaaat gcttggtgta gacatcgatt    14760
atgtgaccaa gatccttagc agtttcgctt ggggaccgct ccgaccagaa ataccgaagt   14820
gaactgacgc caatgacagg aatcccttcc gtctgcagat aggtaccatc gatagatctg   14880
ctgcctcgcg cgtttcggtg atgacggtga aaacctctga cacatgcagc tcccggagac   14940
ggtcacagct tgtctgtaag cggatgccgg gagcagacaa gcccgtcagg gcgcgtcagc   15000
gggtgttggc gggtgtcggg gcgcagccat gacccagtca cgtagcgata gcggagtgta   15060
tactggctta actatgcggc atcagagcag attgtactga gagtgcacca tatgcggtgt   15120
```

```
gaaataccgc acagatgcgt aaggagaaaa taccgcatca ggcgctcttc cgcttcctcg   15180
ctcactgact cgctgcgctc ggtcgttcgg ctgcggcgag cggtatcagc tcactcaaag   15240
gcggtaatac ggttatccac agaatcaggg gataacgcag gaaagaacat gtgagcaaaa   15300
ggccagcaaa aggccaggaa ccgtaaaaag gccgcgttgc tggcgttttt ccataggctc   15360 cgccccctg acgagcatca caaaaatcga cgctcaagtc agaggtggcg aaacccgaca   15420
ggactataaa gataccaggc gtttccccct ggaagctccc tcgtgcgctc tcctgttccg   15480
accctgccgc ttaccggata cctgtccgcc tttctccctt cgggaagcgt ggcgctttct   15540
catagctcac gctgtaggta tctcagttcg gtgtaggtcg ttcgctccaa gctgggctgt   15600
gtgcacgaac cccccgttca gcccgaccgc tgcgccttat ccggtaacta tcgtcttgag   15660
tccaacccgg taagacacga cttatcgcca ctggcagcag ccactggtaa caggattagc   15720
agagcgaggt atgtaggcgg tgctacagag ttcttgaagt ggtggcctaa ctacggctac   15780
actagaagga cagtatttgg tatctgcgct ctgctgaagc cagttacctt cggaaaaaga   15840
gttggtagct cttgatccgg caaacaaacc accgctggta gcggtggttt ttttgtttgc   15900
aagcagcaga ttacgcgcag aaaaaaagga tctcaagaag atcctttgat cttttctacg   15960
gggtctgacg ctcagtggaa cgaaaactca cgttaaggga ttttggtcat gagattatca   16020
aaaaggatct tcacctagat ccttttaaat taaaaatgaa gttttaaatc aatctaaagt   16080
atatatgagt aaacttggtc tgacagttac caatgcttaa tcagtgaggc acctatctca   16140
gcgatctgtc tatttcgttc atccatagtt gcctgactcc ccgtcgtgta gataactacg   16200
atacgggagg gcttaccatc tggccccagt gctgcaatga taccgcgaga cccacgctca   16260
ccggctccag atttatcagc aataaaccag ccagccggaa gggccgagcg cagaagtggt   16320
cctgcaactt tatccgcctc catccagtct attaattgtt gccgggaagc tagagtaagt   16380
agttcgccag ttaatagttt gcgcaacgtt gttgccattg ctgcagggg ggggggggg   16440 gggttccatt gttcattcca cggacaaaaa cagagaaagg aaacgacaga ggccaaaaag   16500
ctcgctttca gcacctgtcg tttcctttct tttcagaggg tattttaaat aaaaacatta   16560
agttatgacg aagaagaacg gaaacgcctt aaaccggaaa attttcataa atagcgaaaa   16620
cccgcgaggt ccctgtcgga tcaccggaaa ggacccgtaa agtgataatg attatcatct   16680
acatatcaca acgtgcgtgg aggccatcaa accacgtcaa ataatcaatt atgacgcagg   16740
tatcgtatta attgatctgc atcaacttaa cgtaaaaaca acttcagaca atacaaatca   16800
gcgacactga atacggggca acctcatgtc cccccccccc ccccccctgc aggcatcgtg   16860
gtgtcacgct cgtcgtttgg tatggcttca ttcagctccg gttcccaacg atcaaggcga   16920
gttacatgat cccccatgtt gtgcaaaaaa gcggttagct ccttcggtcc tccgatcgtt   16980
gtcagaagta agttggccgc agtgttatca ctcatggtta tggcagcact gcataattct   17040
cttactgtca tgccatccgt aagatgcttt tctgtgactg gtgagtactc aaccaagtca   17100
ttctgagaat agtgtatgcg gcgaccgagt tgctcttgcc cggcgtcaac acgggataat   17160
accgcgccac atagcagaac tttaaaagtg ctcatcattg gaaaacgttc ttcggggcga   17220
aaactctcaa ggatcttacc gctgttgaga tccagttcga tgtaacccac tcgtgcaccc   17280
aactgatctt cagcatcttt tactttcacc agcgtttctg ggtgagcaaa aacaggaagg   17340
caaaatgccg caaaaaaggg aataagggcg acacggaaat gttgaatact catactcttc   17400 cttttcaat attattgaag catttatcag ggttattgtc tcatgagcgg atacatattt   17460
gaatgtattt agaaaaataa acaaatagg gttccgcgca catttccccg aaaagtgcca   17520
```

```
cctgacgtct aagaaaccat tattatcatg acattaacct ataaaaatag gcgtatcacg    17580
aggccctttc gtcttcaaga attggtcgac gatcttgctg cgttcggata ttttcgtgga    17640
gttcccgcca cagacccgga ttgaaggcga gatccagcaa ctcgcgccag atcatcctgt    17700
gacggaactt tggcgcgtga tgactggcca ggacgtcggc cgaaagagcg acaagcagat    17760
cacgcttttc gacagcgtcg gatttgcgat cgaggatttt tcggcgctgc gctacgtccg    17820
cgaccgcgtt gagggatcaa gccacagcag cccactcgac cttctagccg acccagacga    17880
gccaagggat ctttttggaa tgctgctccg tcgtcaggct ttccgacgtt tgggtggttg    17940
aacagaagtc attatcgtac ggaatgccaa gcactcccga ggggaaccct gtggttggca    18000
tgcacataca aatggacgaa cggataaacc ttttcacgcc cttttaaata tccgttattc    18060
taataaacgc tcttttctct taggtttacc cgccaatata tcctgtcaaa cactgatagt    18120
ttaaactgaa ggcgggaaac gacaatctga tcatgagcgg agaattaagg gagtcacgtt    18180 atgaccccg ccgatgacgc gggacaagcc gttttacgtt tggaactgac agaaccgcaa    18240
cgttgaagga gccactcagc aagctggtac gattgtaata cgactcacta tagggcgaat    18300
tgagcgctgt ttaaacgctc ttcaactgga agagcggtta ccagagctgg tcacctttgt    18360
ccaccaagat ggaactgcgg ccgctcatta attaagtcag gcgcgcctct agttgaagac    18420
acgttcatgt cttcatcgta agaagacact cagtagtctt cggccagaat ggccatctgg    18480
attcagcagg cctagaaggc catttaaatc ctgaggatct ggtcttccta aggacccggg    18540
atatcgctat caactttgta tagaaaagtt gggccgaatt cgcccttgtt taaacttaat    18600
atttgtttaa acttttact aaattcatgt aataattaat gtatgcgtta tatatatg     18660 tctaggttta taattattca tatgaatatg aacataaaaa tctagggcta aaacgactac    18720
tattttgaaa acggaaggag tagtaagtta tttaagcgga ggggaaccat gatgggctag    18780
tgatttaatt tacatatata tattggtgtt ctgggctctt acatgagaag atctagttaa    18840
ctgttgttac tgaacagcga agacaaatat ataatttaag ctccccaact gctagtgatt    18900
ctgttaagag gtaatgttta aagtaaattt acaagagccc gtctagctca gtcggtagag    18960
cgcaaggctc ttaaccttgt ggtcgtgggt tcgagcccca cggtgggcgc acaatttttt    19020
gttttttgac attttttgtt tgcttagttg cagacggttt ttcccctgct aggagatttc    19080
cgagagaaaa aaaaggcact acaggttaac caaaaccacc aacctttgga gcgtcgaggc    19140
gacggggcat ttgcgtagtt gaagcttaca aagttgcata tgagatgagt gccgacatg    19200 aagcggataa cgttttaaac tggcaacaat atctagctgt ttcaaattca ggcgtgggaa    19260
gctacgccta cgcgccctgg acggcgtgta aagagccagc atcggcatca ttgtcaaacg    19320
atcgacaagg ccaagaaatt ccaaatatat tattaataaa aagaaggca ccaaattagt    19380 ttttgttttt tagtatgtgt ggcggaggaa attttgagaa cgaacgtatc caaagaaggc    19440
acaagacgat atagattgac gcggctagaa agttgcagca agacagtggg tacggtctta    19500
tatatcctaa taaataaaaa ataaaactat agtgtgtcaa atgtcaacaa gaggaggagg    19560
cagccaaatt agcagaggga gacaagtaga gcacgcctta ttagcttgct tatttatcgt    19620
ggtggtgtac ttgttaatta ctggcacgca ttatcaacaa cgcagttctg gatgtgaatc    19680
tagacaaaca tttgtctagg ttccgcacgt atagtttttt ttctttttt tggggggggg    19740 gggggaacgg aagctgtaat aaacggtact aggaacgaaa gcaaccgccg cgcgcatgtt    19800
tttgcaatag attacggtga ccttgatgca ccaccgcgtg ctataaaaac cagtgtcccc    19860
gagtctactc atcaaccaat ccataactcg aaacctttc ttgtgctctg ttctgtctgt    19920
```

```
gtgtttccaa agcaagcgaa agaggtcgag gggatcagct tcaagtttgt acaaaaaagc    19980
aggctccgcg gccgcccct tcaccatggc tcggcagcaa agcgtgcagg ccttgtgtgt     20040
gctggcggcg cttctcttcg ccgcctccct gccgtcgccg gccgccgcgg gggtgcacct    20100
ctcctcgctg cccaaagcgc tcgacgtcac cacctccgcc aaacccggcc aagtcctgca    20160
cgccggcgtg gactcgctga cggtgacgtg gagcctgaac gccacggagc cggccggcgc    20220
cgacgccggg tacaagggcg tgaaggtgaa gctgtgctac gcgccggcga gccagaagga    20280
ccgcgggtgg cgcaagtccg aggacgacat cagcaaggac aaggcgtgcc agttcaaggt    20340
caccgagcag gcgtacgcgg cggcggcgcc cggcagcttc cagtacgccg tcgcccgcga    20400
cgtcccctcg ggctcctact acctgcgcgc cttcgccacg gacgcgtcgg gcgccgaggt    20460
ggcctacggc cagacggcgc ccaccgccgc cttcgacgtc gccggcatca ccggcatcca    20520
cgcctctctc aagatcgccg ccggcgtctt ctcggccttc tccgtcgtcg cgctcgcctt    20580
cttcttcgtc atcgagaccc gcaagaagaa caagtagaag ggtgggcgcg ccgacccagc    20640
tttcttgtac aaagtggccg ttaacggatc cagacttgtc catcttctgg attggccaac    20700
ttaattaatg tatgaaataa aaggatgcac acatagtgac atgctaatca ctataatgtg    20760
ggcatcaaag ttgtgtgtta tgtgtaatta ctagttatct gaataaaaga gaaagagatc    20820
atccatattt cttatcctaa atgaatgtca cgtgtcttta taattctttg atgaaccaga    20880
tgcatttcat taaccaaatc catatacata taaatattaa tcatatataa ttaatatcaa    20940
ttgggttagc aaaacaaatc tagtctaggt gtgttttgcg aattgcggca agcttgcggc    21000
cgccccgggc aactttatta tacaaagttg atagatatcg gaccgattaa actttaattc    21060
ggtccgaagc ttgcatgcct gcagtgcagc gtgacccggt cgtgcccctc tctagagata    21120
atgagcattg catgtctaag ttataaaaaa ttaccacata ttttttttgt cacacttgtt    21180
tgaagtgcag tttatctatc tttatacata tatttaaact ttactctacg aataatataa    21240
tctatagtac tacaataata tcagtgtttt agagaatcat ataaatgaac agttagacat    21300
ggtctaaagg acaattgagt attttgacaa caggactcta cagttttatc ttttttagtgt    21360
gcatgtgttc tccttttttt ttgcaaatag cttcacctat ataatacttc atccatttta    21420
ttagtacatc catttagggt ttagggttaa tggtttttat agactaattt ttttagtaca    21480
tctatttttat tctatttag cctctaaatt aagaaaacta aaactctatt ttagtttttt    21540
tatttaataa tttagatata aaatagaata aaataaagtg actaaaaatt aaacaaatac    21600
cctttaagaa attaaaaaaa ctaaggaaac attttcttg tttcgagtag ataatgccag    21660
cctgttaaac gccgtcgacg agtctaacgg acaccaacca gcgaaccagc agcgtcgcgt    21720
cgggccaagc gaagcagacg gcacggcatc tctgtcgctg cctctggacc cctctcgaga    21780
gttccgctcc accgttggac ttgctccgct gtcggcatcc agaaattgcg tggcggagcg    21840
gcagacgtga gccggcacgg caggcggcct cctcctcctc tcacgcacc ggcagctacg    21900
ggggattcct ttcccaccgc tccttcgctt tccttcctc gcccgccgta ataaatagac    21960
accccctcca caccctcttt ccccaacctc gtgttgttcg gagcgcacac acacacaacc    22020
agatctcccc caaatccacc cgtcggcacc tccgcttcaa ggtacgccgc tcgtcctccc    22080
cccccccct ctctaccttc tctagatcgg cgttccggtc catgcatggt tagggccgg     22140
tagttctact tctgttcatg tttgtgttag atccgtgttt gtgttagatc cgtgctgcta    22200
gcgttcgtac acggatgcga cctgtacgtc agacacgttc tgattgctaa cttgccagtg    22260
tttctctttg gggaatcctg ggatggctct agccgttccg cagacgggat cgatttcatg    22320
```

```
attttttttg tttcgttgca tagggtttgg tttgcccttt tcctttattt caatatatgc    22380
cgtgcacttg tttgtcgggt catcttttca tgcttttttt tgtcttggtt gtgatgatgt    22440
ggtctggttg ggcggtcgtt ctagatcgga gtagaattct gtttcaaact acctggtgga    22500
tttattaatt ttggatctgt atgtgtgtgc catacatatt catagttacg aattgaagat    22560
gatggatgga aatatcgatc taggataggt atacatgttg atgcgggttt tactgatgca    22620
tatacagaga tgcttttttgt tcgcttggtt gtgatgatgt ggtgtggttg ggcggtcgtt    22680
cattcgttct agatcggagt agaatactgt ttcaaactac ctggtgtatt tattaatttt    22740
ggaactgtat gtgtgtgtca tacatcttca tagttacgag tttaagatgg atggaaatat    22800
cgatctagga taggtataca tgttgatgtg ggttttactg atgcatatac atgatggcat    22860
atgcagcatc tattcatatg ctctaacctt gagtacctat ctattataat aaacaagtat    22920
gttttataat tattttgatc ttgatatact tggatgatgg catatgcagc agctatatgt    22980 ggatttttt agccctgcct tcatacgcta tttatttgct tggtactgtt tcttttgtcg    23040
atgctcaccc tgttgtttgg tgttacttct gcaggtcgac tttaacttag cctaggatcc    23100
acacgacacc atgtcccccg agcgccgccc cgtcgagatc cgcccggcca ccgccgccga    23160
catggccgcc gtgtgcgaca tcgtgaacca ctacatcgag acctccaccg tgaacttccg    23220
caccgagccg cagaccccgc aggagtggat cgacgacctg gagcgcctcc aggaccgcta    23280
cccgtggctc gtggccgagg tggagggcgt ggtggccggc atcgcctacg ccggcccgtg    23340
gaaggcccgc aacgcctacg actggaccgt ggagtccacc gtgtacgtgt cccaccgcca    23400
ccagcgcctc ggcctcggct ccaccctcta cacccacctc ctcaagagca tggaggccca    23460
gggcttcaag tccgtggtgg ccgtgatcgg cctcccgaac gacccgtccg tgcgcctcca    23520
cgaggccctc ggctacaccg cccgcggcac cctccgcgcc gccggctaca gcacggcgg    23580 ctggcacgac gtcggcttct ggcagcgcga cttcgagctg ccggcccgc cgcgcccggt    23640 gcgcccggtg acgcagatct gagtcgaaac ctagacttgt ccatcttctg gattggccaa    23700
cttaattaat gtatgaaata aaaggatgca cacatagtga catgctaatc actataatgt    23760
gggcatcaaa gttgtgtgtt atgtgtaatt actagttatc tgaataaaag agaaagagat    23820
catccatatt tcttatccta aatgaatgtc acgtgtcttt ataattcttt gatgaaccag    23880
atgcatttca ttaaccaaat ccatatacat ataaatatta atcatatata attaatatca    23940
attgggttag caaaacaaat ctagtctagg tgtgttttgc gaatgcggcc gccaccgcgg    24000
tggagctcga attcattccg attaatcgtg gcctcttgct cttcaggatg aagagctatg    24060
tttaaacgtg caagcgctac tagacaattc agtacattaa aaacgtccgc aatgtgttat    24120
taagttgtct aagcgtcaat ttgtttacac cacaatatat cctgccacca gccagccaac    24180
agctccccga ccggcagctc ggcacaaaat caccactcga tacaggcagc ccatcagtcc    24240
gggacggcgt cagcgggaga gccgttgtaa ggcggcagac tttgctcatg ttaccgatgc    24300
tattcggaag aacggcaact aagctgccgg gtttgaaaca cggatgatct cgcggagggt    24360
agcatgttga ttgtaacgat gacagagcgt tgctgcctgt gatcaaatat catctcccctc    24420 gcagagatcc gaattatcag ccttcttatt catttctcgc ttaaccgtga caggctgtcg    24480
atcttgagaa ctatgccgac ataataggaa atcgctggat aaagccgctg aggaagctga    24540
gtggcgctat ttctttagaa gtgaacgttg acgatcgtcg accgtacccc gatgaattaa    24600
ttcggacgta cgttctgaac acagctggat acttacttgg gcgattgtca tacatgacat    24660
caacaatgta cccgtttgtg taaccgtctc ttggaggttc gtatgacact agtggttccc    24720
```

```
ctcagcttgc gactagatgt tgaggcctaa cattttatta gagagcaggc tagttgctta   24780
gatacatgat cttcaggccg ttatctgtca gggcaagcga aaattggcca tttatgacga   24840
ccaatgcccc gcagaagctc ccatctttgc cgccatagac gccgcgcccc ccttttgggg   24900
tgtagaacat cctttgcca gatgtggaaa agaagttcgt tgtcccattg ttggcaatga   24960
cgtagtagcc ggcgaaagtg cgagacccat ttgcgctata tataagccta cgatttccgt   25020
tgcgactatt gtcgtaattg gatgaactat tatcgtagtt gctctcagag ttgtcgtaat   25080
ttgatggact attgtcgtaa ttgcttatgg agttgtcgta gttgcttgga gaaatgtcgt   25140
agttggatgg ggagtagtca tagggaagac gagcttcatc cactaaaaca attggcaggt   25200
cagcaagtgc ctgccccgat gccatcgcaa gtacgaggct tagaaccacc ttcaacagat   25260
cgcgcatagt cttccccagc tctctaacgc ttgagttaag ccgcgccgcg aagcggcgtc   25320
ggcttgaacg aattgttaga cattatttgc cgactacctt ggtgatctcg cctttcacgt   25380
agtgaacaaa ttcttccaac tgatctgcgc gcgaggccaa gcgatcttct tgtccaagat   25440
aagcctgcct agcttcaagt atgacgggct gatactgggc cggcaggcgc tccattgccc   25500
agtcggcagc gacatccttc ggcgcgattt tgccggttac tgcgctgtac caaatgcggg   25560
acaacgtaag cactacattt cgctcatcgc cagcccagtc gggcggcgag ttccatagcg   25620
ttaaggtttc atttagcgcc tcaaatagat cctgttcagg aaccggatca aagagttcct   25680
ccgccgctgg acctaccaag gcaacgctat gttctcttgc ttttgtcagc aagatagcca   25740
gatcaatgtc gatcgtggct ggctcgaaga tacctgcaag aatgtcattg cgctgccatt   25800
ctccaaattg cagttcgcgc ttagctggat aacgccacgg aatgatgtcg tcgtgcacaa   25860
caatggtgac ttctacagcg cggagaatct cgctctctcc aggggaagcc gaagtttcca   25920
aaaggtcgtt gatcaaagct cgccgcgttg tttcatcaag ccttacagtc accgtaacca   25980
gcaaatcaat atcactgtgt ggcttcaggc cgccatccac tgcggagccg tacaaatgta   26040
cggccagcaa cgtcggttcg agatggcgct cgatgacgcc aactacctct gatagttgag   26100
tcgatacttc ggcgatcacc gcttccctca tgatgtttaa ctcctgaatt aagccgcgcc   26160
gcgaagcggt gtcggcttga atgaattgtt aggcgtcatc ctgtgctccc gagaaccagt   26220
accagtacat cgctgtttcg ttcgagactt gaggtctagt tttatacgtg aacaggtcaa   26280
tgccgccgag agtaaagcca catttttgcgt acaaattgca ggcaggtaca ttgttcgttt   26340
gtgtctctaa tcgtatgcca aggagctgtc tgcttagtgc ccacttttc gcaaattcga   26400 tgagactgtg cgcgactcct ttgcctcggt gcgtgtgcga cacaacaatg tgttcgatag   26460
aggctagatc gttccatgtt gagttgagtt caatcttccc gacaagctct tggtcgatga   26520
atgcgccata gcaagcagag tcttcatcag agtcatcatc cgagatgtaa tccttccggt   26580 agggggctcac acttctggta gatagttcaa agccttggtc ggataggtgc acatcgaaca   26640
cttcacgaac aatgaaatgg ttctcagcat ccaatgtttc cgccacctgc tcagggatca   26700
ccgaaatctt catatgacgc ctaacgcctg gcacagcgga tcgcaaacct ggcgcggctt   26760
ttggcacaaa aggcgtgaca ggtttgcgaa tccgttgctg ccacttgtta acccttttgc   26820
cagatttggt aactataatt tatgttagag gcgaagtctt gggtaaaaac tggcctaaaa   26880
ttgctgggga tttcaggaaa gtaaacatca ccttccggct cgatgtctat tgtagatata   26940
tgtagtgtat ctacttgatc gggggatctg ctgcctcgcg cgtttcggtg atgacggtga   27000
aaacctctga cacatgcagc tcccggagac ggtcacagct tgtctgtaag cggatgccgg   27060
gagcagacaa gcccgtcagg gcgcgtcagc gggtgttggc gggtgtcggg gcgcagccat   27120
```

```
gacccagtca cgtagcgata gcggagtgta tactggctta actatgcggc atcagagcag   27180
attgtactga gagtgcacca tatgcggtgt gaaataccgc acagatgcgt aaggagaaaa   27240
taccgcatca ggcgctcttc cgcttcctcg ctcactgact cgctgcgctc ggtcgttcgg   27300
ctgcggcgag cggtatcagc tcactcaaag gcggtaatac ggttatccac agaatcaggg   27360
gataacgcag gaaagaacat gtgagcaaaa ggccagcaaa aggccaggaa ccgtaaaaag   27420
gccgcgttgc tggcgttttt ccataggctc cgcccccctg acgagcatca caaaaatcga   27480
cgctcaagtc agaggtggcg aaacccgaca ggactataaa gataccaggc gtttccccct   27540
ggaagctccc tcgtgcgctc tcctgttccg accctgccgc ttaccggata cctgtccgcc   27600
tttctccctt cgggaagcgt ggcgctttct catagctcac gctgtaggta tctcagttcg   27660
gtgtaggtcg ttcgctccaa gctgggctgt gtgcacgaac cccccgttca gcccgaccgc   27720
tgcgccttat ccggtaacta tcgtcttgag tccaacccgg taagacacga cttatcgcca   27780
ctggcagcag ccactggtaa caggattagc agagcgaggt atgtaggcgg tgctacagag   27840
ttcttgaagt ggtggcctaa ctacggctac actagaagga cagtatttgg tatctgcgct   27900
ctgctgaagc cagttacctt cggaaaaaga gttggtagct cttgatccgg caaacaaacc   27960
accgctggta gcggtggttt ttttgtttgc aagcagcaga ttacgcgcag aaaaaaagga   28020
tctcaagaag atcctttgat cttttctacg ggtctgacg ctcagtggaa cgaaaactca   28080
cgttaaggga ttttggtcat gagattatca aaaaggatct tcacctagat ccttttaaat   28140
taaaaatgaa gttttaaatc aatctaaagt atatatgagt aaacttggtc tgacagttac   28200
caatgcttaa tcagtgaggc acctatctca gcgatctgtc tatttcgttc atccatagtt   28260
gcctgactcc ccgtcgtgta gataactacg atacgggagg gcttaccatc tggccccagt   28320
gctgcaatga taccgcgaga cccacgctca ccggctccag atttatcagc aataaaccag   28380
ccagccggaa gggccgagcg cagaagtggt cctgcaactt tatccgcctc catccagtct   28440
attaattgtt gccgggaagc tagagtaagt agttcgccag ttaatagttt gcgcaacgtt   28500
gttgccattg ctgcagggg ggggggggg gggacttcc attgttcatt ccacggacaa   28560
aaacagagaa aggaaacgac agaggccaaa aagcctcgct ttcagcacct gtcgtttcct   28620 ttctttttcag agggtatttt aaataaaaac attaagttat gacgaagaag aacgaaaacg   28680
ccttaaaccg gaaaattttc ataaatagcg aaaacccgcg aggtcgccgc cccgtaagcc   28740
gccccgtaac ctgtcggatc accggaaagg accccgtaaag tgataatgat tatcatctac   28800
atatcacaac gtgcgtggag gccatcaaac cacgtcaaat aatcaattat gacgcaggta   28860
tcgtattaat tgatctgcat caacttaacg taaaaacaac ttcagacaat acaaatcagc   28920
gacactgaat acggggcaac ctcatgtccc cccccccc cccctgcag gcatcgtggt   28980 gtcacgctcg tcgtttggta tggcttcatt cagctccggt tcccaacgat caaggcgagt   29040
tacatgatcc cccatgttgt gcaaaaaagc ggttagctcc ttcggtcctc cgatcgttgt   29100
cagaagtaag ttggccgcag tgttatcact catggttatg gcagcactgc ataattctct   29160
tactgtcatg ccatccgtaa gatgcttttc tgtgactggt gagtactcaa ccaagtcatt   29220
ctgagaatag tgtatgcggc gaccgagttg ctcttgcccg gcgtcaacac gggataatac   29280
cgcgccacat agcagaactt taaaagtgct catcattgga aaacgttctt cggggcgaaa   29340
actctcaagg atcttaccgc tgttgagatc cagttcgatg taacccactc gtgcacccaa   29400
ctgatcttca gcatctttta ctttcaccag cgtttctggg tgagcaaaaa caggaaggca   29460
aaatgccgca aaaaagggaa taagggcgac acggaaatgt tgaatactca tactcttcct   29520
```

```
ttttcaatat tattgaagca tttatcaggg ttattgtctc atgagcggat acatatttga   29580
atgtatttag aaaataaac aaatagggt tccgcgcaca tttccccgaa aagtgccacc    29640
tgacgtctaa gaaaccatta ttatcatgac attaacctat aaaaataggc gtatcacgag   29700 gcccttcgt cttcaagaat tcggagcttt tgccattctc accggattca gtcgtcactc    29760
atggtgattt ctcacttgat aaccttattt ttgacgaggg gaaattaata ggttgtattg   29820
atgttggacg agtcggaatc gcagaccgat accaggatct tgccatccta tggaactgcc   29880
tcggtgagtt ttctccttca ttacagaaac ggcttttca aaaatatggt attgataatc    29940
ctgatatgaa taaattgcag tttcatttga tgctcgatga gttttctaa tcagaattgg    30000 ttaattggtt gtaacactgg cagagcatta cgctgacttg acgggacggc ggctttgttg   30060
aataaatcga acttttgctg agttgaagga tcagatcacg catcttcccg acaacgcaga   30120
ccgttccgtg gcaaagcaaa agttcaaaat caccaactgg tccacctaca acaaagctct   30180
catcaaccgt ggctccctca ctttctggct ggatgatggg gcgattcagg cctggtatga   30240
gtcagcaaca ccttcttcac gaggcagacc tcagcgccag aaggccgcca gagaggccga   30300
gcgcggccgt gaggcttgga cgctagggca gggcatgaaa aagcccgtag cgggctgcta   30360
cgggcgtctg acgcggtgga aaggggagg ggatgttgtc tacatggctc tgctgtagtg    30420
agtgggttgc gctccggcag cggtcctgat caatcgtcac cctttctcgg tccttcaacg   30480
ttcctgacaa cgagcctcct tttcgccaat ccatcgacaa tcaccgcgag tccctgctcg   30540
aacgctgcgt ccgaccggc ttcgtcgaag gcgtctatcg cggcccgcaa cagcggcgag    30600
agcggagcct gttcaacggt gccgccgcgc tcgccggcat cgctgtcgcc ggcctgctcc   30660
tcaagcacgg ccccaacagt gaagtagctg attgtcatca gcgcattgac ggcgtccccg   30720
gccgaaaaac ccgcctcgca gaggaagcga agctgcgcgt cggccgtttc catctgcggt   30780
gcgcccggtc gcgtgccggc atggatgcgc gcgccatcgc ggtaggcgag cagcgcctgc   30840
ctgaagctgc gggcattccc gatcagaaat gagcgccagt cgtcgtcggc tctcggcacc   30900
gaatgcgtat gattctccgc cagcatggct tcggccagtg cgtcgagcag cgcccgcttg   30960
ttcctgaagt gccagtaaag cgccggctgc tgaaccccca accgttccgc cagtttgcgt   31020
gtcgtcagac cgtctacgcc gacctcgttc aacaggtcca gggcggcacg gatcactgta   31080
ttcggctgca acttttgtcat gcttgacact ttatcactga taaacataat atgtccacca   31140
acttatcagt gataaagaat ccgcgcgttc aatcggacca gcggaggctg gtccggaggc   31200
cagacgtgaa acccaacata cccctgatcg taattctgag cactgtcgcg ctcgacgctg   31260
tcggcatcgg cctgattatg ccggtgctgc cgggcctcct gcgcgatctg gttcactcga   31320
acgacgtcac cgcccactat ggcattctgc tggcgctgta tgcgttggtg caatttgcct   31380
gcgcacctgt gctgggcgcg ctgtcggatc gtttcgggcg gcgccaatc ttgctcgtct    31440 cgctggccgg cgccactgtc gactacgcca tcatggcgac agcgcctttc ctttgggttc   31500
tctatatcgg gcggatcgtg gccggcatca ccggggcgac tggggcggta gccggcgctt   31560
atattgccga tatcactgat ggcgatgagc gcgcgcggca cttcggcttc atgagcgcct   31620
gtttcgggtt cggatggtc gcgggacctg tgctcggtgg gctgatgggc ggttctcccc    31680
cccacgctcc gttcttcgcc gcggcagcct tgaacggcct caatttcctg acgggctgtt   31740
tccttttgcc ggagtcgcac aaaggcgaac gccggccgtt acgcgggag gctctcaacc    31800 cgctcgcttc gttccggtgg gcccggggca tgaccgtcgt cgccgccctg atggcggtct   31860
tcttcatcat gcaacttgtc ggacaggtgc cggccgcgct ttgggtcatt tcggcgagg    31920
```

```
atcgctttca ctgggacgcg accacgatcg gcatttcgct tgccgcattt ggcattctgc  31980
attcactcgc ccaggcaatg atcaccggcc ctgtagccgc ccggctcggc gaaaggcggg  32040
cactcatgct cggaatgatt gccgacggca caggctacat cctgcttgcc ttcgcgacac  32100
ggggatggat ggcgttcccg atcatggtcc tgcttgcttc gggtggcatc ggaatgccgg  32160
cgctgcaagc aatgttgtcc aggcaggtgg atgaggaacg tcaggggcag ctgcaaggct  32220
cactggcggc gctcaccagc ctgacctcga tcgtcggacc cctcctcttc acggcgatct  32280
atgcggcttc tataacaacg tggaacgggt gggcatggat tgcaggcgct gccctctact  32340
tgctctgcct gccggcgctg cgtcgcgggc tttggagcgg cgcagggcaa cgagccgatc  32400
gctgatcgtg gaaacgatag gcctatgcca tgcgggtcaa ggcgacttcc ggcaagctat  32460
acgcgcccta ggagtgcggt tggaacgttg gcccagccag atactcccga tcacgagcag  32520
gacgccgatg atttgaagcg cactcagcgt ctgatccaag aacaaccatc ctagcaacac  32580
ggcggtcccc gggctgagaa agcccagtaa ggaaacaact gtaggttcga gtcgcgagat  32640
cccccggaac caaaggaagt aggttaaacc cgctccgatc aggccgagcc acgccaggcc  32700
gagaacattg gttcctgtag gcatcgggat tggcggatca aacactaaag ctactggaac  32760
gagcagaagt cctccggccg ccagttgcca ggcggtaaag gtgagcagag gcacgggagg  32820
ttgccacttg cgggtcagca cggttccgaa cgccatggaa accgccccg ccaggcccgc  32880
tgcgacgccg acaggatcta gcgctgcgtt tggtgtcaac accaacagcg ccacgcccgc  32940
agttccgcaa atagccccca ggaccgccat caatcgtatc gggctaccta gcagagcggc  33000
agagatgaac acgaccatca gcggctgcac agcgcctacc gtcgccgcga ccccgcccgg  33060
caggcggtag accgaaataa acaacaagct ccagaatagc gaaatattaa gtgcgccgag  33120
gatgaagatg cgcatccacc agattcccgt tggaatctgt cggacgatca tcacgagcaa  33180
taaacccgcc ggcaacgccc gcagcagcat accggcgacc cctcggcctc gctgttcggg  33240
ctccacgaaa acgccggaca gatgcgcctt gtgagcgtcc ttggggccgt cctcctgttt  33300
gaagaccgac agcccaatga tctcgccgtc gatgtaggcg ccgaatgcca cggcatctcg  33360
caaccgttca gcgaacgcct ccatgggctt tttctcctcg tgctcgtaaa cggacccgaa  33420
catctctgga gctttcttca gggccgacaa tcggatctcg cggaaatcct gcacgtcggc  33480
cgctccaagc cgtcgaatct gagccttaat cacaattgtc aattttaatc ctctgtttat  33540
cggcagttcg tagagcgcgc cgtgcgtccc gagcgatact gagcgaagca agtgcgtcga  33600
gcagtgcccg cttgttcctg aaatgccagt aaagcgctgg ctgctgaacc cccagccgga  33660
actgacccca caaggcccta gcgtttgcaa tgcaccaggt catcattgac ccaggcgtgt  33720
tccaccaggc cgctgcctcg caactcttcg caggcttcgc cgacctgctc gcgccacttc  33780
ttcacgcggg tggaatccga tccgcacatg aggcggaagg tttccagctt gagcgggtac  33840
ggctcccggt gcgagctgaa atagtcgaac atccgtcggg ccgtcggcga cagcttgcgg  33900
tacttctccc atatgaattt cgtgtagtgg tcgccagcaa acagcacgac gatttcctcg  33960
tcgatcagga cctggcaacg ggacgttttc ttgccacggt ccaggacgcg gaagcggtgc  34020
agcagcgaca ccgattccag gtgcccaacg cggtcggacg tgaagcccat cgccgtcgcc  34080
tgtaggcgcg acaggcattc ctcggccttc gtgtaatacc ggccattgat cgaccagccc  34140
aggtcctggc aaagctcgta gaacgtgaag gtgatcggct cgccgatagg ggtgcgcttc  34200
gcgtactcca acacctgctg ccacaccagt tcgtcatcgt cggcccgcag ctcgacgccg  34260
gtgtaggtga tcttcacgtc cttgttgacg tggaaaatga ccttgttttg cagcgcctcg  34320
```

```
cgcgggattt tcttgttgcg cgtggtgaac agggcagagc gggccgtgtc gtttggcatc   34380
gctcgcatcg tgtccggcca cggcgcaata tcgaacaagg aaagctgcat ttccttgatc   34440
tgctgcttcg tgtgtttcag caacgcggcc tgcttggcct cgctgacctg ttttgccagg   34500
tcctcgccgg cggttttttcg cttcttggtc gtcatagttc ctcgcgtgtc gatggtcatc   34560
gacttcgcca aacctgccgc ctcctgttcg agacgacgcg aacgctccac ggcggccgat   34620
ggcgcgggca gggcagggggg agccagttgc acgctgtcgc gctcgatctt ggccgtagct   34680
tgctggacca tcgagccgac ggactggaag gtttcgcggg gcgcacgcat gacggtgcgg   34740
cttgcgatgg tttcggcatc ctcggcggaa accccgcgt cgatcagttc ttgcctgtat   34800
gccttccggt caaacgtccg attcattcac cctccttgcg ggattgcccc gactcacgcc   34860
ggggcaatgt gcccttattc ctgatttgac ccgcctggtg ccttggtgtc cagataatcc   34920
accttatcgg caatgaagtc ggtcccgtag accgtctggc cgtccttctc gtacttggta   34980
ttccgaatct tgccctgcac gaataccagc gaccccttgc ccaaatactt gccgtgggcc   35040
tcggcctgag agccaaaaca cttgatgcgg aagaagtcgg tgcgctcctg cttgtcgccg   35100
gcatcgttgc gccactcttc attaaccgct atatcgaaaa ttgcttgcgg cttgttagaa   35160
ttgccatgac gtacctcggt gtcacgggta agattaccga taaactggaa ctgattatgg   35220
ctcatatcga aagtctcctt gagaaaggag actctagttt agctaaacat tggttccgct   35280
gtcaagaact ttagcggcta aaattttgcg ggccgcgacc aaaggtgcga ggggcggctt   35340
ccgctgtgta caaccagata ttttttcacca acatccttcg tctgctcgat gagcgggca   35400
tgacgaaaca tgagctgtcg gagagggcag gggtttcaat ttcgttttta tcagacttaa   35460
ccaacggtaa ggccaacccc tcgttgaagg tgatggaggc cattgccgac gccctggaaa   35520
ctcccctacc tcttctcctg gagtccaccg accttgaccg cgaggcactc gcggagattg   35580
cgggtcatcc tttcaagagc agcgtgccgc ccggatacga acgcatcagt gtggttttgc   35640
cgtcacataa ggcgtttatc gtaaagaaat ggggcgacga cacccgaaaa aagctgcgtg   35700
gaaggctctg acgccaaggg ttagggcttg cacttccttc tttagccgct aaaacggccc   35760
cttctctgcg ggccgtcggc tcgcgcatca tatcgacatc ctcaacggaa gccgtgccgc   35820
gaatggcatc gggcgggtgc gctttgacag ttgttttcta tcagaacccc tacgtcgtgc   35880
ggttcgatta gctgtttgtc ttgcaggcta aacactttcg gtatatcgtt tgcctgtgcg   35940
ataatgttgc taatgatttg ttgcgtaggg gttactgaaa agtgagcggg aaagaagagt   36000
ttcagaccat caaggagcgg gccaagcgca agctggaacg cgacatgggt gcggacctgt   36060
tggccgcgct caacgacccg aaaaccgttg aagtcatgct caacgcggac ggcaaggtgt   36120
ggcacgaacg ccttggcgag ccgatgcggt acatctgcga catgcggccc agccagtcgc   36180
aggcgattat agaaacggtg gccggattcc acggcaaaga ggtcacgcgg cattcgccca   36240
tcctggaagg cgagttcccc ttggatggca gccgctttgc cggccaattg ccgccggtcg   36300
tggccgcgcc aacctttgcg atccgcaagc gcgcggtcgc catcttcacg ctggaacagt   36360
acgtcgaggc gggcatcatg acccgcgagc aatacgaggt cattaaaagc gccgtcgcgg   36420
cgcatcgaaa catcctcgtc attggcggta ctggctcggg caagaccacg ctcgtcaacg   36480
cgatcatcaa tgaaatggtc gccttcaacc cgtctgagcg cgtcgtcatc atcgaggaca   36540
ccggcgaaat ccagtgcgcc gcagagaacg ccgtccaata ccacaccagc atcgacgtct   36600
cgatgacgct gctgctcaag acaacgctgc gtatgcgccc cgaccgcatc ctggtcggtg   36660
aggtacgtgg ccccgaagcc cttgatctgt tgatggcctg gaacaccggg catgaaggag   36720
```

```
gtgccgccac cctgcacgca aacaacccca aagcgggcct gagccggctc gccatgctta   36780
tcagcatgca cccggattca ccgaaaccca ttgagccgct gattggcgag gcggttcatg   36840
tggtcgtcca tatcgccagg accctagcg gccgtcgagt gcaagaaatt ctcgaagttc    36900
ttggttacga gaacggccag tacatcacca aaaccctgta aggagtattt ccaatgacaa   36960
cggctgttcc gttccgtctg accatgaatc gcggcatttt gttctacctt gccgtgttct   37020
tcgttctcgc tctcgcgtta tccgcgcatc cggcgatggc ctcggaaggc accggcggca   37080
gcttgccata tgagagctgg ctgacgaacc tgcgcaactc cgtaaccggc ccggtggcct   37140
tcgcgctgtc catcatcggc atcgtcgtcg ccggcggcgt gctgatcttc ggcggcgaac   37200
tcaacgcctt cttccgaacc ctgatcttcc tggttctggt gatggcgctg ctggtcggcg   37260
cgcagaacgt gatgagcacc ttcttcggtc gtggtgccga atcgcggcc ctcggcaacg    37320 gggcgctgca ccaggtgcaa gtcgcggcg cggatgccgt gcgtgcggta gcggctggac    37380
ggctcgccta atcatggctc tgcgcacgat ccccatccgt cgcgcaggca accgagaaaa   37440
cctgttcatg ggtggtgatc gtgaactggt gatgttctcg ggcctgatgg cgtttgcgct   37500
gattttcagc gcccaagagc tgcgggccac cgtggtcggt ctgatcctgt ggttcggggc   37560
gctctatgcg ttccgaatca tggcgaaggc cgatccgaag atgcggttcg tgtacctgcg   37620
tcaccgccgg tacaagccgt attacccggc ccgctcgacc ccgttccgcg agaacaccaa   37680
tagccaaggg aagcaatacc gatgatccaa gcaattgcga ttgcaatcgc gggcctcggc   37740
gcgcttctgt tgttcatcct ctttgcccgc atccgcgcgg tcgatgccga actgaaactg   37800
aaaaagcatc gttccaagga cgccggcctg gccgatctgc tcaactacgc cgctgtcgtc   37860
gatgacggcg taatcgtggg caagaacggc agctttatgg ctgcctggct gtacaagggc   37920
gatgacaacg caagcagcac cgaccagcag cgcgaagtag tgtccgcccg catcaaccag   37980
gccctcgcgg gcctgggaag tgggtggatg atccatgtgg acgccgtgcg gcgtcctgct   38040
ccgaactacg cggagcgggg cctgtcggcg ttccctgacc gtctgacggc agcgattgaa   38100
gaagagcgct cggtcttgcc ttgctcgtcg gtgatgtact tcaccagctc cgcgaagtcg   38160
ctcttcttga tggagcgcat ggggacgtgc ttggcaatca cgcgcaccccc cggccgtttt   38220 tagcggctaa aaaagtcatg gctctgccct cgggcggacc acgcccatca tgaccttgcc   38280
aagctcgtcc tgcttctctt cgatcttcgc cagcagggcg aggatcgtgg catcaccgaa   38340
ccgcgccgtg cgcgggtcgt cggtgagcca gagtttcagc aggccgccca ggcggcccag   38400
gtcgccattg atgcgggcca gctcgcggac gtgctcatag tccacgacgc ccgtgatttt   38460
gtagccctgg ccgacggcca gcaggtaggc cgacaggctc atgccggccg ccgccgcctt   38520
ttcctcaatc gctcttcgtt cgtctggaag gcagtacacc ttgataggtg ggctgccctt   38580
cctggttggc ttggtttcat cagccatccg cttgccctca tctgttacgc cggcggtagc   38640
cggccagcct cgcagagcag gattcccgtt gagcaccgcc aggtgcgaat aagggacagt   38700
gaagaaggaa cacccgctcg cgggtgggcc tacttcacct atcctgcccg gctgacgccg   38760
ttggatacac caaggaaagt ctacacgaac cctttggcaa aatcctgtat atcgtgcgaa   38820
aaaggatgga tataccgaaa aaatcgctat aatgaccccg aagcagggtt atgcagcgga   38880
aaagcgctgc ttccctgctg ttttgtggaa tatctaccga ctggaaacag gcaaatgcag   38940
gaaattactg aactgagggg acaggcgaga gacgatgcca aagagctaca ccgacgagct   39000
ggccgagtgg gttgaatccc gcgcggccaa gaagcgccgg cgtgatgagg ctgcggttgc   39060
gttcctggcg gtgagggcgg atgtcgaggc ggcgttagcg tccggctatg cgctcgtcac   39120
```

| | |
|---|---|
| catttgggag cacatgcggg aaacggggaa ggtcaagttc tcctacgaga cgttccgctc | 39180 |
| gcacgccagg cggcacatca aggccaagcc cgccgatgtg cccgcaccgc aggccaaggc | 39240 |
| tgcggaaccc gcgccggcac ccaagacgcc ggagccacgg cggccgaagc agggggcaa | 39300 |
| ggctgaaaag ccggcccccg ctgcggcccc gaccggcttc accttcaacc caacaccgga | 39360 |
| caaaaaggat ctactgtaat ggcgaaaatt cacatggttt tgcagggcaa gggcggggtc | 39420 |
| ggcaagtcgg ccatcgccgc gatcattgcg cagtacaaga tggacaaggg gcagacaccc | 39480 |
| ttgtgcatcg acaccgaccc ggtgaacgcg acgttcgagg gctacaaggc cctgaacgtc | 39540 |
| cgccggctga acatcatggc cggcgacgaa attaactcgc gcaacttcga caccctggtc | 39600 |
| gagctgattg cgccgaccaa ggatgacgtg gtgatcgaca acggtgccag ctcgttcgtg | 39660 |
| cctctgtcgc attacctcat cagcaaccag gtgccggctc tgctgcaaga aatggggcat | 39720 |
| gagctggtca tccataccgt cgtcaccggc ggccaggctc tcctggacac ggtgagcggc | 39780 |
| ttcgcccagc tcgccagcca gttcccggcc gaagcgcttt tcgtggtctg gctgaacccg | 39840 |
| tattggggc ctatcgagca tgagggcaag agctttgagc agatgaaggc gtacacggcc | 39900 |
| aacaaggccc gcgtgtcgtc catcatccag attccggccc tcaaggaaga aacctacggc | 39960 |
| cgcgatttca gcgacatgct gcaagagcgg ctgacgttcg accaggcgct ggccgatgaa | 40020 |
| tcgctcacga tcatgacgcg gcaacgcctc aagatcgtgc ggcgcggcct gtttgaacag | 40080 |
| ctcgacgcgg cggccgtgct atgagcgacc agattgaaga gctgatccgg gagattgcgg | 40140 |
| ccaagcacgg catcgccgtc ggccgcgacg acccggtgct gatcctgcat accatcaacg | 40200 |
| cccggctcat ggccgacagt gcggccaagc aagaggaaat ccttgccgcg ttcaaggaag | 40260 |
| agctggaagg gatcgcccat cgttggggcg aggacgccaa ggccaaagcg gagcggatgc | 40320 |
| tgaacgcggc cctggcggcc agcaaggacg caatggcgaa ggtaatgaag gacagcgccg | 40380 |
| cgcaggcggc cgaagcgatc cgcagggaaa tcgacgacgg ccttggccgc cagctcgcgg | 40440 |
| ccaaggtcgc ggacgcgcgg cgcgtggcga tgatgaacat gatcgccggc ggcatggtgt | 40500 |
| tgttcgcggc cgccctggtg gtgtgggcct cgttatgaat cgcagaggcg cagatgaaaa | 40560 |
| agcccggcgt tgccgggctt tgtttttgcg ttagctgggc ttgtttgaca ggcccaagct | 40620 |
| ctgactgcgc ccgcgctcgc gctcctgggc ctgtttcttc tcctgctcct gcttgcgcat | 40680 |
| cagggcctgg tgccgtcggg ctgcttcacg catcgaatcc cagtcgccgg ccagctcggg | 40740 |
| atgctccgcg cgcatcttgc gcgtcgccag ttcctcgatc ttgggcgcgt gaatgcccat | 40800 |
| gccttccttg atttcgcgca ccatgtccag ccgcgtgtgc agggtctgca agcgggcttg | 40860 |
| ctgtttgggcc tgctgctgct gccaggcggc ctttgtacgc ggcagggaca gcaagccggg | 40920 |
| ggcattggac tgtagctgct gcaaacgcgc ctgctgacgg tctacgagct gttctaggcg | 40980 |
| gtcctcgatg cgctccacct ggtcatgctt tgcctgcacg tagagcgcaa gggtctgctg | 41040 |
| gtaggtctgc tcgatgggcg cggattctaa gagggcctgc tgttccgtct cggcctcctg | 41100 |
| ggccgcctgt agcaaatcct cgccgctgtt gccgctggac tgctttactg ccggggactg | 41160 |
| ctgttgccct gctcgcgccg tcgtcgcagt tcggcttgcc cccactcgat tgactgcttc | 41220 |
| atttcgagcc gcagcgatgc gatctcggat tgcgtcaacg gacggggcag cgcggaggtg | 41280 |
| tccggcttct ccttgggtga gtcggtcgat gccatagcca aagtttcct tccaaaatgc | 41340 |
| gtccattgct ggaccgtgtt tctccattgat gcccgcaagc atcttcggct tgaccgccag | 41400 |
| gtcaagcgcg ccttcatggg cggtcatgac ggacgccgcc atgaccttgc cgccgttgtt | 41460 |
| ctcgatgtag ccgcgtaatg aggcaatggt gccgcccatc gtcagcgtgt catcgacaac | 41520 |

```
gatgtacttc tggccgggga tcacctcccc ctcgaaagtc gggttgaacg ccaggcgatg    41580
atctgaaccg gctccggttc gggcgacctt ctcccgctgc acaatgtccg tttcgacctc    41640
aaggccaagg cggtcggcca gaacgaccgc catcatggcc ggaatcttgt tgttccccgc    41700
cgcctcgacg gcgaggactg gaacgatgcg gggcttgtcg tcgccgatca gcgtcttgag    41760
ctgggcaaca gtgtcgtccg aaatcaggcg ctcgaccaaa ttaagcgccg cttccgcgtc    41820
gccctgcttc gcagcctggt attcaggctc gttggtcaaa gaaccaaggt cgccgttgcg    41880
aaccaccttc gggaagtctc cccacggtgc gcgctcggct ctgctgtagc tgctcaagac    41940
gcctcccttt ttagccgcta aaactctaac gagtgcgccc gcgactcaac ttgacgcttt    42000
cggcacttac ctgtgccttg ccacttgcgt cataggtgat gcttttcgca ctcccgattt    42060
caggtacttt atcgaaatct gaccgggcgt gcattacaaa gttcttcccc acctgttggt    42120
aaatgctgcc gctatctgcg tggacgatgc tgccgtcgtg gcgctgcgac ttatcggcct    42180
tttgggccat atagatgttg taaatgccag gtttcagggc cccggcttta tctaccttct    42240
ggttcgtcca tgcgccttgg ttctcggtct ggacaattct ttgcccattc atgaccagga    42300
ggcggtgttt cattgggtga ctcctgacgg ttgcctctgg tgttaaacgt gtcctggtcg    42360
cttgccggct aaaaaaaagc cgacctcggc agttcgaggc cggctttccc tagagccggg    42420
cgcgtcaagg ttgttccatc tattttagtg aactgcgttc gatttatcag ttactttcct    42480
cccgctttgt gtttcctccc actcgtttcc gcgtctagcc gacccctcaa catagcggcc    42540
tcttcttggg ctgcctttgc ctcttgccgc gcttcgtcac gctcggcttg caccgtcgta    42600
aagcgctcgg cctgcctggc cgcctcttgc gccgccaact tcctttgctc ctggtgggcc    42660
tcggcgtcgg cctgcgcctt cgcttttcacc gctgccaact ccgtgcgcaa actctccgct    42720
tcgcgcctgg tggcgtcgcg ctcgccgcga agcgcctgca tttcctggtt ggccgcgtcc    42780
agggtcttgc ggctctcttc tttgaatgcg cgggcgtcct ggtgagcgta gtccagctcg    42840
gcgcgcagct cctgcgctcg acgctccacc tcgtcggccc gctgcgtcgc cagcgcggcc    42900
cgctgctcgg ctcctgccag ggcggtgcgt gcttcggcca gggcttgccg ctggcgtgcg    42960
gccagctcgg ccgcctcggc ggcctgctgc tctagcaatg taacgcgcgc ctgggcttct    43020
tccagctcgc gggcctgcgc ctcgaaggcg tcggccagct ccccgcgcac ggcttccaac    43080
tcgttgcgct cacgatccca gccggcttgc gctgcctgca acgattcatt ggcaagggcc    43140
tgggcggctt gccagagggc ggccacggcc tggttgccgg cctgctgcac cgcgtccggc    43200
acctggactg ccagcggggc ggcctgcgcc gtgcgctggc gtcgccattc gcgcatgccg    43260
gcgctggcgt cgttcatgtt gacgcgggcg gccttacgca ctgcatccac ggtcgggaag    43320
ttctcccggt cgccttgctc gaacagctcg tccgcagccg caaaaatgcg gtcgcgcgtc    43380
tctttgttca gttccatgtt ggctccggta attggtaaga ataataatac tcttacctac    43440
cttatcagcg caagagttta gctgaacagt tctcgactta acggcaggtt ttttagcggc    43500
tgaagggcag gcaaaaaaag ccccgcacgg tcggcggggg caagggtca gcggaaggg    43560 gattagcggg cgtcgggctt cttcatgcgt cggggccgcg cttcttggga tggagcacga    43620
cgaagcgcgc acgcgcatcg tcctcggccc tatcggcccg cgtcgcggtc aggaacttgt    43680
cgcgcgctag gtcctccctg gtgggcacca ggggcatgaa ctcggcctgc tcgatgtagg    43740
tccactccat gaccgcatcg cagtcgaggc cgcgttcctt caccgtctct gcaggtcgc    43800 ggtacgcccg ctcgttgagc ggctggtaac gggccaattg gtcgtaaatg gctgtcggcc    43860
atgagcggcc tttcctgttg agccagcagc cgacgacgaa gccggcaatg caggcccctg    43920
```

-continued

```
gcacaaccag gccgacgccg ggggcagggg atggcagcag ctcgccaacc aggaaccccg    43980
ccgcgatgat gccgatgccg gtcaaccagc ccttgaaact atccggcccc gaaacacccc    44040
tgcgcattgc ctggatgctg cgccggatag cttgcaacat caggagccgt ttcttttgtt    44100
cgtcagtcat ggtccgccct caccagttgt tcgtatcggt gtcggacgaa ctgaaatcgc    44160
aagagctgcc ggtatcggtc cagccgctgt ccgtgtcgct gctgccgaag cacggcgagg    44220
ggtccgcgaa cgccgcagac ggcgtatccg gccgcagcgc atcgcccagc atggcccgg    44280 tcagcgagcc gccggccagg tagcccagca tggtgctgtt ggtcgccccg gccaccaggg    44340
ccgacgtgac gaaatcgccg tcattccctc tggattgttc gctgctcggc ggggcagtgc    44400
gccgcgccgg cggcgtcgtg gatggctcgg gttggctggc ctgcgacggc cggcgaaagg    44460
tgcgcagcag ctcgttatcg accggctgcg gcgtcggggc cgccgccttg cgctgcggtc    44520
ggtgttcctt cttcggctcg cgcagcttga acagcatgat cgcggaaacc agcagcaacg    44580
ccgcgcctac gcctcccgcg atgtagaaca gcatcggatt cattcttcgg tcctccttgt    44640
agcggaaccg ttgtctgtgc ggcgcgggtg gcccgcgccg ctgtctttgg ggatcagccc    44700
tcgatgagcg cgaccagttt cacgtcggca aggttcgcct cgaactcctg gccgtcgtcc    44760
tcgtacttca accaggcata gccttccgcc ggcggccgac ggttgaggat aaggcgggca    44820
gggcgctcgt cgtgctcgac ctggacgatg gcctttttca gcttgtccgg gtccggctcc    44880
ttcgcgccct tttccttggc gtccttaccg tcctggtcgc cgtcctcgcc gtcctggccg    44940
tcgccggcct ccgcgtcacg ctcggcatca gtctggccgt tgaaggcatc gacggtgttg    45000
ggatcgcggc ccttctcgtc caggaactcg cgcagcagct tgaccgtgcc gcgcgtgatt    45060
tcctgggtgt cgtcgtcaag ccacgcctcg acttcctccg ggcgcttctt gaaggccgtc    45120
accagctcgt tcaccacggt cacgtcgcgc acgcggccgg tgttgaacgc atcggcgatc    45180
ttctccggca ggtccagcag cgtgacgtgc tgggtgatga acgccggcga cttgccgatt    45240
tccttggcga tatcgccttt cttcttgccc ttcgccagct cgcggccaat gaagtcggca    45300
atttcgcgcg gggtcagctc gttgcgttgc aggttctcga taacctggtc ggcttcgttg    45360
tagtcgttgt cgatgaacgc cgggatggac ttcttgccgg cccacttcga gccacggtag    45420
cggcgggcgc cgtgattgat gatatagcgg cccggctgct cctggttctc gcgcaccgaa    45480
atgggtgact tcaccccgcg ctctttgatc gtggcaccga tttccgcgat gctctccggg    45540
gaaaagccgg ggttgtcggc cgtccgcggc tgatgcggat cttcgtcgat caggtccagg    45600
tccagctcga tagggccgga accgccctga gacgccgcag gagcgtccag gaggctcgac    45660
aggtcgccga tgctatccaa ccccaggccg gacggctgcg ccgcgcctgc ggcttcctga    45720
gcggccgcag cggtgttttt cttggtggtc ttggcttgag ccgcagtcat tgggaaatct    45780
ccatcttcgt gaacacgtaa tcagccaggg cgcgaacctc tttcgatgcc ttgcgcgcgg    45840
ccgttttctt gatcttccag accggcacac cggatgcgag ggcatcggcg atgctgctgc    45900
gcaggccaac ggtggccgga atcatcatct tggggtacgc ggccagcagc tcggcttggt    45960
ggcgcgcgtg gcgcggattc cgcgcatcga ccttgctggg caccatgcca aggaattgca    46020
gcttggcgtt cttctggcgc acgttcgcaa tggtcgtgac catcttcttg atgccctgga    46080
tgctgtacgc ctcaagctcg atgggggaca gcacatagtc ggccgcgaag agggcggccg    46140
ccaggccgac gccaagggtc ggggccgtgt cgatcaggca cacgtcgaag ccttggttcg    46200
ccagggcctt gatgttcgcc ccgaacagct cgcgggcgtc gtccagcgac agccgttcgg    46260
cgttcgccag taccggggttg gactcgatga gggcgaggcg cgcggcctgg ccgtcgccgg    46320
```

-continued

```
ctgcgggtgc ggtttcggtc cagccgccgg cagggacagc gccgaacagc ttgcttgcat    46380
gcaggccggt agcaaagtcc ttgagcgtgt aggacgcatt gccctggggg tccaggtcga    46440
tcacggcaac ccgcaagccg cgctcgaaaa agtcgaaggc aagatgcaca agggtcgaag    46500
tcttgccgac gccgcctttc tggttggccg tgaccaaagt tttcatcgtt tggtttcctg    46560
tttttcttg gcgtccgctt cccacttccg gacgatgtac gcctgatgtt ccggcagaac     46620
cgccgttacc cgcgcgtacc cctcgggcaa gttcttgtcc tcgaacgcgg cccacacgcg    46680
atgcaccgct tgcgacactg cgccctggt cagtcccagc gacgttgcga acgtcgcctg     46740
tggcttccca tcgactaaga cgccccgcgc tatctcgatg gtctgctgcc ccacttccag    46800
cccctggatc gcctcctgga actggctttc ggtaagccgt ttcttcatgg ataacaccca    46860
taatttgctc cgcgccttgg ttgaacatag cggtgacagc cgccagcaca tgagagaagt    46920
ttagctaaac atttctcgca cgtcaacacc tttagccgct aaaactcgtc cttggcgtaa    46980
caaaacaaaa gcccggaaac cgggctttcg tctcttgccg cttatggctc tgcacccggc    47040
tccatcacca acaggtcgcg cacgcgcttc actcggttgc ggatcgacac tgccagccca    47100
acaaagccgg ttgccgccgc cgccaggatc gcgccgatga tgccgccac accggccatc     47160
gcccaccagg tcgccgcctt ccggttccat tcctgctggt actgcttcgc aatgctggac    47220
ctcggctcac cataggctga ccgctcgatg gcgtatgccg cttctcccct tggcgtaaaa    47280
cccagcgccg caggcggcat tgccatgctg cccgccgctt tcccgaccac gacgcgcgca    47340
ccaggcttgc ggtccagacc ttcggccacg gcgagctgcg caaggacata atcagccgcc    47400
gacttggctc cacgcgcctc gatcagctct tgcactcgcg cgaaatcctt ggcctccacg    47460
gccgccatga atcgcgcacg cggcgaaggc tccgcagggc cggcgtcgtg atcgccgccg    47520
agaatgccct tcaccaagtt cgacgacacg aaaatcatgc tgacggctat caccatcatg    47580
cagacggatc gcacgaaccc gctgaattga acacgagcac ggcacccgcg accactatgc    47640
caagaatgcc caaggtaaaa attgccggcc ccgccatgaa gtccgtgaat gccccgacgg    47700
ccgaagtgaa gggcaggccg ccacccaggc cgccgccctc actgcccggc acctggtcgc    47760
tgaatgtcga tgccagcacc tgcggcacgt caatgcttcc gggcgtcgcg ctcgggctga    47820
tcgcccatcc cgttactgcc ccgatcccgg caatggcaag gactgccagc gctgccattt    47880
ttggggtgag gccgttcgcg gccgaggggc gcagccctg ggggatggg aggcccgcgt      47940
tagcgggccg ggagggttcg agaagggggg gcacccccct tcggcgtgcg cggtcacgcg    48000
cacagggcgc agccctggtt aaaaacaagg tttataaata ttggtttaaa agcaggttaa    48060
aagacaggtt agcggtggcc gaaaaacggg cggaaccct tgcaaatgct ggattttctg     48120
cctgtggaca gcccctcaaa tgtcaatagg tgcgcccctc atctgtcagc actctgcccc    48180
tcaagtgtca aggatcgcgc ccctcatctg tcagtagtcg cgcccctcaa gtgtcaatac    48240
cgcagggcac ttatccccag gcttgtccac atcatctgtg ggaaactcgc gtaaaatcag    48300
gcgttttcgc cgatttgcga ggctggccag ctccacgtcg ccggccgaaa tcgagcctgc    48360
ccctcatctg tcaacgccgc gccgggtgag tcggcccctc aagtgtcaac gtccgcccct    48420
catctgtcag tgagggccaa gttttccgcg aggtatccac aacgccggcg gccgcggtgt    48480
ctcgcacacg gcttcgacgg cgtttctggc gcgtttgcag ggccatagac ggccgccagc    48540
ccagcggcga gggcaaccag cccggtgagc gtcggaaagg cgctggaagc cccgtagcga    48600
cgcggagagg ggcgagacaa gccaaggcg caggctcgat gcgcagcacg acatagccgg     48660
ttctcgcaag gacgagaatt tccctgcggt gccctcaag tgtcaatgaa agtttccaac     48720
```

```
gcgagccatt cgcgagagcc ttgagtccac gctagatgag agctttgttg taggtggacc    48780
agttggtgat tttgaacttt tgctttgcca cggaacggtc tgcgttgtcg ggaagatgcg    48840
tgatctgatc cttcaactca gcaaaagttc gatttattca acaaagccac gttgtgtctc    48900
aaaatctctg atgttacatt gcacaagata aaaatatatc atcatgaaca ataaaactgt    48960
ctgcttacat aaacagtaat acaaggggtg ttatgagcca tattcaacgg gaaac         49015

<210> SEQ ID NO 96
<211> LENGTH: 48997
<212> TYPE: DNA
<213> ORGANISM: Artificial Seqeunce
<220> FEATURE:
<223> OTHER INFORMATION: Vector

<400> SEQUENCE: 96
gtcttgctcg actctagagc tcgttcctcg aggcctcgag gcctcgagga acggtacctg       60
cggggaagct tacaataatg tgtgttgtta agtcttgttg cctgtcatcg tctgactgac      120
tttcgtcata aatcccggcc tccgtaaccc agctttgggc aagctcacgg atttgatccg      180
gcggaacggg aatatcgaga tgccgggctg aacgctgcag ttccagcttt ccctttcggg      240
acaggtactc cagctgattg attatctgct gaagggtctt ggttccacct cctggcacaa      300
tgcgaatgat tacttgagcg cgatcgggca tccaattttc tcccgtcagg tgcgtggtca      360
agtgctacaa ggcacctttc agtaacgagc gaccgtcgat ccgtcgccgg gatacggaca      420
aaatggagcg cagtagtcca tcgagggcgg cgaaagcctc gccaaaagca atacgttcat      480
ctcgcacagc ctccagatcc gatcgagggt cttcggcgta ggcagataga agcatggata      540
cattgcttga gagtattccg atggactgaa gtatggcttc catctttttct cgtgtgtctg      600 catctatttc gagaaagccc ccgatgcggc gcaccgcaac gcgaattgcc atactatccg      660
aaagtcccag caggcgcgct tgataggaaa aggtttcata ctcggccgat cgcagacggg      720
cactcacgac cttgaaccct tcaactttca gggatcgatg ctggttgatg gtagtctcac      780
tcgacgtggc tctggtgtgt tttgacatag cttcctccaa agaaagcgga aggtctggat      840
actccagcac gaaatgtgcc cgggtagacg gatggaagtc tagccctgct caatatgaaa      900
tcaacagtac atttacagtc aatactgaat atacttgcta catttgcaat tgtcttataa      960
cgaatgtgaa ataaaaatag tgtaacaacg cttttactca tcgataatca caaaaacatt     1020
tatacgaaca aaaatacaaa tgcactccgg tttcacagga taggcgggat cagaatatgc     1080
aacttttgac gttttgttct ttcaaagggg gtgctggcaa aaccaccgca ctcatgggcc     1140
tttgcgctgc tttggcaaat gacggtaaac gagtggccct cttttgatgcc gacgaaaacc     1200 ggcctctgac gcgatggaga gaaaacgcct tacaaagcag tactgggatc ctcgctgtga     1260
agtctattcc gccgacgaaa tgccccttct tgaagcagcc tatgaaaatg ccagctcga     1320 aggatttgat tatgcgttgg ccgatacgcg tggcggctcg agcgagctca acaacacaat     1380
catcgctagc tcaaacctgc ttctgatccc caccatgcta acgccgctcg acatcgatga     1440
ggcactatct acctaccgct acgtcatcga gctgctgttg agtgaaaatt tggcaattcc     1500
tacagctgtt ttgcgccaac gcgtcccggt cggccgattg acaacatcgc aacgcaggat     1560
gtcagagacg ctagagagcc ttccagttgt accgtctccc atgcatgaaa gagatgcatt     1620
tgccgcgatg aaagaacgcg gcatgttgca tcttacatta ctaaacacgg gaactgatcc     1680
gacgatgcgc ctcatagaga ggaatcttcg gattgcgatg gaggaagtcg tggtcatttc     1740
gaaactgatc agcaaaatct tggaggcttg aagatggcaa ttcgcaagcc cgcattgtcg     1800
```

```
gtcggcgaag cacggcggct tgctggtgct cgacccgaga tccaccatcc caacccgaca    1860
cttgttcccc agaagctgga cctccagcac ttgcctgaaa aagccgacga gaaagaccag    1920
caacgtgagc ctctcgtcgc cgatcacatt tacagtcccg atcgacaact taagctaact    1980
gtggatgccc ttagtccacc tccgtccccg aaaaagctcc aggtttttct ttcagcgcga    2040
ccgcccgcgc ctcaagtgtc gaaaacatat gacaacctcg ttcggcaata cagtccctcg    2100
aagtcgctac aaatgatttt aaggcgcgcg ttggacgatt tcgaaagcat gctggcagat    2160
ggatcatttc gcgtggcccc gaaaagttat ccgatcccct caactacaga aaaatccgtt    2220
ctcgttcaga cctcacgcat gttcccggtt gcgttgctcg aggtcgctcg aagtcatttt    2280
gatccgttgg ggttggagac cgctcgagct ttcggccaca agctggctac cgccgcgctc    2340
gcgtcattct ttgctggaga aagccatcg agcaattggt gaagagggac ctatcggaac    2400
ccctcaccaa atattgagtg taggtttgag gccgctggcc gcgtcctcag tcaccttttg    2460
agccagataa ttaagagcca aatgcaattg gctcaggctg ccatcgtccc cccgtgcgaa    2520
acctgcacgt ccgcgtcaaa gaaataaccg gcacctcttg ctgtttttat cagttgaggg    2580
cttgacggat ccgcctcaag tttgcggcgc agccgcaaaa tgagaacatc tatactcctg    2640
tcgtaaacct cctcgtcgcg tactcgactg gcaatgagaa gttgctcgcg cgatagaacg    2700
tcgcggggtt tctctaaaaa cgcgaggaga agattgaact cacctgccgt aagtttcacc    2760
tcaccgccag cttcggacat caagcgacgt tgcctgagat taagtgtcca gtcagtaaaa    2820
caaaaagacc gtcggtcttt ggagcggaca acgttgggc gcacgcgcaa ggcaacccga    2880
atgcgtgcaa gaaactctct cgtactaaac ggcttagcga taaaatcact tgctcctagc    2940
tcgagtgcaa caactttatc cgtctcctca aggcggtcgc cactgataat tatgattgga    3000
atatcagact ttgccgccag atttcgaacg atctcaagcc catcttcacg acctaaattt    3060
agatcaacaa ccacgacatc gaccgtcgcg gaagagagta ctctagtgaa ctgggtgctg    3120
tcggctaccg cggtcacttt gaaggcgtgg atcgtaaggt attcgataat aagatgccgc    3180
atagcgacat cgtcatcgat aagaagaacg tgtttcaacg gctcacctt caatctaaaa    3240 tctgaaccct tgttcacagc gcttgagaaa ttttcacgtg aaggatgtac aatcatctcc    3300
agctaaatgg gcagttcgtc agaattgcgg ctgaccgcgg atgacgaaaa tgcgaaccaa    3360
gtatttcaat tttatgacaa aagttctcaa tcgttgttac aagtgaaacg cttcgaggtt    3420
acagctacta ttgattaagg gatcgccta tggtctcgcc ccggcgtcgt gcgtccgccg    3480
cgagccagat ctcgcctact tcataaacgt cctcataggc acggaatgga atgatgacat    3540
cgatcgccgt agagagcatg tcaatcagtg tgcgatcttc caagctagca ccttgggcgc    3600
tacttttgac aagggaaaac agtttcttga atccttggat tggattcgcg ccgtgtattg    3660
ttgaaatcga tcccggatgt cccgagacga cttcactcag ataagcccat gctgcatcgt    3720
cgcgcatctc gccaagcaat atccggtccg gccgcatacg cagacttgct tggagcaagt    3780
gctcggcgct cacagcaccc agcccagcac cgttcttgga gtagagtagt ctaacatgat    3840
tatcgtgtgg aatgacgagt tcgagcgtat cttctatggt gattagcctt tcctgggggg    3900
ggatggcgct gatcaaggtc ttgctcattg ttgtcttgcc gcttccggta gggccacata    3960
gcaacatcgt cagtcggctg acgacgcatg cgtgcagaaa cgcttccaaa tccccgttgt    4020
caaaatgctg aaggatagct tcatcatcct gattttggcg tttccttcgt gtctgccact    4080
ggttccacct cgaagcatca taacgggagg agacttcttt aagaccagaa acacgcgagc    4140
ttggccgtcg aatggtcaag ctgacggtgc ccgagggaac ggtcggcggc agacagattt    4200
```

```
gtagtcgttc accaccagga agttcagtgg cgcagagggg gttacgtggt ccgacatcct   4260
gctttctcag cgcgcccgct aaaatagcga tatcttcaag atcatcataa gagacgggca   4320
aaggcatctt ggtaaaaatg ccggcttggc gcacaaatgc ctctccaggt cgattgatcg   4380
caatttcttc agtcttcggg tcatcgagcc attccaaaat cggcttcaga agaaagcgta   4440
gttgcggatc cacttccatt tacaatgtat cctatctcta agcggaaatt tgaattcatt   4500
aagagcggcg gttcctcccc cgcgtggcgc cgccagtcag gcggagctgg taaacaccaa   4560
agaaatcgag gtcccgtgct acgaaaatgg aaacggtgtc ccctgattc ttcttcaggg    4620
ttggcggtat gttgatggtt gccttaaggg ctgtctcagt tgtctgctca ccgttatttt   4680
gaaagctgtt gaagctcatc ccgccacccg agctgccggc gtaggtgcta gctgcctgga   4740
aggcgccttg aacaacactc aagagcatag ctccgctaaa acgctgccag aagtggctgt   4800
cgaccgagcc cggcaatcct gagcgaccga gttcgtccgc gcttggcgat gttaacgaga   4860
tcatcgcatg gtcaggtgtc tcggcgcgat cccacaacac aaaaacgcgc ccatctccct   4920
gttgcaagcc acgctgtatt tcgccaacaa cggtggtgcc acgatcaaga agcacgatat   4980
tgttcgttgt tccacgaata tcctgaggca agacacactt tacatagcct gccaaatttg   5040
tgtcgattgc ggtttgcaag atgcacggaa ttattgtccc ttgcgttacc ataaaatcgg   5100
ggtgcggcaa gagcgtggcg ctgctgggct gcagctcggt gggtttcata cgtatcgaca   5160
aatcgttctc gccggacact tcgccattcg gcaaggagtt gtcgtcacgc ttgcctttctt  5220
gtcttcggcc cgtgtcgccc tgaatggcgc gtttgctgac cccttgatcg ccgctgctat   5280
atgcaaaaat cggtgtttct tccggccgtg gctcatgccg ctccggttcg ccctcggcg    5340
gtagaggagc agcaggctga acagcctctt gaaccgctgg aggatccggc ggcacctcaa   5400
tcggagctgg atgaaatggc ttggtgtttg ttgcgatcaa agttgacggc gatgcgttct   5460
cattcacctt cttttggcgc ccacctagcc aaatgaggct taatgataac gcagaacga    5520
cacctccgac gatcaatttc tgagaccccg aaagacgccg gcgatgtttg tcggagacca   5580
gggatccaga tgcatcaacc tcatgtgccg cttgctgact atcgttattc atcccttcgc   5640
ccccttcagg acgcgtttca catcgggcct caccgtgccc gtttgcggcc tttggccaac   5700
gggatcgtaa gcggtgttcc agatacatag tactgtgtgg ccatccctca gacgccaacc   5760
tcgggaaacc gaagaaatct cgacatcgct ccctttaact gaatagttgg caacagcttc   5820
cttgccatca ggattgatgg tgtagatgga gggtatgcgt acattgcccg gaaagtggaa   5880
taccgtcgta aatccattgt cgaagacttc gagtggcaac agcgaacgat cgccttgggc   5940
gacgtagtgc caattactgt ccgccgcacc aagggctgtg acaggctgat ccaataaatt   6000
ctcagctttc cgttgatatt gtgcttccgc gtgtagtctg tccacaacag ccttctgttg   6060
tgcctccctt cgccgagccg ccgcatcgtc ggcggggtag gcgaattgga cgctgtaata   6120
gagatcgggc tgctctttat cgaggtggga cagagtcttg aacttatac tgaaaacata    6180
acggcgcatc ccggagtcgc ttgcggttag cacgattact ggctgaggcg tgaggacctg   6240
gcttgccttg aaaaatagat aatttccccg cggtagggct gctagatctt tgctatttga   6300
aacggcaacc gctgtcaccg tttcgttcgt ggcgaatgtt acgaccaaag tagctccaac   6360
cgccgtcgag aggcgcacca cttgatcggg attgtaagcc aaataacgca tgcgcggatc   6420
tagcttgccc gccattggag tgtcttcagc ctccgcacca gtcgcagcgg caaataaaca   6480
tgctaaaatg aaaagtgctt ttctgatcat ggttcgctgt ggcctacgtt tgaaacggta   6540
tcttccgatg tctgatagga ggtgacaacc agacctgccg ggttggttag tctcaatctg   6600
```

```
ccgggcaagc tggtcacctt ttcgtagcga actgtcgcgg tccacgtact caccacaggc   6660
attttgccgt caacgacgag ggtccttttg tagcgaattt gctgcgtgct tggagttaca   6720
tcatttgaag cgatgtgctc gacctccacc ctgccgcgtt tgccaagaat gacttgaggc   6780
gaactgggat tgggatagtt gaagaattgc tggtaatcct ggcgcactgt tggggcactg   6840
aagttcgata ccaggtcgta ggcgtactga gcggtgtcgg catcataact ctcgcgcagg   6900
cgaacgtact cccacaatga ggcgttaacg acggcctcct cttgagttgc aggcaatcgc   6960
gagacagaca cctcgctgtc aacggtgccg tccggccgta tccatagata tacgggcaca   7020
agcctgctca acggcaccat tgtggctata gcgaacgctt gagcaacatt tcccaaaatc   7080
gcgatagctg cgacagctgc aatgagtttg gagagacgtc gcgccgattt cgctcgcgcg   7140
gtttgaaagg cttctacttc cttatagtgc tcggcaaggc tttcgcgcgc cactagcatg   7200
gcatattcag gccccgtcat agcgtccacc cgaattgccg agctgaagat ctgacggagt   7260
aggctgccat cgcccacat tcagcgggaa gatcgggcct ttgcagctcg ctaatgtgtc   7320
gtttgtctgg cagccgctca aagcgacaac taggcacagc aggcaatact tcatagaatt   7380
ctccattgag gcgaattttt gcgcgaccta gcctcgctca acctgagcga agcgacggta   7440
caagctgctg gcagattggg ttgcgccgct ccagtaactg cctccaatgt tgccggcgat   7500
cgccggcaaa gcgacaatga gcgcatcccc tgtcagaaaa aacatatcga gttcgtaaag   7560
accaatgatc ttggccgcgg tcgtaccggc gaaggtgatt acaccaagca taagggtgag   7620
cgcagtcgct tcggttagga tgacgatcgt tgccacgagg tttaagagga gaagcaagag   7680
accgtaggtg ataagttgcc cgatccactt agctgcgatg tcccgcgtgc gatcaaaaat   7740
atatccgacg aggatcagag gcccgatcgc gagaagcact ttcgtgagaa ttccaacggc   7800
gtcgtaaact ccgaaggcag accagagcgt gccgtaaagg acccactgtg cccccttggaa   7860 agcaaggatg tcctggtcgt tcatcggacc gatttcggat gcgattttct gaaaaacggc   7920
ctgggtcacg gcgaacattg tatccaactg tgccggaaca gtctgcagag gcaagccggt   7980
tacactaaac tgctgaacaa agtttgggac cgtcttttcg aagatggaaa ccacatagtc   8040
ttggtagtta gcctgcccaa caattagagc aacaacgatg gtgaccgtga tcacccgagt   8100
gataccgcta cgggtatcga cttcgccgcg tatgactaaa ataccctgaa caataatcca   8160
aagagtgaca caggcgatca atggcgcact caccgcctcc tggatagtct caagcatcga   8220
gtccaagcct gtcgtgaagg ctacatcgaa gatcgtatga atggccgtaa acggcgccgg   8280
aatcgtgaaa ttcatcgatt ggacctgaac ttgactggtt tgtcgcataa tgttggataa   8340
aatgagctcg cattcggcga ggatgcgggc ggatgaacaa atcgcccagc cttaggggag   8400
ggcaccaaag atgacagcgg tcttttgatg ctccttgcgt tgagcggccg cctcttccgc   8460
ctcgtgaagg ccggcctgcg cggtagtcat cgttaatagg cttgtcgcct gtacattttg   8520
aatcattgcg tcatggatct gcttgagaag caaaccattg gtcacggttg cctgcatgat   8580
attgcgagat cgggaaagct gagcagacgt atcagcattc gccgtcaagc gtttgtccat   8640
cgtttccaga ttgtcagccg caatgccagc gctgtttgcg gaaccggtga tctgcgatcg   8700
caacaggtcc gcttcagcat cactacccac gactgcacga tctgtatcgc tggtgatcgc   8760
acgtgccgtg gtcgacattg gcattcgcgg cgaaaacatt tcattgtcta ggtccttcgt   8820
cgaaggatac tgattttcct ggttgagcga agtcagtagt ccagtaacgc cgtaggccga   8880
cgtcaacatc gtaaccatcg ctatagtctg agtgagattc tccgcagtcg cgagcgcagt   8940
cgcgagcgtc tcagcctccg ttgccgggtc gctaacaaca aactgcgccc gcgcgggctg   9000
```

```
aatatataga aagctgcagg tcaaaactgt tgcaataagt tgcgtcgtct tcatcgtttc   9060
ctaccttatc aatcttctgc ctcgtggtga cgggccatga attcgctgag ccagccagat   9120
gagttgcctt cttgtgcctc gcgtagtcga gttgcaaagc gcaccgtgtt ggcacgcccc   9180
gaaagcacgg cgacatattc acgcatatcc cgcagatcaa attcgcagat gacgcttcca   9240
ctttctcgtt taagaagaaa cttacggctg ccgaccgtca tgtcttcacg gatcgcctga   9300
aattcctttt cggtacattt cagtccatcg acataagccg atcgatctgc ggttggtgat   9360
ggatagaaaa tcttcgtcat acattgcgca accaagctgg ctcctagcgg cgattccaga   9420
acatgctctg gttgctgcgt tgccagtatt agcatcccgt tgttttttcg aacggtcagg   9480
aggaatttgt cgacgacagt cgaaaattta gggtttaaca aataggcgcg aaactcatcg   9540
cagctcatca caaaacggcg gccgtcgatc atggctccaa tccgatgcag gagatatgct   9600
gcagcgggag cgcatacttc ctcgtattcg agaagatgcg tcatgtcgaa gccggtaatc   9660
gacggatcta actttacttc gtcaacttcg ccgtcaaatg cccagccaag cgcatggccc   9720
cggcaccagc gttggagccg cgctcctgcg ccttcggcgg gcccatgcaa caaaaattca   9780
cgtaaccccg cgattgaacg catttgtgga tcaaacgaga gctgacgatg gataccacgg   9840
accagacggc ggttctcttc cggagaaatc ccaccccgac catcactctc gatgagagcc   9900
acgatccatt cgcgcagaaa atcgtgtgag gctgctgtgt tttctaggcc acgcaacggc   9960
gccaacccgc tgggtgtgcc tctgtgaagt gccaaatatg ttcctcctgt ggcgcgaacc  10020
agcaattcgc caccccggtc cttgtcaaag aacacgaccg tacctgcacg gtcgaccatg  10080
ctctgttcga gcatggctag aacaaacatc atgagcgtcg tcttacccct cccgataggc  10140
ccgaatattg ccgtcatgcc aacatcgtgc tcatgcggga tatagtcgaa aggcgttccg  10200
ccattggtac gaaatcgggc aatcgcgttg ccccagtggc ctgagctggc gccctctgga  10260
aagttttcga aagagacaaa ccctgcgaaa ttgcgtgaag tgattgcgcc agggcgtgtg  10320
cgccacttaa aattccccgg caattgggac caataggccg cttccatacc aatacctcct  10380
tggacaacca cggcacctgc atccgccatt cgtgtccgag cccgcgcgcc cctgtcccca  10440
agactattga gatcgtctgc atagacgcaa aggctcaaat gatgtgagcc cataacgaat  10500
tcgttgctcg caagtgcgtc ctcagcctcg gataatttgc cgatttgagt cacggcttta  10560
tcgccggaac tcagcatctg gctcgatttg aggctaagtt tcgcgtgcgc ttgcgggcga  10620
gtcaggaacg aaaaactctg cgtgagaaca agtggaaaat cgagggatag cagcgcgttg  10680
agcatgcccg gccgtgtttt tgcagggtat tcgcgaaacg aatagatgga tccaacgtaa  10740
ctgtcttttg gcgttctgat ctcgagtcct cgcttgccgc aaatgactct gtcggtataa  10800
atcgaagcgc cgagtgagcc gctgacgacc ggaaccggtg tgaaccgacc agtcatgatc  10860
aaccgtagcg cttcgccaat ttcggtgaag agcacaccct gcttctcgcg gatgccaaga  10920
cgatgcaggc catacgcttt aagagagcca gcgacaacat gccaaagatc ttccatgttc  10980
ctgatctggc ccgtgagatc gttttccctt tttccgctta gcttggtgaa cctcctcttt  11040
accttcccta aagccgcctg tgggtagaca atcaacgtaa ggaagtgttc attgcggagg  11100
agttggccgg agagcacgcg ctgttcaaaa gcttcgttca ggctagcggc gaaaacacta  11160
cggaagtgtc gcggcgccga tgatggcacg tcggcatgac gtacgaggtg agcatatatt  11220
gacacatgat catcagcgat attgcgcaac agcgtgttga acgcacgaca acgcgcattg  11280
cgcatttcag tttcctcaag ctcgaatgca acgccatcaa ttctcgcaat ggtcatgatc  11340
gatccgtctt caagaaggac gatatggtcg ctgaggtggc caatataagg gagatagatc  11400
```

```
tcaccggatc tttcggtcgt tccactcgcg ccgagcatca caccattcct ctccctcgtg   11460
ggggaaccct aattggattt gggctaacag tagcgccccc ccaaactgca ctatcaatgc   11520
ttcttcccgc ggtccgcaaa aatagcagga cgacgctcgc cgcattgtag tctcgctcca   11580
cgatgagccg ggctgcaaac cataacggca cgagaacgac ttcgtagagc gggttctgaa   11640
cgataacgat gacaaagccg gcgaacatca tgaataaccc tgccaatgtc agtggcaccc   11700
caagaaacaa tgcgggccgt gtggctgcga ggtaaagggt cgattcttcc aaacgatcag   11760
ccatcaacta ccgccagtga gcgtttggcc gaggaagctc gccccaaaca tgataacaat   11820
gccgccgacg acgccggcaa ccagcccaag cgaagcccgc ccgaacatcc aggagatccc   11880
gatagcgaca atgccgagaa cagcgagtga ctggccgaac ggaccaagga taaacgtgca   11940
tatattgtta accattgtgg cggggtcagt gccgccaccc gcagattgcg ctgcggcggg   12000
tccggatgag gaaatgctcc atgcaattgc accgcacaag cttggggcgc agctcgatat   12060
cacgcgcatc atcgcattcg agagcgagag gcgatttaga tgtaaacggt atctctcaaa   12120
gcatcgcatc aatgcgcacc tccttagtat aagtcgaata agacttgatt gtcgtctgcg   12180
gatttgccgt tgtcctggtg tggcggtggc ggagcgatta aaccgccagc gccatcctcc   12240
tgcgagcggc gctgatatga cccccaaaca tcccacgtct cttcggattt tagcgcctcg   12300
tgatcgtctt ttggaggctc gattaacgcg ggcaccagcg attgagcagc tgtttcaact   12360
tttcgcacgt agccgtttgc aaaaccgccg atgaaattac cggtgttgta agcggagatc   12420
gcccgacgaa gcgcaaattg cttctcgtca atcgtttcgc cgcctgcata acgacttttc   12480
agcatgtttg cagcggcaga taatgatgtg cacgcctgga gcgcaccgtc aggtgtcaga   12540
ccgagcatag aaaaatttcg agagtttatt tgcatgaggc caacatccag cgaatgccgt   12600
gcatcgagac ggtgcctgac gacttgggtt gcttggctgt gatcttgcca gtgaagcgtt   12660
tcgccggtcg tgttgtcatg aatcgctaaa ggatcaaagc gactctccac cttagctatc   12720
gccgcaagcg tagatgtcgc aactgatggg gcacacttgc gagcaacatg gtcaaactca   12780
gcagatgaga gtggcgtggc aaggctcgac gaacagaagg agaccatcaa ggcaagagaa   12840
agcgaccccg atctcttaag cataccttat ctccttagct cgcaactaac accgcctctc   12900
ccgttggaag aagtgcgttg ttttatgttg aagattatcg ggagggtcgg ttactcgaaa   12960
attttcaatt gcttctttat gatttcaatt gaagcgagaa acctcgcccg gcgtcttgga   13020
acgcaacatg gaccgagaac cgcgcatcca tgactaagca accggatcga cctattcagg   13080
ccgcagttgg tcaggtcagg ctcagaacga aaatgctcgg cgaggttacg ctgtctgtaa   13140
acccattcga tgaacgggaa gcttccttcc gattgctctt ggcaggaata ttggcccatg   13200
cctgcttgcg ctttgcaaat gctcttatcg cgttggtatc atatgccttg tccgccagca   13260
gaaacgcact ctaagcgatt atttgtaaaa atgtttcggt catgcggcgg tcatgggctt   13320
gacccgctgt cagcgcaaga cggatcggtc aaccgtcggc atcgacaaca gcgtgaatct   13380
tggtggtcaa accgccacgg gaacgtccca tacagccatc gtcttgatcc cgctgtttcc   13440
cgtcgccgca tgttggtgga cgcggacaca ggaactgtca atcatgacga cattctatcg   13500
aaagccttgg aaatcacact cagaatatga tcccagacgt ctgcctcacg ccatcgtaca   13560
aagcgattgt agcaggttgt acaggaaccg tatcgatcag gaacgtctgc ccagggcggg   13620
cccgtccgga agcgccacaa gatgacattg atcacccgcg tcaacgcgcg gcacgcgacg   13680
cggcttattt gggaacaaag gactgaacaa cagtccattc gaaatcggtg acatcaaagc   13740
ggggacgggt tatcagtggc ctccaagtca agcctcaatg aatcaaaatc agaccgattt   13800
```

```
gcaaacctga tttatgagtg tgcggcctaa atgatgaaat cgtccttcta gatcgcctcc   13860
gtggtgtagc aacacctcgc agtatcgccg tgctgacctt ggccagggaa ttgactggca   13920
agggtgcttt cacatgaccg ctcttttggc cgcgatagat gatttcgttg ctgctttggg   13980
cacgtagaag gagagaagtc atatcggaga aattcctcct ggcgcgagag cctgctctat   14040
cgcgacggca tcccactgtc gggaacagac cggatcattc acgaggcgaa agtcgtcaac   14100
acatgcgtta taggcatctt cccttgaagg atgatcttgt tgctgccaat ctggaggtgc   14160
ggcagccgca ggcagatgcg atctcagcgc aacttgcggc aaaacatctc actcacctga   14220
aaaccactag cgagtctcgc gatcagacga aggccttta cttaacgaca caatatccga   14280
tgtctgcatc acaggcgtcg ctatcccagt caatactaaa gcggtgcagg aactaaagat   14340
tactgatgac ttaggcgtgc cacgaggcct gagacgacgc gcgtagacag tttttgaaa   14400 tcattatcaa agtgatggcc tccgctgaag cctatcacct ctgcgccggt ctgtcggaga   14460
gatgggcaag cattattacg gtcttcgcgc ccgtacatgc attggacgat tgcagggtca   14520
atggatctga gatcatccag aggattgccg cccttacctt ccgtttcgag ttggagccag   14580
cccctaaatg agacgacata gtcgacttga tgtgacaatg ccaagagaga gatttgctta   14640
acccgatttt tttgctcaag cgtaagccta ttgaagcttg ccggcatgac gtccgcgccg   14700
aaagaatatc ctacaagtaa aacattctgc acaccgaaat gcttggtgta gacatcgatt   14760
atgtgaccaa gatccttagc agtttcgctt ggggaccgct ccgaccagaa ataccgaagt   14820
gaactgacgc caatgacagg aatcccttcc gtctgcagat aggtaccatc gatagatctg   14880
ctgcctcgcg cgtttcggtg atgacggtga aaacctctga cacatgcagc tcccggagac   14940
ggtcacagct tgtctgtaag cggatgccgg gagcagacaa gcccgtcagg gcgcgtcagc   15000
gggtgttggc gggtgtcggg gcgcagccat gacccagtca cgtagcgata gcggagtgta   15060
tactggctta actatgcggc atcagagcag attgtactga gagtgcacca tatgcggtgt   15120
gaaataccgc acagatgcgt aaggagaaaa taccgcatca ggcgctcttc cgcttcctcg   15180
ctcactgact cgctgcgctc ggtcgttcgg ctgcggcgag cggtatcagc tcactcaaag   15240
gcggtaatac ggttatccac agaatcaggg gataacgcag gaaagaacat gtgagcaaaa   15300
ggccagcaaa aggccaggaa ccgtaaaaag gccgcgttgc tggcgttttt ccataggctc   15360
cgcccccctg acgagcatca caaaaatcga cgctcaagtc agaggtggcg aaacccgaca   15420
ggactataaa gataccaggc gtttccccct ggaagctccc tcgtgcgctc tcctgttccg   15480
accctgccgc ttaccggata cctgtccgcc tttctccctt cgggaagcgt ggcgctttct   15540
catagctcac gctgtaggta tctcagttcg gtgtaggtcg ttcgctccaa gctgggctgt   15600
gtgcacgaac cccccgttca gcccgaccgc tgcgccttat ccggtaacta tcgtcttgag   15660
tccaacccgg taagacacga cttatcgcca ctggcagcag ccactggtaa caggattagc   15720
agagcgaggt atgtaggcgg tgctacagag ttcttgaagt ggtggcctaa ctacggctac   15780
actagaagga cagtatttgg tatctgcgct ctgctgaagc cagttacctt cggaaaaaga   15840
gttggtagct cttgatccgg caaacaaacc accgctggta gcggtggttt ttttgtttgc   15900
aagcagcaga ttacgcgcag aaaaaaagga tctcaagaag atcctttgat cttttctacg   15960
gggtctgacg ctcagtggaa cgaaaactca cgttaaggga ttttggtcat gagattatca   16020
aaaaggatct tcacctagat ccttttaaat taaaaatgaa gttttaaatc aatctaaagt   16080
atatatgagt aaacttggtc tgacagttac caatgcttaa tcagtgaggc acctatctca   16140
gcgatctgtc tatttcgttc atccatagtt gcctgactcc ccgtcgtgta gataactacg   16200
```

```
atacgggagg gcttaccatc tggcccagt gctgcaatga taccgcgaga cccacgctca   16260
ccggctccag atttatcagc aataaaccag ccagccggaa gggccgagcg cagaagtggt   16320
cctgcaactt tatccgcctc catccagtct attaattgtt gccgggaagc tagagtaagt   16380
agttcgccag ttaatagttt gcgcaacgtt gttgccattg ctgcaggggg gggggggggg   16440
gggttccatt gttcattcca cggacaaaaa cagagaaagg aaacgacaga ggccaaaaag   16500
ctcgctttca gcacctgtcg tttcctttct tttcagaggg tattttaaat aaaaacatta   16560
agttatgacg aagaagaacg gaaacgcctt aaaccggaaa attttcataa atagcgaaaa   16620
cccgcgaggt ccctgtcgga tcaccggaaa ggacccgtaa agtgataatg attatcatct   16680
acatatcaca acgtgcgtgg aggccatcaa accacgtcaa ataatcaatt atgacgcagg   16740
tatcgtatta attgatctgc atcaacttaa cgtaaaaaca acttcagaca atacaaatca   16800
gcgacactga atacggggca acctcatgtc ccccccccc cccccctgc aggcatcgtg    16860 gtgtcacgct cgtcgtttgg tatggcttca ttcagctccg gttcccaacg atcaaggcga   16920
gttacatgat cccccatgtt gtgcaaaaaa gcggttagct ccttcggtcc tccgatcgtt   16980
gtcagaagta agttggccgc agtgttatca ctcatggtta tggcagcact gcataattct   17040
cttactgtca tgccatccgt aagatgcttt tctgtgactg gtgagtactc aaccaagtca   17100
ttctgagaat agtgtatgcg gcgaccgagt tgctcttgcc cggcgtcaac acgggataat   17160
accgcgccac atagcagaac tttaaaagtg ctcatcattg gaaaacgttc ttcggggcga   17220
aaactctcaa ggatcttacc gctgttgaga tccagttcga tgtaacccac tcgtgcaccc   17280
aactgatctt cagcatcttt tactttcacc agcgtttctg ggtgagcaaa aacaggaagg   17340
caaaatgccg caaaaaaggg aataagggcg acacggaaat gttgaatact catactcttc   17400
ctttttcaat attattgaag catttatcag ggttattgtc tcatgagcgg atacatattt   17460
gaatgtattt agaaaaataa acaaataggg gttccgcgca catttccccg aaaagtgcca   17520
cctgacgtct aagaaaccat tattatcatg acattaacct ataaaaatag gcgtatcacg   17580
aggccctttc gtcttcaaga attggtcgac gatcttgctg cgttcggata ttttcgtgga   17640
gttcccgcca cagacccgga ttgaaggcga gatccagcaa ctcgcgccag atcatcctgt   17700
gacgaacctt ggcgcgtga tgactggcca ggacgtcggc cgaaagagcg acaagcagat    17760
cacgcttttc gacagcgtcg gatttgcgat cgaggatttt tcggcgctgc gctacgtccg   17820
cgaccgcgtt gagggatcaa gccacagcag cccactcgac cttctagccg acccagacga   17880
gccaagggat cttttttggaa tgctgctccg tcgtcaggct ttccgacgtt tgggtggttg   17940
aacagaagtc attatcgtac ggaatgccaa gcactcccga ggggaaccct gtggttggca   18000
tgcacataca aatggacgaa cggataaacc ttttcacgcc cttttaaata tccgttattc   18060
taataaacgc tcttttctct taggtttacc cgccaatata tcctgtcaaa cactgatagt   18120
ttaaactgaa ggcgggaaac gacaatctga tcatgagcgg agaattaagg gagtcacgtt   18180
atgacccccg ccgatgacgc gggacaagcc gttttacgtt tggaactgac agaaccgcaa   18240
cgttgaagga gccactcagc aagctggtac gattgtaata cgactcacta tagggcgaat   18300
tgagcgctgt ttaaacgctc ttcaactgga agagcggtta ccagagctgg tcacctttgt   18360
ccaccaagat ggaactgcgg ccgctcatta attaagtcag gcgcgcctct agttgaagac   18420
acgttcatgt cttcatcgta agaagacact cagtagtctt cggccagaat ggccatctgg   18480
attcagcagg cctagaaggc catttaaatc ctgaggatct ggtcttccta aggacccggg   18540
atatcgctat caactttgta tagaaaagtt gggccgaatt cgcccttgtt taaacttaat   18600
```

```
atttgtttaa acttttttact aaattcatgt aataattaat gtatgcgtta tatatatatg  18660
tctaggttta taattattca tatgaatatg aacataaaaa tctagggcta aaacgactac  18720
tattttgaaa acggaaggag tagtaagtta tttaagcgga ggggaaccat gatgggctag  18780
tgatttaatt tacatatata tattggtgtt ctgggctctt acatgagaag atctagttaa  18840
ctgttgttac tgaacagcga agacaaatat ataatttaag ctccccaact gctagtgatt  18900
ctgttaagag gtaatgttta aagtaaattt acaagagccc gtctagctca gtcggtagag  18960
cgcaaggctc ttaaccttgt ggtcgtgggt tcgagcccca cggtgggcgc acaatttttt  19020
gtttttttgac atttttttgtt tgcttagttg cagacggttt ttcccctgct aggagatttc  19080
cgagagaaaa aaaaggcact acaggttaac caaaaccacc aacctttgga gcgtcgaggc  19140
gacgggcat ttgcgtagtt gaagcttaca aagttgcata tgagatgagt gccggacatg  19200
aagcggataa cgttttaaac tggcaacaat atctagctgt ttcaaattca ggcgtgggaa  19260
gctacgccta cgcgccctgg acggcgtgta aagagccagc atcggcatca ttgtcaaacg  19320
atcgacaagg ccaagaaatt ccaaatatat tattaataaa aaagaaggca ccaaattagt  19380
ttttgttttt tagtatgtgt ggcggaggaa attttgagaa cgaacgtatc caagaaggc  19440
acaagacgat atagattgac gcggctagaa agttgcagca agacagtggg tacggtctta  19500
tatatcctaa taaataaaaa ataaaactat agtgtgtcaa atgtcaacaa gaggaggagg  19560
cagccaaatt agcagaggga gacaagtaga gcacgcctta ttagcttgct tatttatcgt  19620
ggtggtgtac ttgttaatta ctggcacgca ttatcaacaa cgcagttctg gatgtgaatc  19680
tagacaaaca tttgtctagg ttccgcacgt atagttttttt ttctttttttt ttgggggggg  19740
gggggaacgg aagctgtaat aaacggtact aggaacgaaa gcaaccgccg cgcgcatgtt  19800
tttgcaatag attacggtga ccttgatgca ccaccgcgtg ctataaaaac cagtgtcccc  19860
gagtctactc atcaaccaat ccataactcg aaacctttttc ttgtgctctg ttctgtctgt  19920
gtgtttccaa agcaagcgaa agaggtcgag gggatcagct tcaagtttgt acaaaaaagc  19980
aggctccgcg gccgcccccct tcaccatgac gatggctcgt cctggggcgg ctttgccgct  20040
gctgctggtc gtggtcggcg cttgctgcgc gcgcctggcg gcggcagtgc acctctccgc  20100
gctcggcagg acactcatcg tcgaggcgtc gccgaaggcc ggacaagtcc tgcacgccgg  20160
cgaggacacg ataaccgtga catggcacct caacgcgtcg gcgtccagcg tcgggtacaa  20220
ggcgctggag gtgaccctct gctacgcgcc ggcgagccag gaggaccgcg ggtggcgcaa  20280
ggccaacgac gacttgagca aggacaaggc gtgccagttc aggatcgccc ggcatgcata  20340
cgccggcggc caggggacgc tccggtacag ggtcgcccgc gacgtcccca ccgcgtccta  20400
ccacgtgcgc gcctacgcgc tggacgcgtc cggggcgccg gtgggctacg gccagaccgc  20460
gcccgcctac tacttccacg tcgcgggcgt ctcgggcgtc cacgcgtccc tccgggtcgc  20520
cgccgccgtg ctctccgcgt tctccatcgc cgcgctcgcc ttctttgtcg tcgtcgagaa  20580
gaggaggaag gacgagtaga agggtgggcg cgccgaccca gctttcttgt acaaagtggc  20640
cgttaacgga tccagacttg tccatcttct ggattggcca acttaattaa tgtatgaaat  20700
aaaaggatgc acacatagtg acatgctaat cactataatg tgggcatcaa agttgtgtgt  20760
tatgtgtaat tactagttat ctgaataaaa gagaaagaga tcatccatat ttcttatcct  20820
aaatgaatgt cacgtgtctt tataattctt tgatgaacca gatgcatttc attaaccaaa  20880
tccatataca tataaatatt aatcatatat aattaatatc aattgggtta gcaaaacaaa  20940
tctagtctag gtgtgttttg cgaattgcgg caagcttgcg gccgccccgg gcaactttat  21000
```

```
tatacaaagt tgatagatat cggaccgatt aaactttaat tcggtccgaa gcttgcatgc    21060
ctgcagtgca gcgtgacccg gtcgtgcccc tctctagaga taatgagcat tgcatgtcta    21120
agttataaaa aattaccaca tattttttt gtcacacttg tttgaagtgc agtttatcta     21180
tctttataca tatatttaaa ctttactcta cgaataatat aatctatagt actacaataa    21240
tatcagtgtt ttagagaatc atataaatga acagttagac atggtctaaa ggacaattga    21300
gtattttgac aacaggactc tacagtttta tcttttagt gtgcatgtgt tctccttttt     21360
ttttgcaaat agcttcacct atataatact tcatccattt tattagtaca tccatttagg    21420
gtttagggtt aatggttttt atagactaat ttttagta catctatttt attctatttt      21480
agcctctaaa ttaagaaaac taaaactcta ttttagtttt tttatttaat aatttagata    21540
taaaatagaa taaaataaag tgactaaaaa ttaaacaaat acccctttaag aaattaaaaa   21600 aactaaggaa acattttct tgtttcgagt agataatgcc agcctgttaa acgccgtcga     21660
cgagtctaac ggacaccaac cagcgaacca gcagcgtcgc gtcgggccaa gcgaagcaga    21720
cggcacggca tctctgtcgc tgcctctgga cccctctcga gagttccgct ccaccgttgg    21780
acttgctccg ctgtcggcat ccagaaattg cgtggcggag cggcagacgt gagccggcac    21840
ggcaggcggc ctcctcctcc tctcacggca ccggcagcta cgggggattc ctttcccacc    21900
gctccttcgc tttcccttcc tcgcccgccg taataaatag acacccctc cacaccctct     21960 ttccccaacc tcgtgttgtt cggagcgcac acacacacaa ccagatctcc cccaaatcca    22020
cccgtcggca cctccgcttc aaggtacgcc gctcgtcctc cccccccccc ctctctacct    22080
tctctagatc ggcgttccgg tccatgcatg gttagggccc ggtagttcta cttctgttca    22140
tgtttgtgtt agatccgtgt ttgtgttaga tccgtgctgc tagcgttcgt acacggatgc    22200
gacctgtacg tcagacacgt tctgattgct aacttgccag tgtttctctt tggggaatcc    22260
tgggatggct ctagccgttc cgcagacggg atcgatttca tgatttttt tgtttcgttg     22320 catagggttt ggtttgccct tttcctttat ttcaatatat gccgtgcact tgtttgtcgg    22380
gtcatctttt catgcttttt tttgtcttgg ttgtgatgat gtggtctggt tgggcggtcg    22440
ttctagatcg gagtagaatt ctgtttcaaa ctacctggtg gatttattaa ttttggatct    22500
gtatgtgtgt gccatacata ttcatagtta cgaattgaag atgatggatg gaaatatcga    22560
tctaggatag gtatacatgt tgatgcgggt tttactgatg catatacaga gatgcttttt    22620
gttcgcttgg ttgtgatgat gtggtgtggt tgggcggtcg ttcattcgtt ctagatcgga    22680
gtagaatact gtttcaaact acctggtgta tttattaatt ttggaactgt atgtgtgtgt    22740
catacatctt catagttacg agtttaagat ggatggaaat atcgatctag gataggtata    22800
catgttgatg tgggttttac tgatgcatat acatgatggc atatgcagca tctattcata    22860
tgctctaacc ttgagtacct atctattata ataaacaagt atgttttata attattttga    22920
tcttgatata cttggatgat ggcatatgca gcagctatat gtggattttt ttagccctgc    22980
cttcatacgc tatttatttg cttggtactg tttctttgt cgatgctcac cctgttgttt     23040
ggtgttactt ctgcaggtcg actttaactt agcctaggat ccacacgaca ccatgtcccc    23100
cgagcgccgc cccgtcgaga tccgcccggc caccgccgcc gacatggccg ccgtgtgcga    23160
catcgtgaac cactacatcg agacctccac cgtgaacttc cgcaccgagc cgcagacccc    23220
gcaggagtgg atcgacgacc tggagcgcct ccaggaccgc tacccgtggc tcgtggccga    23280
ggtggagggc gtggtggccg gcatcgccta cgccggcccg tggaaggccc gcaacgccta    23340
cgactggacc gtggagtcca ccgtgtacgt gtcccaccgc caccagcgcc tcggcctcgg    23400
```

```
ctccaccctc tacacccacc tcctcaagag catggaggcc cagggcttca agtccgtggt   23460
ggccgtgatc ggcctcccga acgacccgtc cgtgcgcctc cacgaggccc tcggctacac   23520
cgcccgcggc accctccgcg ccgccggcta caagcacggc ggctggcacg acgtcggctt   23580
ctggcagcgc gacttcgagc tgccggcccc gccgcgcccg gtgcgcccgg tgacgcagat   23640
ctgagtcgaa acctagactt gtccatcttc tggattggcc aacttaatta atgtatgaaa   23700
taaaaggatg cacacatagt gacatgctaa tcactataat gtgggcatca aagttgtgtg   23760
ttatgtgtaa ttactagtta tctgaataaa agagaaagag atcatccata tttcttatcc   23820
taaatgaatg tcacgtgtct ttataattct ttgatgaacc agatgcattt cattaaccaa   23880
atccatatac atataaatat taatcatata taattaatat caattgggtt agcaaaacaa   23940
atctagtcta ggtgtgtttt gcgaatgcgg ccgccaccgc ggtggagctc gaattcattc   24000
cgattaatcg tggcctcttg ctcttcagga tgaagagcta tgtttaaacg tgcaagcgct   24060
actagacaat tcagtacatt aaaaacgtcc gcaatgtgtt attaagttgt ctaagcgtca   24120
atttgtttac accacaatat atcctgccac cagccagcca acagctcccc gaccggcagc   24180
tcggcacaaa atcaccactc gatacaggca gcccatcagt ccgggacggc gtcagcggga   24240
gagccgttgt aaggcggcag actttgctca tgttaccgat gctattcgga agaacggcaa   24300
ctaagctgcc gggtttgaaa cacgatgat ctcgcgagg gtagcatgtt gattgtaacg   24360
atgacagagc gttgctgcct gtgatcaaat atcatctccc tcgcagagat ccgaattatc   24420
agccttctta ttcatttctc gcttaaccgt gacaggctgt cgatcttgag aactatgccg   24480
acataatagg aaatcgctgg ataaagccgc tgaggaagct gagtggcgct atttctttag   24540
aagtgaacgt tgacgatcgt cgaccgtacc ccgatgaatt aattcggacg tacgttctga   24600
acacagctgg atacttactt gggcgattgt catacatgac atcaacaatg tacccgtttg   24660
tgtaaccgtc tcttggaggt tcgtatgaca ctagtggttc ccctcagctt gcgactagat   24720
gttgaggcct aacattttat tagagagcag gctagttgct tagatacatg atcttcaggc   24780
cgttatctgt cagggcaagc gaaaattggc catttatgac gaccaatgcc ccgcagaagc   24840
tcccatcttt gccgccatag acgccgcgcc cccctttgg ggtgtagaac atccttttgc   24900
cagatgtgga aaagaagttc gttgtcccat tgttggcaat gacgtagtag ccggcgaaag   24960
tgcgagaccc atttgcgcta tatataagcc tacgatttcc gttgcgacta ttgtcgtaat   25020
tggatgaact attatcgtag ttgctctcag agttgtcgta atttgatgga ctattgtcgt   25080
aattgcttat ggagttgtcg tagttgcttg gagaaatgtc gtagttggat ggggagtagt   25140
catagggaag acgagcttca tccactaaaa caattggcag gtcagcaagt gcctgccccg   25200
atgccatcgc aagtacgagg cttagaacca ccttcaacag atcgcgcata gtcttcccca   25260
gctctctaac gcttgagtta agccgcgccg cgaagcggcg tcggcttgaa cgaattgtta   25320
gacattattt gccgactacc ttggtgatct cgcctttcac gtagtgaaca aattcttcca   25380
actgatctgc gcgcgaggcc aagcgatctt cttgtccaag ataagcctgc ctagcttcaa   25440
gtatgacggg ctgatactgg gccggcaggc gctccattgc ccagtcggca gcgacatcct   25500
tcggcgcgat tttgccggtt actgcgctgt accaaatgcg ggacaacgta agcactacat   25560
ttcgctcatc gccagcccag tcgggcggcg agttccatag cgttaaggtt tcatttagcg   25620
cctcaaatag atcctgttca ggaaccggat caaagagttc ctccgccgct ggacctacca   25680
aggcaacgct atgttctctt gcttttgtca gcaagatagc cagatcaatg tcgatcgtgg   25740
ctggctcgaa gatacctgca agaatgtcat tgcgctgcca ttctccaaat tgcagttcgc   25800
```

```
gcttagctgg ataacgccac ggaatgatgt cgtcgtgcac aacaatggtg acttctacag    25860
cgcggagaat ctcgctctct ccaggggaag ccgaagtttc caaaaggtcg ttgatcaaag    25920
ctcgccgcgt tgtttcatca agccttacag tcaccgtaac cagcaaatca atatcactgt    25980
gtggcttcag gccgccatcc actgcggagc cgtacaaatg tacggccagc aacgtcggtt    26040
cgagatggcg ctcgatgacg ccaactacct ctgatagttg agtcgatact tcggcgatca    26100
ccgcttccct catgatgttt aactcctgaa ttaagccgcg ccgcgaagcg gtgtcggctt    26160
gaatgaattg ttaggcgtca tcctgtgctc ccgagaacca gtaccagtac atcgctgttt    26220
cgttcgagac ttgaggtcta gttttatacg tgaacaggtc aatgccgccg agagtaaagc    26280
cacattttgc gtacaaattg caggcaggta cattgttcgt ttgtgtctct aatcgtatgc    26340
caaggagctg tctgcttagt gcccactttt tcgcaaattc gatgagactg tgcgcgactc    26400
ctttgcctcg gtgcgtgtgc gacacaacaa tgtgttcgat agaggctaga tcgttccatg    26460
ttgagttgag ttcaatcttc ccgacaagct cttggtcgat gaatgcgcca tagcaagcag    26520
agtcttcatc agagtcatca tccgagatgt aatccttccg gtaggggctc acacttctgg    26580
tagatagttc aaagccttgg tcggataggt gcacatcgaa cacttcacga acaatgaaat    26640
ggttctcagc atccaatgtt tccgccacct gctcagggat caccgaaaatc ttcatatgac    26700 gcctaacgcc tggcacagcg gatcgcaaac ctggcgcggc ttttggcaca aaaggcgtga    26760
caggtttgcg aatccgttgc tgccacttgt taaccctttt gccagatttg gtaactataa    26820
tttatgttag aggcgaagtc ttgggtaaaa actggcctaa aattgctggg gatttcagga    26880
aagtaaacat caccttccgg ctcgatgtct attgtagata tatgtagtgt atctacttga    26940
tcgggggatc tgctgcctcg cgcgtttcgg tgatgacggt gaaaacctct gacacatgca    27000
gctcccggag acggtcacag cttgtctgta agcggatgcc gggagcagac aagcccgtca    27060
gggcgcgtca gcgggtgttg gcgggtgtcg ggcgcagcc atgacccagt cacgtagcga    27120
tagcggagtg tatactggct taactatgcg gcatcagagc agattgtact gagagtgcac    27180
catatgcggt gtgaaatacc gcacagatgc gtaaggagaa aataccgcat caggcgctct    27240
tccgcttcct cgctcactga ctcgctgcgc tcggtcgttc ggctgcggcg agcggtatca    27300
gctcactcaa aggcggtaat acggttatcc acagaatcag gggataacgc aggaaagaac    27360
atgtgagcaa aaggccagca aaaggccagg aaccgtaaaa aggccgcgtt gctggcgttt    27420
ttccataggc tccgcccccc tgacgagcat cacaaaaatc gacgctcaag tcagaggtgg    27480
cgaaacccga caggactata agataccag gcgtttcccc ctggaagctc cctcgtgcgc    27540
tctcctgttc cgaccctgcc gcttaccgga tacctgtccg cctttctccc ttcgggaagc    27600
gtggcgcttt ctcatagctc acgctgtagg tatctcagtt cggtgtaggt cgttcgctcc    27660
aagctgggct gtgtgcacga accccccgtt cagcccgacc gctgcgcctt atccggtaac    27720
tatcgtcttg agtccaaccc ggtaagacac gacttatcgc cactggcagc agccactggt    27780
aacaggatta gcagagcgag gtatgtaggc ggtgctacag agttcttgaa gtggtggcct    27840
aactacggct acactagaag gacagtattt ggtatctgcg ctctgctgaa gccagttacc    27900
ttcggaaaaa gagttggtag ctcttgatcc ggcaaacaaa ccaccgctgg tagcggtggt    27960 tttttgttt gcaagcagca gattacgcgc agaaaaaaag gatctcaaga atcctttg    28020 atcttttcta cggggtctga cgctcagtgg aacgaaaact cacgttaagg gattttggtc    28080
atgagattat caaaaaggat cttcacctag atccttttaa attaaaaatg aagttttaaa    28140
tcaatctaaa gtatatatga gtaaacttgg tctgacagtt accaatgctt aatcagtgag    28200
```

```
gcacctatct cagcgatctg tctatttcgt tcatccatag ttgcctgact ccccgtcgtg  28260
tagataacta cgatacggga gggcttacca tctggcccca gtgctgcaat gataccgcga  28320
gacccacgct caccggctcc agatttatca gcaataaacc agccagccgg aagggccgag  28380
cgcagaagtg gtcctgcaac tttatccgcc tccatccagt ctattaattg ttgccgggaa  28440
gctagagtaa gtagttcgcc agttaatagt ttgcgcaacg ttgttgccat tgctgcaggg  28500
gggggggggg gggggactt ccattgttca ttccacggac aaaaacagag aaaggaaacg  28560
acagaggcca aaaagcctcg ctttcagcac ctgtcgtttc ctttcttttc agagggtatt  28620
ttaaataaaa acattaagtt atgacgaaga agaacggaaa cgccttaaac cggaaaattt  28680
tcataaatag cgaaaacccg cgaggtcgcc gccccgtaag ccgccccgta acctgtcgga  28740
tcaccggaaa ggacccgtaa agtgataatg attatcatct acatatcaca acgtgcgtgg  28800
aggccatcaa accacgtcaa ataatcaatt atgacgcagg tatcgtatta attgatctgc  28860
atcaacttaa cgtaaaaaca acttcagaca atacaaatca gcgacactga atacggggca  28920
acctcatgtc ccccccccc ccccccctgc aggcatcgtg gtgtcacgct cgtcgtttgg  28980
tatggcttca ttcagctccg gttcccaacg atcaaggcga gttacatgat cccccatgtt  29040
gtgcaaaaaa gcggttagct ccttcggtcc tccgatcgtt gtcagaagta agttggccgc  29100
agtgttatca ctcatggtta tggcagcact gcataattct cttactgtca tgccatccgt  29160
aagatgcttt tctgtgactg gtgagtactc aaccaagtca ttctgagaat agtgtatgcg  29220
gcgaccgagt tgctcttgcc cggcgtcaac acgggataat accgcgccac atagcagaac  29280
tttaaaagtg ctcatcattg gaaaacgttc ttcggggcga aaactctcaa ggatcttacc  29340
gctgttgaga tccagttcga tgtaacccac tcgtgcaccc aactgatctt cagcatcttt  29400
tactttcacc agcgtttctg ggtgagcaaa aacaggaagg caaaatgccg caaaaaaggg  29460
aataagggcg acacggaaat gttgaatact catactcttc cttttcaat attattgaag  29520 catttatcag ggttattgtc tcatgagcgg atacatattt gaatgtattt agaaaaataa  29580
acaaataggg gttccgcgca catttccccg aaaagtgcca cctgacgtct aagaaaccat  29640
tattatcatg acattaacct ataaaaatag gcgtatcacg aggcccttc gtcttcaaga  29700 attcggagct tttgccattc tcaccggatt cagtcgtcac tcatggtgat ttctcacttg  29760
ataaccttat ttttgacgag gggaaattaa taggttgtat tgatgttgga cgagtcggaa  29820
tcgcagaccg ataccaggat cttgccatcc tatggaactg cctcggtgag ttttctcctt  29880
cattacagaa acggcttttt caaaaatatg gtattgataa tcctgatatg aataaattgc  29940
agtttcattt gatgctcgat gagttttct aatcagaatt ggttaattgg ttgtaacact  30000
ggcagagcat tacgctgact tgacgggacg gcggctttgt tgaataaatc gaacttttgc  30060
tgagttgaag gatcagatca cgcatcttcc cgacaacgca gaccgttccg tggcaaagca  30120
aaagttcaaa atcaccaact ggtccaccta caacaaagct ctcatcaacc gtggctccct  30180
cactttctgg ctggatgatg gggcgattca ggcctggtat gagtcagcaa caccttcttc  30240
acgaggcaga cctcagcgcc agaaggccgc agagaggcc gagcgcggcc gtgaggcttg  30300
gacgctaggg cagggcatga aaagcccgt agcgggctgc tacgggcgtc tgacgcggtg  30360 gaaagggga ggggatgttg tctacatggc tctgctgtag tgagtgggtt gcgctccggc  30420
agcggtcctg atcaatcgtc acccttcctc ggtccttcaa cgttcctgac aacgagcctc  30480
cttttcgcca atccatcgac aatcaccgcg agtccctgct cgaacgctgc gtccggaccg  30540
gcttcgtcga aggcgtctat cgcggcccgc aacagcggcg agagcggagc ctgttcaacg  30600
```

```
gtgccgccgc gctcgccggc atcgctgtcg ccggcctgct cctcaagcac ggccccaaca    30660
gtgaagtagc tgattgtcat cagcgcattg acggcgtccc cggccgaaaa acccgcctcg    30720
cagaggaagc gaagctgcgc gtcggccgtt tccatctgcg gtgcgcccgg tcgcgtgccg    30780
gcatggatgc gcgcgccatc gcggtaggcg agcagcgcct gcctgaagct gcgggcattc    30840
ccgatcagaa atgagcgcca gtcgtcgtcg gctctcggca ccgaatgcgt atgattctcc    30900
gccagcatgg cttcggccag tgcgtcgagc agcgcccgct tgttcctgaa gtgccagtaa    30960
agcgccggct gctgaacccc caaccgttcc gccagtttgc gtgtcgtcag accgtctacg    31020
ccgacctcgt tcaacaggtc cagggcggca cggatcactg tattcggctg caactttgtc    31080
atgcttgaca ctttatcact gataaacata atatgtccac caacttatca gtgataaaga    31140
atccgcgcgt tcaatcggac cagcggaggc tggtccggag gccagacgtg aaacccaaca    31200 taccctgat cgtaattctg agcactgtcg cgctcgacgc tgtcggcatc ggcctgatta    31260
tgccggtgct gccgggcctc ctgcgcgatc tggttcactc gaacgacgtc accgcccact    31320
atggcattct gctggcgctg tatgcgttgg tgcaatttgc ctgcgcacct gtgctgggcg    31380
cgctgtcgga tcgtttcggg cggcggccaa tcttgctcgt ctcgctggcc ggcgccactg    31440
tcgactacgc catcatggcg acagcgcctt cctttgggt tctctatatc gggcggatcg    31500
tggccggcat caccggggcg actggggcgg tagccggcgc ttatattgcc gatatcactg    31560
atggcgatga gcgcgcgcgg cacttcggct tcatgagcgc ctgtttcggg ttcgggatgg    31620
tcgcgggacc tgtgctcggt gggctgatgg gcggtttctc cccccacgct ccgttcttcg    31680
ccgcggcagc cttgaacggc ctcaatttcc tgacgggctg tttccttttg ccggagtcgc    31740
acaaaggcga acgccggccg ttacgccggg aggctctcaa cccgctcgct tcgttccggt    31800
gggcccgggg catgaccgtc gtcgccgccc tgatggcggt cttcttcatc atgcaacttg    31860
tcggacaggt gccggccgcg cttttgggtca ttttcggcga ggatcgcttt cactgggacg    31920
cgaccacgat cggcatttcg cttgccgcat ttggcattct gcattcactc gcccaggcaa    31980
tgatcaccgg ccctgtagcc gcccggctcg gcgaaaggcg ggcactcatg ctcggaatga    32040
ttgccgacgg cacaggctac atcctgcttg ccttcgcgac acggggatgg atggcgttcc    32100
cgatcatggt cctgcttgct tcgggtggca tcggaatgcc ggcgctgcaa gcaatgttgt    32160
ccaggcaggt ggatgaggaa cgtcaggggc agctgcaagg ctcactggcg gcgctcacca    32220
gcctgacctc gatcgtcgga cccctcctct tcacggcgat ctatgcgct tctataacaa    32280 cgtggaacgg gtgggcatgg attgcaggcg ctgccctcta cttgctctgc ctgccggcgc    32340
tgcgtcgcgg gctttggagc ggcgcagggc aacgagccga tcgctgatcg tggaaacgat    32400
aggcctatgc catgcgggtc aaggcgactt ccggcaagct atacgcgccc taggagtgcg    32460
gttggaacgt tgcccagcc agatactccc gatcacgagc aggacgccga tgatttgaag    32520
cgcactcagc gtctgatcca agaacaacca tcctagcaac acggcggtcc ccgggctgag    32580
aaagcccagt aaggaaacaa ctgtaggttc gagtcgcgag atcccccgga accaaaggaa    32640
gtaggttaaa cccgctccga tcaggccgag ccacgccagg ccgagaacat tggttcctgt    32700
aggcatcggg attggcggat caaacactaa agctactgga acgagcagaa gtcctccggc    32760
cgccagttgc caggcggtaa aggtgagcag aggcacggga ggttgccact tgcgggtcag    32820
cacggttccg aacgccatgg aaaccgcccc cgccaggccc gctgcgacgc cgacaggatc    32880
tagcgctgcg tttggtgtca acaccaacag cgccacgccc gcagttccgc aaatagcccc    32940
caggaccgcc atcaatcgta tcgggctacc tagcagagcg gcagagatga acacgaccat    33000
```

```
cagcggctgc acagcgccta ccgtcgccgc gaccccgccc ggcaggcggt agaccgaaat   33060
aaacaacaag ctccagaata gcgaaatatt aagtgcgccg aggatgaaga tgcgcatcca   33120
ccagattccc gttggaatct gtcggacgat catcacgagc aataaacccg ccggcaacgc   33180
ccgcagcagc ataccggcga cccctcggcc tcgctgttcg ggctccacga aaacgccgga   33240
cagatgcgcc ttgtgagcgt ccttggggcc gtcctcctgt ttgaagaccg acagcccaat   33300
gatctcgccg tcgatgtagg cgccgaatgc cacggcatct cgcaaccgtt cagcgaacgc   33360
ctccatgggc ttttctcct cgtgctcgta aacggacccg aacatctctg gagctttctt   33420
cagggccgac aatcggatct cgcggaaatc ctgcacgtcg gccgctccaa gccgtcgaat   33480
ctgagcctta atcacaattg tcaattttaa tcctctgttt atcggcagtt cgtagagcgc   33540
gccgtgcgtc ccgagcgata ctgagcgaag caagtgcgtc gagcagtgcc cgcttgttcc   33600
tgaaatgcca gtaaagcgct ggctgctgaa cccccagccg gaactgaccc cacaaggccc   33660
tagcgtttgc aatgcaccag gtcatcattg acccaggcgt gttccaccag gccgctgcct   33720
cgcaactctt cgcaggcttc gccgacctgc tcgcgccact tcttcacgcg ggtggaatcc   33780
gatccgcaca tgaggcggaa ggtttccagc ttgagcgggg acggctcccg gtgcgagctg   33840
aaatagtcga acatccgtcg ggccgtcggc gacagcttgc ggtacttctc ccatatgaat   33900
ttcgtgtagt ggtcgccagc aaacagcacg acgatttcct cgtcgatcag gacctggcaa   33960
cgggacgttt tcttgccacg gtccaggacg cggaagcggt gcagcagcga caccgattcc   34020
aggtgcccaa cgcggtcgga cgtgaagccc atcgccgtcg cctgtaggcg cgacaggcat   34080
tcctcggcct tcgtgtaata ccggccattg atcgaccagc ccaggtcctg gcaaagctcg   34140
tagaacgtga aggtgatcgg ctcgccgata ggggtgcgct tcgcgtactc caacacctgc   34200
tgccacacca gttcgtcatc gtcggcccgc agctcgacgc cggtgtaggt gatcttcacg   34260
tccttgttga cgtggaaaat gaccttgttt tgcagcgcct cgcgcgggat tttcttgttg   34320
cgcgtggtga acagggcaga gcgggccgtg tcgtttggca tcgctcgcat cgtgtccggc   34380
cacggcgcaa tatcgaacaa ggaaagctgc atttccttga tctgctgctt cgtgtgtttc   34440
agcaacgcgg cctgcttggc ctcgctgacc tgttttgcca ggtcctcgcc ggcggttttt   34500
cgcttcttgg tcgtcatagt tcctcgcgtg tcgatggtca tcgacttcgc caaacctgcc   34560
gcctcctgtt cgagacgacg cgaacgctcc acggcggccg atggcgcggg cagggcaggg   34620
ggagccagtt gcacgctgtc gcgctcgatc ttggccgtag cttgctggac catcgagccg   34680
acggactgga aggtttcgcg gggcgcacgc atgacggtgc ggcttgcgat ggtttcggca   34740
tcctcggcgg aaaaccccgc gtcgatcagt tcttgcctgt atgccttccg gtcaaacgtc   34800
cgattcattc accctccttg cgggattgcc ccgactcacg ccggggcaat gtgcccttat   34860
tcctgatttg acccgcctgg tgccttggtg tccagataat ccaccttatc ggcaatgaag   34920
tcggtcccgt agaccgtctg gccgtccttc tcgtacttgg tattccgaat cttgccctgc   34980
acgaatacca gcgacccctt gcccaaatac ttgccgtggg cctcggcctg agagccaaaa   35040
cacttgatgc ggaagaagtc ggtgcgctcc tgcttgtcgc cggcatcgtt gcgccactct   35100
tcattaaccg ctatatcgaa aattgcttgc ggcttgttag aattgccatg acgtacctcg   35160
gtgtcacggg taagattacc gataaactgg aactgattat ggctcatatc gaaagtctcc   35220
ttgagaaagg agactctagt ttagctaaac attggttccg ctgtcaagaa ctttagcggc   35280
taaaattttg cgggccgcga ccaaaggtgc gaggggcggg ttccgctgtg tacaaccaga   35340 tattttcac caacatcctt cgtctgctcg atgagcgggg catgacgaaa catgagctgt   35400
```

```
cggagagggc aggggtttca atttcgtttt tatcagactt aaccaacggt aaggccaacc    35460
cctcgttgaa ggtgatggag gccattgccg acgccctgga aactcccta cctcttctcc     35520 tggagtccac cgaccttgac cgcgaggcac tcgcggagat tgcgggtcat cctttcaaga    35580
gcagcgtgcc gcccggatac gaacgcatca gtgtggtttt gccgtcacat aaggcgttta    35640
tcgtaaagaa atggggcgac gacacccgaa aaaagctgcg tggaaggctc tgacgccaag    35700
ggttagggct tgcacttcct tctttagccg ctaaaacggc cccttctctg cgggccgtcg    35760
gctcgcgcat catatcgaca tcctcaacgg aagccgtgcc gcgaatggca tcgggcgggt    35820
gcgctttgac agttgttttc tatcagaacc cctacgtcgt gcggttcgat tagctgtttg    35880
tcttgcaggc taaacacttt cggtatatcg tttgcctgtg cgataatgtt gctaatgatt    35940
tgttgcgtag gggttactga aaagtgagcg ggaaagaaga gtttcagacc atcaaggagc    36000
gggccaagcg caagctggaa cgcgacatgg gtgcggacct gttggccgcg ctcaacgacc    36060
cgaaaaccgt tgaagtcatg ctcaacgcgg acggcaaggt gtggcacgaa cgccttggcg    36120
agccgatgcg gtacatctgc gacatgcggc ccagccagtc gcaggcgatt atagaaacgg    36180
tggccggatt ccacggcaaa gaggtcacgc ggcattcgcc catcctggaa ggcgagttcc    36240
ccttggatgg cagccgcttt gccggccaat tgccgccggt cgtggccgcg ccaacctttg    36300
cgatccgcaa gcgcgcggtc gccatcttca cgctggaaca gtacgtcgag gcgggcatca    36360
tgacccgcga gcaatacgag gtcattaaaa gcgccgtcgc ggcgcatcga aacatcctcg    36420
tcattggcgg tactgctcg ggcaagacca cgctcgtcaa cgccgatcatc aatgaaatgg    36480 tcgccttcaa cccgtctgag cgcgtcgtca tcatcgagga caccggcgaa atccagtgcg    36540
ccgcagagaa cgccgtccaa taccacacca gcatcgacgt ctcgatgacg ctgctgctca    36600
agacaacgct gcgtatgcgc cccgaccgca tcctggtcgg tgaggtacgt ggccccgaag    36660
cccttgatct gttgatggcc tggaacaccg ggcatgaagg aggtgccgcc accctgcacg    36720
caaacaaccc caaagcgggc ctgagccggc tcgccatgct tatcagcatg cacccggatt    36780
caccgaaacc cattgagccg ctgattggcg aggcggttca tgtggtcgtc catatcgcca    36840 ggaccctag cggccgtcga gtgcaagaaa ttctcgaagt tcttggttac gagaacggcc     36900
agtacatcac caaaaccctg taaggagtat ttccaatgac aacggctgtt ccgttccgtc    36960
tgaccatgaa tcgcggcatt ttgttctacc ttgccgtgtt cttcgttctc gctctcgcgt    37020
tatccgcgca tccggcgatg gcctcggaag gcaccggcgg cagcttgcca tatgagagct    37080
ggctgacgaa cctgcgcaac tccgtaaccg gcccggtggc cttcgcgctg tccatcatcg    37140
gcatcgtcgt cgccggcggc gtgctgatct tcgcggcga actcaacgcc ttcttccgaa     37200
ccctgatctt cctggttctg gtgatggcgc tgctggtcgg cgcgcagaac gtgatgagca    37260
ccttcttcgg tcgtggtgcc gaaatcgcgc ccctcggcaa cggggcgctg caccaggtgc    37320
aagtcgcggc ggcggatgcc gtgcgtgcgg tagcggctgg acggctcgcc taatcatggc    37380
tctgcgcacg atccccatcc gtcgcgcagg caaccgagaa aacctgttca tgggtggtga    37440
tcgtgaactg gtgatgttct cgggcctgat ggcgtttgcg ctgattttca gcgcccaaga    37500
gctgcgggcc accgtggtcg gtctgatcct gtggttcggg gcgctctatg cgttccgaat    37560
catggcgaag gccgatccga agatgcggtt cgtgtacctg cgtcaccgcc ggtacaagcc    37620
gtattacccg gcccgctcga ccccgttccg cgagaacacc aatagccaag ggaagcaata    37680
ccgatgatca aagcaattgc gattgcaatc gcgggcctcg gcgcgcttct gttgttcatc    37740
ctctttgccc gcatccgcgc ggtcgatgcc gaactgaaac tgaaaaagca tcgttccaag    37800
```

```
gacgccggcc tggccgatct gctcaactac gccgctgtcg tcgatgacgg cgtaatcgtg   37860
ggcaagaacg gcagctttat ggctgcctgg ctgtacaagg gcgatgacaa cgcaagcagc   37920
accgaccagc agcgcgaagt agtgtccgcc cgcatcaacc aggccctcgc gggcctggga   37980
agtgggtgga tgatccatgt ggacgccgtg cggcgtcctg ctccgaacta cgcggagcgg   38040
ggcctgtcgg cgttccctga ccgtctgacg gcagcgattg aagaagagcg ctcggtcttg   38100
ccttgctcgt cggtgatgta cttcaccagc tccgcgaagt cgctcttctt gatggagcgc   38160
atggggacgt gcttggcaat cacgcgcacc ccccggccgt tttagcggct aaaaaagtca   38220
tggctctgcc ctcgggcgga ccacgcccat catgaccttg ccaagctcgt cctgcttctc   38280
ttcgatcttc gccagcaggg cgaggatcgt ggcatcaccg aaccgcgccg tgcgcgggtc   38340
gtcggtgagc cagagtttca gcaggccgcc caggcggccc aggtcgccat tgatgcgggc   38400
cagctcgcgg acgtgctcat agtccacgac gcccgtgatt ttgtagccct ggccgacggc   38460
cagcaggtag gccgacaggc tcatgccggc cgccgccgcc ttttcctcaa tcgctcttcg   38520
ttcgtctgga aggcagtaca ccttgatagg tgggctgccc ttcctggttg gcttggtttc   38580
atcagccatc cgcttgccct catctgttac gccggcggta gccggccagc ctcgcagagc   38640
aggattcccg ttgagcaccg ccaggtgcga ataagggaca gtgaagaagg aacacccgct   38700
cgcgggtggg cctacttcac ctatcctgcc cggctgacgc cgttggatac accaaggaaa   38760
gtctacacga acccttggc aaaatcctgt atatcgtgcg aaaaaggatg gatataccga   38820
aaaaatcgct ataatgaccc cgaagcaggg ttatgcagcg aaaagcgct gcttccctgc    38880 tgttttgtgg aatatctacc gactggaaac aggcaaatgc aggaaattac tgaactgagg   38940
ggacaggcga gagacgatgc caaagagcta caccgacgag ctggccgagt gggttgaatc   39000
ccgcgcggcc aagaagcgcc ggcgtgatga ggctgcggtt gcgttcctgg cggtgagggc   39060
ggatgtcgag gcggcgttag cgtccggcta tgcgctcgtc accatttggg agcacatgcg   39120
ggaaacgggg aaggtcaagt tctcctacga gacgttccgc tcgcacgcca ggcggcacat   39180
caaggccaag cccgccgatg tgcccgcacc gcaggccaag gctgcggaac ccgcgccggc   39240
acccaagacg ccggagccac ggcggccgaa gcagggggc aaggctgaaa agccggcccc    39300
cgctgcggcc ccgaccggct tcaccttcaa cccaacaccg gacaaaaagg atctactgta   39360
atggcgaaaa ttcacatggt tttgcagggc aagggcgggg tcggcaagtc ggccatcgcc   39420
gcgatcattg cgcagtacaa gatggacaag gggcagacac ccttgtgcat cgacaccgac   39480
ccggtgaacg cgacgttcga gggctacaag gccctgaacg tccgccggct gaacatcatg   39540
gccggcgacg aaattaactc gcgcaacttc gacacccttgg tcgagctgat tgcgccgacc   39600
aaggatgacg tggtgatcga caacggtgcc agctcgttcg tgcctctgtc gcattacctc   39660
atcagcaacc aggtgccggc tctgctgcaa gaaatggggc atgagctggt catccatacc   39720
gtcgtcaccg gcggccaggc tctcctggac acggtgagcg gcttcgccca gctcgccagc   39780
cagttcccgg ccgaagcgct tttcgtggtc tggctgaacc cgtattgggg gcctatcgag   39840
catgagggca agagctttga gcagatgaag gcgtacacgg ccaacaaggc ccgcgtgtcg   39900
tccatcatcc agattccggc cctcaaggaa gaaacctacg gccgcgattt cagcgacatg   39960
ctgcaagagc ggctgacgtt cgaccaggcg ctggccgatg aatcgctcac gatcatgacg   40020
cggcaacgcc tcaagatcgt gcggcgcggc ctgtttgaac agctcgacgc ggcggccgtg   40080
ctatgagcga ccagattgaa gagctgatcc gggagattgc ggccaagcac ggcatcgccg   40140
tcggccgcga cgacccggtg ctgatcctgc ataccatcaa cgcccggctc atggccgaca   40200
```

```
gtgcggccaa gcaagaggaa atccttgccg cgttcaagga agagctggaa gggatcgccc   40260
atcgttgggg cgaggacgcc aaggccaaag cggagcggat gctgaacgcg gccctggcgg   40320
ccagcaagga cgcaatggcg aaggtaatga aggacagcgc cgcgcaggcg gccgaagcga   40380
tccgcaggga aatcgacgac ggccttggcc gccagctcgc ggccaaggtc gcggacgcgc   40440
ggcgcgtggc gatgatgaac atgatcgccg gcggcatggt gttgttcgcg gccgccctgg   40500
tggtgtgggc ctcgttatga atcgcagagg cgcagatgaa aaagcccggc gttgccgggc   40560 tttgttttg cgttagctgg gcttgtttga caggcccaag ctctgactgc gcccgcgctc    40620
gcgctcctgg gcctgtttct tctcctgctc ctgcttgcgc atcagggcct ggtgccgtcg   40680
ggctgcttca cgcatcgaat cccagtcgcc ggccagctcg ggatgctccg cgcgcatctt   40740
gcgcgtcgcc agttcctcga tcttgggcgc gtgaatgccc atgccttcct tgatttcgcg   40800
caccatgtcc agccgcgtgt gcagggtctg caagcgggct tgctgttggg cctgctgctg   40860
ctgccaggcg gcctttgtac gcggcaggga cagcaagccg ggggcattgg actgtagctg   40920
ctgcaaacgc gcctgctgac ggtctacgag ctgttctagg cggtcctcga tgcgctccac   40980
ctggtcatgc tttgcctgca cgtagagcgc aagggtctgc tggtaggtct gctcgatggg   41040
cgcggattct aagagggcct gctgttccgt ctcggcctcc tgggccgcct gtagcaaatc   41100
ctcgccgctg ttgccgctgg actgctttac tgccggggac tgctgttgcc ctgctcgcgc   41160
cgtcgtcgca gttcggcttg cccccactcg attgactgct tcatttcgag ccgcagcgat   41220
gcgatctcgg attgcgtcaa cggacggggc agcgcggagg tgtccggctt ctccttgggt   41280
gagtcggtcg atgccatagc caaaggtttc cttccaaaat gcgtccattg ctggaccgtg   41340
tttctcattg atgcccgcaa gcatcttcgg cttgaccgcc aggtcaagcg cgccttcatg   41400
ggcggtcatg acggacgccg ccatgacctt gccgccgttg ttctcgatgt agccgcgtaa   41460
tgaggcaatg gtgccgccca tcgtcagcgt gtcatcgaca acgatgtact tctggccggg   41520
gatcacctcc ccctcgaaag tcggttgaa cgccaggcga tgatctgaac cggctccggt    41580
tcgggcgacc ttctcccgct gcacaatgtc cgtttcgacc tcaaggccaa ggcggtcggc   41640
cagaacgacc gccatcatgg ccggaatctt gttgttcccc gccgcctcga cggcgaggac   41700
tggaacgatg cggggcttgt cgtcgccgat cagcgtcttg agctgggcaa cagtgtcgtc   41760
cgaaatcagg cgctcgacca aattaagcgc cgcttccgcg tcgccctgct tcgcagcctg   41820
gtattcaggc tcgttggtca aagaaccaag gtcgccgttg cgaaccacct tcgggaagtc   41880
tccccacggt gcgcgctcgg ctctgctgta gctgctcaag acgcctccct ttttagccgc   41940
taaaactcta acgagtgcgc ccgcgactca acttgacgct ttcggcactt acctgtgcct   42000
tgccacttgc gtcataggtg atgctttttcg cactcccgat ttcaggtact ttatcgaaat   42060
ctgaccgggc gtgcattaca aagttcttcc ccacctgttg gtaaatgctg ccgctatctg   42120
cgtggacgat gctgccgtcg tggcgctgcg acttatcggc cttttgggcc atatagatgt   42180
tgtaaatgcc aggtttcagg gccccggctt tatctacctt ctggttcgtc catgcgcctt   42240
ggttctcggt ctggacaatt ctttgcccat tcatgaccag gaggcggtgt ttcattgggt   42300
gactcctgac ggttgcctct ggtgttaaac gtgtcctggt cgcttgccgg ctaaaaaaaa   42360
gccgacctcg gcagttcgag gccggctttc cctagagccg ggcgcgtcaa ggttgttcca   42420
tctattttag tgaactgcgt tcgatttatc agttactttc ctcccgcttt gtgtttcctc   42480
ccactcgttt ccgcgtctag ccgacccctc aacatagcgg cctcttcttg ggctgccttt   42540
gcctcttgcc gcgcttcgtc acgctcggct tgcaccgtcg taaagcgctc ggcctgcctg   42600
```

```
gccgcctctt gcgccgccaa cttcctttgc tcctggtggg cctcggcgtc ggcctgcgcc   42660
ttcgctttca ccgctgccaa ctccgtgcgc aaactctccg cttcgcgcct ggtggcgtcg   42720
cgctcgccgc gaagcgcctg catttcctgg ttggccgcgt ccagggtctt gcggctctct   42780
tctttgaatg cgcgggcgtc ctggtgagcg tagtccagct cggcgcgcag ctcctgcgct   42840
cgacgctcca cctcgtcggc ccgctgcgtc gccagcgcgg cccgctgctc ggctcctgcc   42900
agggcggtgc gtgcttcggc cagggcttgc cgctggcgtg cggccagctc ggccgcctcg   42960
gcggcctgct gctctagcaa tgtaacgcgc gcctgggctt cttccagctc gcgggcctgc   43020
gcctcgaagg cgtcggccag ctccccgcgc acggcttcca actcgttgcg ctcacgatcc   43080
cagccggctt gcgctgcctg caacgattca ttggcaaggg cctgggcggc ttgccagagg   43140
gcggccacgg cctggttgcc ggcctgctgc accgcgtccg gcacctggac tgccagcggg   43200
gcggcctgcg ccgtgcgctg gcgtcgccat tcgcgcatgc cggcgctggc gtcgttcatg   43260
ttgacgcggg cggccttacg cactgcatcc acggtcggga agttctcccg gtcgccttgc   43320
tcgaacagct cgtccgcagc cgcaaaaatg cggtcgcgcg tctctttgtt cagttccatg   43380
ttggctccgg taattggtaa gaataataat actcttacct accttatcag cgcaagagtt   43440
tagctgaaca gttctcgact taacggcagg ttttttagcg gctgaagggc aggcaaaaaa   43500
agccccgcac ggtcggcggg ggcaaagggt cagcgggaag gggattagcg ggcgtcgggc   43560
ttcttcatgc gtcggggccg cgcttcttgg gatggagcac gacgaagcgc gcacgcgcat   43620
cgtcctcggc cctatcggcc cgcgtcgcgg tcaggaactt gtcgcgcgct aggtcctccc   43680
tggtgggcac caggggcatg aactcggcct gctcgatgta ggtccactcc atgaccgcat   43740
cgcagtcgag gccgcgttcc ttcaccgtct cttgcaggtc gcggtacgcc cgctcgttga   43800
gcggctggta acgggccaat tggtcgtaaa tggctgtcgg ccatgagcgg cctttcctgt   43860
tgagccagca gccgacgacg aagccggcaa tgcaggcccc tggcacaacc aggccgacgc   43920
cggggcagg ggatggcagc agctcgccaa ccaggaaccc cgccgcgatg atgccgatgc   43980
cggtcaacca gcccttgaaa ctatccggcc ccgaaacacc cctgcgcatt gcctggatgc   44040
tgcgccggat agcttgcaac atcaggagcc gtttctttg ttcgtcagtc atggtccgcc   44100
ctcaccagtt gttcgtatcg gtgtcggacg aactgaaatc gcaagagctg ccggtatcgg   44160
tccagccgct gtccgtgtcg ctgctgccga agcacggcga ggggtccgcg aacgccgcag   44220
acggcgtatc cggccgcagc gcatcgccca gcatggcccc ggtcagcgag ccgccggcca   44280
ggtagcccag catggtgctg ttggtcgccc cggccaccag ggccgacgtg acgaaatcgc   44340
cgtcattccc tctggattgt tcgctgctcg gcggggcagt gcgccgcgcc ggcggcgtcg   44400
tggatggctc gggttggctg gcctgcgacg gccggcgaaa ggtgcgcagc agctcgttat   44460
cgaccggctg cggcgtcggg gccgccgcct tgcgctgcgg tcggtgttcc ttcttcggct   44520
cgcgcagctt gaacagcatg atcgcggaaa ccagcagcaa cgccgcgcct acgcctcccg   44580
cgatgtagaa cagcatcgga ttcattcttc ggtcctcctt gtagcggaac cgttgtctgt   44640
gcggcgcggg tggcccgcgc cgctgtcttt ggggatcagc cctcgatgag cgcgaccagt   44700
ttcacgtcgg caaggttcgc ctcgaactcc tggccgtcgt cctcgtactt caaccaggca   44760
tagccttccg ccggcggccg acggttgagg ataaggcggg cagggcgctc gtcgtgctcc   44820
acctggacga tggcctttt cagcttgtcc gggtccggct ccttcgcgcc cttttccttg   44880
gcgtccttac cgtcctggtc gccgtcctcg ccgtcctggc cgtcgccggc ctccgcgtca   44940
cgctcggcat cagtctggcc gttgaaggca tcgacggtgt tgggatcgcg gcccttctcg   45000
```

```
tccaggaact cgcgcagcag cttgaccgtg ccgcgcgtga tttcctgggt gtcgtcgtca   45060
agccacgcct cgacttcctc cgggcgcttc ttgaaggccg tcaccagctc gttcaccacg   45120
gtcacgtcgc gcacgcggcc ggtgttgaac gcatcggcga tcttctccgg caggtccagc   45180
agcgtgacgt gctgggtgat gaacgccggc gacttgccga tttccttggc gatatcgcct   45240
ttcttcttgc cctcgccag ctcgcggcca atgaagtcgg caatttcgcg cggggtcagc   45300
tcgttgcgtt gcaggttctc gataacctgg tcggcttcgt tgtagtcgtt gtcgatgaac   45360
gccgggatgg acttcttgcc ggcccacttc gagccacggt agcggcgggc gccgtgattg   45420
atgatatagc ggcccggctg ctcctggttc tcgcgcaccg aaatgggtga cttcaccccg   45480
cgctctttga tcgtggcacc gatttccgcg atgctctccg gggaaaagcc ggggttgtcg   45540
gccgtccgcg gctgatgcgg atcttcgtcg atcaggtcca ggtccagctc gatagggccg   45600
gaaccgccct gagacgccgc aggagcgtcc aggaggctcg acaggtcgcc gatgctatcc   45660
aaccccaggc cggacggctg cgccgcgcct gcggcttcct gagcggccgc agcggtgttt   45720
ttcttggtgg tcttggcttg agccgcagtc attgggaaat ctccatcttc gtgaacacgt   45780
aatcagccag ggcgcgaacc tctttcgatg ccttgcgcgc ggccgttttc ttgatcttcc   45840
agaccggcac accggatgcg agggcatcgg cgatgctgct gcgcaggcca acggtggccg   45900
gaatcatcat cttggggtac gcggccagca gctcggcttg gtggcgcgcg tggcgcggat   45960
tccgcgcatc gaccttgctg gcaccatgc caaggaattg cagcttggcg ttcttctggc   46020
gcacgttcgc aatggtcgtg accatcttct tgatgccctg gatgctgtac gcctcaagct   46080
cgatggggga cagcacatag tcggccgcga agagggcggc cgccaggccg acgccaaggg   46140
tcggggccgt gtcgatcagg cacacgtcga agccttggtt cgccagggcc ttgatgttcg   46200
ccccgaacag ctcgcgggcg tcgtccagcg acagccgttc ggcgttcgcc agtaccgggt   46260
tggactcgat gagggcgagg cgcgcggcct ggccgtcgcc ggctgcgggt gcggtttcgg   46320
tccagccgcc ggcagggaca gcgccgaaca gcttgcttgc atgcaggccg gtagcaaagt   46380
ccttgagcgt gtaggacgca ttgccctggg ggtccaggtc gatcacggca acccgcaagc   46440
cgcgctcgaa aaagtcgaag gcaagatgca caagggtcga agtcttgccg acgccgcctt   46500
tctggttggc cgtgaccaaa gttttcatcg tttggtttcc tgtttttttct tggcgtccgc   46560 ttcccacttc cggacgatgt acgcctgatg ttccggcaga accgccgtta cccgcgcgta   46620
cccctcgggg aagttcttgt cctcgaacgc ggcccacacg cgatgcaccg cttgcgacac   46680
tgcgcccctg gtcagtccca gcgacgttgc gaacgtcgcc tgtggcttcc catcgactaa   46740
gacgccccgc gctatctcga tggtctgctg ccccacttcc agccctgga tcgcctcctg   46800 gaactggctt tcggtaagcc gtttcttcat ggataacacc cataatttgc tccgcgcctt   46860
ggttgaacat agcggtgaca gccgccagca catgagagaa gtttagctaa acatttctcg   46920
cacgtcaaca cctttagccg ctaaaactcg tccttggcgt aacaaaacaa aagcccggaa   46980
accgggcttt cgtctcttgc cgcttatggc tctgcacccg gctccatcac caacaggtcg   47040
cgcacgcgct tcactcggtt gcggatcgac actgccagcc caacaaagcc ggttgccgcc   47100
gccgccagga tcgcgccgat gatgccggcc acaccggcca tcgcccacca ggtcgccgcc   47160
ttccggttcc attcctgctg gtactgcttc gcaatgctgg acctcggctc accataggct   47220
gaccgctcga tggcgtatgc cgcttctccc cttggcgtaa acccagcgc gcaggcggc   47280 attgccatgc tgcccgccgc tttcccgacc acgacgcgcg caccaggctt gcggtccaga   47340
ccttcggcca cggcgagctg cgcaaggaca taatcagccg ccgacttggc tccacgcgcc   47400
```

-continued

```
tcgatcagct cttgcactcg cgcgaaatcc ttggcctcca cggccgccat gaatcgcgca  47460
cgcggcgaag gctccgcagg gccggcgtcg tgatcgccgc cgagaatgcc cttcaccaag  47520
ttcgacgaca cgaaaatcat gctgacggct atcaccatca tgcagacgga tcgcacgaac  47580
ccgctgaatt gaacacgagc acggcacccg cgaccactat gccaagaatg cccaaggtaa  47640
aaattgccgg ccccgccatg aagtccgtga atgccccgac ggccgaagtg aagggcaggc  47700
cgccacccag gccgccgccc tcactgcccg gcacctggtc gctgaatgtc gatgccagca  47760
cctgcggcac gtcaatgctt ccgggcgtcg cgctcgggct gatcgcccat cccgttactg  47820
ccccgatccc ggcaatggca aggactgcca gcgctgccat ttttggggtg aggccgttcg  47880
cggccgaggg gcgcagcccc tgggggatg ggaggcccgc gttagcgggc cgggagggtt  47940
cgagaagggg gggcaccccc cttcggcgtg cgcggtcacg cgcacagggc gcagccctgg  48000
ttaaaaacaa ggtttataaa tattggttta aaagcaggtt aaaagacagg ttagcggtgg  48060
ccgaaaaacg ggcggaaacc cttgcaaatg ctggattttc tgcctgtgga cagcccctca  48120
aatgtcaata ggtgcgcccc tcatctgtca gcactctgcc cctcaagtgt caaggatcgc  48180
gcccctcatc tgtcagtagt cgcgcccctc aagtgtcaat accgcagggc acttatcccc  48240
aggcttgtcc acatcatctg tgggaaactc gcgtaaaatc aggcgttttc gccgatttgc  48300
gaggctggcc agctccacgt cgccggccga aatcgagcct gcccctcatc tgtcaacgcc  48360
gcgccgggtg agtcggcccc tcaagtgtca acgtccgccc ctcatctgtc agtgagggcc  48420
aagttttccg cgaggtatcc acaacgccgg cggccgcggt gtctcgcaca cggcttcgac  48480
ggcgtttctg gcgcgtttgc agggccatag acggccgcca gcccagcggc gagggcaacc  48540
agcccggtga gcgtcggaaa ggcgctggaa gccccgtagc gacgcggaga ggggcgagac  48600
aagccaaggg cgcaggctcg atgcgcagca cgacatagcc ggttctcgca aggacgagaa  48660
tttccctgcg gtgcccctca agtgtcaatg aaagtttcca acgcgagcca ttcgcgagag  48720
ccttgagtcc acgctagatg agagctttgt tgtaggtgga ccagttggtg attttgaact  48780
tttgctttgc cacggaacgg tctgcgttgt cgggaagatg cgtgatctga tccttcaact  48840
cagcaaaagt tcgatttatt caacaaagcc acgttgtgtc tcaaaatctc tgatgttaca  48900
ttgcacaaga taaaaatata tcatcatgaa caataaaact gtctgcttac ataaacagta  48960
atacaagggg tgttatgagc catattcaac gggaaac                            48997
```

NITRATE TRANSPORT COMPONENTS

CROSS REFERENCE TO RELATED APPLICATIONS

This application is a divisional of U.S. patent application Ser. No. 11/504,116 filed Aug. 15, 2006, now U.S. Pat. No. 7,999,093, issued Aug. 16, 2011, which claims the benefit of U.S. Provisional Application No. 60/708,318, filed Aug. 15, 2005, U.S. Provisional Application No. 60/784,618, filed Mar. 22, 2006 and U.S. Provisional Application No. 60/785,143, filed Mar. 23, 2006. The entire contents of each of these applications is incorporated herein by reference.

FIELD OF THE INVENTION

This invention is in the field of plant molecular biology. More specifically, this invention pertains to nucleic acid fragments encoding high affinity nitrate transporters in plants and seeds.

BACKGROUND OF THE INVENTION

Higher plants are autotrophic organisms that can synthesize all of their molecular components from inorganic nutrients obtained from the local environment. Nitrogen is a key element in many compounds present in plant cells. It is found in the nucleoside phosphates and amino acids that form the building blocks of nucleic acids and proteins, respectively. Availability of nitrogen for crop plants is an important limiting factor in agricultural production, and the importance of nitrogen is demonstrated by the fact that only oxygen, carbon, and hydrogen are more abundant in higher plant cells. Nitrogen present in the form of ammonia or nitrate is readily absorbed and assimilated by higher plants.

Nitrate is the principal source of nitrogen that is available to higher plants under normal field conditions. Thus, the nitrate assimilation pathway is the major point of entry of inorganic nitrogen into organic compounds (Hewitt et al. (1976) Plant Biochemistry, pp 633-6812, Bonner, and Varner, eds. Academic Press, NY). Although some plants directly utilize ammonia, under certain conditions, nitrate is generally the major form of nitrogen available to plants.

Nitrate uptake by root cells is the first step of the nitrate assimilation pathway in higher plants (Orsel et al. (2002) Plant Physiology 129: 886-896). Plants have developed two different uptake systems to cope with the varying availability of nitrate in cultivated soils. The low-affinity nitrate transport system is used preferentially when external nitrate concentration is high, whereas the high-affinity transport system (HATS) takes place at very low external concentrations.

In higher plants, two gene families have been identified: the NRT1 and NRT2 families involved in the low-affinity transport system and HATs, respectively. The complexity of nitrate/nitrite transport is enhanced by the fine regulation that occurs at the transcriptional level: both low and high-affinity systems have constitutive and inducible components that are clearly distinct. Furthermore, some members of the nitrate transporters require a second gene product, a NAR2-type polypeptide for function (Tong et al. (2005) The Plant Journal 41: 442-450).

The nucleotide sequences of the instant application and the methods of their use can increase the efficiency by which nitrogen can be used.

SUMMARY OF THE INVENTION

The present invention includes isolated polynucleotides encoding a polypeptide required for high affinity nitrate transport, wherein the amino acid sequence of the polypeptide and the amino acid sequence of SEQ ID NO: 36 or 49, have at least 80%, 85%, 90%, 95%, 99% or 100% identity (b) the complement of the nucleotide sequence, wherein the complement and the nucleotide sequence contain the same number of nucleotides and are 100% complementary. The polypeptide preferably comprises the amino acid sequence of SEQ ID NO: 36 or 49. The nucleotide sequence preferably comprises the nucleotide sequence of SEQ ID NO: 35 or 48.

In a first embodiment, the present invention includes an isolated polynucleotide comprising: (a) a nucleotide sequence encoding a polypeptide required for high affinity nitrate transport, wherein the polypeptide has an amino acid sequence of at least 80%, 85%, 90%, 95%, 99% or 100% sequence identity based on the Clustal V method of alignment when compared to a polypeptide SEQ ID NO: 36 or 49.

(b) a complement of the nucleotide sequence, wherein the complement and the nucleotide sequence contain the same number of nucleotides and are 100% complementary.

In a second embodiment, this invention concerns such isolated nucleotide sequence or its complement which comprises at least two motifs corresponding substantially to any of the amino acid sequences set forth in SEQ ID NO: 50, 51 or 52, wherein said motif is substantially a conserved subsequence. Examples of such motifs, among others that can be identified, are shown in SEQ ID NO: 50, 51 or 52. Also of interest is the use of such fragment or a part thereof in anti-sense inhibition or co-suppression in a transformed plant.

In a third embodiment this invention concerns such isolated nucleotide fragment complement thereof wherein the fragment or a part thereof is useful in antisense inhibition or co-suppression of a protein altering nitrate transport in a transformed plant.

In a fourth embodiment, this invention concerns an isolated nucleic acid fragment comprising a promoter wherein said promoter consists essentially of the nucleotide sequence set forth in SEQ ID NO: 37, 38, 46, 47, 56, 65, 67, 68, 69, 70, 71, 72, 73, 74, 89 or 90, or said promoter consists essentially of a fragment or subfragment that is substantially similar and functionally equivalent to the nucleotide sequence set forth in SEQ ID NO:: 37, 38, 46, 47, 56, 65, 67, 68, 69, 70, 71, 72, 73, 74, 89 or 90.

In a fifth embodiment, this invention concerns recombinant DNA constructs comprising any of the foregoing nucleic acid fragment or complement thereof or part of either operably linked to at least one regulatory sequence. Also, of interest are plants comprising such recombinant DNA constructs in their genome, plant tissue or cells obtained from such plants and seeds obtained from these plants.

In a sixth embodiment, this invention concerns a method of altering nitrate transport in plants which comprises:
(a) transforming a plant with a recombinant DNA construct comprising:
 i) a first recombinant DNA construct comprising an isolated polynucleotide encoding a HAT polypeptide, operably linked to at least one regulatory sequence; and
 ii) at least one additional recombinant DNA construct comprising an isolated polynucleotide encoding a NAR polypeptide, operably linked to at least one regulatory sequence,
(b) growing the transformed plant of (a) under conditions suitable for the expression of the recombinant DNA constructs; and selecting those transformed plants having altered nitrate transport. Corn plants comprising these recombinant constructs are also part of this invention.

In a seventh embodiment, this invention concerns a method to isolate nucleic acid fragments encoding polypeptides associated with altering nitrate transport which comprises:

(a) comparing SEQ ID NO: 36, 49, 55, or 58 with other polypeptide sequences associated with altering plant nitrate transport;

(b) identifying the conserved sequences(s) or 4 or more amino acids obtained in step (a);

(c) making region-specific nucleotide probe(s) or oligomer(s) based on the conserved sequences identified in step (b); and (d) using the nucleotide probe(s) or oligomer(s) of step (c) to isolate sequences associated with altering nitrate transport by sequence dependent protocols.

In an eighth embodiment, this invention also concerns a method of mapping genetic variations related to altering plant nitrate transport:

(a) crossing two plant varieties; and (b) evaluating genetic variations with respect to:
(i) a nucleic acid sequence selected from the group consisting of SEQ ID NOs: 35, 48, 54, and 57; or
(ii) a nucleic acid sequence encoding a polypeptide selected from the group consisting of SEQ ID NOs: 36, 49, 55, and 58;

in progeny plants resulting from the cross of step (a) wherein the evaluation is made using a method selected from the group consisting of: RFLP analysis, SNP analysis, and PCR-based analysis.

In a ninth embodiment, this invention concerns a method of molecular breeding to obtain altered plant nitrate transport, comprising:

(a) crossing two plant varieties; and (b) evaluating genetic variations with respect to:
(i) a nucleic acid sequence selected from the group consisting of SEQ ID NOs: 35, 48, 54, and 57; or
(ii) a nucleic acid sequence encoding a polypeptide selected from the group consisting of SEQ ID NOs: 36, 49, 55, and 58;

in progeny plants resulting from the cross of step (a) wherein the evaluation is made using a method selected from the group consisting of: RFLP analysis, SNP analysis, and PCR-based analysis.

In a tenth embodiment, this invention concerns a method of altering the level of expression of a high affinity nitrate transporter polypeptide in a host cell comprising: (a) transforming a host cell with a recombinant DNA construct comprising:

(b) a nucleotide sequence encoding a high affinity nitrate transporter polypeptide, wherein the polypeptide has an amino acid sequence of at least 80% sequence identity, based on the Clustal V method of alignment, when compared to one of SEQ ID NO: 36 or 49 and the polypeptide alters nitrate transport, the complement thereof or at least two motifs corresponding substantially to any of the amino acid sequences set forth in SEQ ID NOs: 50, 51 and 52, wherein said motif is a substantially conserved subsequence operably linked to at least one regulatory sequence; and (c) growing the transformed host cell under conditions that are suitable for expression of the recombinant DNA construct wherein expression of the recombinant DNA construct results in production of altered levels of the polypeptide required for nitrate transport in the transformed host cell.

In an eleventh embodiment, this invention concerns a corn plant, comprising a first DNA construct comprising an isolated HAT polypeptide, operably linked to at least one regulatory sequence; and at least one additional recombinant DNA construct comprising an isolated polynucleotide, operably linked to at least one regulatory sequence, encoding a polypeptide selected from the group consisting of a NAR 2.

An additional embodiment of this invention concerns a method for altering plant nitrogen transport, comprising:

(a) transforming a plant with a recombinant DNA construct comprising:
i) a first recombinant DNA construct comprising an isolated polynucleotide encoding a HAT polypeptide, operably linked to at least one regulatory sequence; and
ii) at least one additional recombinant DNA construct comprising an isolated polynucleotide, operably linked to at least one regulatory sequence, encoding a polypeptide selected from the group consisting of a NAR;

(b) growing the transformed plant of (a) under conditions suitable for the expression of the recombinant DNA construct; and (c) selecting those transformed plants having altered nitrate transport.

Further embodiments of this invention include shuffled HAT variants with improved kinetic parameters, recombinant DNA constructs comprising the nucleotide sequences encoding these variants and plants and transformed cells comprising in their genome these recombinant DNA construct. Also included in this invention are corn plants comprising a first recombinant DNA construct comprising a nucleotide sequence encoding a shuffled HAT variant, operably linked to at least one regulatory sequence and at least one additional recombinant DNA construct comprising an isolated polynucleotide, operably linked to at least one regulatory sequence, encoding a polypeptide selected from the group consisting of a NAR.

Yet another embodiment of this invention sets forth a method for altering plant nitrogen transport, comprising: a) transforming a plant with a recombinant DNA construct comprising a first recombinant DNA construct comprising a nucleotide sequence encoding a shuffled HAT variant, operably linked to at least one regulatory sequence and at least one additional recombinant DNA construct comprising an isolated polynucleotide, operably linked to at least one regulatory sequence, encoding a polypeptide selected from the group consisting of a NAR; and b) growing the transformed plant of (a) under conditions suitable for the expression of the recombinant DNA construct; and selecting those transformed plants having altered nitrate transport.

BIOLOGICAL DEPOSITS

The following plasmid has been deposited with the American Type Culture Collection (ATCC), 10801 University Boulevard, Manassas, Va. 20110-2209, and bears the following identification, deposit designation, and date of deposit.

| Plasmid | ATCC Patent Deposit Designation | Date of Deposit |
|---|---|---|
| PHP27621 | PTA-7787 | Aug. 11, 2006 |

BRIEF DESCRIPTION OF THE SEQUENCE LISTINGS

The invention can be more fully understood from the following detailed description and the accompanying drawings and Sequence Listing, which form a part of this application.

FIG. 1 is a schematic of vector PHP27621.

Figure 2:
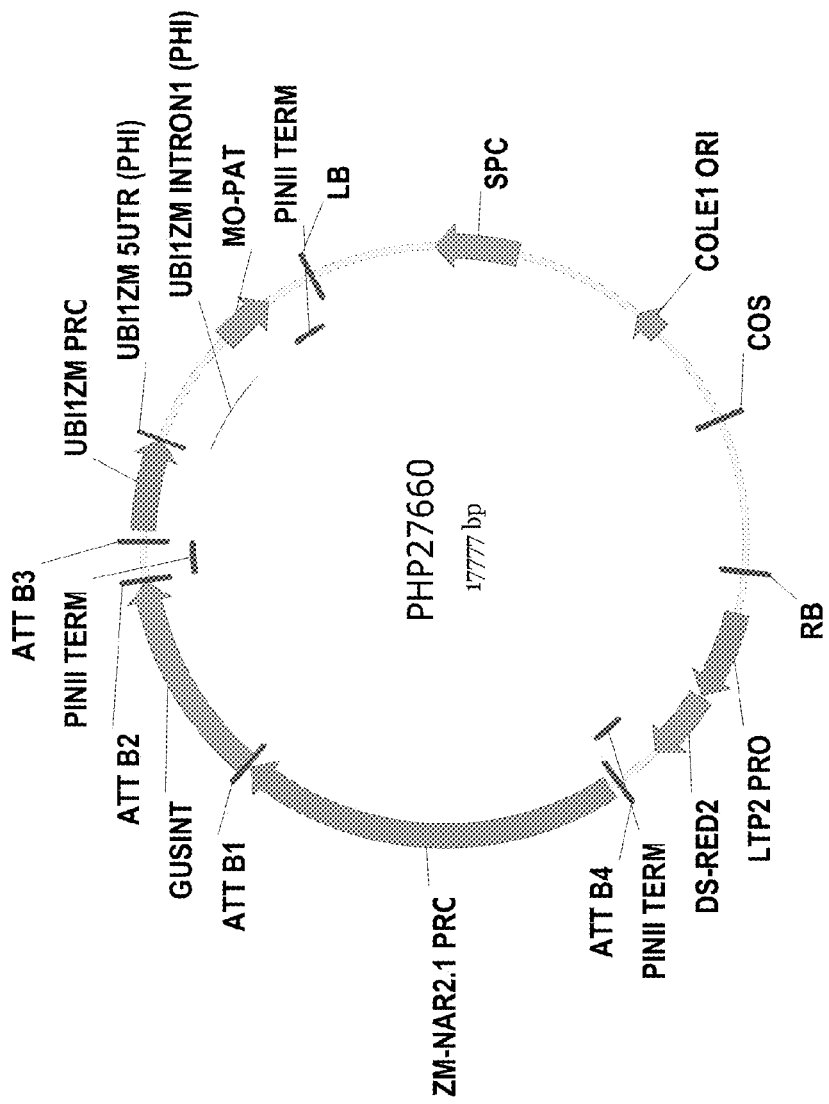
Figure 3:
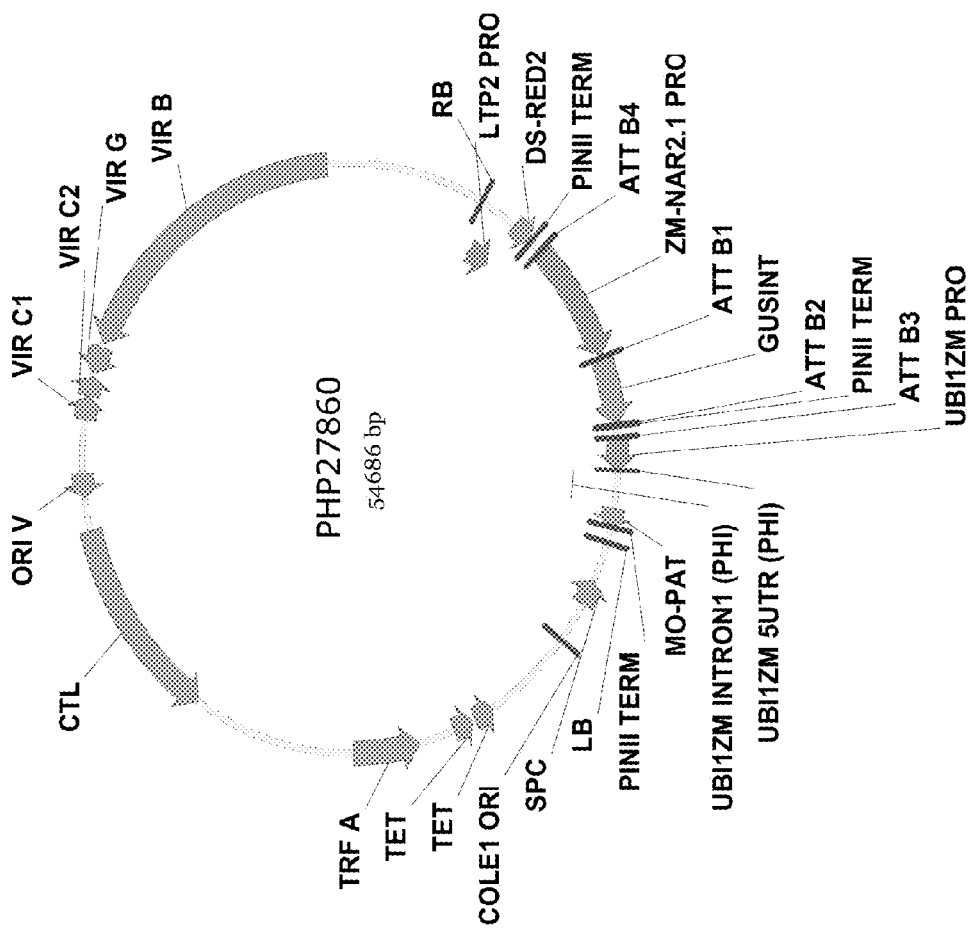
Figure 4:
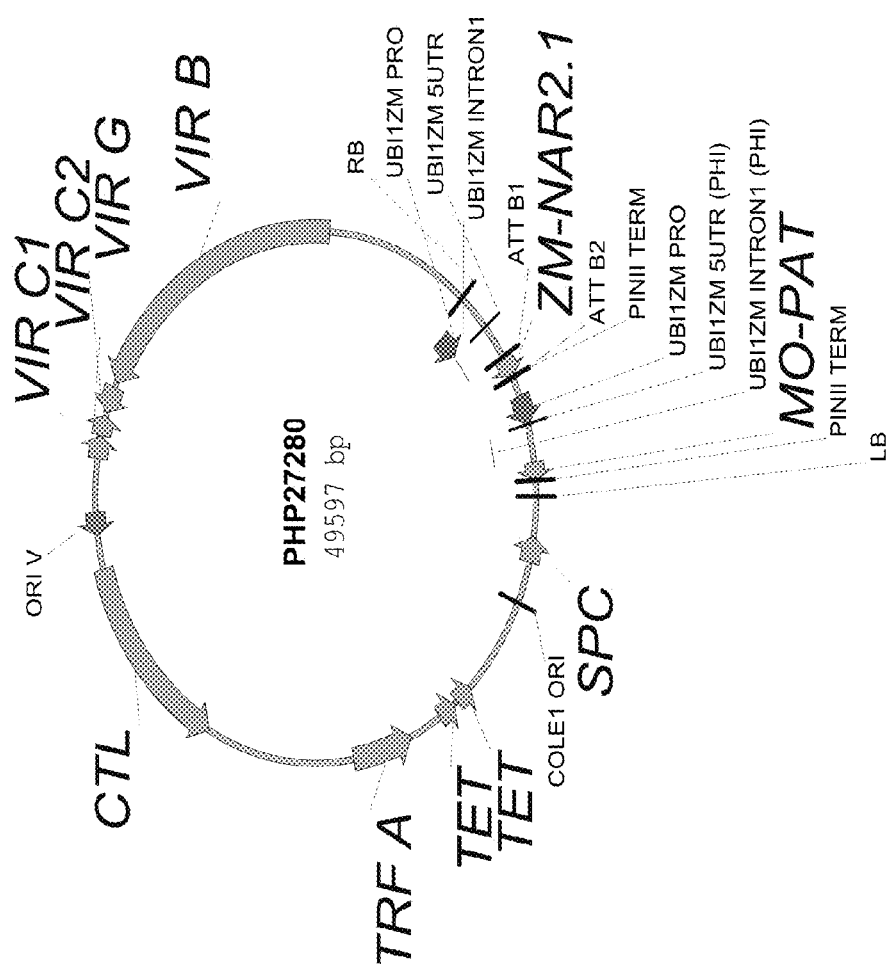
Figure 5:
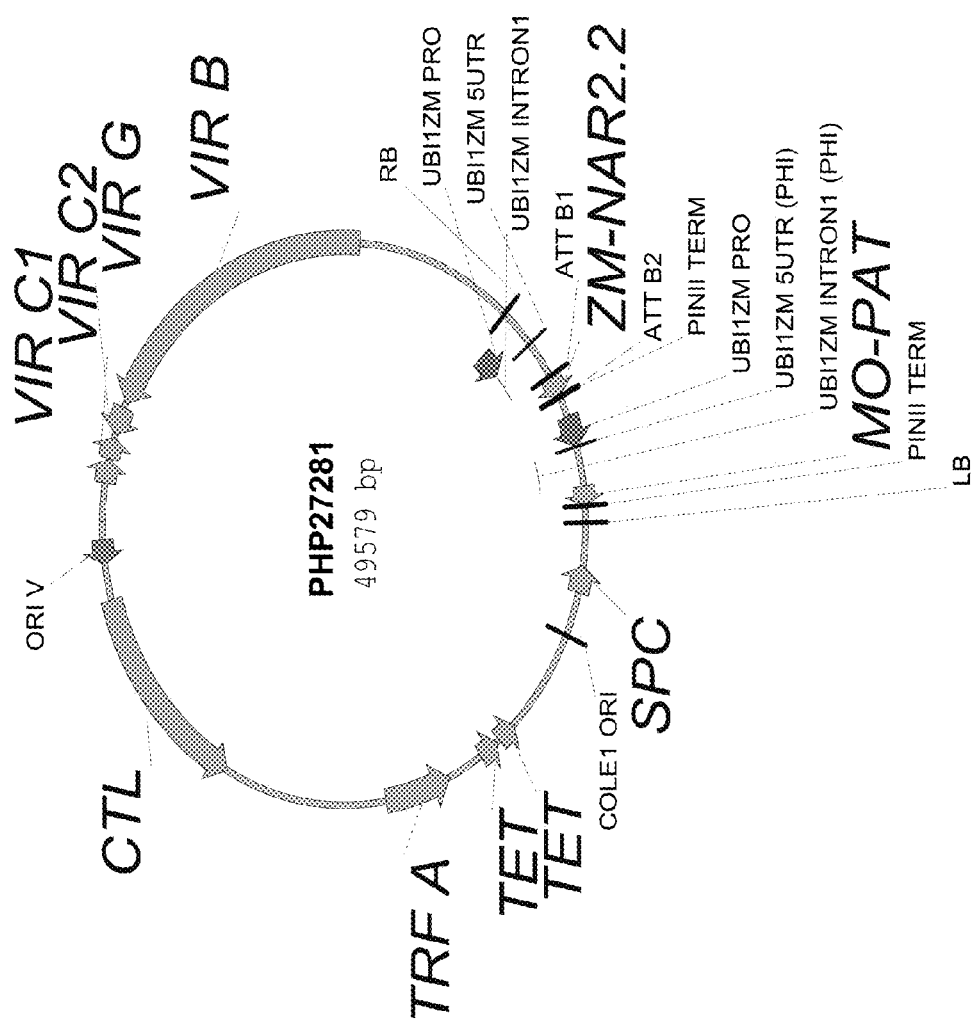
Figure 6:
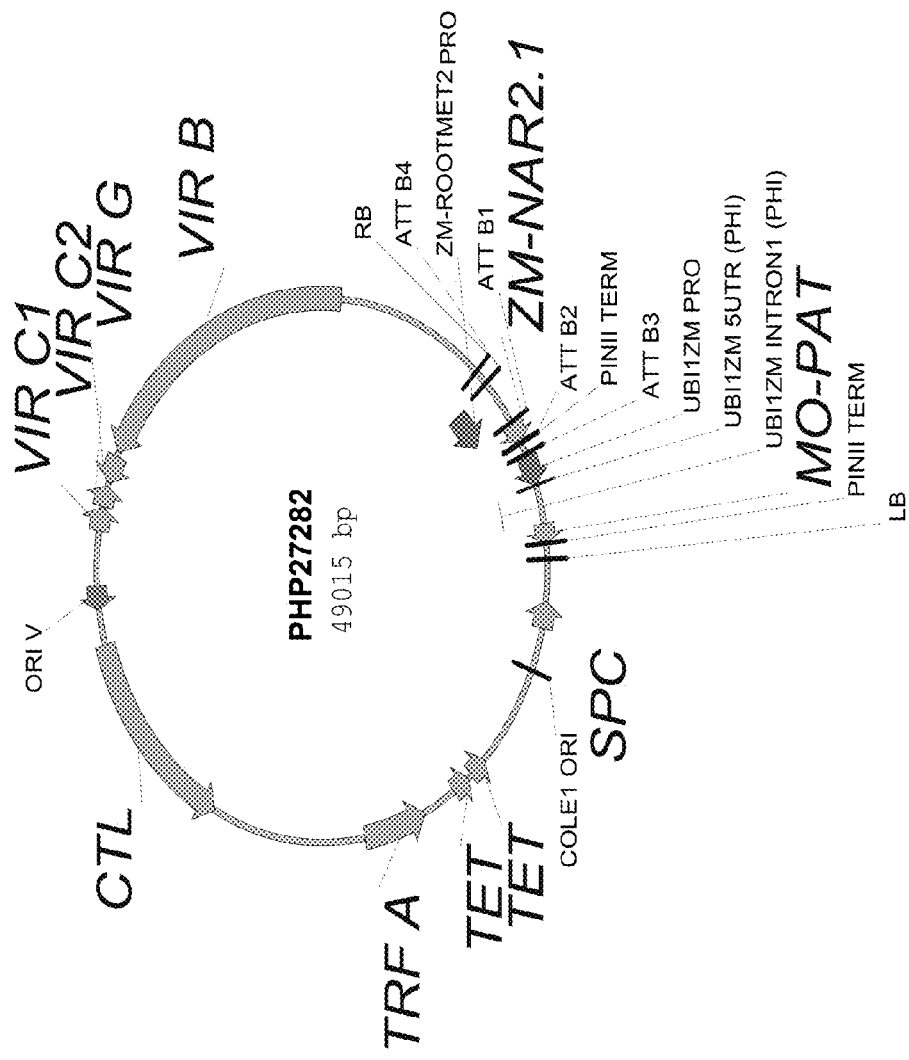

FIG. 2 is a schematic of vector PHP27660.
FIG. 3 is a schematic of vector PHP27860.
FIG. 4 is a schematic of vector PHP27280.
FIG. 5 is a schematic of vector PHP27281.
FIG. 6 is a schematic of vector PHP27282.
FIG. 7 is a schematic of vector PHP27283.

SEQ ID NO: 1 is the forward primer used in Example 3.

SEQ ID NO: 2 is the reverse primer used in Example 3.

SEQ ID NO: 3 is the T7 primer used in Example 3 for confirmatory BAC ends sequencing.

SEQ ID NO: 4 is the SP6 primer used in Example 3 for confirmatory BAC ends sequencing.

SEQ ID NO: 5 through 33 are the sequencing primers used to cover the region on BAC clone bacc.pk139.d24 containing the HAT4 gene.

SEQ ID NO: 34 represents the 3924 bp of the maize genomic sequence containing the ORF (Nucleotides 2015-3583 (Stop)) of the gene encoding the high affinity nitrate transporter (HAT4) isolated from BAC clone bacc.pk139.d24.

SEQ ID NO: 35 is 1569 bp of the nucleotide sequence of the ORF of SEQ ID NO: 34.

SEQ ID NO: 36 is the amino acid sequence encoded by nucleotides 2015-3580 of SEQ ID NO: 34.

SEQ ID NO: 37 is the 2014 bp, extending from Nucleotides 1-2014 of the putative promoter of the maize high affinity nitrate transporter genomic sequence shown in SEQ ID NO: 34.

SEQ ID NO: 38 is 1014 bp, extending from Nucleotide 1001-2014 of the putative promoter of the maize high affinity nitrate transporter genomic sequence shown in SEQ ID NO: 34.

SEQ ID NO: 43 is the T3 primer used in Example 4.

SEQ ID NO: 44 is the T7 primer used in Example 4.

SEQ ID NO: 45 represents the 5812 bp of the maize genomic sequence containing the ORF (Nucleotides 2264-3450 and 5087-5357 (Stop)) of the gene encoding a high affinity nitrate transporter (HAT7).

SEQ ID NO: 46 is the 2263 bp, extending from Nucleotides 1-2263 of the putative promoter of the maize high affinity nitrate transporter genomic sequence shown in SEQ ID NO: 45.

SEQ ID NO: 47 is the 1263 bp, extending from Nucleotides 1001-2263 of the putative promoter of the maize high affinity nitrate transporter genomic sequence shown in SEQ ID NO: 45.

SEQ ID NO: 48 is 1455 bp of the coding sequence, extending from Nucleotides 2264-3450 and 5087-5354 of SEQ ID NO: 45.

SEQ ID NO: 49: is the amino acid sequence encoded by SEQ ID NO: 48.

SEQ ID NO: 50 is a conserved sequence motif useful in identifying genes belonging to the high affinity nitrate transporter of genes.

SEQ ID NO: 51 is a conserved sequence motif useful in identifying genes belonging to the high affinity nitrate transporter of genes.

SEQ ID NO: 52 is a conserved sequence motif useful in identifying genes belonging to the high affinity nitrate transporter of genes.

SEQ ID NO: 53 is the 1561 bp of the sequence containing the ORF (nucleotides 757-1368 (Stop)) encoding a corn NAR2-type polypeptide (NAR2.1).

SEQ ID NO: 54 is the 612 bp of the coding sequence, extending from nucleotides 758-1369 (Stop) of SEQ ID NO: 53.

SEQ ID NO: 55 is the amino acid sequence encoded by nucleotides 758-1366 of SEQ ID NO: 54.

SEQ ID NO: 56 is the 756 bp, extending from Nucleotides 1-756 of the putative promoter of the sequence shown in SEQ ID NO: 53.

SEQ ID NO: 57 is the 594 bp of the ORF (nucleotides 1-594 (Stop)) encoding a NAR2-type polypeptide (NAR2.2).

SEQ ID NO: 58 is the amino acid sequence encoded by nucleotides 1-591 of the ORF of SEQ ID NO: 57.

SEQ ID NO: 59 is the NAR2.1 specific outer primer used in Example 6.

SEQ ID NO: 60 is the NAR2.1 specific inner primer used in Example 6.

SEQ ID NO: 61-64 are the sequencing primers used to sequence the NAR2.1 promoter upstream region.

SEQ ID NO: 65 shows an additional 2917 bp of the putative NAR2.1 promoter.

SEQ ID NO: 66 shows the 4498 bp of the complete NAR2.1 gene, including an intron extending from nucleotides 3655-3841.

SEQ ID NO: 67 is the 3506 bp, extending from Nucleotides 1-3506 of the putative promoter of the NAR2.1 genomic sequence shown in SEQ ID NO: 66.

SEQ ID NO: 68 is 1014 bp, extending from Nucleotide 1001-2014 of the putative promoter of the NAR2.1genomic sequence shown in SEQ ID NO: 66.

SEQ ID NO: 69 is 1492 bp, extending from Nucleotide 2015-3506 of the putative promoter of the NAR2.1 genomic sequence shown in SEQ ID NO: 66.

SEQ ID NO: 70 is 3621 bp of the genomic fragment isolated in Example 14.

SEQ ID NO: 71 is 3236 bp of the putative Nar promoter from B73, extending from Nucleotides 1-3236 of SEQ ID NO: 70.

SEQ ID NO: 72 is 1000 bp of the putative Nar promoter from B73, extending from Nucleotides 1-1000 of SEQ ID NO: 70.

SEQ ID NO: 73 is 2236 bp of the putative Nar promoter from B73, extending from Nucleotides 1001-3236 of SEQ ID NO: 70.

SEQ ID NO: 74 is 1237 bp of the putative Nar promoter from B73, extending from Nucleotides 2000-3236 of SEQ ID NO: 70.

SEQ ID NO: 75 through 78 are the forward and reverse primers described in Example 14.

SEQ ID NO: 79-84 are the sequencing primers used to sequence the Nar promoter from B73 as described in Example 14.

SEQ ID NO: 85 is the sequence of vector pENTR-5' described in Example 14.

SEQ ID NO: 86 is the sequence of vector PHP27621 described in Example 16.

SEQ ID NO: 87 is the sequence of vector PHP27660 described in Example 17.

SEQ ID NO: 88 is the sequence of vector PHP27860 described in Example 17.

SEQ ID NO: 89 is 3324 bp of the putative Nar promoter from B73, comprising Nucleotides 1-1523 and 1821-3324 of SEQ ID NO: 70.

SEQ ID 90: is 500 bp of the putative Nar promoter from B73, extending from Nucleotides 2825-3324 of SEQ ID NO: 70.

SEQ ID NO:91: represents the 2025 bp of the maize sequence containing the ORF (Nucleotides 250-1812(Stop)) of the gene encoding the high affinity nitrate transporter (HAT5) isolated from clone cfp4n.pk008.p6:fis.

SEQ ID NO:92 is the amino acid sequence encoded by the ORF of SEQ ID NO: 91.

SEQ ID NO: 93 is the sequence of vector PHP27280 described in Example 20.

SEQ ID NO: 94 is the sequence of vector PHP27281 described in Example 20.

SEQ ID NO: 95 is the sequence of vector PHP27282 described in Example 20.

SEQ ID NO: 96 is the sequence of vector PHP27283 described in Example 20.

The Sequence Listing contains the one letter code for nucleotide sequence characters and the three letter codes for amino acids as defined in conformity with the IUPAC-IUBMB standards described in *Nucleic Acids Research* 13:3021-3030 (1985) and in the *Biochemical Journal* 219 (No. 2): 345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

The disclosure of each reference set forth herein is incorporated herein by reference in its entirety.

The term "NAR" refers to nitrate assimilation related genes. These type of genes and the NAR polypeptides encoded by them are a component of the high affinity nitrate uptake system in plants.

The term "HAT" is used interchangeably with high affinity nitrate transporter.

As used herein, an "isolated nucleic acid fragment" is used interchangeably with "isolated polynucleotide" and is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the portion or subsequence encodes an active enzyme or functional protein (for example, the portion or subsequence may be a portion of coding and/or non-coding regions and need not encode an active enzyme or functional protein. For example, the fragment or subfragment can be used in the design of recombinant DNA constructs to produce the desired phenotype in a transformed plant. Recombinant DNA constructs can be designed for use in co-suppression or antisense by linking a nucleic acid fragment or subfragment thereof, whether or not it encodes an active enzyme or functional protein, in the appropriate orientation relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 1×SSC, 0.1% SDS, 60° C.) with the sequences exemplified herein, or to any portion of the nucleotide sequences reported herein and which are functionally equivalent to the gene or the promoter of the invention. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

With respect to the degree of substantial similarity between the target (endogenous) mRNA and the RNA region in the construct having homology to the target mRNA, such sequences should be at least 25 nucleotides in length, preferably at least 50 nucleotides in length, more preferably at least 100 nucleotides in length, again more preferably at least 200 nucleotides in length, and most preferably at least 300 nucleotides in length; and should be at least 80% identical, preferably at least 85% identical, more preferably at least 90% identical, and most preferably at least 95% identical.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. A "foreign" gene refers to a gene not normally found in the host organism, but that is introduced into the host organism by gene transfer. Foreign genes can comprise native genes inserted into a non-native organism, or recombinant DNA constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of an isolated nucleic acid fragment in different tissues or cell types, or at different stages of development, or in response to different environmental conditions. Promoters, which cause an isolated nucleic acid fragment to be expressed in most cell types, at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82.

It is further recognized that since in most cases the exact boundaries of regulatory sequences have not been completely defined, DNA fragments of some variation may have identical promoter activity. As used herein, "substantially similar and functionally equivalent subfragment of a promoter" refers to a portion or subsequence of a promoter sequence which is capable of controlling the expression of a coding sequence or functional RNA.

Specific examples of promoters that may be useful in expressing the nucleic acid fragments of the invention include, but are not limited to, the promoters disclosed in this application (SEQ ID NOs:: 37, 38, 46, 47, 56, 65, 67, 68, 69, 70, 71, 72, 73, 74, 89 or 90).

An "intron" is an intervening sequence in a gene that does not encode a portion of the protein sequence. Thus, such sequences are transcribed into RNA but are then excised and are not translated. The term is also used for the excised RNA sequences.

An "exon" is a portion of the sequence of a gene that is transcribed and is found in the mature messenger RNA derived from the gene, but is not necessarily a part of the sequence that encodes the final gene product.

The term "deduced nucleotide sequence" refers to a DNA sequence after removal of intervening sequences, based on homology to other DNA sequences encoding the same protein.

The term "deduced amino acid sequence" refers to a polypeptide sequence derived from a DNA sequence after removal of intervening sequences, based on homology to other proteins encoded by DNA sequences encoding the same protein.

The term "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or anti-sense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of an isolated nucleic acid fragment involves transcription of the isolated nucleic acid fragment and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature* (London) 327:70-73; U.S. Pat. No. 4,945,050), or an *Agrobacterium*-mediated method using an appropriate Ti plasmid containing the transgene (Ishida Y. et al., 1996, Nature Biotech. 14:745-750). The term "transformation and "transformed" as used herein refer to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al, *Cold Spring Harbor Symp. Quant. Biol.* 51:263-273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) Plant J 16:651-659; and Gura (2000) Nature 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al. (1998) Plant Cell 10:1747-1757).

In one aspect, this invention includes an isolated polynucleotide comprising a nucleotide sequence encoding a polypeptide required for high affinity nitrate transport, wherein the polypeptide has an amino acid sequence of at least 80%, 85%, 90%, 95%, or 99% sequence identity, based on the Clustal V method of alignment, when compared to one of SEQ ID NO: 36 or 49. The polypeptide may also comprise SEQ ID NO: 36 or 49, and the nucleotide sequence may comprise SEQ ID NO: 35 or 48.

Also included in the present invention is a complement of any of the foregoing nucleotide sequences, wherein the complement and the nucleotide sequence consist of the same number of nucleotides and are 100% complementary.

In another aspect, this invention includes isolated polynucleotides as described herein (or complements), wherein the nucleotide sequence comprises at least two, three, four, or five motifs selected from group consisting of SEQ ID NOs: 50, 51 and 52, wherein said motif is a substantially conserved subsequence.

"Motifs" or "subsequences" refer to short regions of conserved sequences of nucleic acids or amino acids that comprise part of a longer sequence. For example, it is expected that such conserved subsequences (for example SEQ ID NOs: 50, 51 and 52) would be important for function, and could be used to identify new homologues of high affinity nitrate transporter-homologues in plants. It is expected that some or all of the elements may be found in a high affinity nitrate transporter—homologue. Also, it is expected that at least one or two of the conserved amino acids in any given motif may differ in a true high affinity nitrate transporter—homologue.

In another aspect, a polynucleotide of this invention or a functionally equivalent subfragment thereof is useful in antisense inhibition or cosuppression of expression of nucleic acid sequences encoding proteins required for high affinity nitrate transport, most preferably in antisense inhibition or cosuppression of an endogenous high affinity nitrate transporter or heterologous high affinity nitrate transporter gene.

Protocols for antisense inhibition or co-suppression are well known to those skilled in the art and are described above.

In still a further aspect, this invention includes an isolated nucleic acid fragment comprising (a) a promoter consisting essentially of SEQ ID NO:: 37, 38, 46, 47, 56, 65, 67, 68, 69, 70, 71, 72, 73, 74, 89 or 90 or (b) a substantially similar and functionally equivalent subfragment of said promoter.

Also of interest are recombinant DNA constructs comprising any of the above-identified isolated nucleic acid fragments or isolated polynucleotides or complements thereof or parts of such fragments or complements, operably linked to at least one regulatory sequence.

Plants, plant tissue or plant cells comprising such recombinant DNA constructs in their genome are also within the scope of this invention. Transformation methods are well known to those skilled in the art and are described above. Any plant, dicot or monocot can be transformed with such recombinant DNA constructs.

Examples of monocots include, but are not limited to, corn, wheat, rice, sorghum, millet, barley, palm, lily, Alstroemeria, rye, and oat. Examples of dicots include, but are not limited to, soybean, rape, sunflower, canola, grape, guayule, columbine, cotton, tobacco, peas, beans, flax, safflower, alfalfa.

Plant tissue includes differentiated and undifferentiated tissues or plants, including but not limited to, roots, stems, shoots, leaves, pollen, seeds, tumor tissue, and various forms of cells and culture such as single cells, protoplasm, embryos, and callus tissue. The plant tissue may be in plant or in organ, tissue or cell culture.

In another aspect, this invention includes a method of altering plant nitrate transport, comprising:
(a) transforming a plant with a recombinant DNA construct comprising:
  i) A recombinant DNA construct comprising an isolated polynucleotide encoding a HAT polypeptide, operably linked to at least one regulatory sequence; and
  ii) at least one additional recombinant DNA construct comprising an isolated polynucleotide encoding a NAR polypeptide, operably linked to at least one regulatory sequence.
(b) growing the transformed plant of (a) under conditions suitable for the expression of the recombinant DNA construct; and selecting those transformed plants having altered nitrate transport.

As used herein, altering plant nitrate transport may result in increased or decreased changes.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue.

The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., *BioTechnology* 6:923 (1988), Christou et al., *Plant Physiol.* 87:671-674 (1988)); *Brassica* (U.S. Pat. No. 5,463,174); peanut (Cheng et al., *Plant Cell Rep.* 15:653-657 (1996), McKently et al., *Plant Cell Rep.* 14:699-703 (1995)); papaya; and pea (Grant et al., *Plant Cell Rep.* 15:254-258, (1995)).

Transformation of monocotyledons using electroporation, particle bombardment, and *Agrobacterium* have also been reported. Transformation and plant regeneration have been achieved in asparagus (Bytebier et al., *Proc. Natl. Acad. Sci.* (USA) 84:5354, (1987)); barley (Wan and Lemaux, *Plant Physiol* 104:37 (1994)); Zea mays (Rhodes et al., *Science* 240:204 (1988), Gordon-Kamm et al., *Plant Cell* 2:603-618 (1990), Fromm et al., *BioTechnology* 8:833 (1990), Koziel et al., *BioTechnology* 11: 194, (1993), Armstrong et al., *Crop Science* 35:550-557 (1995)); oat (Somers et al., *BioTechnology* 10: 15 89 (1992)); orchard grass (Horn et al., *Plant Cell Rep.* 7:469 (1988)); rice (Toriyama et al., *TheorAppl. Genet.* 205:34, (1986); Part et al., *Plant Mol. Biol.* 32:1135-1148, (1996); Abedinia et al., *Aust. J. Plant Physiol.* 24:133-141 (1997); Zhang and Wu, *Theor. Appl. Genet.* 76:835 (1988); Zhang et al. *Plant Cell Rep.* 7:379, (1988); Battraw and Hall, *Plant Sci.* 86:191-202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *BioTechnology* 10:691 (1992)), and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)).

Transient expression systems may be used to functionally dissect isolated nucleic acid fragment constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, New York (1998); Birren et al., Genome Analysis: Analyzing DNA, 2, Cold Spring Harbor, New York (1998); Plant Molecular Biology: A Laboratory Manual, eds. Clark, Springer, N.Y. (1997)).

In a still further aspect, this invention includes a method to isolate nucleic acid fragments encoding polypeptides associated with altering plant nitrate transport, which comprises:

(a) comparing SEQ ID NO: 36 or 49 with other polypeptide sequences associated with altering plant nitrate transport;

(b) identifying conserved sequences of 4 or more amino acids obtained in step (a);

(c) making region-specific nucleotide probe(s) or oligomer(s) based on the conserved sequences identified in step (b); and (d) using the nucleotide probe(s) or oligomer(s) of step (c) to isolate sequences associated with altering plant nitrate transport by sequence dependent protocols.

Examples of conserved sequence elements that would be useful in identifying other plant sequences associated with altering plant nitrate transport can be found in the group comprising, but not limited to, the nucleotides encoding the polypeptides of SEQ ID NOs: 50, 51, and 52.

In another aspect, this invention also includes a method of mapping genetic variations related to altering plant nitrate transport comprising:

(a) crossing two plant varieties; and (b) evaluating genetic variations with respect to:

(i) a nucleic acid sequence selected from the group consisting of SEQ ID NO: 35 and 48; or (ii) a nucleic acid sequence encoding a polypeptide selected from the group consisting of SEQ ID NOs: 36 and 49 in progeny plants resulting from the cross of step (a) wherein the evaluation is made using a method selected from the group consisting of: RFLP analysis, SNP analysis, and PCR-based analysis.

In another embodiment, this invention includes a method of molecular breeding to obtain altered plant nitrate transport:

(a) crossing two plant varieties; and (b) evaluating genetic variations with respect to:

(i) a nucleic acid sequence selected from the group consisting of SEQ ID NOs: 35 and 48; or (ii) a nucleic acid sequence encoding a polypeptide selected from the group consisting of SEQ ID NOs: 36 and 49 in progeny plants resulting from the cross of step (a) wherein the evaluation is made using a method selected from the group consisting of: RFLP analysis, SNP analysis, and PCR-based analysis.

The terms "mapping genetic variation" or "mapping genetic variability" are used interchangeably and define the process of identifying changes in DNA sequence, whether from natural or induced causes, within a genetic region that differentiates between different plant lines, cultivars, varieties, families, or species. The genetic variability at a particular locus (gene) due to even minor base changes can alter the pattern of restriction enzyme digestion fragments that can be generated. Pathogenic alterations to the genotype can be due to deletions or insertions within the gene being analyzed or even single nucleotide substitutions that can create or delete a restriction enzyme recognition site. RFLP (restriction fragment length polymorphisms) analysis takes advantage of this and utilizes Southern blotting with a probe corresponding to the isolated nucleic acid fragment of interest.

Thus, if a polymorphism (i.e., a commonly occurring variation in a gene or segment of DNA; also, the existence of several forms of a gene (alleles) in the same species) creates or destroys a restriction endonuclease cleavage site, or if it results in the loss or insertion of DNA (e.g., a variable nucleotide tandem repeat (VNTR) polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed RFLPs. RFLPs have been widely used in human and plant genetic analyses (Glassberg, UK Patent Application 2135774; Skolnick et al, Cytogen. *Cell Genet.* 32:58-67 (1982); Botstein et al, *Ann. J. Hum. Genet.* 32:314-331 (1980); Fischer et al (PCT Application WO 90/13668; Uhlen, PCT Application WO 90/11369).

A central attribute of "single nucleotide polymorphisms" or "SNPs" is that the site of the polymorphism is at a single nucleotide. SNPs have certain reported advantages over RFLPs or VNTRs. First, SNPs are more stable than other classes of polymorphisms. Their spontaneous mutation rate is approximately $10^{-9}$ (Kornberg, DNA Replication, W.H. Freeman & Co., San Francisco, 1980), approximately, 1,000 times less frequent than VNTRs (U.S. Pat. No. 5,679,524). Second, SNPs occur at greater frequency, and with greater uniformity than RFLPs and VNTRs. As SNPs result from sequence variation, sequencing random genomic or cDNA molecules can identify new polymorphisms. SNPs can also result from deletions, point mutations and insertions. Any single base alteration, whatever the cause, can be a SNP. The greater frequency of SNPs means that they can be more readily identified than the other classes of polymorphisms.

SNPs can be characterized using any of a variety of methods. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism or by other biochemical interpretation. SNPs can be sequenced by a number of methods. Two basic methods may be used for DNA sequencing, the chain termination method of Sanger et al, *Proc. Natl. Acad. Sci.* (U.S.A.) 74:5463-5467 (1977), and the chemical degradation method of Maxam and Gilbert, *Proc. Natl. Acad. Sci.* (U.S.A.) 74: 560-564 (1977).

Furthermore, single point mutations can be detected by modified PCR techniques such as the ligase chain reaction ("LCR") and PCR-single strand conformational polymorphisms ("PCR-SSCP") analysis. The PCR technique can also be used to identify the level of expression of genes in extremely small samples of material, e.g., tissues or cells from a body. The technique is termed reverse transcription-PCR ("RT-PCR").

The term "molecular breeding" defines the process of tracking molecular markers during the breeding process. It is common for the molecular markers to be linked to phenotypic traits that are desirable. By following the segregation of the molecular marker or genetic trait, instead of scoring for a phenotype, the breeding process can be accelerated by growing fewer plants and eliminating assaying or visual inspection for phenotypic variation. The molecular markers useful in this process include, but are not limited to, any marker useful in identifying mapable genetic variations previously mentioned, as well as any closely linked genes that display synteny across plant species. The term "synteny" refers to the conservation of gene placement/order on chromosomes between different organisms. This means that two or more genetic loci, that may or may not be closely linked, are found on the same chromosome among different species. Another term for synteny is "genome colinearity".

The nucleic acid fragments of the instant invention may be used to create transgenic plants in which the disclosed polypeptides are present at higher or lower levels than normal or in cell types or developmental stages in which they are not normally found. This would have the effect of altering the level of nitrogen transport and accumulation in those cells. Nitrogen deficiency in plants results in stunted growth, and many times in slender and often woody stems. In many plants the first signal of nitrogen deficiency is chlorosis (yellowing of the leaves).

Overexpression of the proteins of the instant invention may be accomplished by first making a recombinant DNA construct in which the coding region is operably linked to a promoter capable of directing expression of a gene in the desired tissues at the desired stage of development. For reasons of convenience, the recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant recombinant DNA construct can then be made. The choice of plasmid vector is dependent upon the method that will be used to transform host plants. The skilled artisan is well aware of the genetic elements that must be present on the plasmid vector in order to successfully transform, select and propagate host cells containing the recombinant DNA construct. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct described above may be further supplemented by altering the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.*100:1627-1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded ammonium transporter. An example of a vector for high level expression of the instant polypeptides in a bacterial host is provided (Example 7).

Additionally, the instant polypeptides can be used as targets to facilitate design and/or identification of inhibitors of those enzymes that may be useful as herbicides. This is desirable because the polypeptides described herein catalyze various steps in nitrogen uptake. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4(1):37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Research* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nature Genetics* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

The function of the high affinity nitrate transporters and polypeptides required for high affinity nitrate transport can be confirmed using the TUSC Mutant population. The Trait Utility System for Corn (TUSC) is a method that employs genetic and molecular techniques to facilitate the study of gene function in maize. Studying gene function implies that the gene's sequence is already known, thus the method works in reverse: from sequence to phenotype. This kind of application is referred to as "reverse genetics", which contrasts with "forward" methods (such as transposon tagging) that are designed to identify and isolate the gene(s) responsible for a particular trait (phenotype).

Pioneer Hi-Bred International, Inc., has its proprietary collection of maize genomic DNA from approximately 42,000 individual $F_1$ plants (Reverse genetics for maize; Meeley, R and Briggs, S, 1995, Maize Genet. Coop. Newslett. 69:67, 82).

The genome of each of these individuals contains multiple copies of the transposable element family, Mutator (Mu). The Mu family is highly mutagenic; in the presence of the active element Mu-DR, these elements transpose throughout the genome, inserting into genic regions, and often disrupting gene function. By collecting genomic DNA from a large number of individuals (42,000), Pioneer has assembled a library of the mutagenized maize genome. Mu insertion events are predominately heterozygous so; given the recessive nature of most insertional mutations, the $F_1$ plants appear wild-type. Each of the plants was selfed to produce $F_2$ seed, which was collected. In generating the $F_2$ progeny, insertional mutations segregate in a Mendelian fashion and therefore are useful for investigating a mutant allele's effect on the phenotype. The TUSC system has been successfully used by a number of laboratories to identify the function of a variety of genes (Cloning and characterization of the maize An1 gene, Bensen, R J et al., 1995, Plant Cell 7:75-84; Diversification of C-function activity in maize flower development, Mena, M et al., 1996, Science 274:1537-1540; Analysis of a chemical plant defense mechanism in grasses, Frey, M et al., 1997, Science 277:696-699; The control of maize spikelet meristem fate by the APETALA2-like gene Indeterminate spikelet 1, Chuck, G, Meeley, R B, and Hake, S, 1998, Genes & Development 12:1145-1154; A SecY homologue is required for the elaboration of the chloroplast thylakoid membrane and for normal chloroplast gene expression, Roy, L M and Barkan, A., 1998, J. Cell Biol. 141:1-11).

Polynucleotide sequences produced by diversity generation methods or recursive sequence recombination ("RSR") methods (e.g., DNA shuffling) are a feature of the invention. Mutation and recombination methods using the nucleic acids described herein are a feature of the invention. For example, one method of the invention includes recursively recombining one or more nucleotide sequences of the invention as described above and below with one or more additional nucleotides. The recombining steps are optionally performed in vivo, ex vivo, in silico or in vitro. This diversity generation or recursive sequence recombination produces at least one library of recombinant modified HAT polynucleotides. Polypeptides encoded by members of this library are included in the invention.

Descriptions of a variety of diversity generating procedures, including multigene shuffling and methods for generating modified nucleic acid sequences encoding multiple enzymatic domains, are found the following publications and the references cited therein: Soong, N. et al. (2000) "Molecular breeding of viruses" Nat Genet 25(4):436-39; Stemmer, et al. (1999) "Molecular breeding of viruses for targeting and other clinical properties" Tumor Targeting 4:1-4; Ness et al. (1999) "DNA Shuffling of subgenomic sequences of subtilisin" Nature Biotechnology 17:893-896; Chang et al. (1999) "Evolution of a cytokine using DNA family shuffling" Nature Biotechnology 17:793-797; Minshull and Stemmer (1999) "Protein evolution by molecular breeding" Current Opinion in Chemical Biology 3:284-290; Christians et al. (1999) "Directed evolution of thymidine kinase for AZT phosphorylation using DNA family shuffling" Nature Biotechnology 17:259-264; Crameri et al. (1998) "DNA shuffling of a family of genes from diverse species accelerates directed evolution" Nature 391:288-291; Crameri et al. (1997) "Molecular evolution of an arsenate detoxification pathway by DNA shuffling," Nature Biotechnology 15:436-438; Zhang et al. (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Crameri et al. (1996) "Improved green fluorescent protein by molecular evolution using DNA shuffling" Nature Biotechnology 14:315-319; Gates et al. (1996) "Affinity selective isolation of ligands from peptide libraries through display on a lac repressor 'headpiece dimer'" Journal of Molecular Biology 255: 373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al., (1995) "Single-step assembly of a gene and entire plasmid from large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751. Additional details regarding various diversity generating methods can be found in the following U.S. patents, PCT publications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;"

U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in Vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in Vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" W000/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter.

Certain U.S. applications provide additional details regarding various diversity generating methods, including "SHUFFLING OF CODON ALTERED GENES" by Patten et al. filed Sep. 28, 1999, (U.S. Ser. No, 09/407,800); "EVOLUTION OF WHOLE CELLS AND ORGANISMS BY RECURSIVE SEQUENCE RECOMBINATION", by del Cardayre et al. filed Jul. 15, 1998 (U.S. Ser. No. 09/166,188), and Jul. 15, 1999 (U.S. Pat. No. 6,379,964); "OLIGONUCLEOTIDE MEDIATED NUCLEIC ACID RECOMBINATION" by Crameri et al., filed Sep. 28, 1999 (U.S. Pat. No. 6,376,246); "OLIGONUCLEOTIDE MEDIATED NUCLEIC ACID RECOMBINATION" by Crameri et al., filed Jan. 18, 2000 (WO 00/42561); "USE OF CODON-BASED OLIGONUCLEOTIDE SYNTHESIS FOR SYNTHETIC SHUFFLING" by Welch et al., filed Sep. 28, 1999 (U.S. Pat. No. 6,436,675); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (WO 00/42560); "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer (WO 00/42559), filed Jan. 18, 2000; and "SINGLE-STRANDED NUCLEIC ACID TEMPLATE-MEDIATED RECOMBINATION AND NUCLEIC ACID FRAGMENT ISOLATION" by Affholter (U.S. Ser. No. 60/186,482, filed Mar. 2, 2000). Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., WO 00/42561 by Crameri et al., "Oligonucleotide Mediated Nucleic Acid Recombination;" WO 01/23401 by Welch et al., "Use of Codon-Varied Oligonucleotide Synthesis for Synthetic Shuffling;" WO 00/42560 by Selifonov et al., "Methods for Making Character Strings, Polynucleotides and Polypeptides Having Desired Characteristics;" and WO 00/42559 by Selifonov and Stemmer "Methods of Populating Data Structures for Use in Evolutionary Simulations."

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids, which correspond to the recombined sequences, e.g., in concert with oligonucleotide synthesis gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on crossover site selection) as well as designed, pseudo-random or random recombination methods are described in WO 00/42560 by Selifonov et al., "Methods for Making Character Strings, Polynucleotides and Polypeptides Having Desired Characteristics" and WO 00/42559 by Selifonov and Stemmer "Methods of Populating Data Structures for Use in Evolutionary Simulations." Extensive details regarding in silico recombination methods are found in these applications. This methodology is generally applicable to the present invention in providing for recombination of nucleic acid sequences and/or gene fusion constructs encoding proteins involved in various metabolic pathways (such as, for example, carotenoid biosynthetic pathways, ectoine biosynthetic pathways, polyhydroxyalkanoate biosynthetic pathways, aromatic polyketide biosynthetic pathways, and the like) in silico and/or the generation of corresponding nucleic acids or proteins.

Many of the above-described methodologies for generating modified polynucleotides generate a large number of diverse variants of a parental sequence or sequences. In some preferred embodiments of the invention, the modification technique (e.g., some form of shuffling) is used to generate a library of variants that is then screened for a modified polynucleotide or pool of modified polynucleotides encoding some desired functional attribute, e.g., improved HAT activity. Exemplary enzymatic activities that can be screened for include, but are not limited to, catalytic rates (conventionally characterized in terms of kinetic constants such as $k_{cat}$ and $K_M$), substrate specificity, and susceptibility to activation or inhibition by substrate, product or other molecules (e.g., inhibitors or activators) and the maximum velocity of an enzymatic reaction when the binding site is saturated with substrate (Vmax).

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn tissues were prepared. The characteristics of the libraries are described in Table 1.

cDNA libraries may be prepared by any one of many available methods. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651-1656). The resulting ESTs are analyzed using a Perkin Elmer Model 377 fluorescent sequencer.

TABLE 1 cDNA Libraries and clones containing NAR2-like sequences from Corn

| Library | Tissue | Clone |
|---------|--------|-------|
| Cnr1c | Corn (Zea mays). Plants were Nitrogen starved until all seed reserves were depleted of a Nitrogen source. Plants were induced with addition of Nitrogen, then samples were collected at 30 min-1 hr and 2 hr after Nitrogen. | cnr1c.pk003.m9.f:fis |
| Cbn2 | Corn (Zea mays L.) developing kernel two days after pollination | cbn2.pk0042.g4:fis |

Example 2

Identification of cDNA Clones cDNA clones encoding components associated with nitrate transport were identified by conducting BLAST (Basic Local Alignment Search Tool; Altschul et al. (1993) *J. Mol. Biol.* 215:403-410;) and are shown in Table 1.

cDNA clones encoding transporters or components associated with nitrate transport can be identified by conducting BLAST (Basic Local Alignment Search Tool; Altschul et al. (1993) *J. Mol. Biol.* 215:403-410;) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained can be analyzed for similarity to all publicly available DNA sequences contained in the "nr" database using the BLASTN algorithm provided by the National Center for Biotechnology Information (NCBI). The DNA sequences can be translated in all reading frames and compared for similarity to all publicly available protein sequences contained in the "nr" database using the BLASTX algorithm (Gish and States (1993) *Nature Genetics* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Identification and Sequencing of Corn High Affinity Nitrate Transporters (HAT4 and HAT5)

In order to identify homologs of HATs, a public HAT gene (Genbank accession number AY129953), was used to screen Iowa State University MAGI version 2.31 maize genome assembly. A partial clone, MAGI 17514 that showed 85% identity at the nucleotide level and appeared to be a previously unidentified HAT was identified using Blast in the ISU MAGI assembly. This sequence was used to screen the Genbank GSS dataset and some additional homologs of the MAGI sequence were identified; these added about 0.5 kb to the sequence. The GSS dataset consists of sequences set forth in general identification numbers: 33941728, 34245424, 32105143, 34245411, 34082540 and 33992813. The translation of the assembly covered about one half of the gene, at the 3' end. It completely lacked the 5' half of the gene.

In order to isolate the full length HAT4 sequence, BAC clones from two BAC libraries derived from the Maize B73 inbred line were screened using PCR. The libraries had previously been constructed by partial digestion of genomic DNA and inserted in the BamHI and EcoRI sites of the pCUGI (Tomkins, J. P., et al. 2002. Construction and characterization of a deep-coverage bacterial artificial chromosome library for maize. Crop Science 42:928-933) and pTARBAC (pTARBAC2.1 library, Osoegawa, K., et al, Construction Of New Maize, Bovine, Equine And Zebrafish Bac Libraries. Plant And Animal Genome Conference Proceedings. 2001). To facilitate a PCR-based screening, a set of 36 four-dimensional superpools was requested from Amplicon Express (Amplicon Express, 1610NE Eastgate Blvd Pullman, Wash. 99163). Each superpool was derived after the independent growth, isolation and pooling of 4608 clones, more than 165,000 arrayed BAC clones in total. Superpools were subject to PCR reactions, followed by fragment plus-minus determination in agarose gel electrophoresis. PCR primers were designed to amplify a 495-bp fragment located 289 by downstream the stop codon of a HAT homolog located at the Tigr assembly ID AZM4_32787, which is identical to the sequences assembled from the MAGI and GSS databases described above. PCR reactions were performed with 5 ng Template DNA in a 10-µL reaction that included 5 µL of Hotstar Taq Polymerase Mix (Qiagen) and 5 pmol of the forward and reverse primers (SEQ ID NO:1 and SEQ ID NO:2, respectively). Cycle conditions were an initial denaturation step at 95° C. for 15 minutes, followed by 35 cycles of 95° C. for 30 seconds, 60° C. for 30 seconds and 72° C. for 1 minute. A second round of PCR was performed in matrix plates consisting of lower-complexity combinatorial pools derived from clones represented in positive pools. This narrowed down the positives to particular clones. Two clones, bacc.pk139.d24 and bacc.pk142.b21, were identified and confirmed by PCR analysis. Clone bacc.pk139.d24 was used in subsequent work.

BAC DNA from clone bacc.pk139.d24 was isolated from overnight 250-ml 2xYT+cloramphenicol cultures using a modified alkaline lysis method. Cells were harvested by centrifugation and resuspended in 20 ml of 10-mM EDTA, then lysed by gently adding 40 ml of 0.2-N NaOH/1-% SDS and neutralized with 30 ml of cold 3-M potassium acetate (pH 4.8). Cell debris were removed by centrifugation at 4° C. 15 minutes at 15000×g, followed by filtration through Miracloth. DNA in supernatant was precipitated with 0.7 volumes of isopropanol and resuspended in 9 ml of 50-mM Tris/50-mM EDTA, mixed with 4.5 ml of 7.5-M potassium acetate, placed at −70° C., thawed and centrifuged for 20 minutes at 3500×g. The supernatant was decanted, precipitated with ethanol and resuspended in 0.7 ml of 50-mM Tris/50-mM EDTA. DNase-free RNase A was added to a final concentration of 150 µg/ml and incubated 1 hour at 37° C., followed by phenol:chloroform extraction and ethanol precipitation. Final DNA was resuspended in a total of 400 µl sterile nuclease-free water. DNA insert size, quantity and quality was assessed by Pulsed Field Gel Electrophoresis using a CHEF-Mapper III (Bio-Rad). For confirmatory BAC end sequencing, the T7 (SEQ ID NO:3) and SP6 (SEQ ID NO: 4) primers were used using sequencing conditions described below.

The general strategy to obtain double-strand, contiguous sequence information along the HAT4 gene was by walking from the known "start" sequence defined by the PCR identification primers, previously described. BAC bacc.pk139.d24 DNA was used as template. Sequencing was performed in a AB13730 capillary sequencer according to manufacturer protocols. Sequencing reactions consisted of 2 µL of BigDye V3.1Terminator mix (Applied Biosystems), 2 µL of dilution buffer (600 mM Tris HCl pH 9.0, 15 mM MgCl2), 20 pmol of primer, and approximately 1 µg of template DNA in a final reaction volume of 20 µL. Cycle conditions were an initial denaturation at 95° C. for 5 minutes, followed by 99 cycles of 95° C. for 30 seconds, 58° C. for 30 seconds and 64° C. for 4 minutes. Some hard-to-read regions had to be re-sequenced using special cycle and reaction conditions. Excess dye terminator was removed by ethanol precipitation. Trace evaluation, base calling and assembly was based on Phred/Phrap software (Ewing et al. (1998) Genome Res. 8:186-194; Ewing et al. (1998) Genome Res. 8:175-185). Consed (Gordon et al. (1998) Genome Res. 8:195-202) was used for assembly analysis. After every sequence walking step, primers were designed at the ends, avoiding regions of high homology to other genes and to DNA repeats. Homology search was performed using the BLAST program (Basic Local Alignment Search Tool; Altschul et al. (1993) J. Mol. Biol. 215:403-410) against gss, TIGR 4.0, nonredundant, EST, and protein databases (Altschul et al. 1990). Vector NTI was used for primer design and primers were synthesized commercially by MWG Biotech. Primers (SEQ ID NO: 5 through SEQ ID NO: 33) were designed, tested and used to cover region including the HAT gene. SEQ ID NO: 34 describes the genomic sequence containing the HAT 4 gene. SEQ ID NOs: 35 and 36 describe the coding nucleotide and amino acid sequence of the corn HAT4, respectively.

SEQ ID NOs: 37 and 38 show the 2014 bp and 1014 bp putative promoter sequences of the HAT4 gene.

The HAT-5 family was identified via blast homology to the public HATs. One 3' clone cco1n.pk072.i13 had homology to MAGI_56254, which appeared to represent the entire sequence. The TIGR assembly AZM4_2103 corresponded well to the MAGI clone. Databases containing nitrogen induced libraries were re-blasted using this clone and clone cfp4n.pk008.p6 was identified. This clone was sequenced and contains the complete HAT5 gene sequence (SEQ ID NO:91 and 92).

Example 4

Identification and Sequencing of an Additional Corn High Affinity Nitrate Transporter (HAT 7)

A public HAT gene (HAT1, Genbank accession number AY129953) was used to search with Blast, Genbank maize genomic survey sequences (GSS) and maize genomic assemblies (Iowa State University MAGI and Tigr), to try to identify paralogs of AY129953. Along with the HAT4 gene (Example 3) there were other more distant homologs, including MAGI_65216 which corresponded to AZM4_79242, which contained slightly more sequence information than MAGI_65216). Neither of these two clones contained a start Methionine. AN additional hit to AZM4_79246 exhibited similar percent identity when compared to AY129953. AZM4_79246 encoded a start Methionine at nucleotide 2264-2266 and approximately 110 amino acids of coding sequence. Further examination showed that these two assemblies shared clone mates, OGUKX93 and OGUCS47 from the Tigr methylation filtrated library. Therefore it was assumed that AZM4_79242 and AZM4_79246 encode the same gene but have no sequence overlap.

In order to retrieve the full length sequence, PCR was performed using two different forward and two different reverse primers (SEQ ID NOs: 39, 40 and 41, 42, repectively) with T3 (SEQ ID NO: 43) and T7 extensions (SEQ ID NO: 44 at the 5' and 3' end, respectively. HotStart PCR, with an annealing temperature of 58° C. was performed using DNA from eight maize inbred lines (B73, Co159, GT119, Mo17, T218, Oh43 and W23) as templates. All 32 PCR reaction products were run on a agarose 1x TBE gel, excised and cleaned up and sequenced on a 3100 ABI Capillary Sequencer using methods known to those of ordinary skill in the art. The sequences were aligned and the missing sequence information was retrieved. The complete nucleotide sequence of the HAT7 gene is shown in SEQ ID NO: 45. SEQ ID NOs: 46 and 47 describe the 2263 bp and 1263 bp putative promoter sequences of the HAT7 gene and SEQ ID NOs: 48 and 49 describe the coding nucleotide and amino acid sequence of the corn HAT7, respectively.

Example 5

Characterization of Polypeptides Encoding High Affinity Nitrate Transporter

The data in Table 2 represent a calculation of the percent identity of the amino acid sequences set forth in SEQ ID NOs: 36 and 49 and the *Oryza sativa* sequences (NCBI General Identifier Nos. 34913806 and 50904699).

TABLE 2

Percent Identity of Amino Acid Sequences Deduced From the Nucleotide Sequences of cDNA Clones Encoding Polypeptides Homologous to High Affinity Nitrate Transporter (HAT)

| | Percent Identity to | |
|---|---|---|
| SEQ ID NO. | 34913806 | 50904699 |
| 36 | 38.0 | 75.3 |
| 49 | 78.2 | 39.4 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode corn high affinity nitrogen transporters.

Example 6

Identification and Sequencing of Corn Nitrogen Transport Related Genes, (NAR2-1 & NAR2-2)

Examination of blast hits from the maize root library cnr1c, described in Example 1 and Table 2, showed a number of Nitrogen transport related genes. Blast hits were searched with keywords such as nitrate, nitrogen, and transporter. A few of these were homologous to NCBI Accession number: CAC36942, a putative component of high affinity nitrate transporter (NAR2 gene). A TblastN search of maize ESTs, using the sequence of CAC36942 as a query, produced a number of significant hits from different maize libraries. The most 5'clone was identified by aligning the full-length query and the blast hits. A clone from the cnr1c library (cnr1c.pk003.m9.f) showed a methionine that was in the same region as the start methionine from CAC36942. This clone also showed an in frame stop codon upstream of the methionine. This clone was submitted for standard full insert sequencing (FIS) and contained the 971 bp of the NAR2.1, spanning nucleotides 591 through 1561 of SEQ ID NO: 53. SEQ ID NO: 53 shows the 1561 bp sequence of the NAR2.1 gene, which was assembled from the sequence information obtained from clone cnr1c.pk003.m9.f:fis and from Tigr sequence AZM4_81138. SEQ ID NOs: 54 and 55 show the coding nucleotide and amino acid sequence of the NAR2.1 gene, respectively. SEQ ID NO: 56 shows 756 bp of the putative promoter of the NAR2.1. Using CAC36942 as a query also showed a different NAR2 homolog, cbn2.pk0042.g4. This clone also had a start Methionine, but because of the quality of the EST sequence the homology to CAC36942 was short. A complete version (Tigr clone AZM4_1475) of this family member was identified by searching the Tigr maize genomic assembly using cbn2.pk0042.g4 as a query. SEQ ID NOs: 57 and 58 show the coding nucleotide and amino acid sequence of the NAR2.2 (Tigr clone AZM4_1475), repectively.

NAR2.1 Promoter Isolation

The sequence information on the NAR2.1 promoter was extended further upstream by performing Genome Walker™ DNA walking (BD BioSciences). This method employs PCR to facilitate the cloning of unknown genomic DNA sequences adjacent to a known sequence. First, pools of unknown genomic DNA were digested with different restriction enzymes that leave blunt ends. Each pool was ligated to adaptors to create Genome Walker" libraries. Eight different corn HG11 libraries were obtained. These libraries were digested with the following restriction enzymes: StuI, EcoRV, PmlI, PvuII, ScaI, DraI, SmaI, and PmeI.

Then two rounds of nested PCR amplification per library were performed. For the first round the outer adaptor primer (AP1, provided with kit) and the Nar2.1 specific outer primer (SEQ ID NO: 59) were used.

PCR was performed using the Advantage®-GC Genomic Polymerase Mix (BD Biosciences) in a 50 µL reaction containing 1 µL 1 library DNA, 0.5 µL each primer (10 µM), 4 µL dNTPs (2.5 mM), 2.2 µL Mg (OAc)$_2$, 10 µL 15× GC Genomic PCR Reaction Buffer, 10 µL GC-Melt (5M), 20.8 µL ddH$_2$O, and 1 µL Advantage-GC Genomic Polymerase. The cycling conditions were as follows: 7 cycles of denaturation at 94° C. for 25 seconds and annealing/extension at 72° C. for 6 minutes followed by 32 cycles of denaturation at 94° C. for 25 seconds and annealing/extension at 67° C. for 6 minutes capped off by annealing/extension at 67° C. for 7 minutes.

The primary PCR product was then diluted 1:50 and 1 µL served as the template for the second round of PCR which used the same PCR set-up as the first round. The second round primers were the inner adaptor primer (AP2, provided with the kit) and the Nar2.1 specific inner primer (SEQ ID NO: 60). The cycling conditions for the second round were as follows: 5 cycles of denaturation at 94° C. for 25 seconds and annealing/extension at 72° C. for 6 minutes followed by 25 cycles of denaturation at 94 C for 25 seconds and annealing/extension at 67° C. for 6 minutes capped off by annealing/extension at 67° C. for 7 minutes.

A major PCR product (about 3 kb) was observed in the StuI library. This band was cut-out of the gel and purified using the Qiaquick Gel Extraction Kit (Qiagen) and ligated to a pGEM®-T Easy Vector (Promega). The 20 µL ligation reaction was as follows: 10 µL 2× Rapid Ligation Buffer, 1 µL pGEM®-T Easy Vector (50 ng), 1 µL T4 DNA Ligase (3 Weiss units/µL), and 8 µL insert DNA (13 ng/µL). The reaction was incubated at 4° C. overnight.

The ligation product was transformed into Max Efficiency DH10B (Invitrogen) competent cells. One µL of ligate was added to 20 µL of cells and put on ice for 30 minutes. The cells were heat shocked at 42° C. for 45 seconds and then placed again on ice for 2 minutes. The cells were added to 1 mL of SOC and placed on a shaker at 250 rpm for 1 hr at 37° C. Then, 100 µL of cells were plated onto LB media with Ampicillin, IPTG, and X-Gal to allow for blue/white selection. Only one white colony was obtained.

Plasmid DNA was purified using the Plasmid Mini Kit (Qiagen). The plasmid insert representing the NAR2 upstream promoter region was sequenced using standard primers (SP6 and T7) and custom primers (SEQ ID NOs: 61, 62, 63 and 64). SEQ ID NO: 65 shows the sequence of the additional 2917 bp putative NAR 2.1 promoter.

The sequence of the complete NAR2.1 gene is shown in SEQ ID NO: 66.

Example 7

Expression Pattern of Polypeptides of Instant Application

The expression pattern of high affinity nitrate transporters (HAT) and other polypeptides (NAR) required for high affinity nitrate transport was analyzed via Lynx MPSS Brenner et al (2000) *Proc Natl Acad Sci USA* 97:1665-70).

The expression patterns of NAR2.1 and HAT 1 genes are similar across more than 200 libraries as studied via Lynx MPSS (Brenner et al (2000) *Proc Natl Acad Sci USA* 97:1665-70). They are both expressed only in the cortical cylinder of the root tissue and are similarly induced by nitrate, indicating that the polypeptide products of these two genes form a functional complex for nitrate transport in maize roots.

Tissue-specific expression of NAR2.1 and HAT-1 in maize: Of the 210 libraries from different tissues encompassing the whole of maize plant, NAR2.1 and HAT-1 are expressed only in the root libraries. This indicates the root-specific function for each of these genes.

Expression analysis of NAR2.1 and HAT-1 in maize tissues. MPSS tag abundances were averaged over different tissue libraries. The number of libraries for each tissue was: anther, 3; ear, 15; kernel, 44; leaf, 39; pollen, 1; root, 36; silk, 9; stalk, 19; and tassel, 14.

Induction of nitrate uptake and localization within maize roots: Among the root libraries derived from an inbred line A63, the expression of both NAR2.1 and HAT-1 is similarly induced by nitrate.

Corn roots from etiolated seedlings obtained 7-days after growing in paper rolls in water, were harvested and subjected to different treatments in parallel. The freshly harvested roots were kept on ice as controls. The roots were incubated in an aerated solution containing different nutrients for different lengths of time and then either quickly frozen in liquid N and stored at −80° C. until used for expression analyses or saved between two layers of wet paper towels in ice for further manipulation. A batch of roots that had been treated for four hours in nitrate was manually dissected into cortical cylinder and stele.

Response of NAR2.1 and HAT 1 expression to different nutrient treatments. The roots were treated for either half hour or four hours in a medium containing either 1 mM nitrate (0.5 mM $KNO_3$ and 0.25 mM $Ca(NO_3)_2$) or 1 mM chloride (0.5 mM KCl and 0.25 mM $CaCl_2$). A batch of roots treated for 4 hours with nitrate was separated into cortical cylinder and stele and subjected to MPSS.

Both the NAR2.1 and HAT 1 genes from maize exhibit a similar response to nitrate (N) in the incubation medium which is incremental with time when compared to the parallel control roots incubated in a chloride solution. Also, both these genes are nearly exclusively located in the cortical sleeve and not in the stele. Their similar response to nitrate and their localization strongly indicate that the protein products of these genes make a functional nitrate transport complex in maize roots.

Opposite regulation of expression of NAR2.1 in Illinois High Protein (IHP) and Illinois Low Protein (ILP) maize lines: IHP and ILP are two sets of lines that are derived from a maize population after ~100 years of divergent selection for grain protein in the high and low grain protein directions, respectively (Uribelarrea et al., 2004). Whereas IHP grains contain >20% protein, those of ILP contain <5%. The roots of these two lines were subjected to Lynx MPSS after various treatments.

Roots were either kept in a nitrate solution all the time, starved for two hours for nitrate, or placed in nitrate solution after two hour starvation. Whereas NAR2.1 in IHP responded to nitrate treatment like A63, ILP exhibited an opposite response Given the level of expression of this gene in ILP in nitrate starved roots, which is similar to that of IHP roots kept in nitrate, these results suggest that mechanisms to respond to nitrate in both the directions do exist in maize. However, the mechanism for positive response appears to have been selected as indicated by similar response between IHP and A63, an inbred line with normal grain protein content of ~10%.

Only IHP contained the tag for HAT 1 sequence and showed a similar pattern of expression as for NAR2.1, lending further support to the aforementioned suggestion that NAR2.1 and HAT 1 form a functional complex in maize roots.

Expression of other HAT genes in A63: HAT 4G was expressed at >10 ppm only in four libraries, all derived from the root tissue. Thus, this gene appears to be root-specific. HAT 7 is expressed in chilled seedlings and three leaf libraries, suggesting that this gene may encode a protein for nitrate uptake from the xylem apoplast into the leaf cells. It is expected that the HAT sequences of the instant application form a functional nitrate transport complex with a NAR sequence.

Example 8

Confirmation of Function of the High Affinity Nitrate Transporters and Polypeptides Required for High Affinity Nitrate Transport using the TUSC Mutant Population The full genomic sequence for the high affinity nitrate transporter locus can be used to design primers to screen for Mu-insertion mutants in the TUSC population (U.S. Pat. No. 5,962,764, issued Oct. 5, 1999). The pooled TUSC population can be screened with gene specific primers. Alleles of the corn high affinity nitrate transporters and polypeptides required for high affinity nitrate transport can be recovered from this screen, and characterized. Furthermore, function of the sequences of the instant application can be confirmed by complementation studies.

Example 9

Expression of Recombinant DNA Constructs in Monocot Cells

A recombinant DNA construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Ncol or Smal) can be incorporated into the oligonucleotides to provide proper orientation of the DNA fragment when inserted into the digested vector pML103 as described below. Amplification is then performed in a standard PCR. The amplified DNA is then digested with restriction enzymes Ncol and Smal and fractionated on an agarose gel. The appropriate band can be isolated from the gel and combined with a 4.9 kb Ncol-Smal fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb Sall-Ncol promoter fragment of the maize 27 kD zein gene and a 0.96 kb Smal-Sall fragment from the 3' end of the maize 10 kD zein gene in the vector pGem9Zf(+) (Promega). Vector and insert DNA can be ligated at 15° C. overnight, essentially as described in Maniatis. The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0242236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2, 4-D. After two weeks the tissue can be transferred to regeneration medium (Fromm et al. (1990) *Bio/Technology* 8:833-839).

Example 10

Expression of Recombinant DNA Constructs in Dicot Cells

A seed-specific expression cassette composed of the promoter and transcription terminator from the gene encoding the α-subunit of the seed storage protein phaseolin from the bean Phaseolus vulgaris (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a recombinant DNA construct composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefacien*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 11

Expression of Recombinant DNA Construct in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-beta-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 12

Electroporation of *Agrobacterium tumefaciens* LBA4404

Electroporation competent cells (40 pt), such as *Agrobacterium tumefaciens* LBA4404 (containing PHP10523), are thawed on ice (20-30 min). PHP10523 contains VIR genes for T-DNA transfer, an *Agrobacterium* low copy number plasmid origin of replication, a tetracycline resistance gene, and a Cos site for in vivo DNA bimolecular recombination. PHP10523 is further described in Example 17. Meanwhile the electroporation cuvette is chilled on ice. The electroporator settings are adjusted to 2.1 kV. A DNA aliquot (0.5 µL parental DNA at a concentration of 0.2 µg-1.0 µg in low salt buffer or twice distilled $H_2O$) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2×YT medium (or SOC medium) are added to the cuvette and transferred to a 15 mL snap-cap tube (e.g., Falcon™ tube). The cells are incubated at 28-30° C., 200-250 rpm for 3 h.

Aliquots of 250 pt are spread onto plates containing YM medium and 50 µg/mL spectinomycin and incubated three days at 28-30° C. To increase the number of transformants one of two optional steps can be performed:

Option 1: Overlay plates with 30 µL of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 µg/mL spectinomycin for isolation of single colonies. The plates are incubated at 28° C. for two to three days. A single colony for each putative co-integrate is picked and inoculated with 4 mL of 10 g/L bactopeptone, 10 g/L yeast extract, 5 g/L sodium chloride and 50 mg/L spectinomycin. The mixture is incubate for 24 h at 28° C. with shaking. Plasmid DNA from 4 mL of culture is isolated using Qiagen Miniprep and an optional Buffer PB wash. The DNA is eluted in 30 µL. Aliquots of 2 µL are used to electroporate 204 of DH10b+204 of twice distilled $H_2O$ as per above. Optionally a 154 aliquot can be used to transform 75-100 µL of Invitrogen Library Efficiency DH5a. The cells are spread on plates containing LB medium and 50 µg/mL spectinomycin and incubated at 37° C. overnight.

Three to four independent colonies are picked for each putative co-integrate and inoculated 4 mL of 2×YT medium (10 g/L bactopeptone, 10 g/L yeast extract, 5 g/L sodium chloride) with 50 µg/mL spectinomycin. The cells are incubated at 37° C. overnight with shaking. Next, isolate the plasmid DNA from 4 mL of culture using QIAprep® Miniprep with optional Buffer PB wash (elute in 50 µL). Use 84 for digestion with SalI (using parental DNA and PHP10523 as controls). Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Example 13

Transformation of Maize Using *Agrobacterium*

*Agrobacterium*-mediated transformation of maize is performed essentially as described by Zhao et al. in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium innoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step

PHI-A medium of (1) is removed with 1 mL micropipettor, and 1 mL *Agrobacterium* suspension (including, but not limited to, the *Agrobacterium* described in Example 7) is added. The tube is gently inverted to mix. The mixture is incubated for 5 min at room temperature.

2.2 Co-culture Step

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with parafilm. The plates are incubated in darkness at 28° C. Actively growing putative events, as pale yellow embryonic tissue, are expected to be visible in six to to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 Plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:
1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).
2. PHI-B: PHI-A without glucose, increase 2,4-D to 2 mg/L, reduce sucrose to 30 g/L and supplemente with 0.85 mg/L silver nitrate (filter-sterilized), 3.0 g/L Gelrite®, 100 µM acetosyringone (filter-sterilized), pH 5.8.

3. PHI-C: PHI-B without Gelrite® and acetosyringonee, reduce 2,4-D to 1.5 mg/L and supplemente with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected.

Furthermore, a recombinant DNA construct containing a validated *Arabidopsis* gene can be introduced into an elite maize inbred line either by direct transformation or introgression from a separately transformed line.

Transgenic plants, either inbred or hybrid, can undergo more vigorous field-based experiments to study yield enhancement and/or stability under nitrogen limiting and nitrogen non-limiting conditions.

Subsequent yield analysis can be done to determine whether plants that contain the validated *Arabidopsis* lead gene have an improvement in yield performance (under nitrogen limiting or non-limiting conditions), when compared to the control (or reference) plants that do not contain the validated *Arabidopsis* lead gene. Plants containing the validated *Arabidopsis* lead gene would have less yield loss relative to the control plants, preferably 50% less yield loss, under nitrogen limiting conditions, or would have increased yield relative to the control plants under nitrogen non-limiting conditions.

Example 14

Evaluating Compounds for Their Ability to Inhibit the Activity of Nitrate Transporters The polypeptides described herein may be produced using any number of methods known to those skilled in the art. Such methods include, but are not limited to, expression in bacteria as described in Example 11, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin, which is specific for the fusion protein tag attached to the expressed enzyme or an affinity resin containing ligands, which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions that permit optimal enzymatic activity.

Assays that enable rapid screening for nitrate transport activity have been described in the literature, including, but not limited to an assay that measures $^{15}$N-enriched nitrate uptake into Xenopus oocytes expressing the proteins (Tong et al., The Plant J. (2005) 41:442-450).

Example 15

Expansion of the Linear Nitrate Uptake Range of Higher Plant HATS by Gene Shuffling HATs are known to possess a low Km (in 10 to 100 µM range) and low Vmax (Doddema et al., Kinetics. Physiol. Plant. (1979) 45:332-338, Meharg et al., (1995) J. Membr. Biol. 145:49-66, Touraine et al., Plant Physiol. (1997) 114: 137-144, Liu et al., Plant Cell. (1999) 11(5):865-874). Therefore, the uptake rate of HATs remains constant once the nitrate concentration reaches a level of about 2 to 3 fold higher than their Km.

The most relevant field nitrate concentration is around 2 to 5 mM on a typical modern corn farmland. Within this concentration range, the uptake rate of HATs is well saturated. Extending the linear nitrate uptake of HATs from very low to relevant field concentration would allow maize crop to fully utilize available nitrate for better growth and productivity. Such a transporter would also allow the crop plant to maintain the normal uptake efficiency at lower nitrate input by its enhanced ability to uptake fast at relatively lower nitrate concentration.

Various gene-shuffling methods (Stemmet WP, PNAS (1994) 91: 10747-10751, Crameri et al., Nature (1998) 391: 288-291, Ness et al., Nature Biotech. (1999) 17:893-896) can be used to generate different types of shuffled HATs libraries. For example, libraries can be generated by single gene and family gene shuffling. Additional diversities can be introduced by spiked oligos carrying amino acid mutations.

The shuffled HAT libraries can be functionally expressed in one of the heterologous hosts such as yeast, E. coli, and green algae. Preferably, the host lacks the nitrate assimilation pathway except for an endogenous or introduced nitrate reductase. Nitrate uptake rate by functionally expressed shufflants can be assayed by either direct measurement of depletion of nitrate in the assay medium via HPLC or other analytical means or by measurement of nitrite generated by nitrate reductase within the same cell. Nitrite concentration can be easily determined by colorimetrical assay (such as use of Greiss Reagent) or other analytical means (HPLC). Further characterization of the putative hits from screening various shuffled libraries can be achieved by measuring the uptake rates against different concentrations of nitrate. Such assay will provide uptake kinetic parameters of Km and Vmax.

Hits confirmed with improved properties can then be reshuffled to generate a second round of shuffled libraries and the aforementioned screening scheme can be used for identifying second round hits. This process can be repeated until several shuffled variants are identified that meet the desired kinetic properties.

Example 16

Isolation, Cloning and Sequencing of the Nar Promoter from the Maize B73 Inbred Line Identification of a BAC Clone Carrying the Nar Gene A BAC library derived from maize B71 inbred line was screened by PCR using the forward and reverse primers depicted in SEQ ID NOs: 75 and 76, respectively. Cycle conditions were an initial activation step at 95° C. for 15 minutes, followed by 35 cycles at 94° C. for 1 minute, 60° C. for 1 minute and 72° C. for 1 minute. Final extension was at 72° C. for 10 minutes.

A 377 bp product was obtained. BAC clone ZMMBBb0521 a1 was identified as carrying the Nar gene.
Cloning of the Nar Promoter from Maize B73 Inbred Line The Nar promoter was cloned by PCR using the forward and reverse primer with restriction enzyme sites for BamHI and HindIII depicted in SEQ ID NOs: 77 and 78, repectively.

To 1 μl diluted (1:100) BAC DNA from BAC clone ZMMBBb0521a1, 1 μl primer mix at a concentration of 10 μM each, 4 μl DNTPs at a concentration of 2.5 mM, 10 μl 5× HF buffer and 33.5 μl H₂O and 0.5 μl Phusion High Fidelity DNA Polymerase (Finnzymes) were added. Cycle conditions were an initial activation step at 98° C. for 30 seconds, followed by 35 cycles of 98° C. for 10 seconds, 63° C. for 30 seconds and 72° C. for 1 minute. Final Extension was at 72° C. for 10 minutes.

A product of 3621 bp was obtained.

The 3621 bp product was gel purified using the Qiaquick™ Gel Extraction Kit (Qiagen) and eluted with 88 μl Elution Buffer.

To the purified band 10 μl of buffer E (Promega) and 1 μl of each of the restriction enzyme, BamHI and Hind III (each at 10 U/μl) were added. The assay mixture was incubated at 37° C. for 3 hrs and cleaned up with Qiaquick™ PCR Purification Kit (Qiagen).

The pENTR-5' vector (SEQ ID NO: 85) was digested with BamHI and HindIII and dephosphorylated. The purified PCR band was inserted into the prepared pENTR-5' vector using the Epicentre Fast Link Kit. The ligation reaction mixture contained 1.5 μL buffer (10×), 1.5 μL ATP (10×), 1 μL ligase, 1 μL pENTR-5'vector (~10 ng/μL BamHI/HindIII/dephosphorylated vector), 1 μL promoter insert (~30 ng) and 9 μL H20. The ligaton reaction was allowed to proceed for 15 minutes at room temperature and was stopped by incubating the mixture at 70° C. for 15 minutes.
Transformation into Bacteria and PCR Screen for Insert 1 μL of the ligation mix was added to 20 μL of electro-competent cells (DH10B ElectroMax-Invitrogen) and the mixture was electroporated with a Gibco BRL Cell Porator, then 1 mL SOC media were added and the mixture was incubated in a shaker at 37° C. for 1 hr. 150 μL of cells were plated on LB plates with Kanamycin selection and grown overnight at 37° C.

12 colonies were picked and 30 μL LB media was added. The colonies were screened using PCR. To 1 μL colony DNA (colony/30 μL LB), 5 μL HotTaq 2× master mix (Qiagen), 1 μL (10 mM primer mix, SEQ ID NO: 77 and 78) and 3 μL dH₂0 were added. Cycle conditions were an initial activation at 95° C. for 15 minutes, followed by 35 cycles of 95° C. for 50 seconds, 55° C. for 50 seconds and of 72° C. for 4 minutes. Final Extension was at 72° C. for 10 minutes.
Insert Sequencing DNA carrying the insert was sequenced using the sequence primers depicted in SEQ ID NOs: 79-84. The sequence of the insert is shown in SEQ ID NO: 70. The vector construct carrying the 3621 bp insert was named PHP27621 and is shown in SEQ ID NO: 86 and FIG. 1.

Example 17

Testing the NAR Promoter in Transgenic Maize and *Arabidopsis*

Using Invitrogen's™ gateway LR Clonase technology a MultiSite Gateway® LR Recombination Reaction was performed to create the corn NAR promoter::GUS::PINII, UBI::MO-PAT::PINII and LTP2::DS-RED PINII JT binary vector (PHP27660, SEQ ID NO: 87 and FIG. 2). The vector PHP27660 contains the following expression cassettes:
1. Ubiquitin promoter::MO-PAT::PINII terminator cassette expressing the PAT herbicide resistance gene used for selection during the transformation process.
2. LTP2 promoter::DS-RED2::PinII terminator cassette expressing the DS-RED color marker gene used for seed sorting.
3. NAR promoter::GUS::PINII terminator cassette expressing the GUS gene under control of the corn NAR promoter.

Vector PHP27660 was electroporated using the protocol outlined in Example 16 into LBA4404 *Agrobacterium* cells containing PHP10523 bp electroporation creating the final co-integrate vector PHP27860 (SEQ ID NO: 88 and FIG. 3) was then used for *Agrobacterium*-based maize transformation as described in Example 17. T0 transgenic plants were sampled for GUS expression.

Separately, the same vector (PHP27860) was also used for *Arabidopsis* transformation, following the standard inflorescence-dipping procedures. Transgenic events were selected by herbicide glufosinate spraying on the T1 seedlings. The herbicide-resistant T1 plants were sampled for GUS expression.

Leaf and root tissue samples were collected from transgenic plants at different time points, including seedling stage and at maturity. Freshly collected tissue samples were dissected into small pieces to facilitate penetration of the GUS staining solution. GUS histochemical staining was done following the standard protocol (Jefferson R A, Kavanagh T A, Bevan M W. 1987 GUS fusions: beta-glucuronidase as a sensitive and versatile gene fusion marker in higher plants. EMBO J. 6(13):3901-3907) incubating at 37° C. overnight.

No significant promoter activity was observed in transgenic maize and *Arabidopsis* tissues.

Example 18

Testing the Effects of Extraneous Junction Sequences on the NAR Promoter in Transqenic Maize and Arabidopsis The Gateway cloning system leaves a short fragment of "foot-print" sequences between components, particularly a 21-bp ATT-B1 fragment between the NAR promoter and the GUS coding region. This has been shown to weaken or even abolish promoter activity in certain cases. This likely is related to the physical distance between basal promoter elements and the start codon. To determine if introducing the ATT-B1 site is negatively affecting the NAR promoter, a construct containing the corn NARpromoter::GUS::PINII cassette is built with a conventional cloning method, i.e., without the use of the Gateway system. Transgenic maize plants are produced via *Agrobacterium*-based transformation, and various tissue samples are collected for GUS expression study as described in Example 17.

Example 19

Testing the maize NAR Promoter in a Deletion Series

The NAR gene has a nitrate-inducible and root-specific expression pattern. To determine the fragments that determine NAR promoter activity and specificity, a series of constructs containing truncated NAR promoter fragments linked to the sequences for GUS and the PINII end are constructed and tested as described for the full length promoter in Examples 17 and 18.

Using BLASTN (Basic Local Alignment Search Tool; Altschul et al. (1993) *J. Mol. Biol.* 215:403-410;), sequences within the NAR promoter can be identified that might be important for enhancing or suppressing promoter activity. The sequence around 1.5 to 1.9 kb of the NAR promoter shows homology to another gene and a transposon element. Deletion of this fragment as shown in SEQ ID NO: 89 is therefore expected to add information on NAR promoter activity.

In addition truncation that reduce the length of the promoter as shown in SEQ ID NOs: 71, 72, 73, 74 and 90 can also be tested in the same way as described for the full length promoter in Examples 17 and 18. Additional promoter subfragments can be prepared by using primers derived from the 3.6 Kb NAR promoter sequence in PCR.

Example 20

Evaluation of Nitrate Uptake in Maize using HAT and NAR Sequences and Combinations Thereof The following maize expression constructs were prepared for evaluation of nitrate uptake in maize: PHP27280 (SEQ ID NO: 93 and FIG. 4), PHP27281 (SEQ ID NO:94 and FIG. 5), PHP27282 (SEQ ID NO: 95 and FIG. 6) and PHP27283 (SEQ ID NO:96 and FIG. 7).

Additional constructs comprising HAT sequences and combinations of HAT and Nar sequences will be prepared and tested for their ability to alter Nitrate transport. T0, T1 and subsequenct generations will be evaualted for alterd biomass and total ear weight under 1 mM nitrate conditions.

What is claimed is:

1. An isolated polynucleotide comprising:
   (a) a nucleotide sequence encoding a high affinity nitrate transporter polypeptide, wherein the polypeptide has an amino acid sequence of at least 95% sequence identity, based on the Clustal V method of alignment, when compared to SEQ ID NO: 49; or
   (b) a complement of the nucleotide sequence, wherein the complement and the nucleotide sequence consist of the same number of nucleotides and are 100% complementary.

2. The polynucleotide of claim 1, wherein the amino acid sequence of the polypeptide has at least 99% sequence identity, based on the Clustal V method of alignment, when compared to SEQ ID NO: 49.

3. The polynucleotide of claim 1, wherein the amino acid sequence of the polypeptide comprises SEQ ID NO: 49.

4. The polynucleotide of claim 1 wherein the nucleotide sequence comprises SEQ ID NO: 48.

5. The isolated polynucleotide of claim 1, wherein the polypeptide sequence comprises at least two motifs selected from group consisting of SEQ ID NOs: 50, 51 and 52.

6. A recombinant DNA construct comprising the isolated polynucleotide of claim 1, the polynucleotide operably linked to at least one regulatory sequence.

7. A plant comprising in its genome the recombinant DNA construct of claim 6.

8. A transgenic seed obtained from the plant of claim 7.

9. The plant of claim 7, wherein said plant is selected from the group consisting of rice, corn, sorghum, millet, rye, soybean, canola, wheat, barley, oat, beans, and nuts.

10. A plant cell comprising in its genome the recombinant DNA construct of claim 6.

11. Plant tissue comprising the plant cell of claim 10.

* * * * *